US012116585B2

(12) United States Patent
Armstrong et al.

(10) Patent No.: US 12,116,585 B2
(45) Date of Patent: *Oct. 15, 2024

(54) GENETICALLY MODIFIED REDUCED-BROWNING FRUIT-PRODUCING PLANT AND PRODUCED FRUIT THEREOF, AND METHOD OF OBTAINING SUCH

(71) Applicant: Okanagan Specialty Fruits Inc., Summerland (CA)

(72) Inventors: John Armstrong, Penticton (CA); William David Lane, Summerland (CA)

(73) Assignee: OKANAGAN SPECIALTY FRUITS INC., Summerland (CA)

( * ) Notice: Subject to any disclaimer, the term of this patent is extended or adjusted under 35 U.S.C. 154(b) by 141 days.

This patent is subject to a terminal disclaimer.

(21) Appl. No.: 17/738,230

(22) Filed: May 6, 2022

(65) Prior Publication Data

US 2022/0267786 A1   Aug. 25, 2022

Related U.S. Application Data

(63) Continuation of application No. 16/248,057, filed on Jan. 15, 2019, now Pat. No. 11,359,205, which is a continuation of application No. 15/404,236, filed on Jan. 12, 2017, now Pat. No. 10,227,602, which is a continuation of application No. 14/049,952, filed on Oct. 9, 2013, now Pat. No. 9,580,723, which is a continuation of application No. 12/919,735, filed as application No. PCT/CA2009/000212 on Feb. 26, 2009, now Pat. No. 8,563,805.

(60) Provisional application No. 61/031,821, filed on Feb. 27, 2008.

(51) Int. Cl.
*C12N 15/82* (2006.01)
*C12N 9/02* (2006.01)

(52) U.S. Cl.
CPC ....... *C12N 15/8249* (2013.01); *C12N 9/0059* (2013.01); *C12N 15/8243* (2013.01); *C12Y 110/03001* (2013.01); *C12Y 114/18001* (2013.01)

(58) Field of Classification Search
None
See application file for complete search history.

(56) References Cited

U.S. PATENT DOCUMENTS

| | | | |
|---|---|---|---|
| 5,177,010 A | 1/1993 | Goldman et al. | |
| 5,302,523 A | 4/1994 | Coffee et al. | |
| 5,384,253 A | 1/1995 | Krzyzek et al. | |
| 5,464,765 A | 11/1995 | Coffee et al. | |
| 5,846,531 A | 12/1998 | Weiner et al. | |
| 5,925,395 A | 7/1999 | Chen et al. | |
| 5,939,117 A | 8/1999 | Chen et al. | |
| 6,703,542 B1* | 3/2004 | Robinson ............. | C12N 9/0059 536/25.1 |
| 6,936,748 B1 | 8/2005 | Robinson et al. | |
| 8,563,805 B2 | 10/2013 | Armstrong et al. | |

FOREIGN PATENT DOCUMENTS

| | | |
|---|---|---|
| WO | 1993/002195 A1 | 2/1993 |
| WO | 1994/003607 A1 | 2/1994 |
| WO | 96/37617 A1 | 11/1996 |
| WO | 2008/070845 A2 | 6/2008 |

OTHER PUBLICATIONS

Helliwell et al. Methods in Enzymology 30.4 (2003): 289-295. (Year: 2003).*
Genbank Accession L29450 (1995). (Year: 1995).*
Genbank Accession AF380300 (2001) (Year: 2001).*
Torello et al. "Apple juice evaluation: Qualitative analysis and microsatellite traceability." Aims Agriculture and Food 7.4 (2022): 819-830. (Year: 2022).*
GenBank Accession No. U22922 Jan. 5, 1996.
GenBank Accession No. Z27411 Apr. 18, 2005.
GenBank Accession No. DQ320121 Jan. 15, 2010.
GenBank Accession No. D87669 Feb. 7, 1999.
GenBank Accession No. D87670 Feb. 7, 1999.
GenBank Accession No. AX028784 Sep. 16, 2000.
GenBank Accession No. AF020786 Jun. 29, 2000.
GenBank Accession No. AB038994 Mar. 4, 2000.
GenBank Accession No. D45385 Jan. 22, 2003.
GenBank Accession No. Y12501 Jul. 25, 2016.
GenBank Accession No. Z12838 Apr. 18, 2005.
Office Action for CA2716846 dated Oct. 14, 2014.
Office Action for CA2716846 dated Jun. 9, 2016.
Office Action for CA2716846 dated Oct. 6, 2017.
Helliwell et al., "Constructs and Methods of Hairpin RNA-Mediated Gene Silencing in Plants," Methods in Enzymology 30:289-295 (2003).
Boss et al., "An Apple Polyphenol Oxidase cDNA is Up-Regulated in Wounded Tissues," Plant Mol. Biol. 27(2):429-433 (1995).
Brushett and Lacasse, "Regional Market Analysis for Fresh-out Apple Slices," Cooperative Development Institute, (2006) Deerfield MA.
Buta et al., "Extending Storage Life of Fresh-Cut Apples Using Natural Products and their Derivatives," Journal of Agriculture and Food Chemistry 4 7:1-6 (1999).

(Continued)

*Primary Examiner* — Charles Logsdon
(74) *Attorney, Agent, or Firm* — Troutman Pepper Hamilton Sanders LLP (Rochester)

(57) ABSTRACT

A genetically modified fruit-producing plant, said plant having sufficiently reduced total Polyphenol Oxidase (PPO) activity relative to a wild type of said plant to reduce browning in the fruit of said plant relative to said wild type, wherein the reduced total PPO activity results from a reduction in activity of at least two PPO isoenzymes in said plant relative to said wild type, or a cell, seed, seedling, part, tissue, cell, fruit or progeny of said plant.

19 Claims, 62 Drawing Sheets

Specification includes a Sequence Listing.

(56) References Cited

OTHER PUBLICATIONS

Chen J. et al., "Inactivation of Polyphenol Oxidase by High Pressure Carbon Dioxide," Journal of Agriculture and Food Chemistry 40:2345-2349 (1992).
Fire et al., "Potent and Specific Genetic Interference by Double Stranded RNA in Caenorhabditis Elegans," Nature 391:806-811 (1998).
Garbarino and Belknap, "Isolation of a Ubiquitin-Ribosomal Protein Gene (ubi3) from Potato and Expression of its Promoter in Transgenic Plants," Plant Mol Biol. 24(1):119-127 (1994).
Gnanasekharan et al., "Detection of Color Changes in Green Vegetables," Journal of Food Science. 57:149-154 (1992).
Haruta et al., "Cloning Genomic DNA Encoding Apple Polyphenol Oxidase and Comparison of the Gene Product in *Escherichia coli* and in Apple," Bioscience Biotech Biochem. 62:358-362 (1998).
Heimdal et al., Journal of Food Science (1995) 60:1265-1268.
Jiang and Fu, Food Chemistry, (1998) 62:49-52.
Jorgensen et al., Cold Spring Harb. Symp. Quant. Biol. (2006) 71:481-485.
Karkare et al., Appl Biochem Biotechnol. (2004) 119(1):1-12.
Kim et al., Plant Science (2001) 161:1145-1152.
Kruger et al., Cereal Chem. (1976) 53:201-213.
Lane et al., HortTechnology (2003) 13(4):641-646.
Lindbo et al., Plant Cell (1993) 5:1749-1759.
Lodhi et al., Plant Mol. Biol. Reporter (1994) 12:6-13.
Mar Sojo et al., Journal of Agriculture and Food Chemistry (1998) 46:4931-4936.
Martinez and Whitaker, Trends in Food Science and Technology (1995) 6: 95-200.
Matzke et al., Curr Opin Plant Biol. (Oct. 2007) 10(5): 012-519. Epub Aug. 16, 2007. Review.
Mayer, Phytochemistry (2006) 57: 2318-2331.
Mcevil et al., Critical Reviews in Food Science and Nutrition (1992) 32: 253-273.
Mcguire, HortScience (1992) 27:1254-1255.
Montgomery, PNAS (1998) 95:15502-15507.
Murata et al., Journal of Agriculture and Food Chemistry (2000) 48:5243-5248.
Murata et al., Biosci. Biotechnol .Biochem. (2001) 65:383-388.
Napoli et al., Plant Cell (1990) 2:279-289.
Newman et al., Plant Mal Biol. (1993) 1:1035-1051.
Ossowski et al., The Plant Journal (2008) 53:674-690.
Oszmianski and lee, Journal of Agriculture and Food Chemistry (1990) 38:1892-1895.
Otani et al., Plant Cell Rep (2007) 26(10):1801-1807. Epub Jul. 12, 2007.
Pikaard, Cold Spring Harb Symp Quant Biol. (2006) 71:473-480.
Rojas-Grau Ma et al., Journal of Food Science. (2006) 71:S59-S65.
Sapers, GM Food Technology (1993) 47:75-84.
Sharp, Genes and Development (2001) 15:485-490.
Van Der Krol, A.R. et al. "Flavonoid Genes in Petunia: Addition of a Limited Number of Gene Copies May Lead to a Suppression of Gene Expression". Plant Cell (1990) 2: 291-299.
Weemaes et al. "High pressure inactivation of polyphenoloxidases". Journal of Food Science 2008 63: 1-5.
Whitaker and Lee, "Enzymatic browning and its prevention," American Chemical Society Wash. D.C. (1995) 2-7.
Weirsma P.A. et al. "Survey of the expression of genes for ethylene synthesis and perception during maturation and ripening of "Sunrise" and "Golden Delicious" apple fruit". Postharvest Biology and Technology (2007) 44: 204-211.
Willmann and Poethig, "Conservation and evolution of miRNA regulatory programs in plant development". Curr. Opin. Plant Biol. Oct. 10, 2007(5):503-1 1. Epub Aug. 20, 2007. Review.
Zhao et al., "Transiently Expressed Short Hairpin RNA Targeting 126 kOa Protein of Tobacco Mosaic Virus Interference with Virus Infection". Acta Biochim Biophys Sin (Shanghai). (2006) 38(1) 22-28.
International Search Report from International Application No. PCT/CA2009/00021 dated May 27, 2009.
Written Opinion from International Application No. PCT/CA2009/00021 dated Aug. 27, 2010.
International Preliminary Report on Patentability from International Application No. PCT/CA2009/00021 dated Aug. 31, 2010.
Newman et al., Molecules 2011, 16, 493-517; doi: 10.3390/molecules16010493.
Thomas et al., Plant J., 2001, vol. 25, pp. 417-425.
Klahre et al., PNAS, 2002, vol. 99, pp. 11981-11986.
Thipyapong et al., 2004, Planta 220: 105-117.
Smith et al., 2000, Nature 407: 319-320.
GenBank Accession No. L29450 Jul. 14, 1995.

\* cited by examiner

```
CLUSTAL W (1.83) Multiple Sequence Alignments

Sequence format is Pearson
Sequence 1: GPO3            1850 bp
Sequence 2: AP14             450 bp
Start of Pairwise alignments
Aligning...
Sequences (1:2) Aligned. Score:  90
Guide tree        file created:   [infile.dnd]
Start of Multiple Alignment
There are 1 groups
Aligning...
Group 1: Sequences:   2      Score:7884
Alignment Score 2988
CLUSTAL-Alignment file created  [infile.aln]
```

>GPO3 [SEQ ID NO: 1]

ATGGCTTCTATGTCAGCTCCACTCGTCACCTCCGCCACAAGTATCATCCCCACAACTTCCCTCTCCCCTTTCTCCCAAAA
GTATCACCGAATATCCTTATTTGGAAACCCTAGGCATTCCAATTTACAAGCTGTCTCATGCAAAGCCACAATAATAGTA
GTGACCAAAACAAAAACCCTTCCACTAGCTCCAACGATCACGACCATGAAAACCCTTCTCCAGTAAACCTAGACAGAAGA
AATGTACTTATAGGTCTCGGAAGCCTATACGGTGGAGTGGCTGGTCTTGGCAGCGACCCCTTCGCTGTTGCAAAGCCAGT
GTCGCCGCCTGACCTAGCCAAATGCGGAGCTGCGGACTTTCCAAGTGGAGCAGTCCCGACCAACTGTTGCCCGCCAACGT
CCCAAAAAATCGTAGACTTCAAATTCCCCTCCCCTACCAAACTCCGCGTCAGGCCGGCAGCTCACACCGTGGATAAAGCC
TACATCGAAAAATATTCAAAAGCCATCGAGCTCATGAAAGCCCTCCCGGACGACGATCCGCGTAGCTTCACCCAGCAAGC
CGATATCCACTGTGCCTATTGCGACGGCGCGTACGACCAAGTCGGCTTCCCCAACCTCGAGCTCCAAATCCATCAATGCT
GGCTTTTCTTCCCCTTCCATCGTTACTACCTATACTTCCACGAAAGAATCTTGGCCAAACTCATATACGATCCGACGTTC
GCGTTGCCGTTTTGGAACTGGGACGCGCCAGCTGGCATGCAACTCCCTGCCTTGTTCGCTAACCCGGACTCTCCGCTTTA
CGACGAGCTTCGCGCTGCCAGCCATCAGCCGCCGACTCTCATCGATCTTGACTTCAACGGCACGGATGAAACAATGTCCA
ACGATGCTCAAATCGAAGCCAACCGCAAAATTATGTATAGGCAGATGGTTTCCAACTCCAAGAAACCGCTGTTGTTCTTT
GGTTCTCCCTACAGGGCTGGCACTGAACCAGATCCAGGGGGCGGTTCAATCGAAACGACCCCACATGGTCCGGTTCATTT
ATGGACCGGAGATAACACGCAACCTAATTTTGAAGACATGGGGAATTTTTACTCCGCTGGAAGGGATCCAATATTTTTTT
CGCACCATTCGAATATAGATCGAATGTGGAATATTTGGAAAAGTATAGGGACTAAAAATAAAGATATTAACGATAGGATT
GGTTGGATACGGGGTTTTTGTTTTATGACGAGAATGCTGAGCTTGTTAGGGTCACGGTGAGGGACACTCTTGATAATAAA
AAGCTAGGGTATACGTATGAAGATGTTGAGATTCCATGGCTCAAGTCTAGACCGACGCCACGTCGGACAAAGCTTGCGAG
AAAGGCAAAGGCGGCTGGAGTGGCGAAGGCGGCTGGATTGGCGAAGGCCGCTGAGACGACGTCATCGGGAAGGTGGTGG
CGGGTAAAGATTTTCCAATAAATTTGGAGACGAAGATAAGTACGGTGGTGTCAAGGCCGAAGCCGAAGAAGAGGAGCAAG
AAGGAGAAAGAGGGATGAGGAGGAGATATTGGTGATTCAGGGGATTGAGCTTGACAAAGATGTGGCTGTGAAGTTTGATGT
GTATGTGAATGACGTGGACGATGAGGATGCGGCACCGAGTGGACCCGACAAGAGCGAGTTTGCTGGGAGTTTTGTGAGTG
TGCCACATAAGCAGAAGGAAAAGAGCAAGAGTTGTTTAAGGTTGGGGTTAACGGACCTGTTGGAGGATTTGGGTGCTGAA
GATGATGAGAGTGTGGTGGTGACTTTAGTGCCCAGGTACGGCGCTCAGGCTGTTAAGATCGGTAGCATCAAAATTGAGTT
TCTTGCTTGA

>AP14 [SEQ ID NO: 2]

TCTTCTTCCCGTTCCACCGTTACTATCTATACTTCTACGAAAGAATCTTAGCCAAACTCATCGACGACCCGACGTTCGCG
TTGCCGTTTTGGAACCGGGACGCGCCAGCTGGCATGCAACTCCCTGCCTTGTACGCCAACCCCGACTCTCCGCTATACGA
CGAGCTCCGCGCTTCGAGACATCAGCCGTCGACTCTCATCGATCTTGACTTCAACGGCACGGATGAAACAATGTCCAACG
ACGTTCAAATCGACGCCAACCTCAAAATCATGTATAGGCAGATGGTTTCCAACTCCAAGAAACCGCTGTTGTTCTTTGGT
TCGCCTTTGAGAGCTGGCACTGAACCAGATCCAGGGTCCGGTTAAATCGAAGGTACCCCACATAGTCCAGTTCATAGGTG
GACCGGACGCAACCTAATTTTGAGGACATGGGGAATTTTTACTCCGCTGG

FIGURE 1A

CLUSTAL W (1.83) multiple sequence alignment

```
GPO3    ATGGCTTCTATGTCAGCTCCACTCGTCACCTCCGCCACAAGTATCATCCCCACAACTTCC
AP14    ------------------------------------------------------------

GPO3    CTCTCCCCTTTCTCCCAAAAGTATCACCGAATATCCTTATTTGGAAACCCTAGGCATTCC
AP14    ------------------------------------------------------------

GPO3    AATTTACAAGCTGTCTCATGCAAAGCCACAAATAATAGTAGTGACCAAAACAAAAACCCT
AP14    ------------------------------------------------------------

GPO3    TCCACTAGCTCCAACGATCACGACCATGAAAACCCTTCTCCAGTAAACCTAGACAGAAGA
AP14    ------------------------------------------------------------

GPO3    AATGTACTTATAGGTCTCGGAAGCCTATACGGTGGAGTGGCTGGTCTTGGCAGCGACCCC
AP14    ------------------------------------------------------------

GPO3    TTCGCTGTTGCAAAGCCAGTGTCGCCGCCTGACCTAGCCAAATGCGGAGCTGCGGACTTT
AP14    ------------------------------------------------------------

GPO3    CCAAGTGGAGCAGTCCCGACCAACTGTTGCCCGCCAACGTCCCAAAAAATCGTAGACTTC
AP14    ------------------------------------------------------------

GPO3    AAATTCCCCTCCCCTACCAAACTCCGCGTCAGGCCGGCAGCTCACACCGTGGATAAAGCC
AP14    ------------------------------------------------------------

GPO3    TACATCGAAAAATATTCAAAAGCCATCGAGCTCATGAAAGCCCTCCCGGACGACGATCCG
AP14    ------------------------------------------------------------

GPO3    CGTAGCTTCACCCAGCAAGCCGATATCCACTGTGCCTATTGCGACGGCGCGTACGACCAA
AP14    ------------------------------------------------------------

GPO3    GTCGGCTTCCCCAACCTCGAGCTCCAAATCCATCAATGCTGGCTTTTCTTCCCCTTCCAT
AP14    ---------------------------------------------TCTTCTTCCCGTTCCAC
                                                     * ******** *****

GPO3    CGTTACTACCTATACTTCCACGAAAGAATCTTGGCCAAACTCATATACGATCCGACGTTC
AP14    CGTTACTATCTATACTTCTACGAAAGAATCTTAGCCAAACTCATCGACGACCCGACGTTC
        ******** ********* ************* *********** **** ** *******

GPO3    GCGTTGCCGTTTTGGAACTGGGACGCGCCAGCTGGCATGCAACTCCCTGCCTTGTTCGCT
AP14    GCGTTGCCGTTTTGGAACCGGGACGCGCCAGCTGGCATGCAACTCCCTGCCTTGTACGCC
        ****************** ******************************************  ***
```

FIGURE 1B

```
GPO3    AACCCGGACTCTCCGCTTTACGACGAGCTTCGCGCTGCCAGCCATCAGCCGCCGACTCTC
AP14    AACCCCGACTCTCCGCTATACGACGAGCTCCGCGCTTCGAGACATCAGCCGTCGACTCTC
        ***** ********** ************ ****** * ** ********* *******

GPO3    ATCGATCTTGACTTCAACGGCACGGATGAAACAATGTCCAACGATGCTCAAATCGAAGCC
AP14    ATCGATCTTGACTTCAACGGCACGGATGAAACAATGTCCAACGACGTTCAAATCGACGCC
        ******************************************* * ********* ***

GPO3    AACCGCAAAATTATGTATAGGCAGATGGTTTCCAACTCCAAGAAACCGCTGTTGTTCTTT
AP14    AACCTCAAAATCATGTATAGGCAGATGGTTTCCAACTCCAAGAAACCGCTGTTGTTCTTT
        **** ****** ************************************************

GPO3    GGTTCTCCCTACAGGGCTGGCACTGAACCAGATCCAGGGGGCGGTTCAATCGAAACGACC
AP14    GGTTCGCCTTTGAGAGCTGGCACTGAACCAGATCCAGGGTCCGGTTAAATCGAAGGTACC
        ***** ** *  ** *********************** * ***** ******   ***

GPO3    CCACATGGTCCGGTTCATTTATGGACCGGAGATAACACGCAACCTAATTTTGAAGACATG
AP14    CCACATAGTCCAGTTCATAGGTGGACCGGA------CGCAACCTAATTTTGAGGACATG
        ****** **** ****** ** ********      **************** ******

GPO3    GGGAATTTTTACTCCGCTGGAAGGGATCCAATATTTTTTCGCACCATTCGAATATAGAT
AP14    GGGAATTTTTACTCCGCTGG----------------------------------------
        ********************

GPO3    CGAATGTGGAATATTTGGAAAAGTATAGGGACTAAAAATAAAGATATTAACGATAGGATT
AP14    ------------------------------------------------------------

GPO3    GGTTGGATACGGGGTTTTTGTTTTATGACGAGAATGCTGAGCTTGTTAGGGTCACGGTGA
AP14    ------------------------------------------------------------

GPO3    GGGACACTCTTGATAATAAAAAGCTAGGGTATACGTATGAAGATGTTGAGATTCCATGGC
AP14    ------------------------------------------------------------

GPO3    TCAAGTCTAGACCGACGCCACGTCGGACAAAGCTTGCGAGAAAGGCAAAGGCGGCTGGAG
AP14    ------------------------------------------------------------

GPO3    TGGCGAAGGCGGCTGGAGTGGCGAAGGCCGCTGAGACGACGTCATCAGGGAAGGTGGTGG
AP14    ------------------------------------------------------------

GPO3    CGGGTAAAGATTTTCCAATAAATTTGGAGACGAAGATAAGTACGGTGGTGTCAAGGCCGA
AP14    ------------------------------------------------------------

GPO3    AGCCGAAGAAGAGGAGCAAGAAGGAGAAAGAGGATGAGGAGGAGATATTGGTGATTCAGG
AP14    ------------------------------------------------------------

GPO3    GGATTGAGCTTGACAAAGATGTGGCTGTGAAGTTTGATGTGTATGTGAATGACGTGGACG
AP14    ------------------------------------------------------------
```

FIGURE 1C

```
GPO3         ATGAGGATGCGGCACCGAGTGGACCCGACAAGAGCGAGTTTGCTGGGAGTTTTGTGAGTG
AP14         ------------------------------------------------------------

GPO3         TGCCACATAAGCAGAAGGAAAAGAGCAAGAGTTGTTTAAGGTTGGGGTTAACGGACCTGT
AP14         ------------------------------------------------------------

GPO3         TGGAGGATTTGGGTGCTGAAGATGATGAGAGTGTGGTGGTGACTTTAGTGCCCAGGTACG
AP14         ------------------------------------------------------------

GPO3         GCGCTCAGGCTGTTAAGATCGGTAGCATCAAAATTGAGTTTCTTGCTTGA
AP14         --------------------------------------------------

>GPO3    [SEQ ID NO: 3]
FFPFHRYYLYFHERILAKLIYDPTFALPFWNWDAPAGMQLPALFANPDSPLYDELRAASHQPPTLIDLDFNGTDETMSND
AQIEANRKIMYRQMVSNSKKPLLFFGSPYRAGTEPDPGGGSIETTPHGPVHLWTGDNTQPNFEDMGNFYSA

>AP14    [SEQ ID NO: 4]
FFPFHRYYLYFYERILAKLIDDPTFALPFWNRDAPAGMQLPALYANPDSPLYDELRASRHQPSTLIDLDFNGTDETMSND
VQIDANLKIMYRQMVSNSKKPLLFFGSPLRAGTEPDPGSG-IEGTPHSPVHRWTGRNLILRTWGIFTPL

CLUSTAL W (1.83) Multiple Sequence Alignments

Sequence format is Pearson
Sequence 1: GPO3          151 aa
Sequence 2: AP14          149 aa
Start of Pairwise alignments
Aligning...
Sequences (1:2) Aligned. Score:   81
Guide tree        file created:    [infile.dnd]
Start of Multiple Alignment
There are 1 groups
Aligning...
Group 1: Sequences:    2       Score:2933
Alignment Score 774
CLUSTAL-Alignment file created   [infile.aln]

CLUSTAL W (1.83) multiple sequence alignment

GPO3         FFPFHRYYLYFHERILAKLIYDPTFALPFWNWDAPAGMQLPALFANPDSPLYDELRAASH
AP14         FFPFHRYYLYFYERILAKLIDDPTFALPFWNRDAPAGMQLPALYANPDSPLYDELRASRH
             ***********:******* ***********:***********:*************:  *

GPO3         QPPTLIDLDFNGTDETMSNDAQIEANRKIMYRQMVSNSKKPLLFFGSPYRAGTEPDPGGG
AP14         QPSTLIDLDFNGTDETMSNDVQIDANLKIMYRQMVSNSKKPLLFFGSPLRAGTEPDPGSG
             **.****************.**:** ********************** ********.*

GPO3         SIETTPHGPVHLWTGDNTQPNFEDMGNFYSA
AP14         -IEGTPHSPVHRWTGRN--LILRTWGIFTPL
              ** ***.*** ***        :.  * * .
```

FIGURE 1D

APO5 (L29450) [SEQ ID NO: 5]

ATGACGTCTCTTTCACCTCCGGTAGTCACCACCCCACCGTTCCCAACCCCGCCACAAAACCTCTC
TCCCCCTTCTCTCAAAACAACTCCCAAGTTTCCCTACTCACAAAGCCCAAGCGTTCCTTTGCACGT
AAGGTCTCATGCAAAGCCACAAACAATGACCAAAATGATCAAGCACAGTCCAAACTAGACAGGAGA
AATGTGCTTCTTGGTCTTGGAGGTCTATACGGCGTGGCGGGTATGGGCACAGACCCGTTCGCTTTT
GCCAAGCCTATAGCCCCACCAGACGTATCTAAATGTGGTCCTGCAGACTTGCCACAGGGTGCAGTG
CCCACCAACTGCTGCCCGCCGCCTTCCACAAAAATCATTGACTTTAAGCTGCCTGCCCCCGCCAAA
CTCCGCATCAGGCCACCGGCTCACGCCGTTGACCAAGCCTACAGGGACAAATACTACAAAGCGATG
GAGCTCATGAAGGCCCTACCCGACGACGACCCACGTAGCTTCAAGCAACAGGCAGCCGTGCATTGC
GCTTATTGCGACGGCGCCTATGACCAAGTCGGGTTCCCAGAACTCGAGCTCCAAATCCACAACTCA
TGGCTCTTCTTCCCGTTCCACCGTTACTACTTGTACTTTTTCGAGAAGATCCTAGGCAAACTCATT
AACGACCCGACATTCGCTTTGCCGTTCTGGAACTGGGACTCGCCAGCCGGCATGCCACTGCCCGCA
ATTTACGCTGATCCAAAGTCCCCTCTCTACGACAAGCTCCGATCTGCCAATCATCAGCCCCCGACT
CTGGTCGATCTCGATTACAACGGGACCGAGGACAATGTGTCAAAGGAAACCACAATCAACGCCAAT
CTCAAAATCATGTACAGGCAAATGGTGTCCAATTCCAAGAATGCTAAGTTGTTCTTTGGGAACCCG
TACAGGGCAGGGGACGAGCCTGACCCTGGTGGCGGCTCCATCGAGGGGACACCACACGCGCCGGTT
CATTTATGGACCGGTGACAACACCCAGCCCAACTTTGAGGACATGGGGAATTTTACTCCGCTGGT
CGGGACCCCATATTTTTTGCACACCATTCGAATGTCGATCGAATGTGGAGTATTTGGAAAACTCTT
GGAGGTAAGAGAACTGATCTTACTGACTCGGACTGGTTGGACTCCGGATTCTTGTTTTACAACGAG
AACGCAGAGTTAGTCCGAGTCAAGGTCAGGGACTGCTTGGAGACCAAAAATCTTGGGTATGTATAC
CAAGATGTGGACATTCCTTGGCTCAGCTCCAAGCCAACACCGCGAAGGGCGAAAGTTGCATTGAGC
AAAGTAGCGAAGAAGCTGGGAGTTGCACACGCAGCTGTTGCGTCGTCCAGCAAGGTGGTGGCAGGC
ACTGAGTTCCCGATAAGTCTGGGGTCGAAGATAAGCACGGTGGTGAAGAGACCGAAGCAGAAGAAG
AGGAGCAAGAAGGCCAAGGAGGATGAGGAGGAGATATTGGTGATTGAGGGAATCGAGTTTGACAGG
GACGTGGCTGTGAAGTTTGATGTGTATGTGAATGACGTCGATGACTTGCCGAGTGGGCCTGACAAG
ACGGAGTTTGCCGGAAGCTTTGTAAGTGTGCCGCACAGCCACAAGCACAAGAAGAAGATGAACACT
ATTTTGAGGTTAGGGTTGACAGATTTGTTGGAGGAAATTGAGGCGGAGGACGATGACAGCGTGGTG
GTGACTTTGGTGCCCAAGTTCGGCGCTGTCAAGATTGGTGGTATCAAGATTGAATTTGCTTCTTAG

PPO3 (D87669) [SEQ ID NO: 6]

ATGACGTCTCTTTCACCTCCGGTAGTCACCACCCCACCGCTCCCAACCCCGACACAAAACCTCTC
TCCCCCTTCTCTCAAAACAACTCCCAAGTTTCCCTACTCACAAAGCCCAAGCGTTCCTTGGGACGT
GAGGTCTCATGCAACGCCACAAACAATGACCAATTTGATCAAGCACAGTCCAAACTAGACAGGAGA
AATGTGCTTCTTGGTCTTGGAGGTCTATACGGCGTGGCGGGTATGGTCACAGACCCGCGCGGTTTT
GGCAAGTCTATCGCCCCACCAGACGTATCTAAATGTGGTCCCGGAGACTTGCCACAGGGTGCAGTG
CCCACCAACTGCTGCCCGCCGCCTTCCACAAAAATCATTGACTTTAAGCTGCCTGCCCCCGCCAAT
CTCCGTATCAGGCCACCGGCTCACGCCGTTGACCAAGCCTACAGGGACAAATACTACAAGGCGATG
GAGCTCATGAAGGCCCTACCCGACGACGACTCACGTAGCTTCAAGCAACAGGGAGCCGTGCATTGT
GCTTATTGCGACGGCGCCTATGACCAAGTCGGGTTCCCAGAACTCGAGCTCCAACTCCACAACTCA
TGGCTCTTCTTCCCATTCCACCGTTACTACTTGTACTTTTGCGAGAAGATCCTAGGCAATCTCATT
AACGACCCGACATTCGCTTTGCCGTTCTGGAACTGGGACTCGCCAGCCGGCATGCCACTGCCCGCG
ATTTACGCTGATCCAAAGTCCCCTCTCTACGACAAGCTCCGA

FIGURE 2A

TCTGCCAAACATCAGCCCCCGACTCTAGTCGATCTCGATTACAACGGGACCGAGGACAATGTGTCA
AAGGAAACCACAATCAACGCCAATCTCAAAATCATGTACAGGCAAATGGTGTCCAATTCCAAGAAT
GCTAAGTTGTTCTTTGGGAACCCGTACAGGGCAGGGGACGAGCCTGACCCTGGTGGCGGCTCCATC
GAGGGGACACCACACGCGCCGGTTCATTTATGGACCGGTGACAACACCCAGCCCAACTTTGAGGAC
ATGGGGAATTTTTACTCCGCTGGTCGGGACCCCATATTTTTTGCACACCATTCGAATGTCGATCGA
ATGTGGAGTATTTGGAAAACTCTTGGAGGTAAGAGAGCTGATCTTACTGACTCGGACTGGTTGGAC
TCCGGATTCTTGTTTTACAACGAGAACGCAGAGTTAGTCCGAGTCAAGGTCAGGGACTGCTTGGAG
ACCAAACATCTTGGGTATGTATACCAAGATGTGGACATTCCTTGGCTCAGCTCGAAGCCAACACCG
CGAAGGGCGGAAGTTGCATTGAGCCCAATAGCGAAGAAGCTGGGAGTTGCACACCCAGCTGTTGCG
TCGTCCAGCAAGGTGGTGGCAGGCACTGAGTTCCCGATAAATCTGGGGTCGAAGATAAGCACGGTG
GTGAAGAGACCGAAACAGAAGAAGAGAAGCAAGAAGGCCAAGGAGGATGAGGAGGAGATATTGGTG
ATTGAGGGAATCGAGTTTGACAGGGACGTGGCTGTGAAGTTTGATGTGTATGTGAATGACGTCGAT
GACTTGCCGAGTGGGCCTGACAAGACGGAATTTGCCGGAAGCTTTGTAAGTGTGCCGCACAGCCAC
AAGCACAAGAAGAAGATGAACACTACTTTGAGGTTAGGGTTGACAGATTTGTTGGAGGAAATTGAG
GCGGAGGACGATGACAGCGTGGTGGTGACTTTGGTGCCCAAGTTCGGCGCTGTCAAGATTGGTGGT
ATCAAGATTGAATTTGCTTCTTAG

PPO7 (D87670) [SEQ ID NO: 7]

ATGACGTCTCTTTCACCTCCGGTAGTCACCACCCCCACCGTTCCCAACCCCGACACAAAACCTCTC
TCCCCCTTCTCTCAAAACAACTCCCAAGTTTCCCTACTCACAAAGCCCAAGCGTTCCTTTGGACGT
AAGGTCTCATGCAAAGACACAAACAATGACGAAATTGATCAAGCACAGTCCAAACTAGAGAGGAGA
AATGTGCTTCTTGGTCTTGGGGGTCTATACGGCGTGGGGGTATGGACACAGACCCGCGCGGTTGG
GGCAAGGCTATAGCCCCACCAGACGTTTCTAAATGTGGCCCTGCAGACTTACCACAGGGTGGAGTG
CCCACCATCTGCTGCCCGCCGCGTTCCACAAAAATCATTGACTTTAAGCTGCCTGCCCCCGCCAAA
CTCCGTATCAGGCCACCGGCTCACGCCGGGGACCAAGCCTACAGGGACAAACACTACAAGGCGATG
GAGCTCATGAAGGCCCTACCCGACGACGACCCACGTAGTTTCAAGCAACAGGGAGCCGTGCATTGC
GCTTATTGCGACGGCGCCTATGACCAAGTCGGGTTCCCAGAACTCGAGCTCCAAATCCACAACTCA
TGGCTCTTCTTCCCGCTCCACCGTTACTACTTGTACTTTTTCGAGAAGATCCTAGGCAAACTCATT
AACGACCCGACATTCGCTGGGCCGTTCTGGAACTGGGACTCGCCAGCCGGCATGCCACTGCCCGCG
ATTTACGCTGATCCAAAGTCCCCTCTCTACGACAAGCTCCGATCTGCCCAACATCAGCCCCCGACT
CTGGTCGATCTCGATTACAACGGGACCGAGGACAATGTGTCAAAGGAAACCACAATCAACGCCAAT
CTCAAAATCATGTACAGGCAAATGGTGTCCAATTCCAAGAATGCTAAGTTGTTCTTTGGGAACCCG
TACAGGGCAGGGGACGAGCCTGACCCTGGTGGCGGCTCCATCGAGGGGACACCACACGCGCCGGTT
CATTTATGGACCGGTGACAACACCCAGCCCAACTTTGAGGACATGGGGAATTTTTACTCCGCTGGT
CGGGACCCCATATTTTTTGCACACCATTCGAATGTCGATCGAATGTGGAGTATTTGGAAAACTCTT
GGAGGTAAGAGAGCTGATCTTACTGACTCGGACTGGTTGGACTCCGGATTCTTGTTTTACAACGAG
AACGCAGAGTTAGTCCGAGTCAAGGTCAGGGACTGCTTGGAGACCAAAAATCTTGGGTATGTATAC
CAAGATGTGGACATTCCTTGGCTCAGCTCGAAGCCAACACCGCGAAGGGCGAAAGTTGCATTGAGC
AAAATAGCGAAGAAGCTGGGAGTTGCACACGCAGCTGTTGCGTCGTCCAGCAAGGTGGTGGCAGGC
ACTGAGTTCCCGATAAATCTGGGGTCGAAGATAAGCACGGTGGTGAAGAGACCGAAGCAGAAGAAG
AGAAGCAAGAAGGCCAAGGAGGATGAGGAGGAGATATTGGTGATTGAGGGAATCGAGTTTGACAGG
GACGTGGCTGTGAAGTTTGATGTGTATGTGAATGACGTCGATGACTTGCCGAGTGGGCCTGACAAG
ACGGAATTTGCCGGAAGCTTTGTAAGTGTGCCGCACAGCCACAAGCACAAGAAGAAGATGAACACT
ATTTTGAGGTTAGG

FIGURE 2B

```
GTTGACAGATTTGTTGGAGGAAATTGAGGCGGAGGACGATGACAGCGTGGTGGTGACTTTGGTGCC
CAAGTTCGGCGCTGTCAAGATTGGTGGTATCAAGATTGAATTTGCTTCTTAG
```

PPO2 (AF380300)  [SEQ ID NO: 8]

```
ATGACTTCATCTCCCTTACCACCAACTTCTACAATGGCCGCCCTGCACTCCACCACCACAACCACC
CTCTTCCGCTCTCCTTTATTCCCAAACAAGTCCCAGACTCCACTGCAACGAAAACCCAAACAATGC
CTTGCGGGCAGAGTGCGCTGCAAAGCAACAAAAGGTGACAATGATAACCTAGACCAGGGCTTAGCA
AGACTCGACAGGAGGAACATGCTGATAGGTTTAGGCACTGGGGGTCTCTACAGTGCGGCAGGAAAC
TCATTTGCTTTTGCAGCACCGGTATCCGCCCCAGACCTGACCACATGTGGCCCTGCCGACAAGCCA
GACGGGTCCACCATCGATTGTTGCCCACCCATCACGACCACCATCATCGACTTCAAACTCCCCGAC
CGAGGCCCACTCCGCACAAGGATCGCTGCCCAGGACGTTGCAAAAACCCTGCATACTTGGCTAAA
TACAAAAAGGCCATCGAGCTGATGCGGGCACTTCCAGATGACGACCCGCGCAGTCTCGTCCAACAG
GCCAAAGTCCATTGCTCCTACTGCGACGGTGGATACCCACAAGTCGGATATTCAGATTTGGAGATC
CAAGTTCACTTCTGTTGGCTATTCTTCCCGTTCCATCGTTGGTACCTCTACTTCTACGAGAAAATC
ATGGGCGAGCTCATTGGGGACCCAACCTTCGCCCTCCCCTTCTGGAACAGGGACGCGCCAGCTGGC
ATGTACATTCCTGAGATTTTCACCGATACGTCGTCATCCCTCTACGACCAGAACAGAAATACAGCG
CATCAGCCCCCGAAGCTCCTGGACTTGAATTATGGCGGACCGACGATGACGTCGACGACGCGACA
CGAATCAAAGAGAACCTAACAACGATGTACCAGCAGATGGTGTCGAAGGCCACTTCTACAGACTA
TTCTACGGAGAGCCCTATAGCGCAGGGGACGAACCAGATCCTGGCGCCGGAAACATTGAGACCACT
CCCCATAACAATATTCACCTTTGGGTTGGCGACCCAACCCAGACAAACGGGGAGGACATGGGGACC
TTTTACTCTGCGGGGAGGGATCCGCTGTTTACTCTCACCATTCCAACGTGGACCGCATGTGGTCT
ATATATAAGATAAGTTGGGAGGTACGGACATAGAAAATACCGACTGGCTGGACGCAGAGTTCTTA
TTCTACGACGAGAAAAAGAATCTCGTGCGCGTCAAGGTTCGGGACTCGCTCGACACTAAAAAACTC
GGGTACGTGTACGACGAGAAAGTCCCAATCCCATGGCTGAAGTCGAAGCCGACGCTCGTAAGTCGA
CGAATAAGAGAAAGGCCACAGTTCATCTTCGATCTTACTACAACGTTCCCTGCTACATTGTCGGAT
ACAATCAGCGTCGAGGTGACAAGGCCGTCTGCGACGAAGCGGACAGCTGCCCAGAAGAAGGCACAT
GACGAGGTGCTGGTGATTAAGGGGATTGAGTTTGCCGGGAATGAGCCTGTGAAGTTCGACGTGTAT
GTGAACGATGACGCGGAATCGCTGGCTGGGAAAGACAAGTCGGAGTTTGCTGGGAGTTTTGTTCAC
GTGCCGCATAAGCATAAGAAAAATATTAAGACGAACCTGCGACTGAGCATTATGAGCTTGTTGGAG
GAGTTGGATGCGGAGACAGACAGCAGTTTGGTGGTGACTTTGGTGCCGAAAGTTGGGAAGGGGCCA
ATCACCATCGGAGGGTTTAGCATTGAGCTCATTATACTACCTAA
```

PPOJ (PPO2 like gene, cloned at Okanagan specialty fruit (OSF), used in the PGAS transgene)  [SEQ ID NO: 9]

```
CATTGGGGACCCAACCTTCGCCCTCCCCTTCTGGAACTGGGACGCACCAGCTGGAATGTACATTCC
TGAGATTTTCACTGATACGTCGTCATCCCTCTACGACCAGTATAGAAATGCAGCGCATCAGCCCCC
GAAGCTCTTAGACTTTAATAACAGCGGGACCGACGATAACGTCGACGACGCAACACGAATCAAAGA
GAACTTAACAACAATGTACCAGCAGATGGTGTCAAAGGCCACTTCTCACAGACTCTTTTTTGGAGA
GCCCTACAGCGCAGGGGACGACCCAAGTCCTGGTGCCGGAAACATTGAGAGCATTCCCCATAACAA
TATTCACTTTTGGACTGGCGACCCAACCCAGACAAATGGGGAAGACATGGGGAATTTTTACTCCGC
TGG
```

FIGURE 2C

GPO3  [SEQ ID NO: 10]

CATTGCGCGTATTGCGACGGCGCGTACGACCAAGTCGGCTTCCCCAACCTCGAGCTCCAAATCCAT
CAATGCTGGCTTTTCTTCCCCTTCCATCGTTACTACCTATACTTCCACGAAAGAATCTTGGCCAAA
CTCATAGACGATCCGACGTTCGCGTTGCCGTTTTGGAACTGGGACGCGCCAGCTGGCATGCAACTC
CCTGCCTTGTTCGCTAACCCGGACTCTCCGCTTTACGACGAGCTTCGCGCTGCCAGCCATCAGCCG
CCGACTCTCATCGATCTTGACTTCAACGGCACGGATGAAACAATGTCCAACGATGCTCAAATCGAA
GCCAACCTCAAAATTATGTATAGGCAGATGGTTTCCAACTCCAAGAAACCGCTGTTGTTCTTTGGT
TCGCCCTACAGGGCTGGCACTGAACCAGATCCAGGGGGCGGTTCAATCGAAACGACCCCACATGGT
CCGGTTCATTTATGGACCGGAGATAACACGCAACCTAATTTTGAAGACATGGGGAATTTTTACTCC
GCTGGAAGGGATCCAATATTTTTTTCGCACCATTCGAATATAGATCGAATGTGGAATATT

AP14 (GPO3-like pseudogene, cloned at OSF)  [SEQ ID NO: 11]

TCTTCTTCCCGTTCCACCGTTACTATCTATACTTCTACGAAAGAATCTTAGCCAAACTCATCGACG
ACCCGACGTTCGCGTTGCCGTTTTGGAACCGGGACGCGCCAGCTGGCATGCAACTCCCTGCCTTGT
ACGCCAACCCCGACTCTCCGCTATACGACGAGCTCCGCGCTTCGAGACATCAGCCGTCGACTCTCA
TCGATCTTGACTTCAACGGCACGGATGAAACAATGTCCAACGACGTTCAAATCGACGCCAACCTCA
AAATCATGTATAGGCAGATGGTTTCCAACTCCAAGAAACCGCTGTTGTTCTTTGGTTCGCCTTTGA
GAGCTGGCACTGAACCAGATCCAGGGTCCGGTTAAATCGAAGGTACCCCACATAGTCCAGTTCATA
GGTGGACCGGACGCAACCTAATTTTGAGGACATGGGGAATTTTTACTCCGCTGG pSR7 (A27661, plus fragments 1,2,3,4 i.e. complete sequence of cDNA clone 8 @ HR)  [SEQ ID NO: 12]

GAAGACGACCCGCGTAGCATGGTTCAACAAGCTAAAGTTCACTGTGCCTACTGCAATGGTGCTTAT
CCACAAGTAGGGTTTCCGGACATTGACATCCAAATCCACTTCTCCTGGCTTTTCTTTCCTTTCCAC
CGCATGTACTTGTATTTCTACGAGAGAATCCTTGGCAAGCTCATTGATGACCCAACTTTCGCTCTC
CCATACTGGAATTGGGACTCTCCTGACGGTTTTCCAATTCCCGACATTTACAGATACAACTTCC
CCACTCTATGATCAGTACCGAAACGCCGACCACCAGCCCCCGTGCTGGTGGATCTCAGCTACGGT
GGAACCGATGATGACGTGGACGACCAGACAAGAATAGATGAGAATCTAGCCATCATGTACCGGCAA
ATGGTTTCCGGTGCCAAAACTCCCCATCTATTTTCGGCCATGAGTACAGGGCAGGAGACACAACA
ACAGGGACTTACGCCGGCACCATTGAGAACAGTCCTCATAATAACATCCATCTCTGGTGCGGTGAC
CCGAACCAGACCCACCACGAAGACATGGGTAACTTCTACTCCGCCGGTCGGATCCCTGTTTACGCC
CACCATTGCAGTGACCGCATGTGGAACGTTTGGAAAACCCTCGGAGGCAAGCGCAAGGACCCCACC
GACACCGATTGGCTTGACGCTGAGTTTCTGTTCTACGATGAAAACGCCGAGCTTGTGAGCTGTAAA
GTTCGGGACAGCCTCAAACCTGAGAAAGATCTTCGTTATACTTACGAGCCTGTTAGTGTTCCGTGG
CTGTTCACCAAGCCAACCGCTCGTAAGCCAAAGAGCAAGACAAAAGCCAAGGTGGGGCTACCCAG
CTGACGACAAAGTTCCCGGCCACGTTTGATTCGAAGACGACGGTGGAGGTGGCGAGGCCGAAGCCG
CGGAAGAGGACCAAGAAGGAGAAGATCGACGAGGAGGAGGTGCTGATCATTAAGGACATCGAATTC
GAGAGCAACGAGGCGGTGAAGTTCGATGTGTTTATTAATGATGATGCTGAGTCGCTCAGTAGGAAG
GACAAATCCGAGTTTGCTGGGAGTTTTGTGCACGTGCCGCATAACCAGAAGACTGGGACGAAGAAA
AAGACGAACTTAAAACTGGGGATCACGGACTTGTTGGAGGATTTGGGTGTGGAGGATGATAGCAGT
GTGCTGGTGACGTTGGTGCCTAGGGTTTCGAACTCGCCTATCACCAT

FIGURE 2D

TGGTGGGTTTAAGATCGAGTATTCTTCTTGATCAAAAAGTATGGTTAAGTAATTAAATAATTTCAT
AGTGGAATGGCCTGCTTTCATGCATGCCCTTGTGTTTAGTTAA

APO3 (5′ APO3 sequence)  [SEQ ID NO: 13]

AGGATGCTCAAATCGAAGCCAACCTCAAAATCATGTATAGGCAGATCGTTTCCAACTCCAAGAAAC
CGCTGTTGTTCTTTGGTTCGCCCTACAGGGCTGGCACTGAACCAGATCCAGGGGCCGGTGCAATCG
AACAGACCCCACATGGTCCGGTTCATACATGGACCGGAGATAACACGCAACCTAATTATGAATACA
TGGGGAATTTTTACTCCACTGCA

APO9 (5′ APO9 sequence)  [SEQ ID NO: 14]

CCCCCAAACCCATCATTCCTGGCTTTCTTCCCCCTTCCATCGTAACTACCTATACTTCCACGAAAG
ATTCTGGGCCAAACTCATAGACGATCCGACGTCCGCTTTGCCGTTTTGGAACTGGGACGCGCCAGC
GGGAATGCAACTCCCTGCTTTGTCCGCAAACCCGGACTTTCCGGTTAACGACGAGCTCCGTCGTGA
CAGCCATCA

APO3 (3′ APO3 sequence)  [SEQ ID NO: 15]

TGTGGCTGTGAAGTTTGATGTGTATGTGAATGACGTGGATGATGAGGATGCGGCACCGAGTGGACC
CCACAAGAGCGAGTTTGCTGGGAGTTTTGTGAGTGTGCCACCTGTTGGAGGATTTGGGTGCTGAAG
ATGATGAGAGTGTGGTGGTGACTTTAGTGCCCAGGTACGGCGCTCAGGCTGTTAAGATCGGTAGCA
TCAAAATTGAGTTTCTTGCTTGA

APO9 (3′ APO3 sequence)  [SEQ ID NO: 16]

GACCTGTTGGAGGATTTGGGTGCTGAAGATGATGAGAGTGTGGTGGTGACTTTAGTGCCCAGGTAC
GGCGCTCAGGCTGTTAAGATCGGTAGCATCAAAATTGAGTTTCTTGCTTGA pSR8 (A27663)  [SEQ ID NO: 17]

GAGGATATGGGGAATTTTTACTCTGCGGGGAGGGATCCGCTGTTTTACTCTCACCATTCCAACGTG
GACCGCATGTGGTCTATATATAAAGATAAGTTGGGAGGTACGGACATAGAAAAATACCGACTGCTG
GACGCAGAGTTCTTATTCTACGACGAGAACAAGAATCTTCGTGC

FIGURE 2E

```
CLUSTAL W (1.82) Multiple Sequence Alignments
Align APO5, PPO3 and PPO7. Sequentially add sequences PPO2 and
PPOJ. Sequentially add GALPO3 and AP14 to the APO5/PPO2 group.
Sequentially add pSR7, APO95, APO93, APO35, APO33, pSR8.
```

|       | PPO3 | PPO7 | PPOJ | PPO2 | GPO3 | AP14 | pSR8 | APO95 | APO93 | APO33 | pSR7 | APO35 |
|-------|------|------|------|------|------|------|------|-------|-------|-------|------|-------|
| APO5  | 97   | 97   | 66   | 61   | 78   | 75   | 64   | 72    | 72    | 75    | 62   | 73    |
| PPO3  |      | 97   | 66   | 61   | 77   | 75   | 64   | 71    | 72    | 74    | 61   | 73    |
| PPO7  |      |      | 66   | 61   | 77   | 74   | 64   | 72    | 72    | 74    | 61   | 73    |
| PPOJ  |      |      |      | 90   | 63   | 59   | 14   | 24    | 11    | 6     | 67   | 58    |
| PPO2  |      |      |      |      | 64   | 63   | 96   | 44    | 37    | 28    | 62   | 55    |
| GPO3  |      |      |      |      |      | 91   | 36   | 87    | 11    | 8     | 59   | 94    |
| AP14  |      |      |      |      |      |      | 14   | 73    | 9     | 8     | 58   | 85    |
| pSR8  |      |      |      |      |      |      |      | 10    | 8     | 5     | 59   | 11    |
| APO95 |      |      |      |      |      |      |      |       | 11    | 6     | 49   | 4     |
| APO93 |      |      |      |      |      |      |      |       |       | 99    | 71   | 17    |
| APO33 |      |      |      |      |      |      |      |       |       |       | 37   | 8     |
| pSR7  |      |      |      |      |      |      |      |       |       |       |      | 53    |

FIGURE 3

PPO2  [SEQ ID NO: 18]

ATGACTTCATCTCCCTTACCACCAACTTCTACAATGGCCGCCCTGCACTCCACCACCACAACCACC
CTCTTCCGCTCTCCTTTATTCCCAAACAAGTCCCAGACTCCACTGCAACGAAAACCCAAACAATGC
CTTGCGGGCAGAGTGCGCTGCAAAGCAACAAAAGGTGACAATGATAACCTAGACCAGGGCTTAGCA
AGACTCGACAGGAGGAACATGCTGATAGGTTTAGGCACTGGGGGTCTCTACAGTGCGGCAGGAAAC
TCATTTGCTTTTGCAGCACCGGTATCCGCCCCAGACCTGACCACATGTGGCCCTGCCGACAAGCCA
GACGGGTCCACCATCGATTGTTGCCCACCCATCACGACCACCATCATCGACTTCAAACTCCCCGAC
CGAGGCCCACTCCGCACAAGGATCGCTGCCCAGGACGTTGCAAAAAACCCTGCATACTTGGCTAAA
TACAAAAAGGCCATCGAGCTGATGCGGGCACTTCCAGATGACGACCCGCGCAGTCTCGTCCAACAG
GCCAAAGTCCATTGCTCCTACTGCGACGGTGGATACCCACAAGTCGGATATTCAGATTTGGAGATC
CAAGTTCACTTCTGTTGGCTATTCTTCCCGTTCCATCGTTGGTACCTCTACTTCTACGAGAAAATC
ATGGGCGAGCTCATTGGGGACCCAACCTTCGCCCTCCCCTTCTGGAACAGGGACGCGCCAGCTGGC
ATGTACATTCCTGAGATTTTCACCGATACGTCGTCATCCCTCTACGACCAGAACAGAAATACAGCG
CATCAGCCCCCGAAGCTCCTGGACTTGAATTATGGCGGGACCGACGATGACGTCGACGACGCGACA
CGAATCAAAGAGAACCTAACAACGATGTACCAGCAGATGGTGTCGAAGGCCACTTCTCACAGACTA
TTCTACGGAGAGCCCTATAGCGCAGGGGACGAACCAGATCCTGGCGCCGGAAACATTGAGACCACT
CCCCATAACAATATTCACCTTTGGGTTGGCGACCCAACCCAGACAAACGGGGAGGACATGGGGACC
TTTTACTCTGCGGGGAGGGATCCGCTGTTTTACTCTCACCATTCCAACGTGGACCGCATGTGGTCT
ATATATAAAGATAAGTTGGGAGGTACGGACATAGAAAATACCGACTGGCTGGACGCAGAGTTCTTA
TTCTACGACGAGAAAAAGAATCTCGTGCGCGTCAAGGTTCGGGACTCGCTCGACACTAAAAAACTC
GGGTACGTGTACGACGAGAAAGTCCCAATCCCATGGCTGAAGTCGAAGCCGACGCTCGTAAGTCGA
CGAATAAGAGAAAGGCCACAGTTCATCTTCGATCTTACTACAACGTTCCCTGCTACATTGTCGGAT
ACAATCAGCGTCGAGGTGACAAGGCCGTCTGCGACGAAGCGGACAGCTGCCCAGAAGAAGGCACAT
GACGAGGTGCTGGTGATTAAGGGGATTGAGTTTGCCGGGAATGAGCCTGTGAAGTTCGACGTGTAT
GTGAACGATGACGCGGAATCGCTGGCTGGGAAAGACAAGTCGGAGTTTGCTGGGAGTTTTGTTCAC
GTGCCGCATAAGCATAAGAAAAATATTAAGACGAACCTGCGACTGAGCATTATGAGCTTGTTGGAG
GAGTTGGATGCGGAGACAGACAGCAGTTTGGTGGTGACTTTGGTGCCGAAAGTTGGGAAGGGGCCA
ATCACCATCGGAGGGTTTAGCATTGAGCTCATTAATACTACCTAA

PPO2 (Translation)  [SEQ ID NO: 19]

MTSSPLPPTSTMAALHSTTTTTLFRSPLFPNKSQTPLQRKPKQCLAGRVRCKATKGDNDNLDQGLA
RLDRRNMLIGLGTGGLYSAAGNSFAFAAPVSAPDLTTCGPADKPDGSTIDCCPPITTTIIDFKLPD
RGPLRTRIAAQDVAKNPAYLAKYKKAIELMRALPDDDPRSLVQQAKVHCSYCDGGYPQVGYSDLEI
QVHFCWLFFPFHRWYLYFYEKIMGELIGDPTFALPFWNRDAPAGMYIPEIFTDTSSSLYDQNRNTA
HQPPKLLDLNYGGTDDDVDDATRIKENLTTMYQQMVSKATSHRLFYGEPYSAGDEPDPGAGNIETT
PHNNIHLWVGDPTQTNGEDMGTFYSAGRDPLFYSHHSNVDRMWSIYKDKLGGTDIENTDWLDAEFL
FYDEKKNLVRVKVRDSLDTKKLGYVYDEKVPIPWLKSKPTLVSRRIRERPQFIFDLTTTFPATLSD
TISVEVTRPSATKRTAAQKKAHDEVLVIKGIEFAGNEPVKFDVYVNDDAESLAGKDKSEFAGSFVH
VPHKHKKNIKTNLRLSIMSLLEELDAETDSSLVVTLVPKVGKGPITIGGFSIELINTT-

FIGURE 4A

GPO3 [SEQ ID NO: 20]

ATGGCTTCTATGTCAGCTCCACTCGTCACCTCCGCCACAAGTATCATCCCCACAACTTCCCTCTCC
CCTTTCTCCCAAAAGTATCACCGAATATCCTTATTTGGAAACCCTAGGCATTCCAATTTACAAGCT
GTCTCATGCAAAGCCACAAATAATAGTAGTGACCAAAACAAAAACCCTTCCACTAGCTCCAACGAT
CACGACCATGAAAACCCTTCTCCAGTAAACCTAGACAGAAGAAATGTACTTATAGGTCTCGGAAGC
CTATACGGTGGAGTGGCTGGTCTTGGCAGCGACCCCTTCGCTGTTGCAAAGCCAGTGTCGCCGCCT
GACCTAGCCAAATGCGGAGCTGCGGACTTTCCAAGTGGAGCAGTCCCGACCAACTGTTGCCCGCCA
ACGTCCAAAAAATCGTAGACTTCAAATTCCCCTCCCCTACCAAACTCCGCGTCAGGCCGGCAGCT
CACACCGTGGATAAAGCCTACATCGAAAATATTCAAAAGCCATCGAGCTCATGAAAGCCCTCCCG
GACGACGATCCGCGTAGCTTCACCCAGCAAGCCGATATCCACTGTGCCTATTGCGACGGCGCGTAC
GACCAAGTCGGCTTCCCCAACCTCGAGCTCCAAATCCATCAATGCTGGCTTTTCTTCCCCTTCCAT
CGTTACTACCTATACTTCCACGAAAGAATCTTGGCCAAACTCATATACGATCCGACGTTCGCGTTG
CCGTTTTGGAACTGGGACGCGCCAGCTGGCATGCAACTCCCTGCCTTGTTCGCTAACCCGGACTCT
CCGCTTTACGACGAGCTTCGCGCTGCCAGCCATCAGCCGCCGACTCTCATCGATCTTGACTTCAAC
GGCACGGATGAAACAATGTCCAACGATGCTCAAATCGAAGCCAACCGCAAAATTATGTATAGGCAG
ATGGTTTCCAACTCCAAGAAACCGCTGTTGTTCTTTGGTTCTCCCTACAGGGCTGGCACTGAACCA
GATCCAGGGGCGGTTCAATCGAAACGACCCCACATGGTCCGGTTCATTTATGGACCGGAGATAAC
ACGCAACCTAATTTTGAAGACATGGGGAATTTTACTCCGCTGGAAGGGATCCAATATTTTTTTCG
CACCATTCGAATATAGATCGAATGTGGAATATTTGGAAAAGTATAGGGACTAAAAATAAAGATATT
AACGATAGGATTGGTTGGATACGGGGTTTTTGTTTTATGACGAGAATGCTGAGCTTGTTAGGGTCA
CGGTGAGGGACACTCTTGATAATAAAAAGCTAGGGTATACGTATGAAGATGTTGAGATTCCATGGC
TCAAGTCTAGACCGACGCCACGTCGGACAAAGCTTGCGAGAAAGGCAAAGGCGGCTGGAGTGGCGA
AGGCGGCTGGAGTGGCGAAGGCCGCTGAGACGACGTCATCAGGGAAGGTGGTGGCGGGTAAAGATT
TTCCAATAAATTTGGAGACGAAGATAAGTACGGTGGTGTCAAGGCCGAAGCCGAAGAAGAGGAGCA
AGAAGGAGAAAGAGGATGAGGAGGAGATATTGGTGATTCAGGGGATTGAGCTTGACAAAGATGTGG
CTGTGAAGTTTGATGTGTATGTGAATGACGTGGACGATGAGGATGCGGCACCGAGTGGACCCGACA
GAGCGAGTTTGCTGGAGTTTTGTGAGTGTGCCACATAAGCAGAAGGAAAAGAGCAAGAGTTGTT
TAAGGTTGGGGTTAACGGACCTGTTGGAGGATTTGGGTGCTGAAGATGATGAGAGTGTGGTGGTGA
CTTTAGTGCCCAGGTACGGCGCTCAGGCTGTTAAGATCGGTAGCATCAAAATTGAGTTTCTTGCTT
GA

GPO3 (Translation) [SEQ ID NO: 21]

MASMSAPLVTSATSIIPTTSLSPFSQKYHRISLFGNPRHSNLQAVSCKATNNSSDQNKNPSTSSND
HDHENPSPVNLDRRNVLIGLGSLYGGVAGLGSDPFAVAKPVSPPDLAKCGAADFPSGAVPTNCCPP
TSQKIVDFKFPSPTKLRVRPAAHTVDKAYIEKYSKAIELMKALPDDDPRSFTQQADIHCAYCDGAY
DQVGFPNLELQIHQCWLFFPFHRYYLYFHERILAKLIYDPTFALPFWNWDAPAGMQLPALFANPDS
PLYDELRAASHQPPTLIDLDFNGTDETMSNDAQIEANRKIMYRQMVSNSKKPLLFFGSPYRAGTEP
DPGGGSIETTPHGPVHLWTGDNTQPNFEDMGNFYSAGRDPIFFSHHSNIDRMWNIWKSIGTKNKDI
NDKDWLDTGFLFYDENAELVRVTVRDTLDNKKLGYTYEDVEIPWLKSRPTPRRTKLARKAKAAGVA
KAAGVAKAAETTSSGKVVAGKDFPINLETKISTVVSRPKPKKRSKKEKEDEEEILVIQGIELDKDV
AVKFDVYVNDVDDEDAAPSGPDKSEFAGSFVSVPHKQKEKSKSCLRLGLTDLLEDLGAEDDESVVV
TLVPRYGAQAVKIGSIKIEFLA-

FIGURE 4B

APO5 [SEQ ID NO: 22]

ATGACGTCTCTTTCACCTCCGGTAGTCACCACCCCCACCGTTCCCAACCCCGCCACAAAACCTCTC
TCCCCCTTCTCTCAAAACAACTCCCAAGTTTCCCTACTCACAAAGCCCAAGCGTTCCTTTGCACGT
AAGGTCTCATGCAAAGCCACAAACAATGACCAAAATGATCAAGCACAGTCCAAACTAGACAGGAGA
AATGTGCTTCTTGGTCTTGGAGGTCTATACGGCGTGGCGGGTATGGGCACAGACCCGTTCGCTTTT
GCCAAGCCTATAGCCCCACCAGACGTATCTAAATGTGGTCCTGCAGACTTGCCACAGGGTGCAGTG
CCCACCAACTGCTGCCCGCCGCCTTCCACAAAATCATTGACTTTAAGCTGCCTGCCCCGCCAAA
CTCCGCATCAGGCCACCGGCTCACGCCGTTGACCAAGCCTACAGGGACAAATACTACAAAGCGATG
GAGCTCATGAAGGCCCTACCCGACGACGACCCACGTAGCTTCAAGCAACAGGCAGCCGTGCATTGC
GCTTATTGCGACGGCGCCTATGACCAAGTCGGGTTCCCAGAACTCGAGCTCCAAATCCACAACTCA
TGGCTCTTCTTCCCGTTCCACCGTTACTACTTGTACTTTTTCGAGAAGATCCTAGGCAAACTCATT
AACGACCCGACATTCGCTTTGCCGTTCTGGAACTGGGACTCGCCAGCCGGCATGCCACTGCCCGCA
ATTTACGCTGATCCAAAGTCCCCTCTCTACGACAAGCTCCGATCTGCCAATCATCAGCCCCCGACT
CTGGTCGATCTCGATTACAACGGGACCGAGGACAATGTGTCAAAGGAAACCACAATCAACGCCAAT
CTCAAAATCATGTACAGGCAAATGGTGTCCAATTCCAAGAATGCTAAGTTGTTCTTTGGGAACCCG
TACAGGGCAGGGGACGAGCCTGACCCTGGTGGCGGCTCCATCGAGGGGACACCACACGCGCCGGTT
CATTTATGGACCGGTGACAACACCCAGCCCAACTTTGAGGACATGGGGAATTTTTACTCCGCTGGT
CGGGACCCCATATTTTTTGCACACCATTCGAATGTCGATCGAATGTGGAGTATTTGGAAAACTCTT
GGAGGTAAGAGAACTGATCTTACTGACTCGGACTGGTTGGACTCCGGATTCTTGTTTTACAACGAG
AACGCAGAGTTAGTCCGAGTCAAGGTCAGGGACTGCTTGGAGACCAAAAATCTTGGGTATGTATAC
CAAGATGTGGACATTCCTTGGCTCAGCTCCAAGCCAACACCGCGAAGGGCGAAAGTTGCATTGAGC
AAAGTAGCGAAGAAGCTGGGAGTTGCACACGCAGCTGTTGCGTCGTCCAGCAAGGTGGTGGCAGGC
ACTGAGTTCCCGATAAGTCTGGGGTCGAAGATAAGCACGGTGGTGAAGAGACCGAAGCAGAAGAAG
AGGAGCAAGAAGGCCAAGGAGGATGAGGAGGAGATATTGGTGATTGAGGGAATCGAGTTTGACAGG
GACGTGGCTGTGAAGTTTGATGTGTATGTGAATGACGTCGATGACTTGCCGAGTGGGCCTGACAAG
ACGGAGTTTGCCGGAAGCTTTGTAAGTGTGCCGCACAGCCACAAGCACAAGAAGAAGATGAACACT
ATTTTGAGGTTAGGGTTGACAGATTTGTTGGAGGAAATTGAGGCGGAGGACGATGACAGCGTGGTG
GTGACTTTGGTGCCCAAGTTCGGCGCTGTCAAGATTGGTGGTATCAAGATTGAATTTGCTTCTTAG

APO5 (Translation) [SEQ ID NO: 23]

MTSLSPPVVTTPTVPNPATKPLSPFSQNNSQVSLLTKPKRSFARKVSCKATNNDQNDQAQSKLDRR
NVLLGLGGLYGVAGMGTDPFAFAKPIAPPDVSKCGPADLPQGAVPTNCCPPPSTKIIDFKLPAPAK
LRIRPPAHAVDQAYRDKYYKAMELMKALPDDDPRSFKQQAAVHCAYCDGAYDQVGFPELELQIHNS
WLFFPFHRYYLYFFEKILGKLINDPTFALPFWNWDSPAGMPLPAIYADPKSPLYDKLRSANHQPPT
LVDLDYNGTEDNVSKETTINANLKIMYRQMVSNSKNAKLFFGNPYRAGDEPDPGGGSIEGTPHAPV
HLWTGDNTQPNFEDMGNFYSAGRDPIFFAHHSNVDRMWSIWKTLGGKRTDLTDSDWLDSGFLFYNE
NAELVRVKVRDCLETKNLGYVYQDVDIPWLSSKPTPRRAKVALSKVAKKLGVAHAAVASSSKVVAG
TEFPISLGSKISTVVKRPKQKKRSKKAKEDEEEILVIEGIEFDRDVAVKFDVYVNDVDDLPSGPDK
TEFAGSFVSVPHSHKHKKKMNTILRLGLTDLLEEIEAEDDDSVVVTLVPKFGAVKIGGIKIEFAS-

FIGURE 4C pSR7  [SEQ ID NO: 24]

TACCACCACCACCATGGGCACTTACTCTTCTCTGATCATCTCCACCAATTCCTTCTCTGCCTTCCT
CCCAAACAAATCCCAACTTTCCTTCTCTGGAAAAAGCAAGCACTACATTGCACGTAGATCATCAAT
ATATTGCAAAGCCACAAACCCTAATTATAATAATGAGCAAGATCAACAACAATCTTCTAATTTGTT
GGGAAAATTGGACAGGAGAAATGTCCTAATTGGCCTGGGCGGCCTCTACGGGGCCACCACCCTCGC
CCCAAAGCCGTTGGCCTTTGCCAACCCGCTGGCTCCACCCGACCTAACCAAATGTAAGCCGGCCGA
AATCACCACCGGAGGTGAAACTGTGGAATGCTGTCCACCGGTCTCCACAAAGATCAAAACCTTCAC
TCCGGACCAGTCTATCCCACTGCGGACGAGGCCTGCCGCCCATTTGGTCACGGACGAGTACTTGGC
CAAGTTCAAGAAAGCTCAAGCCCTCATGCGTGCCTTACCCGAAGACGACCCGCGTAGCATGGTTCA
ACAAGCTAAAGTTCACTGTGCCTACTGCAATGGTGCTTATCCACAAGTAGGGTTTCCGGACATTGA
CATCCAAATCCACTTCTCCTGGCTTTTCTTTCCTTTCCACCGCATGTACTTGTATTTCTACGAGAG
AATCCTTGGCAAGCTCATTGATGACCCAACTTTCGCTCTCCATACTGGAATTGGGACTCTCCTGA
CGGTTTTCCAATTCCCGACATTTACACAGATACAACTTCCCCACTCTATGATCAGTACCGAAACGC
CGACCACCAGCCCCCGTGCTGGTGGATCTCAGCTACGGTGGAACCGATGATGACGTGGACGACCA
GACAAGAATAGATGAGAATCTAGCCATCATGTACCGGCAAATGGTTTCCGGTGCCAAAACTCCCCA
TCTATTTTTCGGCCATGAGTACAGGGCAGGAGACACAACAACAGGGACTTACGCCGGCACCATTGA
GAACAGTCCTCATAATAACATCCATCTCTGGTGCGGTGACCCGAACCAGACCCACCACGAAGACAT
GGGTAACTTCTACTCCGCCGGTCGGATCCCTGTTTACGCCCACCATTGCAGTGACCGCATGTGGAA
CGTTTGGAAAACCCTCGGAGGCAAGCGCAAGGACCCCACCGACACCGATTGGCTTGACGCTGAGTT
TCTGTTCTACGATGAAAACGCCGAGCTTGTGAGCTGTAAAGTTCGGGACAGCCTCAAACCTGAGAA
AGATCTTCGTTATACTTACGAGCCTGTTAGTGTTCCGTGGCTGTTCACCAAGCCAACCGCTCGTAA
GCCAAAGAGCAAGACAAAAGCCAAGGTGGGGGCTACCCAGCTGACGACAAAGTTCCCGGCCACGTT
TGATTCGAAGACGACGGTGGAGGTGGCGAGGCCGAAGCCGCGGAAGAGGACCAAGAAGGAGAAGAT
CGACGAGGAGGAGGTGCTGATCATTAAGGACATCGAATTCGAGAGCAACGAGGCGGTGAAGTTCGA
TGTGTTTATTAATGATGATGCTGAGTCGCTCAGTAGGAAGGACAAATCCGAGTTTGCTGGGAGTTT
TGTGCACGTGCCGCATAACCAGAAGACTGGGACGAAGAAAAAGACGAACTTAAAACTGGGGATCAC
GGACTTGTTGGAGGATTTGGGTGTGGAGGATGATAGCAGTGTGCTGGTGACGTTGGTGCCTAGGGT
TTCGAACTCGCCTATCACCATTGGTGGGTTTAAGATCGAGTATTCTTCTTGATCAAAAAGTATGGT
TAAGTAATTAAATAATTTCATAGTGGAATGGCCTGCTTTCATGCATGCCCTTGTGTTTAGTTAA pSR7 (Translation)  [SEQ ID NO: 25]

TTTTMGTYSSLIISTNSFSAFLPNKSQLSFSGKSKHYIARRSSIYCKATNPNYNNEQDQQQSSNLL
GKLDRRNVLIGLGGLYGATTLAPKPLAFANPLAPPDLTKCKPAEITTGGETVECCPPVSTKIKTFT
PDQSIPLRTRPAAHLVTDEYLAKFKKAQALMRALPEDDPRSMVQQAKVHCAYCNGAYPQVGFPDID
IQIHFSWLFFPFHRMYLYFERILGKLIDDPTFALPYWNWDSPDGFPIPDIYTDTTSPLYDQYRNA
DHQPPVLVDLSYGGTDDDVDDQTRIDENLAIMYRQMVSGAKTPHLFFGHEYRAGDTTTGTYAGTIE
NSPHNNIHLWCGDPNQTHHEDMGNFYSAGRIPVYAHHCSDRMWNVWKTLGGKRKDPTDTDWLDAEF
LFYDENAELVSCKVRDSLKPEKDLRYTYEPVSVPWLFTKPTARKPKSKTKAKVGATQLTTKFPATF
DSKTTVEVARPKPRKRTKKEKIDEEEVLIIKDIEFESNEAVKFDVFINDDAESLSRKDKSEFAGSF
VHVPHNQKTGTKKKTNLKLGITDLLEDLGVEDDSSVLVTLVPRVSNSPITIGGFKIEYSS-

FIGURE 4D

PPO2 (PPOJ, Okanagan Specialty Fruits)  [SEQ ID NO: 26]

CGAATTGGCATTGGGGACCCAACCTTCGCCCTCCCCTTCTGGAACTGGGACGCACCAGCTGGAATG
TACATTCCTGAGATTTTCACTGATACGTCGTCATCCCTCTACGACCAGTATAGAAATGCAGCGCAT
CAGCCCCCGAAGCTCTTAGACTTTAATAACAGCGGGACCGACGATAACGTCGACGACGCAACACGA
ATCAAAGAGAACTTAACAACAATGTACCAGCAGATGGTGTCAAAGGCCACTTCTCACAGACTCTTT
TTTGGAGAGCCCTACAGCGCAGGGGACGACCCAAGTCCTGGTGCCGGAAACATTGAGAGCATTCCC
CATAACAATATTCACTTTTGGACTGGCGACCCAACCCAGACAAATGGGGAAGACATGGGGAATTTT
TACTCCGCTGG

GPO3  [SEQ ID NO: 27]

TTTCTTTCCCGTTCCACCGTTACTACTTATACTTCCACGAAAGAATCTTGGCCAAACTCATAGACG
ATCCGACGTTCGCGTTGCCGTTTTGGAACTGGGACGCGCCAGCTGGCATGCAACTCCCTGCCTTGT
TCGCTAACCCGGACTCTCCGCTTTACGACGAGCTTCGCGCTGCCAGCCATCAGCCGCCGACTCTCA
TCGATCTTGACTTCAACGGCACGGATGAAACAATGTCCAACGATGCTCAAATCGAAGCCAACCTCA
AAATTATGTATAGGCAGATGGTTTCCAACTCCAAGAAACCGCTGTTGTTCTTTGGTTCGCCCTACA
GGGCTGGCACTGAACCAGATCCAGGGGGCGGTTCAATCGAAACGACCCCACATGGTCCGGTTCATT
TATGGGCCGGAGATAACACGCAACCTAATTTTGAAGACATGGGGAATTTTTACTCCGCTGG

APO5  [SEQ ID NO: 28]

TCTTCTTCCCGTTCCACCGTTACTATCTCTACTTTTTCGAGAAGATCCTAGGCAAACTCATTAACG
ACCCGACATTCGCTTTGCCGTTCTGGAACTGGGACTCGCCAGCCGGCATGCCACTGCCCGCGATTT
ACGCTGATCCAAAGTCCCCTCTCTACGACAAGCTCCGATCTGCCAATCATCAGCCCCCGACTCTGG
TCGATCTCGATTACAACGGGACCGAGGACAATGTGTCAAAGGAAACCACAATCAACGCCAATCTCA
AAATCATGTACAGGCAAATGGTGTCCAATTCCAAGAATGCTAAGTTGTTCTTTGGGAACCCGTACA
GGGCAGGGGACAAGCCCGACCCTGGTGGCGGCTCCATCGAGGGGACACCACACGCGCCGGTTCATT
TATGGACCGGTGACAACACCCAGCCCAACTTTGAGGATATGGGGAATTTTTACTCCGCTGG pSR7  [SEQ ID NO: 29]

TTCCTTTCCACCGCATGTACTTGTATTTCTACGAGAGAATCCTTGGCAAGCTCATTGATGACCCAA
CTTTCGCTCTCCATACTGGAATTGGGACTCTCCTGACGGTTTTCCAATTCCCGACATTTACACAG
ATACAACTTCCCCACTCTATGATCAGTACCGAAACGCCGACCACCAGCCCCCGTGCTGGTGGATC
TCAGCTACGGTGGAACCGATGATGACGTGGACGACCAGACAAGAATAGATGAGAACCTAGCCATCA
TGTACCGGCAAGTGGTTTCCGGTGCCAAAACTCCCCATCTATTTTTCGGCCATGAGTACAGGGCAG
GAGACACAACAACAGGGACCTACGCCGGCACCATTGAGAACAGTCCTCATAATAACATCCATCTCT
GGTGCGGTGACCCGAACCAGACCCACCACGAAGACATGGGTAACTTCTACTCCGCGG

FIGURE 5A

PPO2    [SEQ ID NO: 30]

CCACATGTGGCCCTGCCGACAAGCCAGACGGGTCCACCATCGATTGTTGCCCACCCATCACGACCA
CCATCATCGACTTCAAACTCCCCGACCGAGGCCCACTCCGCACAAGGATCGCTGCCCAGGACGTTG
CAAAAAACCCTGCATACTTGGCTAAATACAAAAAGGCCATCGAGCTGATGCGGGCACTTCCAGATG
AC

GPO3    [SEQ ID NO: 31]

AATGCGGAGCTGCGGACTTTCCAAGTGGAGCAGTCCCGACCAACTGTTGCCCGCCAACGTCCCAAA
AAATCGTAGACTTCAAATTCCCCTCCCCTACCAAACTCCGCGTCAGGCCGGCAGCTCACACCGTGG
ATAAAGCCTACATCGAAAAATATTCAAAGCCATCGAGCTCATGAAAGCCCTCCCGGACGACGATC
CG

APO5    [SEQ ID NO: 32]

AATGTGGTCCTGCAGACTTGCCACAGGGTGCAGTGCCCACCAACTGCTGCCCGCCGCCTTCCACAA
AAATCATTGACTTTAAGCTGCCTGCCCCCGCCAAACTCCGCATCAGGCCACCGGCTCACGCCGTTG
ACCAAGCCTACAGGGACAAATACTACAAAGCGATGGAGCTCATGAAGGCCCTACCCGACGACGACC
CA pSR7    [SEQ ID NO: 33]

AATGTAAGCCGGCCGAAATCACCACCGGAGGTGAAACTGTGGAATGCTGTCCACCGGTCTCCACAA
AGATCAAAACCTTCACTCCGGACCAGTCTATCCCACTGCGGACGAGGCCTGCCGCCCATTTGGTCA
CGGACGAGTACTTGGCCAAGTTCAAGAAAGCTCAAGCCCTCATGCGTGCCTTACCCGAAGACGACC
CG

ACO2 Intron (AF015788)    [SEQ ID NO: 34]

GTCACACTAATTACAACAAACTTAATTAATTTCCCGCTGATTTGGATTTAACCAAGTTAGCTAAAG
CACCTTGCGGCCCCATTGCACCTAAGTTTGGATCTCGGTTTTGTAGACTAGATTGTATTAGAATAT
CATATTGAGGGCTTGTATATATTTTGAACAATATTTCAG

FIGURE 5B

PGAS (sense orientation) [SEQ ID NO: 35]

CGAATTGGCATTGGGGACCCAACCTTCGCCCTCCCCTTCTGGAACTGGGACGCACCAGCTGGAATG
TACATTCCTGAGATTTTCACTGATACGTCGTCATCCCTCTACGACCAGTATAGAAATGCAGCGCAT
CAGCCCCCGAAGCTCTTAGACTTTAATAACAGCGGGACCGACGATAACGTCGACGACGCAACACGA
ATCAAAGAGAACTTAACAACAATGTACCAGCAGATGGTGTCAAAGGCCACTTCTCACAGACTCTTT
TTTGGAGAGCCCTACAGCGCAGGGGACGACCCAAGTCCTGGTGCCGGAAACATTGAGAGCATTCCC
CATAACAATATTCACTTTTGGACTGGCGACCCAACCCAGACAAATGGGGAAGACATGGGGAATTTT
TACTCCGCTGGAATCACTAGTGAATTCGATTTCTTTCCCGTTCCACCGTTACTACTTATACTTCCA
CGAAAGAATCTTGGCCAAACTCATAGACGATCCGACGTTCGCGTTGCCGTTTTGGAACTGGGACGC
GCCAGCTGGCATGCAACTCCCTGCCTTGTTCGCTAACCCGGACTCTCCGCTTTACGACGAGCTTCG
CGCTGCCAGCCATCAGCCGCCGACTCTCATCGATCTTGACTTCAACGGCACGGATGAAACAATGTC
CAACGATGCTCAAATCGAAGCCAACCTCAAAATTATGTATAGGCAGATGGTTTCCAACTCCAAGAA
ACCGCTGTTGTTCTTTGGTTCGCCCTACAGGGCTGGCACTGAACCAGATCCAGGGGCGGTTCAAT
CGAAACGACCCCACATGGTCCGGTTCATTTATGGCCGGAGATAACACGCAACCTAATTTTGAAGA
CATGGGGAATTTTTACTCCGCTGGAATCACTAGTGAATTCGATATCTTCTTCCCGTTCCACCGTTA
CTATCTCTACTTTTTCGAGAAGATCCTAGGCAAACTCATTAACGACCCGACATTCGCTTTGCCGTT
CTGGAACTGGGACTCGCCAGCCGGCATGCCACTGCCCGCGATTTACGCTGATCCAAAGTCCCCTCT
CTACGACAAGCTCCGATCTGCCAATCATCAGCCCCGACTCTGGTCGATCTCGATTACAACGGGAC
CGAGGACAATGTGTCAAAGGAAACCACAATCAACGCCAATCTCAAAATCATGTACAGGCAAATGGT
GTCCAATTCCAAGAATGCTAAGTTGTTCTTTGGGAACCCGTACAGGGCAGGGACAAGCCCGACCC
TGGTGGCGGCTCCATCGAGGGACACCACACGCGCCGGTTCATTTATGGACCGGTGACAACACCCA
GCCCAACTTTGAGGATATGGGGAATTTTTACTCCGCTGGTATCAAGCTTTTCCTTTCCACCGCATG
TACTTGTATTTCTACGAGAGAATCCTTGGCAAGCTCATTGATGACCCAACTTTCGCTCTCCCATAC
TGGAATTGGGACTCTCCTGACGGTTTTCCAATTCCCGACATTTACACAGATACAACTTCCCCACTC
TATGATCAGTACCGAAACGCCGACCACCAGCCCCCGTGCTGGTGGATCTCAGCTACGGTGGAACC
GATGATGACGTGGACGACCAGACAAGAATAGATGAGAACCTAGCCATCATGTACCGGCAAGTGGTT
TCCGGTGCCAAAACTCCCCATCTATTTTCGGCCATGAGTACAGGGCAGGAGACACAACAACAGGG
ACCTACGCCGGCACCATTGAGAACAGTCCTCATAATAACATCCATCTCTGGTGCGGTGACCCGAAC
CAGACCCACCACGAAGACATGGGTAACTTCTACTCCGCGG

FIGURE 6A

PGAS2 (stem loop) [SEQ ID NO: 36]

CCACATGTGGCCCTGCCGACAAGCCAGACGGGTCCACCATCGATTGTTGCCCACCCATCACGACCA
CCATCATCGACTTCAAACTCCCCGACCGAGGCCCACTCCGCACAAGGATCGCTGCCCAGGACGTTG
CAAAAAACCCTGCATACTTGGCTAAATACAAAAAGGCCATCGAGCTGATGCGGGCACTTCCAGATG
ACAATGCGGAGCTGCGGACTTTCCAAGTGGAGCAGTCCCGACCAACTGTTGCCCGCCAACGTCCCA
AAAAATCGTAGACTTCAAATTCCCCTCCCCTACCAAACTCCGCGTCAGGCCGGCAGCTCACACCGT
GGATAAAGCCTACATCGAAAATATTCAAAAGCCATCGAGCTCATGAAAGCCCTCCCGGACGACGA
TCCGAATGTGGTCCTGCAGACTTGCCACAGGGTGCAGTGCCCACCAACTGCTGCCCGCCGCCTTCC
ACAAAAATCATTGACTTTAAGCTGCCTGCCCCGCCAAACTCCGCATCAGGCCACCGGCTCACGCC
GTTGACCAAGCCTACAGGGACAAATACTACAAAGCGATGGAGCTCATGAAGGCCCTACCCGACGAC
GACCCAAATGTAAGCCGGCCGAAATCACCACCGGAGGTGAAACTGTGGAATGCTGTCCACCGGTCT
CCACAAAGATCAAAACCTTCACTCCGGACCAGTCTATCCCACTGCGGACGAGGCCTGCCGCCCATT
TGGTCACGGACGAGTACTTGGCCAAGTTCAAGAAAGCTCAAGCCCTCATGCGTGCCTTACCCGAAG
ACGACCCGGTCACACTAATTACAACAAACTTAATTAATTTCCCGCTGATTTGGATTTAACCAAGTT
AGCTAAAGCACCTTGCGGCCCCATTGCACCTAAGTTTGGATCTCGGTTTTGTAGACTAGATTGTAT
TAGAATATCATATTGAGGGCTTGTATATATTTTGAACAATATTTCAGCGGGTCGTCTTCGGGTAAG
GCACGCATGAGGGCTTGAGCTTTCTTGAACTTGGCCAAGTACTCGTCCGTGACCAAATGGGCGGCA
GGCCTCGTCCGCAGTGGGATAGACTGGTCCGGAGTGAAGGTTTTGATCTTTGTGGAGACCGGTGGA
CAGCATTCCACAGTTTCACCTCCGGTGGTGATTTCGGCCGGCTTACATTTGGGTCGTCGTCGGGTA
GGGCCTTCATGAGCTCCATCGCTTTGTAGTATTTGTCCCTGTAGGCTTGGTCAACGGCGTGAGCCG
GTGGCCTGATGCGGAGTTTGGCGGGGGCAGGCAGCTTAAAGTCAATGATTTTGTGGAAGGCGGCG
GGCAGCAGTTGGTGGGCACTGCACCCTGTGGCAAGTCTGCAGGACCACATTCGGATCGTCGTCCGG
GAGGGCTTTCATGAGCTCGATGGCTTTTGAATATTTTCGATGTAGGCTTTATCCACGGTGTGAGC
TGCCGGCCTGACGCGGAGTTTGGTAGGGGAGGGAATTTGAAGTCTACGATTTTTGGGACGTTGG
CGGGCAACAGTTGGTCGGGACTGCTCCACTTGGAAAGTCCGCAGCTCCGCATTGTCATCTGGAAGT
GCCCGCATCAGCTCGATGGCCTTTTTGTATTTAGCCAAGTATGCAGGGTTTTTTGCAACGTCCTGG
GCAGCGATCCTTGTGCGGAGTGGGCCTCGGTCGGGGAGTTTGAAGTCGATGATGGTGGTCGTGATG
GGTGGGCAACAATCGATGGTGGACCCGTCTGGCTTGTCGGCAGGGCCACATGTGG

FIGURE 6B

PPO2/PPO2_PGAS [PPO2: SEQ ID NO: 37; PPO2_PGAS: SEQ ID NO: 38]
CLUSTAL W (1.83) multiple sequence alignment

```
PPO2       ATGACTTCATCTCCCTTACCACCAACTTCTACAATGGCCGCCCTGCACTCCACCACCACA
PPO2_PGAS  ------------------------------------------------------------

PPO2       ACCACCCTCTTCCGCTCTCCTTTATTCCCAAACAAGTCCCAGACTCCACTGCAACGAAAA
PPO2_PGAS  ------------------------------------------------------------

PPO2       CCCAAACAATGCCTTGCGGGCAGAGTGCGCTGCAAAGCAACAAAAGGTGACAATGATAAC
PPO2_PGAS  ------------------------------------------------------------

PPO2       CTAGACCAGGGCTTAGCAAGACTCGACAGGAGGAACATGCTGATAGGTTTAGGCACTGGG
PPO2_PGAS  ------------------------------------------------------------

PPO2       GGTCTCTACAGTGCGGCAGGAAACTCATTTGCTTTTGCAGCACCGGTATCCGCCCCAGAC
PPO2_PGAS  ------------------------------------------------------------

PPO2       CTGACCACATGTGGCCCTGCCGACAAGCCAGACGGGTCCACCATCGATTGTTGCCCACCC
PPO2_PGAS  ------------------------------------------------------------

PPO2       ATCACGACCACCATCATCGACTTCAAACTCCCCGACCGAGGCCCACTCCGCACAAGGATC
PPO2_PGAS  ------------------------------------------------------------

PPO2       GCTGCCCAGGACGTTGCAAAAAACCCTGCATACTTGGCTAAATACAAAAAGGCCATCGAG
PPO2_PGAS  ------------------------------------------------------------

PPO2       CTGATGCGGGCACTTCCAGATGACGACCCGCGCAGTCTCGTCCAACAGGCCAAAGTCCAT
PPO2_PGAS  ------------------------------------------------------------

PPO2       TGCTCCTACTGCGACGGTGGATACCCACAAGTCGGATATTCAGATTTGGAGATCCAAGTT
PPO2_PGAS  ------------------------------------------------------------

PPO2       CACTTCTGTTGGCTATTCTTCCCGTTCCATCGTTGGTACCTCTACTTCTACGAGAAAATC
PPO2_PGAS  ------------------------------------------------------------

PPO2       ATGGGCGAGCT--CATTGGGGACCCAACCTTCGCCCTCCCCTTCTGGAACAGGGACGCGC
PPO2_PGAS  -----CGAATTGGCATTGGGGACCCAACCTTCGCCCTCCCCTTCTGGAACTGGGACGCAC
                *** *  ***************************************** *******  *

PPO2       CAGCTGGCATGTACATTCCTGAGATTTTCACCGATACGTCGTCATCCCTCTACGACCAGA
PPO2_PGAS  CAGCTGGAATGTACATTCCTGAGATTTTCACTGATACGTCGTCATCCCTCTACGACCAGT
           ******* *********************** ****************************
```

FIGURE 7A

```
PPO2        ACAGAAATACAGCGCATCAGCCCCCGAAGCTCCTGGACTTGAATTATGGCGGGACCGACG
PPO2_PGAS   ATAGAAATGCAGCGCATCAGCCCCCGAAGCTCTTAGACTTTAATAACAGCGGGACCGACG
            * ***** ************************ * **** *** *  ************

PPO2        ATGACGTCGACGACGCGACACGAATCAAAGAGAACCTAACAACGATGTACCAGCAGATGG
PPO2_PGAS   ATAACGTCGACGACGCAACACGAATCAAAGAGAACTTAACAACAATGTACCAGCAGATGG
            ** ************* ****************** ******* ****************

PPO2        TGTCGAAGGCCACTTCTCACAGACTATTCTACGGAGAGCCCTATAGCGCAGGGGACGAAC
PPO2_PGAS   TGTCAAAGGCCACTTCTCACAGACTCTTTTTGGAGAGCCCTACAGCGCAGGGGACGACC
            **** ******************** **  * ********** ************** *

PPO2        CAGATCCTGGCGCCGGAAACATTGAGACCACTCCCCATAACAATATTCACCTTTGGGTTG
PPO2_PGAS   CAAGTCCTGGTGCCGGAAACATTGAGAGCATTCCCCATAACAATATTCACTTTTGGACTG
            **  ****** **************** ** ****************** ***** ***

PPO2        GCGACCCAACCCAGACAAACGGGGAGGACATGGGGACCTTTTACTCTGCGGGGAGGGATC
PPO2_PGAS   GCGACCCAACCCAGACAAATGGGGAAGACATGGGGAATTTTTACTCCGCTGG--------
            ******************* ***** **********   ******* ** **

PPO2        CGCTGTTTTACTCTCACCATTCCAACGTGGACCGCATGTGGTCTATATATAAAGATAAGT
PPO2_PGAS   ------------------------------------------------------------

PPO2        TGGGAGGTACGGACATAGAAAATACCGACTGGCTGGACGCAGAGTTCTTATTCTACGACG
PPO2_PGAS   ------------------------------------------------------------

PPO2        AGAAAAAGAATCTCGTGCGCGTCAAGGTTCGGGACTCGCTCGACACTAAAAAACTCGGGT
PPO2_PGAS   ------------------------------------------------------------

PPO2        ACGTGTACGACGAGAAAGTCCCAATCCCATGGCTGAAGTCGAAGCCGACGCTCGTAAGTC
PPO2_PGAS   ------------------------------------------------------------

PPO2        GACGAATAAGAGAAAGGCCACAGTTCATCTTCGATCTTACTACAACGTTCCCTGCTACAT
PPO2_PGAS   ------------------------------------------------------------

PPO2        TGTCGGATACAATCAGCGTCGAGGTGACAAGGCCGTCTGCGACGAAGCGGACAGCTGCCC
PPO2_PGAS   ------------------------------------------------------------

PPO2        AGAAGAAGGCACATGACGAGGTGCTGGTGATTAAGGGGATTGAGTTTGCCGGGAATGAGC
PPO2_PGAS   ------------------------------------------------------------

PPO2        CTGTGAAGTTCGACGTGTATGTGAACGATGACGCGGAATCGCTGGCTGGGAAAGACAAGT
PPO2_PGAS   ------------------------------------------------------------
```

FIGURE 7B

```
PPO2       CGGAGTTTGCTGGGAGTTTTGTTCACGTGCCGCATAAGCATAAGAAAAATATTAAGACGA
PPO2_PGAS  ------------------------------------------------------------

PPO2       ACCTGCGACTGAGCATTATGAGCTTGTTGGAGGAGTTGGATGCGGAGACAGACAGCAGTT
PPO2_PGAS  ------------------------------------------------------------

PPO2       TGGTGGTGACTTTGGTGCCGAAAGTTGGGAAGGGGCCAATCACCATCGGAGGGTTTAGCA
PPO2_PGAS  ------------------------------------------------------------

PPO2       TTGAGCTCATTAATACTACCTAA
PPO2_PGAS  -----------------------
```

Figure 7C

GPO3/GPO3_PGAS    [GPO3: SEQ ID NO: 39; GPO3_PGAS: SEQ ID NO: 40]
CLUSTAL W (1.83) multiple sequence alignment

```
GPO3            ATGGCTTCTATGTCAGCTCCACTCGTCACCTCCGCCACAAGTATCATCCCCACAACTTCC
GPO3_PGAS       ------------------------------------------------------------

GPO3            CTCTCCCCTTTCTCCCAAAAGTATCACCGAATATCCTTATTTGGAAACCCTAGGCATTCC
GPO3_PGAS       ------------------------------------------------------------

GPO3            AATTTACAAGCTGTCTCATGCAAAGCCACAAATAATAGTAGTGACCAAAACAAAAACCCT
GPO3_PGAS       ------------------------------------------------------------

GPO3            TCCACTAGCTCCAACGATCACGACCATGAAAACCCTTCTCCAGTAAACCTAGACAGAAGA
GPO3_PGAS       ------------------------------------------------------------

GPO3            AATGTACTTATAGGTCTCGGAAGCCTATACGGTGGAGTGGCTGGTCTTGGCAGCGACCCC
GPO3_PGAS       ------------------------------------------------------------

GPO3            TTCGCTGTTGCAAAGCCAGTGTCGCCGCCTGACCTAGCCAAATGCGGAGCTGCGGACTTT
GPO3_PGAS       ------------------------------------------------------------

GPO3            CCAAGTGGAGCAGTCCCGACCAACTGTTGCCCGCCAACGTCCCAAAAAATCGTAGACTTC
GPO3_PGAS       ------------------------------------------------------------

GPO3            AAATTCCCCTCCCCTACCAAACTCCGCGTCAGGCCGGCAGCTCACACCGTGGATAAAGCC
GPO3_PGAS       ------------------------------------------------------------

GPO3            TACATCGAAAAATATTCAAAAGCCATCGAGCTCATGAAAGCCCTCCCGGACGACGATCCG
GPO3_PGAS       ------------------------------------------------------------

GPO3            CGTAGCTTCACCCAGCAAGCCGATATCCACTGTGCCTATTGCGACGGCGCGTACGACCAA
GPO3_PGAS       ------------------------------------------------------------

GPO3            GTCGGCTTCCCCAACCTCGAGCTCCAAATCCATCAATGCTGGCTTTTCTTCCCCTTCCAT
GPO3_PGAS       ------------------------------------------------TTTCTTTCCCGTTCCAC
                                                                  ***  *****  *****

GPO3            CGTTACTACCTATACTTCCACGAAAGAATCTTGGCCAAACTCATATACGATCCGACGTTC
GPO3_PGAS       CGTTACTACTTATACTTCCACGAAAGAATCTTGGCCAAACTCATAGACGATCCGACGTTC
                ********* ***************************************  *********
```

Figure 7D

```
GPO3       GCGTTGCCGTTTTGGAACTGGGACGCGCCAGCTGGCATGCAACTCCCTGCCTTGTTCGCT
GPO3_PGAS  GCGTTGCCGTTTTGGAACTGGGACGCGCCAGCTGGCATGCAACTCCCTGCCTTGTTCGCT
           ************************************************************

GPO3       AACCCGGACTCTCCGCTTTACGACGAGCTTCGCGCTGCCAGCCATCAGCCGCCGACTCTC
GPO3_PGAS  AACCCGGACTCTCCGCTTTACGACGAGCTTCGCGCTGCCAGCCATCAGCCGCCGACTCTC
           ************************************************************

GPO3       ATCGATCTTGACTTCAACGGCACGGATGAAACAATGTCCAACGATGCTCAAATCGAAGCC
GPO3_PGAS  ATCGATCTTGACTTCAACGGCACGGATGAAACAATGTCCAACGATGCTCAAATCGAAGCC
           ************************************************************

GPO3       AACCGCAAAATTATGTATAGGCAGATGGTTTCCAACTCCAAGAAACCGCTGTTGTTCTTT
GPO3_PGAS  AACCTCAAAATTATGTATAGGCAGATGGTTTCCAACTCCAAGAAACCGCTGTTGTTCTTT
           **** *******************************************************

GPO3       GGTTCTCCCTACAGGGCTGGCACTGAACCAGATCCAGGGGGCGGTTCAATCGAAACGACC
GPO3_PGAS  GGTTCGCCCTACAGGGCTGGCACTGAACCAGATCCAGGGGGCGGTTCAATCGAAACGACC
           ***** ******************************************************

GPO3       CCACATGGTCCGGTTCATTTATGGACCGGAGATAACACGCAACCTAATTTTGAAGACATG
GPO3_PGAS  CCACATGGTCCGGTTCATTTATGGGCCGGAGATAACACGCAACCTAATTTTGAAGACATG
           ************************ ***********************************

GPO3       GGGAATTTTTACTCCGCTGGAAGGGATCCAATATTTTTTCGCACCATTCGAATATAGAT
GPO3_PGAS  GGGAATTTTTACTCCGCTGG----------------------------------------
           ********************

GPO3       CGAATGTGGAATATTTGGAAAAGTATAGGGACTAAAAATAAAGATATTAACGATAAGGAT
GPO3_PGAS  ------------------------------------------------------------

GPO3       TGGTTGGATACGGGGTTTTTGTTTTATGACGAGAATGCTGAGCTTGTTAGGGTCACGGTG
GPO3_PGAS  ------------------------------------------------------------

GPO3       AGGGACACTCTTGATAATAAAAAGCTAGGGTATACGTATGAAGATGTTGAGATTCCATGG
GPO3_PGAS  ------------------------------------------------------------

GPO3       CTCAAGTCTAGACCGACGCCACGTCGGACAAAGCTTGCGAGAAAGGCAAAGGCGGCTGGA
GPO3_PGAS  ------------------------------------------------------------

GPO3       GTGGCGAAGGCGGCTGGAGTGGCGAAGGCCGCTGAGACGACGTCATCAGGGAAGGTGGTG
GPO3_PGAS  ------------------------------------------------------------

GPO3       GCGGGTAAAGATTTTCCAATAAATTTGGAGACGAAGATAAGTACGGTGGTGTCAAGGCCG
GPO3_PGAS  ------------------------------------------------------------

GPO3       AAGCCGAAGAAGAGGAGCAAGAAGGAGAAAGAGGATGAGGAGGAGATATTGGTGATTCAG
```

FIGURE 7E

GPO3_PGAS        ------------------------------------------------------------

GPO3             GGGATTGAGCTTGACAAAGATGTGGCTGTGAAGTTTGATGTGTATGTGAATGACGTGGAC
GPO3_PGAS        ------------------------------------------------------------

GPO3             GATGAGGATGCGGCACCGAGTGGACCCGACAAGAGCGAGTTTGCTGGGAGTTTTGTGAGT
GPO3_PGAS        ------------------------------------------------------------

GPO3             GTGCCACATAAGCAGAAGGAAAAGAGCAAGAGTTGTTTAAGGTTGGGGTTAACGGACCTG
GPO3_PGAS        ------------------------------------------------------------

GPO3             TTGGAGGATTTGGGTGCTGAAGATGATGAGAGTGTGGTGGTGACTTTAGTGCCCAGGTAC
GPO3_PGAS        ------------------------------------------------------------

GPO3             GGCGCTCAGGCTGTTAAGATCGGTAGCATCAAAATTGAGTTTCTTGCTTGA
GPO3_PGAS        --------------------------------------------------

FIGURE 7F

APO5/APO5_PGAS    [APO5: SEQ ID NO: 41; APO5_PGAS: SEQ ID NO: 42]
CLUSTAL W (1.83) multiple sequence alignment

```
APO5          ATGACGTCTCTTTCACCTCCGGTAGTCACCACCCCCACCGTTCCCAACCCCGCCACAAAA
APO5_PGAS     ------------------------------------------------------------

APO5          CCTCTCTCCCCCTTCTCTCAAAACAACTCCCAAGTTTCCCTACTCACAAAGCCCAAGCGT
APO5_PGAS     ------------------------------------------------------------

APO5          TCCTTTGCACGTAAGGTCTCATGCAAAGCCACAAACAATGACCAAAATGATCAAGCACAG
APO5_PGAS     ------------------------------------------------------------

APO5          TCCAAACTAGACAGGAGAAATGTGCTTCTTGGTCTTGGAGGTCTATACGGCGTGGCGGGT
APO5_PGAS     ------------------------------------------------------------

APO5          ATGGGCACAGACCCGTTCGCTTTTGCCAAGCCTATAGCCCCACCAGACGTATCTAAATGT
APO5_PGAS     ------------------------------------------------------------

APO5          GGTCCTGCAGACTTGCCACAGGGTGCAGTGCCCACCAACTGCTGCCCGCCGCCTTCCACA
APO5_PGAS     ------------------------------------------------------------

APO5          AAAATCATTGACTTTAAGCTGCCTGCCCCCGCCAAACTCCGCATCAGGCCACCGGCTCAC
APO5_PGAS     ------------------------------------------------------------

APO5          GCCGTTGACCAAGCCTACAGGGACAAATACTACAAAGCGATGGAGCTCATGAAGGCCCTA
APO5_PGAS     ------------------------------------------------------------

APO5          CCCGACGACGACCCACGTAGCTTCAAGCAACAGGCAGCCGTGCATTGCGCTTATTGCGAC
APO5_PGAS     ------------------------------------------------------------

APO5          GGCGCCTATGACCAAGTCGGGTTCCCAGAACTCGAGCTCCAAATCCACAACTCATGGCTC
APO5_PGAS     -------------------------------------------------------TC
                                                                     **

APO5          TTCTTCCCGTTCCACCGTTACTACTTGTACTTTTTCGAGAAGATCCTAGGCAAACTCATT
APO5_PGAS     TTCTTCCCGTTCCACCGTTACTATCTCTACTTTTTCGAGAAGATCCTAGGCAAACTCATT
              **********************  * *********************************

APO5          AACGACCCGACATTCGCTTTGCCGTTCTGGAACTGGGACTCGCCAGCCGGCATGCCACTG
APO5_PGAS     AACGACCCGACATTCGCTTTGCCGTTCTGGAACTGGGACTCGCCAGCCGGCATGCCACTG
              ************************************************************
```

FIGURE 7G

```
APO5       CCCGCAATTTACGCTGATCCAAAGTCCCCTCTCTACGACAAGCTCCGATCTGCCAATCAT
APO5_PGAS  CCCGCGATTTACGCTGATCCAAAGTCCCCTCTCTACGACAAGCTCCGATCTGCCAATCAT
           **** *******************************************************

APO5       CAGCCCCCGACTCTGGTCGATCTCGATTACAACGGGACCGAGGACAATGTGTCAAAGGAA
APO5_PGAS  CAGCCCCCGACTCTGGTCGATCTCGATTACAACGGGACCGAGGACAATGTGTCAAAGGAA
           ************************************************************

APO5       ACCACAATCAACGCCAATCTCAAAATCATGTACAGGCAAATGGTGTCCAATTCCAAGAAT
APO5_PGAS  ACCACAATCAACGCCAATCTCAAAATCATGTACAGGCAAATGGTGTCCAATTCCAAGAAT
           ************************************************************

APO5       GCTAAGTTGTTCTTTGGGAACCCGTACAGGGCAGGGGACGAGCCTGACCCTGGTGGCGGC
APO5_PGAS  GCTAAGTTGTTCTTTGGGAACCCGTACAGGGCAGGGGACAAGCCCGACCCTGGTGGCGGC
           *************************************** **** **************

APO5       TCCATCGAGGGGACACCACACGCGCCGGTTCATTTATGGACCGGTGACAACACCCAGCCC
APO5_PGAS  TCCATCGAGGGGACACCACACGCGCCGGTTCATTTATGGACCGGTGACAACACCCAGCCC
           ************************************************************

APO5       AACTTTGAGGACATGGGGAATTTTTACTCCGCTGGTCGGGACCCCATATTTTTTGCACAC
APO5_PGAS  AACTTTGAGGATATGGGGAATTTTTACTCCGCTGG--------------------------
           ***********  *********************

APO5       CATTCGAATGTCGATCGAATGTGGAGTATTTGGAAAACTCTTGGAGGTAAGAGAACTGAT
APO5_PGAS  ------------------------------------------------------------

APO5       CTTACTGACTCGGACTGGTTGGACTCCGGATTCTTGTTTTACAACGAGAACGCAGAGTTA
APO5_PGAS  ------------------------------------------------------------

APO5       GTCCGAGTCAAGGTCAGGGACTGCTTGGAGACCAAAAATCTTGGGTATGTATACCAAGAT
APO5_PGAS  ------------------------------------------------------------

APO5       GTGGACATTCCTTGGCTCAGCTCCAAGCCAACACCGCGAAGGGCGAAAGTTGCATTGAGC
APO5_PGAS  ------------------------------------------------------------

APO5       AAAGTAGCGAAGAAGCTGGGAGTTGCACACGCAGCTGTTGCGTCGTCCAGCAAGGTGGTG
APO5_PGAS  ------------------------------------------------------------

APO5       GCAGGCACTGAGTTCCCGATAAGTCTGGGGTCGAAGATAAGCACGGTGGTGAAGAGACCG
APO5_PGAS  ------------------------------------------------------------

APO5       AAGCAGAAGAAGAGGAGCAAGAAGGCCAAGGAGGATGAGGAGGAGATATTGGTGATTGAG
APO5_PGAS  ------------------------------------------------------------

APO5       GGAATCGAGTTTGACAGGGACGTGGCTGTGAAGTTTGATGTGTATGTGAATGACGTCGAT
```

FIGURE 7H

```
APO5_PGAS    ------------------------------------------------------------

APO5         GACTTGCCGAGTGGGCCTGACAAGACGGAGTTTGCCGGAAGCTTTGTAAGTGTGCCGCAC
APO5_PGAS    ------------------------------------------------------------

APO5         AGCCACAAGCACAAGAAGAAGATGAACACTATTTTGAGGTTAGGGTTGACAGATTTGTTG
APO5_PGAS    ------------------------------------------------------------

APO5         GAGGAAATTGAGGCGGAGGACGATGACAGCGTGGTGGTGACTTTGGTGCCCAAGTTCGGC
APO5_PGAS    ------------------------------------------------------------

APO5         GCTGTCAAGATTGGTGGTATCAAGATTGAATTTGCTTCTTAG
APO5_PGAS    -----------------------------------------
```

FIGURE 7I pSR7/pSR7_PGAS    [pSR7: SEQ ID NO: 43; pSR7_PGAS: SEQ ID NO: 44]
CLUSTAL W (1.83) multiple sequence alignment

```
pSR7           TACCACCACCACCATGGGCACTTACTCTTCTCTGATCATCTCCACCAATTCCTTCTCTGC
pSR7_PGAS      ------------------------------------------------------------ pSR7           CTTCCTCCCAAACAAATCCCAACTTTCCTTCTCTGGAAAAAGCAAGCACTACATTGCACG
pSR7_PGAS      ------------------------------------------------------------ pSR7           TAGATCATCAATATATTGCAAAGCCACAAACCCTAATTATAATAATGAGCAAGATCAACA
pSR7_PGAS      ------------------------------------------------------------ pSR7           ACAATCTTCTAATTTGTTGGGAAAATTGGACAGGAGAAATGTCCTAATTGGCCTGGGCGG
pSR7_PGAS      ------------------------------------------------------------ pSR7           CCTCTACGGGGCCACCACCCTCGCCCCAAAGCCGTTGGCCTTTGCCAACCCGCTGGCTCC
pSR7_PGAS      ------------------------------------------------------------ pSR7           ACCCGACCTAACCAAATGTAAGCCGGCCGAAATCACCACCGGAGGTGAAACTGTGGAATG
pSR7_PGAS      ------------------------------------------------------------ pSR7           CTGTCCACCGGTCTCCACAAAGATCAAAACCTTCACTCCGGACCAGTCTATCCCACTGCG
pSR7_PGAS      ------------------------------------------------------------ pSR7           GACGAGGCCTGCCGCCCATTTGGTCACGGACGAGTACTTGGCCAAGTTCAAGAAAGCTCA
pSR7_PGAS      ------------------------------------------------------------ pSR7           AGCCCTCATGCGTGCCTTACCCGAAGACGACCCGCGTAGCATGGTTCAACAAGCTAAAGT
pSR7_PGAS      ------------------------------------------------------------ pSR7           TCACTGTGCCTACTGCAATGGTGCTTATCCACAAGTAGGGTTTCCGGACATTGACATCCA
pSR7_PGAS      ------------------------------------------------------------ pSR7           AATCCACTTCTCCTGGCTTTTCTTTCCTTTCCACCGCATGTACTTGTATTTCTACGAGAG
pSR7_PGAS      ----------------------TTCCTTTCCACCGCATGTACTTGTATTTCTACGAGAG
                                     ************************************ pSR7           AATCCTTGGCAAGCTCATTGATGACCCAACTTTCGCTCTCCCATACTGGAATTGGGACTC
pSR7_PGAS      AATCCTTGGCAAGCTCATTGATGACCCAACTTTCGCTCTCCCATACTGGAATTGGGACTC
               ************************************************************
```

FIGURE 7J

```
pSR7        TCCTGACGGTTTTCCAATTCCCGACATTTACACAGATACAACTTCCCCACTCTATGATCA
pSR7_PGAS   TCCTGACGGTTTTCCAATTCCCGACATTTACACAGATACAACTTCCCCACTCTATGATCA
            ************************************************************ pSR7        GTACCGAAACGCCGACCACCAGCCCCCCGTGCTGGTGGATCTCAGCTACGGTGGAACCGA
pSR7_PGAS   GTACCGAAACGCCGACCACCAGCCCCCCGTGCTGGTGGATCTCAGCTACGGTGGAACCGA
            ************************************************************ pSR7        TGATGACGTGGACGACCAGACAAGAATAGATGAGAATCTAGCCATCATGTACCGGCAAAT
pSR7_PGAS   TGATGACGTGGACGACCAGACAAGAATAGATGAGAACCTAGCCATCATGTACCGGCAAGT
            *********************************  ******************* * pSR7        GGTTTCCGGTGCCAAAACTCCCCATCTATTTTTCGGCCATGAGTACAGGGCAGGAGACAC
pSR7_PGAS   GGTTTCCGGTGCCAAAACTCCCCATCTATTTTTCGGCCATGAGTACAGGGCAGGAGACAC
            ************************************************************ pSR7        AACAACAGGGACTTACGCCGGCACCATTGAGAACAGTCCTCATAATAACATCCATCTCTG
pSR7_PGAS   AACAACAGGGACCTACGCCGGCACCATTGAGAACAGTCCTCATAATAACATCCATCTCTG
            ********** ********************************************* pSR7        GTGCGGTGACCCGAACCAGACCCACCACGAAGACATGGGTAACTTCTACTCCGCCGGTCG
pSR7_PGAS   GTGCGGTGACCCGAACCAGACCCACCACGAAGACATGGGTAACTTCTACTCCGCGG----
            ***************************************************** * pSR7        GATCCCTGTTTACGCCCACCATTGCAGTGACCGCATGTGGAACGTTTGGAAAACCCTCGG
pSR7_PGAS   ------------------------------------------------------------ pSR7        AGGCAAGCGCAAGGACCCCACCGACACCGATTGGCTTGACGCTGAGTTTCTGTTCTACGA
pSR7_PGAS   ------------------------------------------------------------ pSR7        TGAAAACGCCGAGCTTGTGAGCTGTAAAGTTCGGGACAGCCTCAAACCTGAGAAAGATCT
pSR7_PGAS   ------------------------------------------------------------ pSR7        TCGTTATACTTACGAGCCTGTTAGTGTTCCGTGGCTGTTCACCAAGCCAACCGCTCGTAA
pSR7_PGAS   ------------------------------------------------------------ pSR7        GCCAAAGAGCAAGACAAAAGCCAAGGTGGGGGCTACCCAGCTGACGACAAAGTTCCCGGC
pSR7_PGAS   ------------------------------------------------------------ pSR7        CACGTTTGATTCGAAGACGACGGTGGAGGTGGCGAGGCCGAAGCCGCGGAAGAGGACCAA
pSR7_PGAS   ------------------------------------------------------------ pSR7        GAAGGAGAAGATCGACGAGGAGGAGGTGCTGATCATTAAGGACATCGAATTCGAGAGCAA
pSR7_PGAS   ------------------------------------------------------------ pSR7        CGAGGCGGTGAAGTTCGATGTGTTTATTAATGATGATGCTGAGTCGCTCAGTAGGAAGGA
pSR7_PGAS   ------------------------------------------------------------
```

FIGURE 7K

```
pSR7        CAAATCCGAGTTTGCTGGGAGTTTTGTGCACGTGCCGCATAACCAGAAGACTGGGACGAA
pSR7_PGAS   ------------------------------------------------------------ pSR7        GAAAAGACGAACTTAAAACTGGGGATCACGGACTTGTTGGAGGATTTGGGTGTGGAGGA
pSR7_PGAS   ------------------------------------------------------------ pSR7        TGATAGCAGTGTGCTGGTGACGTTGGTGCCTAGGGTTTCGAACTCGCCTATCACCATTGG
pSR7_PGAS   ------------------------------------------------------------ pSR7        TGGGTTTAAGATCGAGTATTCTTCTTGA
pSR7_PGAS   ----------------------------
```

FIGURE 7L

PPO2/PPO2_PGAS2    [PPO2: SEQ ID NO: 45; PPO2_PGAS2: SEQ ID NO: 46]

CLUSTAL W (1.83) multiple sequence alignment

```
PPO2           ATGACTTCATCTCCCTTACCACCAACTTCTACAATGGCCGCCCTGCACTCCACCACCACA
PPO2_PGAS2     ------------------------------------------------------------

PPO2           ACCACCCTCTTCCGCTCTCCTTTATTCCCAAACAAGTCCCAGACTCCACTGCAACGAAAA
PPO2_PGAS2     ------------------------------------------------------------

PPO2           CCCAAACAATGCCTTGCGGGCAGAGTGCGCTGCAAAGCAACAAAAGGTGACAATGATAAC
PPO2_PGAS2     ------------------------------------------------------------

PPO2           CTAGACCAGGGCTTAGCAAGACTCGACAGGAGGAACATGCTGATAGGTTTAGGCACTGGG
PPO2_PGAS2     ------------------------------------------------------------

PPO2           GGTCTCTACAGTGCGGCAGGAAACTCATTTGCTTTTGCAGCACCGGTATCCGCCCCAGAC
PPO2_PGAS2     ------------------------------------------------------------

PPO2           CTGACCACATGTGGCCCTGCCGACAAGCCAGACGGGTCCACCATCGATTGTTGCCCACCC
PPO2_PGAS2     ----CCACATGTGGCCCTGCCGACAAGCCAGACGGGTCCACCATCGATTGTTGCCCACCC
                   ********************************************************

PPO2           ATCACGACCACCATCATCGACTTCAAACTCCCCGACCGAGGCCCACTCCGCACAAGGATC
PPO2_PGAS2     ATCACGACCACCATCATCGACTTCAAACTCCCCGACCGAGGCCCACTCCGCACAAGGATC
               ************************************************************

PPO2           GCTGCCCAGGACGTTGCAAAAAACCCTGCATACTTGGCTAAATACAAAAAGGCCATCGAG
PPO2_PGAS2     GCTGCCCAGGACGTTGCAAAAAACCCTGCATACTTGGCTAAATACAAAAAGGCCATCGAG
               ************************************************************

PPO2           CTGATGCGGGCACTTCCAGATGACGACCCGCGCAGTCTCGTCCAACAGGCCAAAGTCCAT
PPO2_PGAS2     CTGATGCGGGCACTTCCAGATGAC------------------------------------
               ***********************

PPO2           TGCTCCTACTGCGACGGTGGATACCCACAAGTCGGATATTCAGATTTGGAGATCCAAGTT
PPO2_PGAS2     ------------------------------------------------------------

PPO2           CACTTCTGTTGGCTATTCTTCCCGTTCCATCGTTGGTACCTCTACTTCTACGAGAAAATC
PPO2_PGAS2     ------------------------------------------------------------

PPO2           ATGGGCGAGCTCATTGGGGACCCAACCTTCGCCCTCCCCTTCTGGAACAGGGACGCGCCA
PPO2_PGAS2     ------------------------------------------------------------
```

FIGURE 7M

| | |
|---|---|
| PPO2 | GCTGGCATGTACATTCCTGAGATTTTCACCGATACGTCGTCATCCCTCTACGACCAGAAC |
| PPO2_PGAS2 | ------------------------------------------------------------ |
| PPO2 | AGAAATACAGCGCATCAGCCCCCGAAGCTCCTGGACTTGAATTATGGCGGGACCGACGAT |
| PPO2_PGAS2 | ------------------------------------------------------------ |
| PPO2 | GACGTCGACGACGCGACACGAATCAAAGAGAACCTAACAACGATGTACCAGCAGATGGTG |
| PPO2_PGAS2 | ------------------------------------------------------------ |
| PPO2 | TCGAAGGCCACTTCTCACAGACTATTCTACGGAGAGCCCTATAGCGCAGGGGACGAACCA |
| PPO2_PGAS2 | ------------------------------------------------------------ |
| PPO2 | GATCCTGGCGCCGGAAACATTGAGACCACTCCCCATAACAATATTCACCTTTGGGTTGGC |
| PPO2_PGAS2 | ------------------------------------------------------------ |
| PPO2 | GACCCAACCCAGACAAACGGGGAGGACATGGGGACCTTTTACTCTGCGGGGAGGGATCCG |
| PPO2_PGAS2 | ------------------------------------------------------------ |
| PPO2 | CTGTTTTACTCTCACCATTCCAACGTGGACCGCATGTGGTCTATATATAAAGATAAGTTG |
| PPO2_PGAS2 | ------------------------------------------------------------ |
| PPO2 | GGAGGTACGGACATAGAAAATACCGACTGGCTGGACGCAGAGTTCTTATTCTACGACGAG |
| PPO2_PGAS2 | ------------------------------------------------------------ |
| PPO2 | AAAAAGAATCTCGTGCGCGTCAAGGTTCGGGACTCGCTCGACACTAAAAAACTCGGGTAC |
| PPO2_PGAS2 | ------------------------------------------------------------ |
| PPO2 | GTGTACGACGAGAAAGTCCCAATCCCATGGCTGAAGTCGAAGCCGACGCTCGTAAGTCGA |
| PPO2_PGAS2 | ------------------------------------------------------------ |
| PPO2 | CGAATAAGAGAAAGGCCACAGTTCATCTTCGATCTTACTACAACGTTCCCTGCTACATTG |
| PPO2_PGAS2 | ------------------------------------------------------------ |
| PPO2 | TCGGATACAATCAGCGTCGAGGTGACAAGGCCGTCTGCGACGAAGCGGACAGCTGCCCAG |
| PPO2_PGAS2 | ------------------------------------------------------------ |
| PPO2 | AAGAAGGCACATGACGAGGTGCTGGTGATTAAGGGGATTGAGTTTGCCGGGAATGAGCCT |
| PPO2_PGAS2 | ------------------------------------------------------------ |
| PPO2 | GTGAAGTTCGACGTGTATGTGAACGATGACGCGGAATCGCTGGCTGGGAAAGACAAGTCG |

FIGURE 7N

```
PPO2_PGAS2      ------------------------------------------------------------

PPO2            GAGTTTGCTGGGAGTTTTGTTCACGTGCCGCATAAGCATAAGAAAAATATTAAGACGAAC
PPO2_PGAS2      ------------------------------------------------------------

PPO2            CTGCGACTGAGCATTATGAGCTTGTTGGAGGAGTTGGATGCGGAGACAGACAGCAGTTTG
PPO2_PGAS2      ------------------------------------------------------------

PPO2            GTGGTGACTTTGGTGCCGAAAGTTGGGAAGGGGCCAATCACCATCGGAGGGTTTAGCATT
PPO2_PGAS2      ------------------------------------------------------------

PPO2            GAGCTCATTAATACTACCTAA
PPO2_PGAS2      ---------------------
```

FIGURE 70

GPO3/GPO3_PGAS2    [GPO3: SEQ ID NO: 47; GPO3_PGAS2: SEQ ID NO: 48]
CLUSTAL W (1.83) multiple sequence alignment

```
GPO3            ATGGCTTCTATGTCAGCTCCACTCGTCACCTCCGCCACAAGTATCATCCCCACAACTTCC
GPO3_PGAS2      ------------------------------------------------------------

GPO3            CTCTCCCCTTTCTCCCAAAAGTATCACCGAATATCCTTATTTGGAAACCCTAGGCATTCC
GPO3_PGAS2      ------------------------------------------------------------

GPO3            AATTTACAAGCTGTCTCATGCAAAGCCACAAATAATAGTAGTGACCAAAACAAAAACCCT
GPO3_PGAS2      ------------------------------------------------------------

GPO3            TCCACTAGCTCCAACGATCACGACCATGAAAACCCTTCTCCAGTAAACCTAGACAGAAGA
GPO3_PGAS2      ------------------------------------------------------------

GPO3            AATGTACTTATAGGTCTCGGAAGCCTATACGGTGGAGTGGCTGGTCTTGGCAGCGACCCC
GPO3_PGAS2      ------------------------------------------------------------

GPO3            TTCGCTGTTGCAAAGCCAGTGTCGCCGCCTGACCTAGCCAAATGCGGAGCTGCGGACTTT
GPO3_PGAS2      ---------------------------------------AATGCGGAGCTGCGGACTTT
                                                       *********************

GPO3            CCAAGTGGAGCAGTCCCGACCAACTGTTGCCCGCCAACGTCCCAAAAAATCGTAGACTTC
GPO3_PGAS2      CCAAGTGGAGCAGTCCCGACCAACTGTTGCCCGCCAACGTCCCAAAAAATCGTAGACTTC
                ************************************************************

GPO3            AAATTCCCCTCCCCTACCAAACTCCGCGTCAGGCCGGCAGCTCACACCGTGGATAAAGCC
GPO3_PGAS2      AAATTCCCCTCCCCTACCAAACTCCGCGTCAGGCCGGCAGCTCACACCGTGGATAAAGCC
                ************************************************************

GPO3            TACATCGAAAATATTCAAAAGCCATCGAGCTCATGAAAGCCCTCCCGGACGACGATCCG
GPO3_PGAS2      TACATCGAAAATATTCAAAAGCCATCGAGCTCATGAAAGCCCTCCCGGACGACGATCCG
                ************************************************************

GPO3            CGTAGCTTCACCCAGCAAGCCGATATCCACTGTGCCTATTGCGACGGCGCGTACGACCAA
GPO3_PGAS2      ------------------------------------------------------------

GPO3            GTCGGCTTCCCCAACCTCGAGCTCCAAATCCATCAATGCTGGCTTTTCTTCCCCTTCCAT
GPO3_PGAS2      ------------------------------------------------------------

GPO3            CGTTACTACCTATACTTCCACGAAAGAATCTTGGCCAAACTCATATACGATCCGACGTTC
GPO3_PGAS2      ------------------------------------------------------------
```

FIGURE 7P

| | |
|---|---|
| GPO3 | GCGTTGCCGTTTTGGAACTGGGACGCGCCAGCTGGCATGCAACTCCCTGCCTTGTTCGCT |
| GPO3_PGAS2 | ------------------------------------------------------------ |
| | |
| GPO3 | AACCCGGACTCTCCGCTTTACGACGAGCTTCGCGCTGCCAGCCATCAGCCGCCGACTCTC |
| GPO3_PGAS2 | ------------------------------------------------------------ |
| | |
| GPO3 | ATCGATCTTGACTTCAACGGCACGGATGAAACAATGTCCAACGATGCTCAAATCGAAGCC |
| GPO3_PGAS2 | ------------------------------------------------------------ |
| | |
| GPO3 | AACCGCAAAATTATGTATAGGCAGATGGTTTCCAACTCCAAGAAACCGCTGTTGTTCTTT |
| GPO3_PGAS2 | ------------------------------------------------------------ |
| | |
| GPO3 | GGTTCTCCCTACAGGGCTGGCACTGAACCAGATCCAGGGGGCGGTTCAATCGAAACGACC |
| GPO3_PGAS2 | ------------------------------------------------------------ |
| | |
| GPO3 | CCACATGGTCCGGTTCATTTATGGACCGGAGATAACACGCAACCTAATTTTGAAGACATG |
| GPO3_PGAS2 | ------------------------------------------------------------ |
| | |
| GPO3 | GGGAATTTTTACTCCGCTGGAAGGGATCCAATATTTTTTTCGCACCATTCGAATATAGAT |
| GPO3_PGAS2 | ------------------------------------------------------------ |
| | |
| GPO3 | CGAATGTGGAATATTTGGAAAAGTATAGGGACTAAAAATAAAGATATTAACGATAAGGAT |
| GPO3_PGAS2 | ------------------------------------------------------------ |
| | |
| GPO3 | TGGTTGGATACGGGGTTTTTGTTTTATGACGAGAATGCTGAGCTTGTTAGGGTCACGGTG |
| GPO3_PGAS2 | ------------------------------------------------------------ |
| | |
| GPO3 | AGGGACACTCTTGATAATAAAAGCTAGGGTATACGTATGAAGATGTTGAGATTCCATGG |
| GPO3_PGAS2 | ------------------------------------------------------------ |
| | |
| GPO3 | CTCAAGTCTAGACCGACGCCACGTCGGACAAAGCTTGCGAGAAAGGCAAAGGCGGCTGGA |
| GPO3_PGAS2 | ------------------------------------------------------------ |
| | |
| GPO3 | GTGGCGAAGGCGGCTGGAGTGGCGAAGGCCGCTGAGACGACGTCATCAGGGAAGGTGGTG |
| GPO3_PGAS2 | ------------------------------------------------------------ |
| | |
| GPO3 | GCGGGTAAAGATTTTCCAATAAATTTGGAGACGAAGATAAGTACGGTGGTGTCAAGGCCG |
| GPO3_PGAS2 | ------------------------------------------------------------ |
| | |
| GPO3 | AAGCCGAAGAAGAGGAGCAAGAAGGAGAAAGAGGATGAGGAGGAGATATTGGTGATTCAG |

FIGURE 7Q

| | |
|---|---|
| GPO3_PGAS2 | ------------------------------------------------------------ |
| | |
| GPO3 | GGGATTGAGCTTGACAAAGATGTGGCTGTGAAGTTTGATGTGTATGTGAATGACGTGGAC |
| GPO3_PGAS2 | ------------------------------------------------------------ |
| | |
| GPO3 | GATGAGGATGCGGCACCGAGTGGACCCGACAAGAGCGAGTTTGCTGGGAGTTTTGTGAGT |
| GPO3_PGAS2 | ------------------------------------------------------------ |
| | |
| GPO3 | GTGCCACATAAGCAGAAGGAAAAGAGCAAGAGTTGTTTAAGGTTGGGGTTAACGGACCTG |
| GPO3_PGAS2 | ------------------------------------------------------------ |
| | |
| GPO3 | TTGGAGGATTTGGGTGCTGAAGATGATGAGAGTGTGGTGGTGACTTTAGTGCCCAGGTAC |
| GPO3_PGAS2 | ------------------------------------------------------------ |
| | |
| GPO3 | GGCGCTCAGGCTGTTAAGATCGGTAGCATCAAAATTGAGTTTCTTGCTTGA |
| GPO3_PGAS2 | --------------------------------------------------- |

FIGURE 7R

APO5/APO5_PGAS2    [APO5: SEQ ID NO: 49; APO5_PGAS2: SEQ ID NO: 50]

CLUSTAL W (1.83) multiple sequence alignment

```
APO5         ATGACGTCTCTTTCACCTCCGGTAGTCACCACCCCCACCGTTCCCAACCCCGCCACAAAA
APO5_PGAS2   ------------------------------------------------------------

APO5         CCTCTCTCCCCCTTCTCTCAAAACAACTCCCAAGTTTCCCTACTCACAAAGCCCAAGCGT
APO5_PGAS2   ------------------------------------------------------------

APO5         TCCTTTGCACGTAAGGTCTCATGCAAAGCCACAAACAATGACCAAAATGATCAAGCACAG
APO5_PGAS2   ------------------------------------------------------------

APO5         TCCAAACTAGACAGGAGAAATGTGCTTCTTGGTCTTGGAGGTCTATACGGCGTGGCGGGT
APO5_PGAS2   ------------------------------------------------------------

APO5         ATGGGCACAGACCCGTTCGCTTTTGCCAAGCCTATAGCCCCACCAGACGTATCTAAATGT
APO5_PGAS2   ------------------------------------------------------AATGT
                                                                   *****

APO5         GGTCCTGCAGACTTGCCACAGGGTGCAGTGCCCACCAACTGCTGCCCGCCGCCTTCCACA
APO5_PGAS2   GGTCCTGCAGACTTGCCACAGGGTGCAGTGCCCACCAACTGCTGCCCGCCGCCTTCCACA
             ************************************************************

APO5         AAAATCATTGACTTTAAGCTGCCTGCCCCCGCCAAACTCCGCATCAGGCCACCGGCTCAC
APO5_PGAS2   AAAATCATTGACTTTAAGCTGCCTGCCCCCGCCAAACTCCGCATCAGGCCACCGGCTCAC
             ************************************************************

APO5         GCCGTTGACCAAGCCTACAGGGACAAATACTACAAAGCGATGGAGCTCATGAAGGCCCTA
APO5_PGAS2   GCCGTTGACCAAGCCTACAGGGACAAATACTACAAAGCGATGGAGCTCATGAAGGCCCTA
             ************************************************************

APO5         CCCGACGACGACCCACGTAGCTTCAAGCAACAGGCAGCCGTGCATTGCGCTTATTGCGAC
APO5_PGAS2   CCCGACGACGACCCA---------------------------------------------
             ***************

APO5         GGCGCCTATGACCAAGTCGGGTTCCCAGAACTCGAGCTCCAAATCCACAACTCATGGCTC
APO5_PGAS2   ------------------------------------------------------------

APO5         TTCTTCCCGTTCCACCGTTACTACTTGTACTTTTTCGAGAAGATCCTAGGCAAACTCATT
APO5_PGAS2   ------------------------------------------------------------

APO5         AACGACCCGACATTCGCTTTGCCGTTCTGGAACTGGGACTCGCCAGCCGGCATGCCACTG
APO5_PGAS2   ------------------------------------------------------------
```

FIGURE 7S

| | |
|---|---|
| APO5 | CCCGCAATTTACGCTGATCCAAAGTCCCCTCTCTACGACAAGCTCCGATCTGCCAATCAT |
| APO5_PGAS2 | ------------------------------------------------------------ |
| | |
| APO5 | CAGCCCCCGACTCTGGTCGATCTCGATTACAACGGGACCGAGGACAATGTGTCAAAGGAA |
| APO5_PGAS2 | ------------------------------------------------------------ |
| | |
| APO5 | ACCACAATCAACGCCAATCTCAAAATCATGTACAGGCAAATGGTGTCCAATTCCAAGAAT |
| APO5_PGAS2 | ------------------------------------------------------------ |
| | |
| APO5 | GCTAAGTTGTTCTTTGGGAACCCGTACAGGGCAGGGGACGAGCCTGACCCTGGTGGCGGC |
| APO5_PGAS2 | ------------------------------------------------------------ |
| | |
| APO5 | TCCATCGAGGGGACACCACACGCGCCGGTTCATTTATGGACCGGTGACAACACCCAGCCC |
| APO5_PGAS2 | ------------------------------------------------------------ |
| | |
| APO5 | AACTTTGAGGACATGGGGAATTTTTACTCCGCTGGTCGGGACCCCATATTTTTTGCACAC |
| APO5_PGAS2 | ------------------------------------------------------------ |
| | |
| APO5 | CATTCGAATGTCGATCGAATGTGGAGTATTTGGAAAACTCTTGGAGGTAAGAGAACTGAT |
| APO5_PGAS2 | ------------------------------------------------------------ |
| | |
| APO5 | CTTACTGACTCGGACTGGTTGGACTCCGGATTCTTGTTTTACAACGAGAACGCAGAGTTA |
| APO5_PGAS2 | ------------------------------------------------------------ |
| | |
| APO5 | GTCCGAGTCAAGGTCAGGGACTGCTTGGAGACCAAAAATCTTGGGTATGTATACCAAGAT |
| APO5_PGAS2 | ------------------------------------------------------------ |
| | |
| APO5 | GTGGACATTCCTTGGCTCAGCTCCAAGCCAACACCGCGAAGGGCGAAAGTTGCATTGAGC |
| APO5_PGAS2 | ------------------------------------------------------------ |
| | |
| APO5 | AAAGTAGCGAAGAAGCTGGGAGTTGCACACGCAGCTGTTGCGTCGTCCAGCAAGGTGGTG |
| APO5_PGAS2 | ------------------------------------------------------------ |
| | |
| APO5 | GCAGGCACTGAGTTCCCGATAAGTCTGGGGTCGAAGATAAGCACGGTGGTGAAGAGACCG |
| APO5_PGAS2 | ------------------------------------------------------------ |
| | |
| APO5 | AAGCAGAAGAAGAGGAGCAAGAAGGCCAAGGAGGATGAGGAGGAGATATTGGTGATTGAG |
| APO5_PGAS2 | ------------------------------------------------------------ |
| | |
| APO5 | GGAATCGAGTTTGACAGGGACGTGGCTGTGAAGTTTGATGTGTATGTGAATGACGTCGAT |

FIGURE 7T

```
APO5_PGAS2      ----------------------------------------------------------

APO5            GACTTGCCGAGTGGGCCTGACAAGACGGAGTTTGCCGGAAGCTTTGTAAGTGTGCCGCAC
APO5_PGAS2      ----------------------------------------------------------

APO5            AGCCACAAGCACAAGAAGAAGATGAACACTATTTTGAGGTTAGGGTTGACAGATTTGTTG
APO5_PGAS2      ----------------------------------------------------------

APO5            GAGGAAATTGAGGCGGAGGACGATGACAGCGTGGTGGTGACTTTGGTGCCCAAGTTCGGC
APO5_PGAS2      ----------------------------------------------------------

APO5            GCTGTCAAGATTGGTGGTATCAAGATTGAATTTGCTTCTTAG
APO5_PGAS2      ----------------------------------------
```

FIGURE 7U pSR7/pSR7_PGAS2    [pSR7: SEQ ID NO: 51; pSR7_PGAS2: SEQ ID NO: 52]
CLUSTAL W (1.83) multiple sequence alignment

```
pSR7            TACCACCACCACCATGGGCACTTACTCTTCTCTGATCATCTCCACCAATTCCTTCTCTGC
pSR7_PGAS2      ------------------------------------------------------------ pSR7            CTTCCTCCCAAACAAATCCCAACTTTCCTTCTCTGGAAAAAGCAAGCACTACATTGCACG
pSR7_PGAS2      ------------------------------------------------------------ pSR7            TAGATCATCAATATATTGCAAAGCCACAAACCCTAATTATAATAATGAGCAAGATCAACA
pSR7_PGAS2      ------------------------------------------------------------ pSR7            ACAATCTTCTAATTTGTTGGGAAAATTGGACAGGAGAAATGTCCTAATTGGCCTGGGCGG
pSR7_PGAS2      ------------------------------------------------------------ pSR7            CCTCTACGGGGCCACCACCCTCGCCCCAAAGCCGTTGGCCTTTGCCAACCCGCTGGCTCC
pSR7_PGAS2      ------------------------------------------------------------ pSR7            ACCCGACCTAACCAAATGTAAGCCGGCCGAAATCACCACCGGAGGTGAAACTGTGGAATG
pSR7_PGAS2      --------------AATGTAAGCCGGCCGAAATCACCACCGGAGGTGAAACTGTGGAATG
                              ********************************************** pSR7            CTGTCCACCGGTCTCCACAAAGATCAAAACCTTCACTCCGGACCAGTCTATCCCACTGCG
pSR7_PGAS2      CTGTCCACCGGTCTCCACAAAGATCAAAACCTTCACTCCGGACCAGTCTATCCCACTGCG
                ************************************************************ pSR7            GACGAGGCCTGCCGCCCATTTGGTCACGGACGAGTACTTGGCCAAGTTCAAGAAAGCTCA
pSR7_PGAS2      GACGAGGCCTGCCGCCCATTTGGTCACGGACGAGTACTTGGCCAAGTTCAAGAAAGCTCA
                ************************************************************ pSR7            AGCCCTCATGCGTGCCTTACCCGAAGACGACCCGCGTAGCATGGTTCAACAAGCTAAAGT
pSR7_PGAS2      AGCCCTCATGCGTGCCTTACCCGAAGACGACCCG--------------------------
                ********************************** pSR7            TCACTGTGCCTACTGCAATGGTGCTTATCCACAAGTAGGGTTTCCGGACATTGACATCCA
pSR7_PGAS2      ------------------------------------------------------------ pSR7            AATCCACTTCTCCTGGCTTTTCTTTCCTTTCCACCGCATGTACTTGTATTTCTACGAGAG
pSR7_PGAS2      ------------------------------------------------------------ pSR7            AATCCTTGGCAAGCTCATTGATGACCCAACTTTCGCTCTCCCATACTGGAATTGGGACTC
pSR7_PGAS2      ------------------------------------------------------------
```

FIGURE 7V

| | |
|---|---|
| pSR7 | TCCTGACGGTTTTCCAATTCCCGACATTTACACAGATACAACTTCCCCACTCTATGATCA |
| pSR7_PGAS2 | ------------------------------------------------------------ |
| pSR7 | GTACCGAAACGCCGACCACCAGCCCCCCGTGCTGGTGGATCTCAGCTACGGTGGAACCGA |
| pSR7_PGAS2 | ------------------------------------------------------------ |
| pSR7 | TGATGACGTGGACGACCAGACAAGAATAGATGAGAATCTAGCCATCATGTACCGGCAAAT |
| pSR7_PGAS2 | ------------------------------------------------------------ |
| pSR7 | GGTTTCCGGTGCCAAAACTCCCCATCTATTTTTCGGCCATGAGTACAGGGCAGGAGACAC |
| pSR7_PGAS2 | ------------------------------------------------------------ |
| pSR7 | AACAACAGGGACTTACGCCGGCACCATTGAGAACAGTCCTCATAATAACATCCATCTCTG |
| pSR7_PGAS2 | ------------------------------------------------------------ |
| pSR7 | GTGCGGTGACCCGAACCAGACCCACCACGAAGACATGGGTAACTTCTACTCCGCCGGTCG |
| pSR7_PGAS2 | ------------------------------------------------------------ |
| pSR7 | GATCCCTGTTTACGCCCACCATTGCAGTGACCGCATGTGGAACGTTTGGAAAACCCTCGG |
| pSR7_PGAS2 | ------------------------------------------------------------ |
| pSR7 | AGGCAAGCGCAAGGACCCCACCGACACCGATTGGCTTGACGCTGAGTTTCTGTTCTACGA |
| pSR7_PGAS2 | ------------------------------------------------------------ |
| pSR7 | TGAAAACGCCGAGCTTGTGAGCTGTAAAGTTCGGGACAGCCTCAAACCTGAGAAAGATCT |
| pSR7_PGAS2 | ------------------------------------------------------------ |
| pSR7 | TCGTTATACTTACGAGCCTGTTAGTGTTCCGTGGCTGTTCACCAAGCCAACCGCTCGTAA |
| pSR7_PGAS2 | ------------------------------------------------------------ |
| pSR7 | GCCAAAGAGCAAGACAAAAGCCAAGGTGGGGGCTACCCAGCTGACGACAAAGTTCCCGGC |
| pSR7_PGAS2 | ------------------------------------------------------------ |
| pSR7 | CACGTTTGATTCGAAGACGACGGTGGAGGTGGCGAGGCCGAAGCCGCGGAAGAGGACCAA |
| pSR7_PGAS2 | ------------------------------------------------------------ |
| pSR7 | GAAGGAGAAGATCGACGAGGAGGAGGTGCTGATCATTAAGGACATCGAATTCGAGAGCAA |
| pSR7_PGAS2 | ------------------------------------------------------------ |
| pSR7 | CGAGGCGGTGAAGTTCGATGTGTTTATTAATGATGATGCTGAGTCGCTCAGTAGGAAGGA |
| pSR7_PGAS2 | ------------------------------------------------------------ |

FIGURE 7W pSR7            CAAATCCGAGTTTGCTGGGAGTTTTGTGCACGTGCCGCATAACCAGAAGACTGGGACGAA
pSR7_PGAS2      ------------------------------------------------------------ pSR7            GAAAAAGACGAACTTAAAACTGGGGATCACGGACTTGTTGGAGGATTTGGGTGTGGAGGA
pSR7_PGAS2      ------------------------------------------------------------ pSR7            TGATAGCAGTGTGCTGGTGACGTTGGTGCCTAGGGTTTCGAACTCGCCTATCACCATTGG
pSR7_PGAS2      ------------------------------------------------------------ pSR7            TGGGTTTAAGATCGAGTATTCTTCTTGA
pSR7_PGAS2      ----------------------------

FIGURE 7X

The M13 ori and geneIII sequences and the ornithine cycledeaminase (OCD) from Agrobacterium plasmid C58 are present in the T-DNA. Also, lacI 5' and 3' regions surround the lacZ and M13 ori regions.

LB [SEQ ID NO: 53]

CTGATGGGCTGCCTGTATCGAGTGGTGATTTTGTGCCGAGCTGCCGGTCGGGGAGCTGTTGGCTGG
CTGGTGGCAGGATATATTGTGGTGTAAACAAATTGACGCTTAGACAACTTAATAACACATTGCGGA
CGTTTTTAATGTACTG $P_{NOS}$ [SEQ ID NO: 54]

AAACTGAAGGCGGGAAACGACAATCTGATCATGAGCGGAGAATTAAGGGAGTCACGTTATGACCCC
CGCCGATGACGCGGGACAAGCCGTTTTACGTTTGGAACTGACAGAACCGCAACGTTGAAGGAGCCA
CTCAGCCGCGGGTTTCTGGAGTTTAATGAGCTAAGCACATACGTCAGAAACCATTATTGCGCGTTC
AAAAGTCGCCTAAGGTCACTATCAGCTAGCAAATATTTCTTGTCAAAAATGCTCCACTGACGTTCC
ATAAATTCCCCTCGGTATCCAATTAGAGTCTCATATTCACTCTCAATCCAAATAATCTGCACCGGA
TCTGGATCGTTTCGC nptII [SEQ ID NO: 55]

ATGATTGAACAAGATGGATTGCACGCAGGTTCTCCGGCCGCTTGGGTGGAGAGGCTATTCGGCTAT
GACTGGGCACAACAGACAATCGGCTGCTCTGATGCCGCCGTGTTCCGGCTGTCAGCGCAGGGGCGC
CCGGTTCTTTTTGTCAAGACCGACCTGTCCGGTGCCCTGAATGAACTGCAGGACGAGGCAGCGCGG
CTATCGTGGCTGGCCACGACGGGCGTTCCTTGCGCAGCTGTGCTCGACGTTGTCACTGAAGCGGGA
AGGGACTGGCTGCTATTGGGCGAAGTGCCGGGGCAGGATCTCCTGTCATCTCACCTTGCTCCTGCC
GAGAAAGTATCCATCATGGCTGATGCAATGCGGCGGCTGCATACGCTTGATCCGGCTACCTGCCCA
TTCGACCACCAAGCGAAACATCGCATCGAGCGAGCACGTACTCGGATGGAAGCCGGTCTTGTCGAT
CAGGATGATCTGGACGAAGAGCATCAGGGGCTCGCGCCAGCCGAACTGTTCGCCAGGCTCAAGGCG
CGCATGCCCGACGGCGATGATCTCGTCGTGACCCATGGCGATGCCTGCTTGCCGAATATCATGGTG
GAAAATGGCCGCTTTTCTGGATTCATCGACTGTGGCCGGCTGGGTGTGGCGGACCGCTATCAGGAC
ATAGCGTTGGCTACCCGTGATATTGCTGAAGAGCTTGGCGGCGAATGGGCTGACCGCTTCCTCGTG
CTTTACGGTATCGCCGCTCCCGATTCGCAGCGCATCGCCTTCTATCGCCTTCTTGACGAGTTCTTC
TGA $T_{NOS}$ [SEQ ID NO: 56]

GATCGTTCAAACATTTGGCAATAAAGTTTCTTAAGATTGAATCCTGTTGCCGGTCTTGCGATGATT
ATCATATAATTTCTGTTGAATTACGTTAAGCATGTAATAATTAACATGTAATGCATGACGTTATTT
ATGAGATGGGTTTTTATGATTAGAGTCCCGC

FIGURE 9A

P<sub>CaMV35s</sub> [SEQ ID NO: 57]

```
TCTAGATAAGGATCCACGAAGCTTGCATGCCTGCAGGTCCGATCTGAGACTTTTCAACAAAGGGTA
ATATCGGGAAACCTCCTCGGATTCCATTGCCCAGCTATCTGTCACTTCATCAAAAGGACAGTAGAA
AAGGAAGGTGGCACCTACAAATGCCATCATTGCGATAAAGGAAAGGCTATCGTTCAAGATGCCTCT
GCCGACAGTGGTCCCAAAGATGGACCCCCACCCACGAGGAGCATCGTGGAAAAGAAGACGTTCCA
ACCACGTCTTCAAAGCAAGTGGATTGATGTGATGGTCCGATCTGAGACTTTTCAACAAAGGGTAAT
ATCGGGAAACCTCCTCGGATTCCATTGCCCAGCTATCTGTCACTTCATCAAAAGGACAGTAGAAAA
GGAAGGTGGCACCTACAAATGCCATCATTGCGATAAAGGAAAGGCTATCGTTCAAGATGCCTCTGC
CGACAGTGGTCCCAAAGATGGACCCCCACCCACGAGGAGCATCGTGGAAAAGAAGACGTTCCAAC
CACGTCTTCAAAGCAAGTGGATTGATGTGATATCTCCACTGACGTAAGGGATGACGCACAATCCCA
CTATCCTTCGCAAGACCCTTCCTCTATATAAGGAAGTTCATTTCATTTGGAGAGGAG
```

PGAS (Sense Transgene) [SEQ ID NO: 58]

```
GAGCCCAGTCACGACGTTGTAAAACGACGGCCAGTGAGCGCGCGTAATACGACTCCTATAGGGCGA
ATTGGCATTGGGGACCCAACCTTCGCCCTCCCCTTCTGGAACTGGGACGCACCAGCTGGAATGTAC
ATTCCTGAGATTTTCACTGATACGTCGTCATCCCTCTACGACCAGTATAGAAATGCAGCGCATCAG
CCCCCGAAGCTCTTAGACTTTAATAACAGCGGGACCGACGATAACGTCGACGACGCAACACGAATC
AAAGAGAACTTAACAACAATGTACCAGCAGATGGTGTCAAAGGCCACTTCTCACAGACTCTTTTTT
GGAGAGCCCTACAGCGCAGGGGACGACCCAAGTCCTGGTGCCGGAAACATTGAGAGCATTCCCCAT
AACAATATTCACTTTTGGACTGGCGACCCAACCCAGACAAATGGGGAAGACATGGGGAATTTTTAC
TCCGCTGGAATCACTAGTGAATTCGATTTCTTTCCCGTTCCACCGTTACTACTTATACTTCCACGA
AAGAATCTTGGCCAAACTCATAGACGATCCGACGTTCGCGTTGCCGTTTTGGAACTGGGACGCGCC
AGCTGGCATGCAACTCCCTGCCTTGTTCGCTAACCCGGACTCTCCGCTTTACGACGAGCTTCGCGC
TGCCAGCCATCAGCCGCCGACTCTCATCGATCTTGACTTCAACGGCACGGATGAAACAATGTCCAA
CGATGCTCAAATCGAAGCCAACCTCAAAATTATGTATAGGCAGATGGTTTCCAACTCCAAGAAACC
GCTGTTGTTCTTTGGTTCGCCCTACAGGGCTGGCACTGAACCAGATCCAGGGGGCGGTTCAATCGA
AACGACCCCACATGGTCCGGTTCATTTATGGGCCGGAGATAACACGCAACCTAATTTTGAAGACAT
GGGGAATTTTTACTCCGCTGGAATCACTAGTGAATTCGATATCTTCTTCCCGTTCCACCGTTACTA
TCTCTACTTTTTCGAGAAGATCCTAGGCAAACTCATTAACGACCCGACATTCGCTTTGCCGTTCTG
GAACTGGGACTCGCCAGCCGGCATGCCACTGCCCGCGATTTACGCTGATCCAAAGTCCCTCTCTA
CGACAAGCTCCGATCTGCCAATCATCAGCCCCCGACTCTGGTCGATCTCGATTACAACGGGACCGA
GGACAATGTGTCAAAGGAAACCACAATCAACGCCAATCTCAAAATCATGTACAGGCAAATGGTGTC
CAATTCCAAGAATGCTAAGTTGTTCTTTGGGAACCCGTACAGGGCAGGGACAAGCCCGACCCTGG
TGGCGGCTCCATCGAGGGGACACCACACGCGCCGGTTCATTTATGGACCGGTGACAACACCCAGCC
CAACTTTGAGGATATGGGGAATTTTTACTCCGCTGGTATCAAGCTTTTCCTTTCCACCGCATGTAC
TTGTATTTCTACGAGAGAATCCTTGGCAAGCTCATTGATGACCCAACTTTCGCTCTCCCATACTGG
AATTGGGACTCTCCTGACGGTTTTCCAATTCCGACATTTACACAGATACAACTTCCCCACTCTAT
GATCAGTACCGAAACGCCGACCACCAGCCCCCGTGCTGGTGGATCTCAGCTACGGTGGAACCGAT
GATGACGTGGACGACCAGACAAGAATAGATGAGAACCTAGCCATCATGTACCGGCAAGTGGTTTCC
GGTGCCAAAACTCCCCATCTATTTTCGGCCATGAGTACAGGGCAGGAGACACAACAACAGGGACC
TACGCCGGCACCATTGAGAACAGTCCTCATAATAACATCCATCTCTGGTGCGGTGACCCGAACCAG
ACCCACCACGAAGACATGGGTAACTTCTACTCCGCGGCTC
```

FIGURE 9B

T_NOS [SEQ ID NO: 59]

GATCGTTCAAACATTTGGCAATAAAGTTTCTTAAGATTGAATCCTGTTGCCGGTCTTGCGATGATT
ATCATATAATTTCTGTTGAATTACGTTAAGCATGTAATAATTAACATGTAATGCATGACGTTATTT
ATGAGATGGGTTTTTATGATTAGAGTCCCGCAATTATACATTTAATACGCGATAGAAAACAAAATA
TAGCGCGCAAACTAGGATAAATTATCGCGCGCGGTGTCATCTATGTTACTAGATC

RB [SEQ ID NO: 60]

AAACTATCAGTGTTTGACAGGATATATTGGCGGGTAAACCTAAGAGAAAAGAGCGTTTATTAGAAT
AATCGGATATTTAAAAGGGCGTGAAAAGGTTTATCCGTTCGTCCATTTGTATGTGCATGCCAACCA
CAGG

FIGURE 9C

RB [SEQ ID NO: 61]

TCCTGTGGTTGGCATGCACATACAAATGGACGAACGGATAAACCTTTTCACGCCCTTTTAAATATC
CGATTATTCTAATAAACGCTCTTTTCTCTTAGGTTTACCCGCCAATATATCCTGTCAAACACTGAT
AGTTTAAACTGAAGGCGGGAAACGACAATCT $P_{BUL409s}$ [SEQ ID NO: 62]

GGCGCGCCAAGCTACTTACCTCTTATATAAAAAGAAAAAGTGTTTCTAATATATACTCAATTTAA
ATAAATATTTTCAATCAAATTTAGATAACAAATACTTATCAATATGAGGTCAATAACAATAAAAA
AATAATGTAAAAAAAGGAGCAATACATAATATAAGAAAAAGATTAAAGTGCGATTATCAACGAG
TATTATACCCTAATTTGCTAATATTTAAACTCTTATATTTAAGGTTATGTTCACAATATACTTAAA
AAGCGCTATATTAGAGCATATATTAATTAATAAAAAGAAATGCTAAATGATCAAAAAATTAGA
TAGAAAATTAAGAAATTATAATATTTTTTTATTTTAAAATAAATTCATATATTCTTTATTTTTA
GTTAAAATGTATTAAAGTTAAAAGAATAAAAATATTTTAAAAAATAAAATAACATAAATAAAATAT
CATTCTAATTAAATTCAGACCAAATTTTTTCCCCAGATTTTGGCCAATACCTAAAATAAAATTAAG
TTATTTTTAGTATATTTTTTTACATTGACCTACATTTTTCTAGTTTTTTCTAAAGGAGCGTGTAAG
CGTCAACCTCATTCTCCTAATTTTCCCCACCACATAAATAAAAAGAAACGGTAGCTTTTGCGTGTT
GTTTTGCTACACTACACCTCATTATTACACGTGTCATCATATAATTGGCTAACCCTATGAGGCGGT
TTCGTCTAGAGTCGGCCATGCCATCTATAAAAGGAACCTTTCTGCACCTCATTTTTTCATCTTCTA
TCTGACTTCTATTATAATTTCTCTCAATTGCCTTTAAATTTCTCTTTCAAGGTTAGAAATCTTCTC
TATTTTTTGGTTTTTGTCTGTTTAGATTCTCGAATTAGCTAAGCAGGTGCTGTTAAAGCCCTAAAA
TTTGAGTTTTTTTTCCGTTGTTTTGATGAAAAGCCCCTAATTTGAGTTTTTTTCCGTCGATTTGA
TGCCAAAGGTTTAAAATTAGAGTTTTTTCGTCGGTTTGATTCTAAAGGCCCAAAATGTGGGGTTTT
CCGGGTGATTTGATGATAATGCCCTAGAATTTGAGTTTTTTTATGGTGGTTTGATGAAAAAGGTCT
TGAATTTGATTTTTTTTTTCCGGTTGATTTGATGAAAAAGCCCTAGAATTTGTGATTTTTCGTCGG
TTTGATTCTAAAGCCCTAAAATTTGAGGTTTTCCGGTTGTTTTGATGAAAAGCCCTAAAATTTGA
GTTTTTTCCCCGTGTTTTAGATTGTTTGGTTTAATTCTCGAATCAGTTAATCAGGGAGTGTGAAA
AGCCCTATAATTTGAGTTTTTTTCCGTTGTTCTGATTGTTGTTTTATGACTTTGCAGATGCAGAT
CTTTGTGAAAACTCTCACCGGAAGACCATCACCCTAGAGGTGGAAAGTTCTGATACAATCGACAA
CGTTAAGGCTAAGATTCAGGATAAGGAAGGGATTCCCCGGATCAGCAAAGGCTTATCTTCGCCGG
AAAGCAGTTGGAGGACGGACGTACTCTAGCTGATTACAACATCCAGAAGGAGTCTACCCTCCATTT
GGTTCTCCGTCTACGTGGTGGTGGATCC

FIGURE 9D

PGAS2 (Stem Loop Transgene) [SEQ ID NO: 63]

CCACATGTGGCCCTGCCGACAAGCCAGACGGGTCCACCATCGATTGTTGCCCACCCATCACGACCA
CCATCATCGACTTCAAACTCCCCGACCGAGGCCCACTCCGCACAAGGATCGCTGCCCAGGACGTTG
CAAAAAACCCTGCATACTTGGCTAAATACAAAAAGGCCATCGAGCTGATGCGGGCACTTCCAGATG
ACAATGCGGAGCTGCGGACTTTCCAAGTGGAGCAGTCCCGACCAACTGTTGCCCGCCAACGTCCCA
AAAAATCGTAGACTTCAAATTCCCCTCCCCTACCAAACTCCGCGTCAGGCCGGCAGCTCACACCGT
GGATAAAGCCTACATCGAAAAATATTCAAAAGCCATCGAGCTCATGAAAGCCCTCCCGGACGACGA
TCCGAATGTGGTCCTGCAGACTTGCCACAGGGTGCAGTGCCCACCAACTGCTGCCCGCCGCCTTCC
ACAAAAATCATTGACTTTAAGCTGCCTGCCCCGCCAAACTCCGCATCAGGCCACCGGCTCACGCC
GTTGACCAAGCCTACAGGGACAAATACTACAAAGCGATGGAGCTCATGAAGGCCCTACCCGACGAC
GACCCAAATGTAAGCCGGCCGAAATCACCACCGGAGGTGAAACTGTGGAATGCTGTCCACCGGTCT
CCACAAAGATCAAAACCTTCACTCCGGACCAGTCTATCCCACTGCGGACGAGGCCTGCCGCCCATT
TGGTCACGGACGAGTACTTGGCCAAGTTCAAGAAAGCTCAAGCCCTCATGCGTGCCTTACCCGAAG
ACGACCCGGTCACACTAATTACAACAAACTTAATTAATTTCCCGCTGATTTGGATTTAACCAAGTT
AGCTAAAGCACCTTGCGGCCCCATTGCACCTAAGTTTGGATCTCGGTTTTGTAGACTAGATTGTAT
TAGAATATCATATTGAGGGCTTGTATATATTTTGAACAATATTTCAGCGGGTCGTCTTCGGGTAAG
GCACGCATGAGGGCTTGAGCTTTCTTGAACTTGGCCAAGTACTCGTCCGTGACCAAATGGGCGGCA
GGCCTCGTCCGCAGTGGGATAGACTGGTCCGGAGTGAAGGTTTTGATCTTTGTGGAGACCGGTGGA
CAGCATTCCACAGTTTCACCTCCGGTGGTGATTTCGGCCGGCTTACATTTGGGTCGTCGTCGGGTA
GGGCCTTCATGAGCTCCATCGCTTTGTAGTATTTGTCCCTGTAGGCTTGGTCAACGGCGTGAGCCG
GTGGCCTGATGCGGAGTTTGGCGGGGGCAGGCAGCTTAAAGTCAATGATTTTGTGGAAGGCGGCG
GGCAGCAGTTGGTGGGCACTGCACCCTGTGGCAAGTCTGCAGGACCACATTCGGATCGTCGTCCGG
GAGGGCTTTCATGAGCTCGATGGCTTTTGAATATTTTCGATGTAGGCTTTATCCACGGTGTGAGC
TGCCGGCCTGACGCGGAGTTTGGTAGGGGAGGGGAATTTGAAGTCTACGATTTTTGGGACGTTGG
CGGGCAACAGTTGGTCGGGACTGCTCCACTTGGAAAGTCCGCAGCTCCGCATTGTCATCTGGAAGT
GCCCGCATCAGCTCGATGGCCTTTTGTATTTAGCCAAGTATGCAGGGTTTTTTGCAACGTCCTGG
GCAGCGATCCTTGTGCGGAGTGGGCCTCGGTCGGGAGTTTGAAGTCGATGATGGTGGTCGTGATG
GGTGGGCAACAATCGATGGTGGACCCGTCTGGCTTGTCGGCAGGGCCACATGTGG $T_{UBI3}$ [SEQ ID NO: 64]

CTAGTTTTTAATGTTTAGCAAATGTCCTATCAGTTTTCTCTTTTTGTCGAACGGTAATTTAGAGTT
TTTTTTGCTATATGGATTTTCGTTTTTGATGTATGTGACAACCCTCGGGATTGTTGATTTATTTCA
AAACTAAGAGTTTTTGCTTATTGTTCTCGTCTATTTTGGATATCAATCTTAGTTTTATATCTTTTC
TAGTTCTCTACGTGTTAAATGTTCAACACACTAGCAATTTGGCTGCAGCGTATGGATTATGGAACT
ATCAAGTCTGTGGGATCGATAAATATGCTTCTCAGGAATTTGAGATTTTACAGTCTTTATGCTCAT
TGGGTTGAGTATAATATAGTAAAAAAATAGG

LB [SEQ ID NO: 65]

AAAACCACCCCAGTACATTAAAAACGTCCGCAATGTGTTATTAAGTTGTCTAAGCGTCAATTTGTT
TACACCACAATATATCCTGCCACCAGCCAGCCAACAGCTCCCCGACCGGCAGCTCGGCACAAAATC
ACCACTCGATACAGGCAGCCCATCAGTCC

FIGURE 9E

| GEN-03 Events | | | | | |
|---|---|---|---|---|---|
| | | Tissue Culture | | | |
| | | PCR Screening | | | PPO Suppression |
| Event | Variety | AP05 | PGAS2 | NptII | 2002 |
| 702 | GD | + | + | + | Moderately |
| 703 | GD | + | + | + | Moderately |
| 705 | GD | + | + | | Highly |
| 707 | GD | + | + | + | Highly |
| 739 | GD | + | - | - | Control |
| 743 | GD | + | + | + | Highly |
| 745 | GD | + | + | + | Not Suppressed |
| 746 | GD | + | + | + | Not Suppressed |
| 773 | GD | + | + | + | Moderately |
| 784 | GS | + | + | + | Highly |
| 792 | GD | + | + | + | Moderately |
| 801 | GD | + | + | + | Moderately |
| 1000 | GD | + | - | - | Control |
| 1001 | GS | + | - | - | Control |

FIGURE 10A

| GEN-03 Events | | | | | |
|---|---|---|---|---|---|
| | | Tissue Culture | | | |
| | | PCR Screening | | | PPO Suppression |
| Event | Variety | APO5 | PGAS2 | NptII | 2002 |
| 704 | GD | + | - | - | Not Suppressed |
| 709 | GD | + | - | + | Not Suppressed |
| 714 | GD | + | + | | Not Suppressed |
| 719 | GD | + | + | + | Not Suppressed |
| 728 | GD | + | + | - | Not Suppressed |
| 730 | GD | + | + | + | Moderately |
| 748 | GD | + | + | + | Not Suppressed |
| 752 | GD | + | + | + | Moderately |
| 753 | GD | + | + | + | Not Suppressed |
| 758 | GD | + | + | + | Not Suppressed |
| 763 | GD | + | + | + | Not Suppressed |
| 811 | GD | + | + | + | Not Suppressed |
| 831 | GD | + | + | - | Moderately |
| 842 | GD | + | + | - | Moderately |
| 845 | GD | + | + | | Highly |
| 846 | GD | + | + | | Highly |
| 872 | Fu | + | + | | Moderately |
| 879 | Ga | + | + | | Not Suppressed |
| 880 | Ga | + | + | | Not Suppressed |
| 885 | Ga | + | + | | Not Suppressed |

FIGURE 10B

| OSF-02 Events | | | | | |
|---|---|---|---|---|---|
| | | Tissue Culture | | | |
| | | PCR Screening | | | PPO Suppression |
| Event | Variety | APO5 | PGAS2 | Backbone | 2008 |
| TNF5002 | Fu | + | + | + | Moderately |
| TNF5003 | Fu | + | + | + | Highly |
| TNF5004 | Fu | + | + | - | Highly |
| TNF5005 | Fu | + | + | - | Moderately |
| TNF5006 | Fu | + | + | - | Not Suppressed |
| TNF5007 | Fu | + | + | - | Not Suppressed |
| TNF5008 | Fu | + | + | - | Highly |
| 7N | Fu | + | - | - | Not Suppressed |
| 12N | Fu | + | - | - | Not Suppressed |
| Fuji | Fu | + | - | - | Control |

FIGURE 10C

| OSF-02 Events | | | | |
|---|---|---|---|---|
| | | Tissue Culture | | |
| | | PCR Screening | | PPO Activity |
| Event | Variety | PGAS2 | Backbone | % |
| N1 | Fu | + | - | 7.9 |
| N2 | Fu | + | - | 2.5 |
| N3 | Fu | + | + | 70.5 |
| N6 | Fu | + | - | 11.6 |
| N8 | Fu | + | + | 11.2 |
| N9 | Fu | + | + | 8.1 |
| N10 | Fu | + | - | 22.4 |
| N12 | Fu | + | - | 18.1 |
| N13 | Fu | + | - | 10.4 |
| N14 | Fu | + | - | 10.4 |
| N15 | Fu | + | - | 5.4 |
| N16 | Fu | + | - | 22.2 |
| N17 | Fu | + | - | 25.7 |
| N18 | Fu | + | - | 18.3 |
| N19 | Fu | + | + | 32.2 |
| N21 | Fu | + | + | 7.3 |
| N22 | Fu | + | - | 11.8 |
| Control | Fu | - | | 100 |

FIGURE 10D

| Event | Variety | Gene Expression in Immature Fruit % Reduction in Gene Expression | | | | Total PPO Activity % Reduction in PPO Activity | Change in Luminosity |
|---|---|---|---|---|---|---|---|
| | | PPO2 | GPO3 | APO5 | pSR7 | Total | DeltaL |
| Control | GD | | | | | | -11.6 |
| 745 | GD | - 6 | - 20 | 1 | 68 | - 21 | Not tested |
| 705 | GD | 83 | 36 | 71 | 97 | 75 | -0.7 |
| 707 | GD | 82 | 60 | 74 | 98 | 86 | -0.4 |
| 743 | GD | 87 | 39 | 69 | 94 | 92 | -1.4 |
| | | | | | | | |
| Control | GS | | | | | | -9.0 |
| 739 | GS | 5 | 33 | 20 | 51 | - 42 | -5.9 |
| 784 | GS | 42 | 73 | 80 | 89 | Not tested | -1.2 |

| Events Sent to Field Trial | | | | | | | |
|---|---|---|---|---|---|---|---|
| | Tissue Culture | | | | | | |
| | PCR Screening | | | PPO Activity | | | PPO Activity |
| Event | APO5 | PGAS | NptII | 2002 | N | STDev | |
| 1000 | - | - | - | 2630 | 37 | 980 | Control |
| 745 | + | + | + | 2400 | | | High |
| 705 | + | + | + | 500 | | | Low |
| 707 | + | + | + | 300 | | | Low |
| 743 | + | + | + | 600 | | | Low |
| | | | | | | | |
| 1001 | - | - | - | 2150 | 13 | 680 | Control |
| 739 | + | - | - | 2500 | | | High |
| 784 | + | + | + | 300 | | | Low |

FIGURE 11

Golden Delicious – Bruised Response
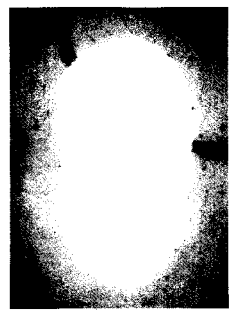 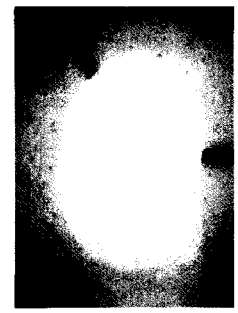
C 743
Granny Smith – Bruised Response
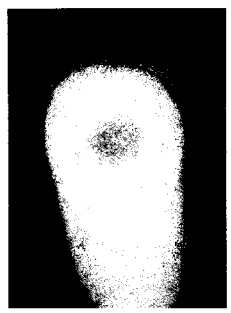 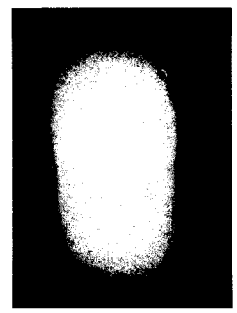
C 784
FIGURE 12

Golden Delicious – Apple Juice
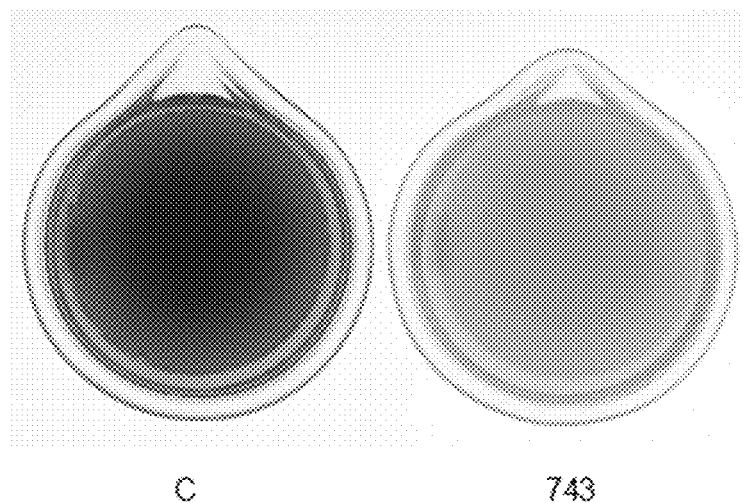
C 743
Granny Smith – Apple Juice
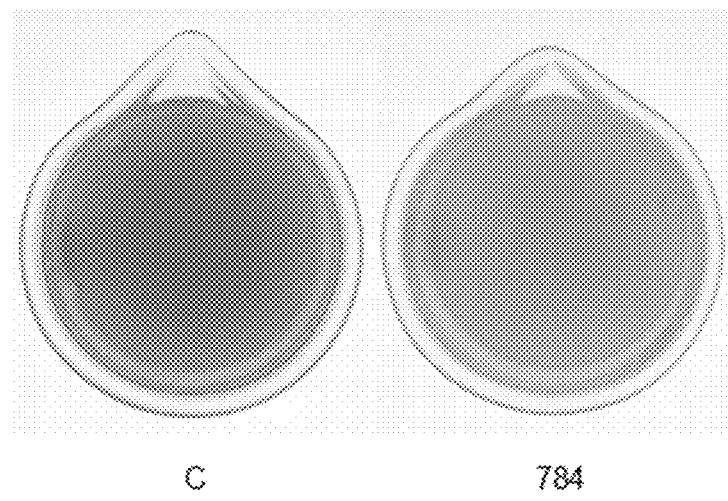
C 784
FIGURE 13

| Measurement of PPO Gene Expression in Immature Fruit ||||||||
|---|---|---|---|---|---|---|---|
| | | | | % Reduction in Gene Expression ||||
| Event ID | Plant ID | Variety | | PPO2 | GPO5 | APO5 | pSR7 |
| 1000 | 0001 0002 | GD | Control | | | | |
| 705 | 0030 0031 | GD | | 83 | 36 | 71 | 97 |
| 707 | 0022 0023 | GD | | 82 | 60 | 74 | 98 |
| 743 | 0008 0014 | GD | | 87 | 39 | 69 | 94 |
| 745 | 0001 0002 | GD | | -6 | -20 | 1 | 68 |
| | | | | | | | |
| 1001 | 0004 0017 | GS | Control | | | | |
| 739 | 0001 0003 | GS | | 5 | 33 | 20 | 51 |
| 784 | 0003 0005 | GS | | 42 | 73 | 80 | 89 |

FIGURE 14A

| Measurement of Total PPO Activity in Immature Fruit | | | |
|---|---|---|---|
| Event ID | Variety | | % Reduction in PPO Activity |
| 1000 | GD | Control | |
| 702 | GD | | 74 |
| 703 | GD | | 77 |
| 705 | GD | | 81 |
| 707 | GD | | 89 |
| 743 | GD | | 94 |
| 745 | GD | | 10 |
| 746 | GD | | 25 |
| 753 | GD | | 56 |
| 773 | GD | | 34 |
| 792 | GD | | 66 |
| 801 | GD | | 71 |
| 811 | GD | | 76 |
| | | | |
| 1001 | GS | Control | |
| 739 | GS | | -26 |

FIGURE 14B

| Controlled Bruising of Whole Fruit | | | | |
|---|---|---|---|---|
| Event ID | Variety | | Change in Luminosity (Delta L) | |
| | | | I | II |
| 1000 | GD | Control | -11.6 | -9.9 |
| 702 | GD | | -1.7 | -3.3 |
| 703 | GD | | -2.8 | -2.1 |
| 705 | GD | | -0.7 | -0.7 |
| 707 | GD | | -0.4 | -0.5 |
| 743 | GD | | -1.4 | -0.7 |
| 792 | GD | | -1.1 | -0.5 |
| 801 | GD | | -1.3 | -1.4 |
| | | | | |
| 1001 | GS | Control | -9.0 | -14.2 |
| 739 | GS | | -5.9 | not tested |
| 784 | GS | | -1.2 | -3.3 |

FIGURE 14C

PearGB (AB011828) [SEQ ID NO: 66]

TCTTCTTCCCGTTCCACCGTTACTACTTGTACTTTTTCGAGAAGATCCTAGGCAAACTCATTAACG
ACCCGACATTCGCTATGCCGTTCTGGAACTGGGACTCGCCAGCCGGCATGCCACTGCCCGCGATTT
ACGCTAATCCAAGGTCCCCTCTCTACGACAAGTTCCGATCTGCCAAACATCAGCCGCCAACTTTGG
TCGATCTCGATTACAACGGGACCGAGGACAACGTGTCAAAGGAAACCACAATCAACGCCAATCTCA
AAATCATGTACAGGCAAATGGTGTCCAATTCCAAGAATGCTCGGTTGTTCTTTGGGAACCCGTACA
GGGCAGGGGACGAGCCTGACCCTGGTGGCGGCTCCATCGAGGGCACCCCACACGGGCCGGTTCATT
TATGGACCGGTGACAACACCCAGCCCAACTTTGAGGACATGGGGAATTTTTACTCCGCTGG

Pear1 (Okanagan Specialty Fruits) [SEQ ID NO: 67]

TTCTTCTTCCCGTTCCACCGTTACTATTTATACTTCTACGAAAGAATCTTAGCCAAACTCATCGAC
GATCTGATGTTCGCGTTACCGTTTTGGAACTGGGACGCGCCAGCTGGCATGCAACTCCCTGCCTTG
TACGCCAACCCCGACTCTCCCCTATACGACGAGCTCCGCGCTTCAAGCCATCAGCCGCCGACTCTC
ATCGATCTGGACTTCAACGGTACGGATGAAACAATGTCCAACGACGTTTAAATCGACGCCAACCTC
AAAATCATGTATAGGCAGATGGTTTCCAACTCCAAGAAACCGCTGTTGTTCTTTGGTTCGCCTTTG
AGAGCTGGCACTGAACCAGATCCAGGGTCCGGTTCAATCGAAGGTACCCCACATGGTCCAGTTCAT
AGGTGGACCGGAGATAACACGCAACCTAATTTTGAGGACATGGGGAATTTTTACTCCGCTGG

Pear2 (Okanagan Specialty Fruits) [SEQ ID NO: 68]

CTTCTTCCCATTCCACCGTTACTATCTATACTTCTACGAAAGAATCTTGGGCAAACTCATAGGCGA
TCCGACGTTCGCGTTGCCGTTTTGGAACTACGACGCGCCAGCTGGCATGCAAATCCCTGCCTTGTA
CACTAACCCGGACTCTCCGCTTTACGACAAGTTCCGCGCTGCCAGCCATCAGCCGCCGACTCTCAT
CGATCTTGACTTCAACGGCACGGATGAAACAATTTCCAACGATGCTCGAATCGACGCCAACCTCAA
ACTCATGTATAGGCAGATGATTTCCAACGCCAAGAAACAGCTGTTGTTCTTTGGTGCGCCCTTGAG
GGCTGGCACTGAACCAGATCCAGGGCAGGGTTCAATCGAAACGGCCCCACATGGTCCGGTTCATTT
ATGGACCGGAGATAACACGCAACCTAATATTGAAGACATGGGGAATTTTTACTCCGCTGG

FIGURE 15

CLUSTAL W (1.82) Multiple Sequence Alignments

|          | PPO2 | GPO3 | pSR7 | PearGB | Pear1 | Pear2 |
|----------|------|------|------|--------|-------|-------|
| APO5     | 66   | 77   | 66   | 96     | 75    | 74    |
| PPO2     |      | 63   | 70   | 65     | 61    | 63    |
| GPO3     |      |      | 59   | 77     | 91    | 93    |
| pSR7     |      |      |      | 67     | 58    | 58    |
| AB011828 |      |      |      |        | 75    | 74    |
| Contig1  |      |      |      |        |       | 89    |

FIGURE 16

| Event Information | | | PPO Activity (TC) | | | PPO Activity (2005) | | | | Bruising (2005) | | | Bruising (2006) | | | Gene Expression (2005) % Reduction in Expression | | | |
|---|---|---|---|---|---|---|---|---|---|---|---|---|---|---|---|---|---|---|---|
| EventID | Generation | Variety | Tissue | average | n | % Reduction | Tissue | average | n | % Reduction | DeltaL | Phenotype | n | DeltaL | Phenotype | n | PPO2 | GPO3 | APO5 | pSR7 |
| 702 | GEN-03 | GD | L | 778 | 3 | 70% | IF | 19293 | 3 | 74% | -1.7 | NB | 13 | -3.3 | LB | 40 | | | | |
| 703 | GEN-03 | GD | L | 569 | 3 | 78% | IF | 17157 | 3 | 77% | -2.8 | LB | 15 | -2.1 | LB | 50 | | | | |
| 705 | GEN-03 | GD | L | 520 | 4 | 80% | IF | 14139 | 3 | 81% | -0.7 | NB | 10 | -0.7 | NB | 50 | 86% | 36% | 71% | 97% |
| 707 | GEN-03 | GD | L | 300 | 5 | 89% | IF | 8035 | 1 | 89% | -0.4 | NB | 2 | -0.5 | NB | 50 | 82% | 60% | 74% | 98% |
| 743 | GEN-03 | GD | L | 593 | 2 | 77% | IF | 4519 | 4 | 94% | -1.4 | NB | 14 | -0.7 | NB | 50 | 87% | 39% | 69% | 94% |
| 745 | GEN-03 | GD | L | 2400 | 3 | 9% | IF | 67801 | 2 | 10% | | B | | | | | -6% | -20% | 1% | 68% |
| 746 | GEN-03 | GD | L | 2276 | 3 | 13% | IF | 56293 | 1 | 25% | | | | | | | | | | |
| 753 | GEN-03 | GD | L | 2568 | 3 | 2% | IF | 33172 | 1 | 56% | | | | | | | | | | |
| 773 | GEN-03 | GD | L | 1320 | 2 | 50% | IF | 49353 | 2 | 34% | -1.1 | NB | 15 | -0.5 | NB | 50 | | | | |
| 792 | GEN-03 | GD | L | 1144 | 2 | 57% | IF | 25521 | 5 | 66% | -1.3 | NB | 15 | -1.4 | NB | 50 | | | | |
| 801 | GEN-03 | GD | L | 906 | 2 | 66% | IF | 21837 | 4 | 71% | | | | | | | | | | |
| 811 | GEN-03 | GD | L | 2526 | 3 | 4% | IF | 17983 | 2 | 76% | -11.6 | B | 15 | -9.9 | B | 50 | | | | |
| 1000 | Control | GD | L | 2630 | 4 | | IF | 75160 | 4 | | -5.9 | B | 10 | | | | | | | |
| 739 | GEN-03 | GS | L | 2500 | 3 | -16% | IF | 79452 | 3 | -26% | -1.2 | NB | 14 | -3.3 | NB | 50 | 5% | 33% | 20% | 51% |
| 784 | GEN-03 | GS | L | 300 | 3 | 86% | IF | | | | -9.0 | B | 9 | -14.2 | B | 50 | 42% | 73% | 80% | 89% |
| 1001 | Control | GS | L | 2150 | 7 | | IF | 63222 | 7 | | | | | | | | | | | |

FIGURE 17

SEQUENCE LISTING

<160> NUMBER OF SEQ ID NOS: 108

<210> SEQ ID NO 1
<211> LENGTH: 1850
<212> TYPE: DNA
<213> ORGANISM: Malus sp.

<400> SEQUENCE: 1

| | | | | | |
|---|---|---|---|---|---|
| atggcttcta | tgtcagctcc | actcgtcacc | tccgccacaa | gtatcatccc | cacaacttcc | 60 |
| ctctcccctt | tctcccaaaa | gtatcaccga | atatccttat | ttggaaaccc | taggcattcc | 120 |
| aatttacaag | ctgtctcatg | caaagccaca | aataatagta | gtgaccaaaa | caaaaaccct | 180 |
| tccactagct | ccaacgatca | cgaccatgaa | aacccttctc | cagtaaacct | agacagaaga | 240 |
| aatgtactta | taggtctcgg | aagcctatac | ggtggagtgg | ctggtcttgg | cagcgacccc | 300 |
| ttcgctgttg | caaagccagt | gtcgccgcct | gacctagcca | aatgcggagc | tgcggacttt | 360 |
| ccaagtggag | cagtcccgac | caactgttgc | ccgccaacgt | cccaaaaaat | cgtagacttc | 420 |
| aaattcccct | ccctaccaa | actccgcgtc | aggccggcag | ctcacaccgt | ggataaagcc | 480 |
| tacatcgaaa | atattcaaa | agccatcgag | ctcatgaaag | ccctcccgga | cgacgatccg | 540 |
| cgtagcttca | cccagcaagc | cgatatccac | tgtgcctatt | gcgacggcgc | gtacgaccaa | 600 |
| gtcggcttcc | ccaacctcga | gctccaaatc | catcaatgct | ggcttttctt | ccccttccat | 660 |
| cgttactacc | tatacttcca | cgaaagaatc | ttggccaaac | tcatatacga | tccgacgttc | 720 |
| gcgttgccgt | tttggaactg | gacgcgcca | gctggcatgc | aactccctgc | cttgttcgct | 780 |
| aacccggact | ctccgcttta | cgacgagctt | cgcgctgcca | gccatcagcc | gccgactctc | 840 |
| atcgatcttg | acttcaacgg | cacgatgaa | acaatgtcca | acgatgctca | aatcgaagcc | 900 |
| aaccgcaaaa | ttatgtatag | gcagatggtt | tccaactcca | agaaaccgct | gttgttcttt | 960 |
| ggttctccct | acagggctgg | cactgaacca | gatccagggg | gcggttcaat | cgaaacgacc | 1020 |
| ccacatggtc | cggttcattt | atggaccgga | gataacacgc | aacctaattt | tgaagacatg | 1080 |
| gggaatttt | actccgctgg | aagggatcca | atattttt | cgcaccattc | gaatatagat | 1140 |
| cgaatgtgga | atatttggaa | agtataggg | actaaaaata | aagatattaa | cgataggatt | 1200 |
| ggttggatac | ggggtttttg | ttttatgacg | agaatgctga | gcttgttagg | gtcacggtga | 1260 |
| gggacactct | tgataataaa | aagctagggt | atacgtatga | agatgttgag | attccatggc | 1320 |
| tcaagtctag | accgacgcca | cgtcggacaa | agcttgcgag | aaaggcaaag | gcggctggag | 1380 |
| tggcgaaggc | ggctggagtg | gcgaaggccg | ctgagacgac | gtcatcaggg | aaggtggtgg | 1440 |
| cgggtaaaga | ttttccaata | aatttggaga | cgaagataag | tacggtggtg | tcaaggccga | 1500 |
| agccgaagaa | gaggagcaag | aaggagaaag | aggatgagga | ggagatattg | gtgattcagg | 1560 |
| ggattgagct | tgacaaagat | gtggctgtga | agtttgatgt | gtatgtgaat | gacgtggacg | 1620 |
| atgaggatgc | ggcaccgagt | ggacccgaca | agagcgagtt | tgctgggagt | tttgtgagtg | 1680 |
| tgccacataa | gcagaaggaa | aagagcaaga | gttgtttaag | gttggggtta | acggacctgt | 1740 |
| tggaggattt | gggtgctgaa | gatgatgaga | gtgtggtgg | gactttagtg | cccaggtacg | 1800 |
| gcgctcaggc | tgttaagatc | ggtagcatca | aaattgagtt | tcttgcttga | | 1850 |

<210> SEQ ID NO 2
<211> LENGTH: 450
<212> TYPE: DNA
<213> ORGANISM: Malus sp.

<400> SEQUENCE: 2

```
tcttcttccc gttccaccgt tactatctat acttctacga aagaatctta gccaaactca    60
tcgacgaccc gacgttcgcg ttgccgtttt ggaaccggga cgcgccagct ggcatgcaac   120
tccctgcctt gtacgccaac cccgactctc cgctatacga cgagctccgc gcttcgagac   180
atcagccgtc gactctcatc gatcttgact tcaacggcac ggatgaaaca atgtccaacg   240
acgttcaaat cgacgccaac ctcaaaatca tgtataggca gatggtttcc aactccaaga   300
aaccgctgtt gttctttggt tcgcctttga gagctggcac tgaaccagat ccagggtccg   360
gttaaatcga aggtacccca catagtccag ttcataggtg gaccggacgc aacctaattt   420
tgaggacatg gggaattttt actccgctgg                                    450
```

<210> SEQ ID NO 3
<211> LENGTH: 151
<212> TYPE: PRT
<213> ORGANISM: Malus sp.

<400> SEQUENCE: 3

```
Phe Phe Pro Phe His Arg Tyr Tyr Leu Tyr Phe His Glu Arg Ile Leu
1               5                   10                  15

Ala Lys Leu Ile Tyr Asp Pro Thr Phe Ala Leu Pro Phe Trp Asn Trp
            20                  25                  30

Asp Ala Pro Ala Gly Met Gln Leu Pro Ala Leu Phe Ala Asn Pro Asp
        35                  40                  45

Ser Pro Leu Tyr Asp Glu Leu Arg Ala Ala Ser His Gln Pro Pro Thr
    50                  55                  60

Leu Ile Asp Leu Asp Phe Asn Gly Thr Asp Glu Thr Met Ser Asn Asp
65                  70                  75                  80

Ala Gln Ile Glu Ala Asn Arg Lys Ile Met Tyr Arg Gln Met Val Ser
                85                  90                  95

Asn Ser Lys Lys Pro Leu Leu Phe Phe Gly Ser Pro Tyr Arg Ala Gly
            100                 105                 110

Thr Glu Pro Asp Pro Gly Gly Gly Ser Ile Glu Thr Thr Pro His Gly
        115                 120                 125

Pro Val His Leu Trp Thr Gly Asp Asn Thr Gln Pro Asn Phe Glu Asp
    130                 135                 140

Met Gly Asn Phe Tyr Ser Ala
145                 150
```

<210> SEQ ID NO 4
<211> LENGTH: 148
<212> TYPE: PRT
<213> ORGANISM: Malus sp.

<400> SEQUENCE: 4

```
Phe Phe Pro Phe His Arg Tyr Tyr Leu Tyr Phe Tyr Glu Arg Ile Leu
1               5                   10                  15

Ala Lys Leu Ile Asp Asp Pro Thr Phe Ala Leu Pro Phe Trp Asn Arg
            20                  25                  30

Asp Ala Pro Ala Gly Met Gln Leu Pro Ala Leu Tyr Ala Asn Pro Asp
        35                  40                  45

Ser Pro Leu Tyr Asp Glu Leu Arg Ala Ser Arg His Gln Pro Ser Thr
    50                  55                  60

Leu Ile Asp Leu Asp Phe Asn Gly Thr Asp Glu Thr Met Ser Asn Asp
65                  70                  75                  80

Val Gln Ile Asp Ala Asn Leu Lys Ile Met Tyr Arg Gln Met Val Ser
```

```
                    85                  90                  95
Asn Ser Lys Lys Pro Leu Leu Phe Phe Gly Ser Pro Leu Arg Ala Gly
            100                 105                 110

Thr Glu Pro Asp Pro Gly Ser Gly Ile Glu Gly Thr Pro His Ser Pro
            115                 120                 125

Val His Arg Trp Thr Gly Arg Asn Leu Ile Leu Arg Thr Trp Gly Ile
            130                 135                 140

Phe Thr Pro Leu
145

<210> SEQ ID NO 5
<211> LENGTH: 1782
<212> TYPE: DNA
<213> ORGANISM: Malus sp.

<400> SEQUENCE: 5
atgacgtctc tttcacctcc ggtagtcacc accccaccg ttcccaaccc cgccacaaaa      60
cctctctccc ccttctctca aaacaactcc caagtttccc tactcacaaa gcccaagcgt    120
tcctttgcac gtaaggtctc atgcaaagcc acaaacaatg accaaaatga tcaagcacag    180
tccaaactag acaggagaaa tgtgcttctt ggtcttggag tctatacgg cgtggcgggt    240 atgggcacag acccgttcgc ttttgccaag cctatagccc caccagacgt atctaaatgt    300
ggtcctgcag acttgccaca gggtgcagtg cccaccaact gctgccccgcc gccttccaca   360 aaaatcattg actttaagct gcctgccccc gccaaactcc gcatcaggcc accggctcac    420
gccgttgacc aagcctacag ggacaaatac tacaaagcga tggagctcat gaaggcccta    480
cccgacgacg acccacgtag cttcaagcaa caggcagccg tgcattgcgc ttattgcgac    540
ggcgcctatg accaagtcgg gttcccgaaa ctcgagctcc aaatccacaa ctcatggctc    600
ttcttcccgt tccaccgtta ctacttgtac ttttttcgaga agatcctagg caaactcatt    660
aacgacccga cattcgcttt gccgttctgg aactgggact cgccagccgg catgccactg   720
cccgcaattt acgctgatcc aaagtcccct ctctacgaca agctccgatc tgccaatcat    780
cagcccccga ctctggtcga tctcgattac aacgggaccg aggacaatgt gtcaaaggaa   840
accacaatca acgccaatct caaaatcatg tacaggcaaa tggtgtccaa ttccaagaat    900
gctaagttgt tctttgggaa cccgtacagg gcagggacg agcctgaccc tggtggcggc    960
tccatcgagg ggacaccaca cgcgccggtt catttatgga ccggtgacaa cacccagccc   1020
aactttgagg acatggggaa ttttactcc gctggtcggg accccatatt ttttgcacac   1080
cattcgaatg tcgatcgaat gtggagtatt tggaaaactc ttggaggtaa gagaactgat   1140
cttactgact cggactggtt ggactccgga ttcttgtttt acaacgagaa cgcagagtta   1200
gtccgagtca aggtcaggga ctgcttggag accaaaaatc ttgggtatgt ataccaagat   1260
gtggacattc cttggctcag ctccaagcca acaccgcgaa gggcgaaagt tgcattgagc   1320
aaagtagcga agaagctggg agttgcacac gcagctgttg cgtcgtccag caaggtggtg   1380
gcaggcactg agttcccgat aagtctgggg tcgaagataa gcacggtggt gaagagaccg   1440
aagcagaaga gaggagcaa gaaggccaag gaggatgagg aggagatatt ggtgattgag   1500
ggaatcgagt ttgacaggga cgtggctgtg aagtttgatg tgtatgtgaa tgacgtcgat   1560
gacttgccga gtgggcctga caagacggag tttgccggaa gctttgtaag tgtgccgcac   1620
agccacaagc acaagaagaa gatgaacact attttgaggt tagggttgac agatttgttg   1680
gaggaaattg aggcggagga cgatgacagc gtggtggtga cttggtgcc caagttcggc   1740
```

```
gctgtcaaga ttggtggtat caagattgaa tttgcttctt ag            1782
```

<210> SEQ ID NO 6
<211> LENGTH: 1782
<212> TYPE: DNA
<213> ORGANISM: Malus sp.

<400> SEQUENCE: 6

```
atgacgtctc tttcacctcc ggtagtcacc accccaccg ctcccaaccc cgacacaaaa     60
cctctctccc ccttctctca aaacaactcc caagtttccc tactcacaaa gcccaagcgt    120
tccttgggac gtgaggtctc atgcaacgcc acaaacaatg accaatttga tcaagcacag    180
tccaaactag acaggagaaa tgtgcttctt ggtcttggag gtctatacgg cgtggcgggt    240
atggtcacag acccgcgcgg ttttggcaag tctatcgccc caccagacgt atctaaatgt    300
ggtcccggag acttgccaca gggtgcagtg cccaccaact gctgcccgcc gccttccaca    360
aaaatcattg actttaagct gcctgccccc gccaatctcc gtatcaggcc accggctcac    420
gccgttgacc aagcctacag ggacaaatac tacaaggcga tggagctcat gaaggcccta    480
cccgacgacg actcacgtag cttcaagcaa cagggagccg tgcattgtgc ttattgcgac    540
ggcgcctatg accaagtcgg gttcccagaa ctcgagctcc aactccacaa ctcatggctc    600
ttcttcccat tccaccgtta ctacttgtac ttttgcgaga gatcctagg caatctcatt     660
aacgacccga cattcgcttt gccgttctgg aactgggact cgccagccgg catgccactg    720
cccgcgattt acgctgatcc aaagtcccct ctctacgaca agctccgatc tgccaaacat    780
cagcccccga ctctagtcga tctcgattac aacgggaccg aggacaatgt gtcaaaggaa    840
accacaatca cgccaatctc aaaatcatg tacaggcaaa tggtgtccaa ttccaagaat    900
gctaagttgt tctttgggaa cccgtacagg gcaggggacg agcctgaccc tggtggcggc    960
tccatcgagg ggacaccaca cgcgccggtt catttatgga ccggtgacaa cacccagccc   1020
aactttgagg acatggggaa tttttactcc gctggtcggg accccatatt ttttgcacac   1080
cattcgaatg tcgatcgaat gtggagtatt tggaaaactc ttggaggtaa gagagctgat   1140
cttactgact cggactggtt ggactccgga ttcttgtttt acaacgagaa cgcagagtta   1200
gtccgagtca aggtcaggga ctgcttggag accaaacatc ttgggtatgt ataccaagat   1260
gtggacattc cttggctcag ctcgaagcca acaccgcgaa gggcggaagt tgcattgagc   1320
ccaatagcga agaagctggg agttgcacac ccagctgttg cgtcgtccag caaggtggtg   1380
gcaggcactg agttcccgat aaatctgggg tcgaagataa gcacggtggt gaagagaccg   1440
aaacagaaga agagaagcaa gaaggccaag gaggatgagg aggagatatt ggtgattgag   1500
ggaatcgagt ttgacaggga cgtggctgtg aagtttgatg tgtatgtgaa tgacgtcgat   1560
gacttgccga gtgggcctga caagacggaa tttgccggaa gctttgtaag tgtgccgcac   1620
agccacaagc acaagaagaa gatgaacact actttgaggt tagggttgac agatttgttg   1680
gaggaaattg aggcggagga cgatgacagc gtggtggtga ctttggtgcc caagttcggc   1740
gctgtcaaga ttggtggtat caagattgaa tttgcttctt ag                      1782
```

<210> SEQ ID NO 7
<211> LENGTH: 1782
<212> TYPE: DNA
<213> ORGANISM: Malus sp.

<400> SEQUENCE: 7

```
atgacgtctc tttcacctcc ggtagtcacc accccaccg ttcccaaccc cgacacaaaa    60
cctctctccc ccttctctca aaacaactcc caagtttccc tactcacaaa gcccaagcgt   120
tcctttggac gtaaggtctc atgcaaagac acaaacaatg acgaaattga tcaagcacag   180
tccaaactag agaggagaaa tgtgcttctt ggtcttgggg gtctatacgg cgtgggggt    240
atggacacag acccgcgcgg ttggggcaag gctatagccc caccagacgt ttctaaatgt   300
ggccctgcag acttaccaca gggtggagtg cccaccatct gctgcccgcc gcgttccaca   360
aaaatcattg actttaagct gcctgccccc gccaaactcc gtatcaggcc accggctcac   420
gccggggacc aagcctacag ggacaaaacac tacaaggcga tggagctcat gaaggccta   480
cccgacgacg acccacgtag tttcaagcaa cagggagccg tgcattgcgc ttattgcgac   540
ggcgcctatg accaagtcgg gttcccagaa ctcgagctcc aaatccacaa ctcatggctc   600
ttcttcccgc tccaccgtta ctacttgtac tttttcgaga agatcctagg caaactcatt   660
aacgacccga cattcgctgg gccgttctgg aactgggact cgccagccgg catgccactg   720
cccgcgattt acgctgatcc aaagtccct ctctacgaca agctccgatc tgcccaacat   780
cagcccccga ctctggtcga tctcgattac aacgggaccg aggacaatgt gtcaaaggaa   840
accacaatca acgccaatct caaaatcatg tacaggcaaa tggtgtccaa ttccaagaat   900
gctaagttgt tctttgggaa cccgtacagg gcagggacg agcctgaccc tggtggcggc   960
tccatcgagg ggacaccaca cgcgccggtt catttatgga ccggtgacaa cacccagccc  1020
aactttgagg acatggggaa ttttttactcc gctggtcggg accccatatt ttttgcacac  1080
cattcgaatg tcgatcgaat gtggagtatt tggaaaactc ttggaggtaa gagagctgat  1140
cttactgact cggactggtt ggactccgga ttcttgtttt acaacgagaa cgcagagtta  1200
gtccgagtca aggtcaggga ctgcttggag accaaaaatc ttgggtatgt ataccaagat  1260
gtggacattc cttggctcag ctcgaagcca acaccgcgaa gggcgaaagt tgcattgagc  1320
aaaatagcga agaagctggg agttgcacac gcagctgttg cgtcgtccag caaggtggtg  1380
gcaggcactg agttcccgat aaatctgggg tcgaagataa gcacggtggt gaagagaccg  1440
aagcagaaga agagaagcaa gaaggccaag gaggatgagg aggagatatt ggtgattgag  1500
ggaatcgagt ttgacaggga cgtggctgtg aagtttgatg tgtatgtgaa tgacgtcgat  1560
gacttgccga gtgggcctga caagacgaa ttttgccggaa gctttgtaag tgtgccgcac   1620
agccacaagc acaagaagaa gatgaacact attttgaggt tagggttgac agatttgttg   1680
gaggaaattg aggcggagga cgatgacagc gtggtggtga ctttggtgcc caagttcggc   1740
gctgtcaaga ttggtggtat caagattgaa tttgcttctt ag                      1782

<210> SEQ ID NO 8
<211> LENGTH: 1760
<212> TYPE: DNA
<213> ORGANISM: Malus sp.

<400> SEQUENCE: 8
atgacttcat ctcccttacc accaacttct acaatggccg ccctgcactc caccaccaca    60
accaccctct tccgctctcc tttattccca aacaagtccc agactccact gcaacgaaaa   120
cccaaacaat gccttgcggg cagagtgcgc tgcaaagcaa caaaggtga caatgataac   180
ctagaccagg gcttagcaag actcgacagg aggaacatgc tgataggttt aggcactggg   240
ggtctctaca gtgcggcagg aaactcattt gcttttgcag caccggtatc cgccccagac   300
ctgaccacat gtggccctgc cgacaagcca gacgggtcca ccatcgattg ttgcccaccc   360
```

```
atcacgacca ccatcatcga cttcaaactc cccgaccgag gcccactccg cacaaggatc    420
gctgcccagg acgttgcaaa aaaccctgca tacttggcta aatacaaaaa ggccatcgag    480
ctgatgcggg cacttccaga tgacgacccg cgcagtctcg tccaacaggc caaagtccat    540
tgctcctact gcgacggtgg atacccacaa gtcggatatt cagatttgga gatccaagtt    600
cacttctgtt ggctattctt cccgttccat cgttggtacc tctacttcta cgagaaaatc    660
atgggcgagc tcattgggga cccaaccttc gccctcccct tctggaacag gacgcgcca     720 gctggcatgt acattcctga gattttcacc gatacgtcgt catccctcta cgaccagaac    780
agaaatacag cgcatcagcc cccgaagctc ctggacttga attatggcgg gaccgacgat    840
gacgtcgacg acgcgacacg aatcaaagag aacctaacaa cgatgtacca gcagatggtg    900
tcgaaggcca cttctcacag actattctac ggagagccct atagcgcagg gacgaacca     960 gatcctggcg ccggaaacat tgagaccact ccccataaca atattcacct ttgggttggc    1020
gacccaaccc agacaaacgg ggaggacatg gggacctttt actctgcggg gagggatccg    1080
ctgttttact ctcaccattc caacgtggac cgcatgtggt ctatatataa agataagttg    1140
ggaggtacgg acatagaaaa taccgactgg ctggacgcag agttcttatt ctacgacgag    1200
aaaaagaatc tcgtgcgcgt caaggttcgg gactcgctcg cactaaaaa actcgggtac     1260 gtgtacgacg agaaagtccc aatcccatgg ctgaagtcga agccgacgct cgtaagtcga    1320
cgaataagag aaaggccaca gttcatcttc gatcttacta caacgttccc tgctacattg    1380
tcggatacaa tcagcgtcga ggtgacaagg ccgtctgcga cgaagcggac agctgcccag    1440
aagaaggcac atgacgaggt gctggtgatt aaggggattg agtttgccgg gaatgagcct    1500
gtgaagttcg acgtgtatgt gaacgatgac gcggaatcgc tggctgggaa agacaagtcg    1560
gagtttgctg ggagttttgt tcacgtgccg cataagcata agaaaaatat taagacgaac    1620
ctgcgactga gcattatgag cttgttggag gagttggatg cggagacaga cagcagtttg    1680
gtggtgactt tggtgccgaa agttgggaag gggccaatca ccatcggagg gtttagcatt    1740
gagctcatta tactacctaa                                                1760

<210> SEQ ID NO 9
<211> LENGTH: 399
<212> TYPE: DNA
<213> ORGANISM: Malus sp.

<400> SEQUENCE: 9
cattggggac ccaaccttcg ccctcccctt ctggaactgg gacgcaccag ctggaatgta     60
cattcctgag attttcactg atacgtcgtc atccctctac gaccagtata gaaatgcagc    120
gcatcagccc ccgaagctct tagactttaa taacagcggg accgacgata acgtcgacga    180
cgcaacacga atcaaagaga acttaacaac aatgtaccag cagatggtgt caaaggccac    240
ttctcacaga ctcttttttg gagagcccta cagcgcaggg acgacccaa gtcctggtgc     300 cggaaacatt gagagcattc cccataacaa tattcacttt tggactggcg acccaaccca    360
gacaaatggg gaagacatgg ggaatttttta ctccgctgg                           399

<210> SEQ ID NO 10
<211> LENGTH: 588
<212> TYPE: DNA
<213> ORGANISM: Malus sp.

<400> SEQUENCE: 10
```

| | | |
|---|---|---|
| cattgcgcgt attgcgacgg cgcgtacgac caagtcggct tccccaacct cgagctccaa | 60 | |
| atccatcaat gctggctttt cttcccctcc catcgttact acctatactt ccacgaaaga | 120 | |
| atcttggcca aactcataga cgatccgacg ttcgcgttgc cgttttggaa ctgggacgcg | 180 | |
| ccagctggca tgcaactccc tgccttgttc gctaacccgg actctccgct ttacgacgag | 240 | |
| cttcgcgctg ccagccatca gccgccgact ctcatcgatc ttgacttcaa cggcacggat | 300 | |
| gaaacaatgt ccaacgatgc tcaaatcgaa gccaacctca aaattatgta taggcagatg | 360 | |
| gtttccaact ccaagaaacc gctgttgttc tttggttcgc cctacagggc tggcactgaa | 420 | |
| ccagatccag ggggcggttc aatcgaaacg accccacatg gtccggttca tttatggacc | 480 | |
| ggagataaca cgcaacctaa ttttgaagac atggggaatt tttactccgc tggaagggat | 540 | |
| ccaatatttt tttcgcacca ttcgaatata gatcgaatgt ggaatatt | 588 | |

<210> SEQ ID NO 11
<211> LENGTH: 450
<212> TYPE: DNA
<213> ORGANISM: Malus sp.

<400> SEQUENCE: 11

| | | |
|---|---|---|
| tcttcttccc gttccaccgt tactatctat acttctacga aagaatctta gccaaactca | 60 | |
| tcgacgaccc gacgttcgcg ttgccgtttt ggaaccggga cgcgccagct ggcatgcaac | 120 | |
| tccctgcctt gtacgccaac cccgactctc cgctatacga cgagctccgc gcttcgagac | 180 | |
| atcagccgtc gactctcatc gatcttgact tcaacggcac ggatgaaaca atgtccaacg | 240 | |
| acgttcaaat cgacgccaac ctcaaaatca tgtataggca gatggtttcc aactccaaga | 300 | |
| aaccgctgtt gttctttggt tcgcctttga gagctggcac tgaaccagat ccagggtccg | 360 | |
| gttaaatcga aggtaccccca catagtccag ttcataggtg gaccggacgc aacctaattt | 420 | |
| tgaggacatg gggaattttt actccgctgg | 450 | |

<210> SEQ ID NO 12
<211> LENGTH: 1344
<212> TYPE: DNA
<213> ORGANISM: Malus sp.

<400> SEQUENCE: 12

| | | |
|---|---|---|
| gaagacgacc cgcgtagcat ggttcaacaa gctaaagttc actgtgccta ctgcaatggt | 60 | |
| gcttatccac aagtagggtt tccggacatt gacatccaaa tccacttctc ctggcttttc | 120 | |
| tttccttttcc accgcatgta cttgtatttc tacgagagaa tccttggcaa gctcattgat | 180 | |
| gacccaactt cgctctcccc atactggaat tgggactctc ctgacggttt tccaattccc | 240 | |
| gacatttaca cagatacaac ttccccactc tatgatcagt accgaaacgc cgaccaccag | 300 | |
| cccccgtgc tggtggatct cagctacggt ggaaccgatg atgacgtgga cgaccagaca | 360 | |
| agaatagatg agaatctagc catcatgtac cggcaaatgg tttccggtgc caaaactccc | 420 | |
| catctatttt tcgccatga gtacagggca ggagacacaa caacagggac ttacgccggc | 480 | |
| accattgaga acagtcctca taataacatc catctctggt gcggtgaccc gaaccagacc | 540 | |
| caccacgaag acatgggtaa cttctactcc gccggtcgga tccctgttta cgcccaccat | 600 | |
| tgcagtgacc gcatgtggaa cgtttggaaa accctcggag gcaagcgcaa ggaccccacc | 660 | |
| gacaccgatt ggcttgacgc tgagtttctg ttctacgatg aaaacgccga gcttgtgagc | 720 | |
| tgtaaagttc gggacagcct caaacctgag aaagatcttc gttatactta cgagcctgtt | 780 | |
| agtgttccgt ggctgttcac caagccaacc gctcgtaagc caaagagcaa gacaaaagcc | 840 | |

```
aaggtggggg ctacccagct gacgacaaag ttcccggcca cgtttgattc gaagacgacg    900
gtggaggtgg cgaggccgaa gccgcggaag aggaccaaga aggagaagat cgacgaggag    960
gaggtgctga tcattaagga catcgaattc gagagcaacg aggcggtgaa gttcgatgtg   1020
tttattaatg atgatgctga gtcgctcagt aggaaggaca aatccgagtt tgctgggagt   1080
tttgtgcacg tgccgcataa ccagaagact gggacgaaga aaagacgaa cttaaaactg   1140 gggatcacgg acttgttgga ggatttgggt gtggaggatg atagcagtgt gctggtgacg   1200
ttggtgccta gggtttcgaa ctcgcctatc accattggtg ggtttaagat cgagtattct   1260
tcttgatcaa aaagtatggt taagtaatta aataatttca tagtggaatg gcctgctttc   1320
atgcatgccc ttgtgtttag ttaa                                          1344

<210> SEQ ID NO 13
<211> LENGTH: 221
<212> TYPE: DNA
<213> ORGANISM: Malus sp.

<400> SEQUENCE: 13
aggatgctca aatcgaagcc aacctcaaaa tcatgtatag gcagatcgtt tccaactcca     60
agaaaccgct gttgttcttt ggttcgccct acagggctgg cactgaacca gatccagggg    120
ccggtgcaat cgaacagacc ccacatggtc cggttcatac atggaccgga gataacacgc    180
aacctaatta tgaatacatg gggaattttt actccactgc a                        221

<210> SEQ ID NO 14
<211> LENGTH: 207
<212> TYPE: DNA
<213> ORGANISM: Malus sp.

<400> SEQUENCE: 14
cccccaaacc catcattcct ggctttcttc cccttccat cgtaactacc tatacttcca     60
cgaaagattc tgggccaaac tcatagacga tccgacgtcc gctttgccgt tttggaactg    120
ggacgcgcca gcgggaatgc aactccctgc tttgtccgca aacccggact ttccggttaa    180
cgacgagctc cgtcgtgaca gccatca                                        207

<210> SEQ ID NO 15
<211> LENGTH: 221
<212> TYPE: DNA
<213> ORGANISM: Malus sp.

<400> SEQUENCE: 15
tgtggctgtg aagtttgatg tgtatgtgaa tgacgtggat gatgaggatg cggcaccgag     60
tggaccccac aagagcgagt ttgctgggag ttttgtgagt gtgccacctg ttggaggatt    120
tgggtgctga agatgatgag agtgtggtgg tgactttagt gcccaggtac ggcgctcagg    180
ctgttaagat cggtagcatc aaaattgagt ttcttgcttg a                        221

<210> SEQ ID NO 16
<211> LENGTH: 117
<212> TYPE: DNA
<213> ORGANISM: Malus sp.

<400> SEQUENCE: 16
gacctgttgg aggatttggg tgctgaagat gatgagagtg tggtggtgac tttagtgccc     60
aggtacggcg ctcaggctgt taagatcggt agcatcaaaa ttgagttcct tgcttga       117
```

<210> SEQ ID NO 17
<211> LENGTH: 176
<212> TYPE: DNA
<213> ORGANISM: Malus sp.

<400> SEQUENCE: 17

| | | | | | |
|---|---|---|---|---|---|
| gaggatatgg | ggaatttta | ctctgcgggg | agggatccgc | tgttttactc | tcaccattcc | 60 |
| aacgtggacc | gcatgtggtc | tatatataaa | gataagttgg | gaggtacgga | catagaaaaa | 120 |
| taccgactgc | tggacgcaga | gttcttattc | tacgacgaga | caagaatct | tcgtgc | 176 |

<210> SEQ ID NO 18
<211> LENGTH: 1761
<212> TYPE: DNA
<213> ORGANISM: Malus sp.

<400> SEQUENCE: 18

| | | | | | |
|---|---|---|---|---|---|
| atgacttcat | ctcccttacc | accaacttct | acaatggccg | ccctgcactc | caccaccaca | 60 |
| accaccctct | tccgctctcc | tttattccca | aacaagtccc | agactccact | gcaacgaaaa | 120 |
| cccaaacaat | gccttgcggg | cagagtgcgc | tgcaaagcaa | caaaaggtga | caatgataac | 180 |
| ctagaccagg | gcttagcaag | actcgacagg | aggaacatgc | tgataggttt | aggcactggg | 240 |
| ggtctctaca | gtgcggcagg | aaactcattt | gcttttgcag | caccggtatc | cgccccagac | 300 |
| ctgaccacat | gtggccctgc | cgacaagcca | gacgggtcca | ccatcgattg | ttgcccaccc | 360 |
| atcacgacca | ccatcatcga | cttcaaactc | cccgaccgag | gcccactccg | cacaaggatc | 420 |
| gctgcccagg | acgttgcaaa | aaaccctgca | tacttggcta | aatacaaaaa | ggccatcgag | 480 |
| ctgatgcggg | cacttccaga | tgacgacccg | cgcagtctcg | tccaacaggc | caaagtccat | 540 |
| tgctcctact | gcgacggtgg | ataccacaa | gtcggatatt | cagatttgga | gatccaagtt | 600 |
| cacttctgtt | ggctattctt | cccgttccat | cgttggtacc | tctacttcta | cgagaaaatc | 660 |
| atgggcgagc | tcattgggga | cccaaccttc | gccctcccct | tctggaacag | ggacgcgcca | 720 |
| gctggcatgt | acattcctga | gattttcacc | gatacgtcgt | catccctcta | cgaccagaac | 780 |
| agaaatacag | cgcatcagcc | cccgaagctc | ctggacttga | attatggcgg | gaccgacgat | 840 |
| gacgtcgacg | acgcgacacg | aatcaaagag | aacctaacaa | cgatgtacca | gcagatggtg | 900 |
| tcgaaggcca | cttctcacag | actattctac | ggagagccct | atagcgcagg | gacgaacca | 960 |
| gatcctggcg | ccggaaacat | tgagaccact | ccccataaca | atattcacct | ttgggttggc | 1020 |
| gacccaaccc | agacaaacgg | ggaggacatg | gggaccttt | actctgcggg | gagggatccg | 1080 |
| ctgttttact | ctcaccattc | caacgtggac | cgcatgtggt | ctatatataa | agataagttg | 1140 |
| ggaggtacgg | acatagaaaa | taccgactgg | ctggacgcag | agttcttatt | ctacgacgag | 1200 |
| aaaaagaatc | tcgtgcgcgt | caaggttcgg | gactcgctcg | acactaaaaa | actcgggtac | 1260 |
| gtgtacgacg | agaaagtccc | aatcccatgg | ctgaagtcga | agccgacgct | cgtaagtcga | 1320 |
| cgaataagag | aaaggccaca | gttcatcttc | gatcttacta | caacgttccc | tgctacattg | 1380 |
| tcggatacaa | tcagcgtcga | ggtgacaagg | ccgtctgcga | cgaagcggac | agctgcccag | 1440 |
| aagaaggcac | atgacgaggt | gctggtgatt | aaggggattg | agtttgccgg | gaatgagcct | 1500 |
| gtgaagttcg | acgtgtatgt | gaacgatgac | gcggaatcgc | tggctgggaa | agacaagtcg | 1560 |
| gagtttgctg | ggagttttgt | tcacgtgccg | cataagcata | agaaaatat | taagacgaac | 1620 |
| ctgcgactga | gcattatgag | cttgttggag | gagttggatg | cggagacaga | cagcagttg | 1680 |
| gtggtgactt | tggtgccgaa | agttgggaag | gggccaatca | ccatcggagg | gtttagcatt | 1740 | gagctcatta atactaccta a	1761

<210> SEQ ID NO 19
<211> LENGTH: 586
<212> TYPE: PRT
<213> ORGANISM: Malus sp.

<400> SEQUENCE: 19

```
Met Thr Ser Ser Pro Leu Pro Thr Ser Thr Met Ala Ala Leu His
1               5                  10                  15

Ser Thr Thr Thr Thr Thr Leu Phe Arg Ser Pro Leu Phe Pro Asn Lys
            20                  25                  30

Ser Gln Thr Pro Leu Gln Arg Lys Pro Lys Gln Cys Leu Ala Gly Arg
        35                  40                  45

Val Arg Cys Lys Ala Thr Lys Gly Asp Asn Asp Asn Leu Asp Gln Gly
50                  55                  60

Leu Ala Arg Leu Asp Arg Arg Asn Met Leu Ile Gly Leu Gly Thr Gly
65                  70                  75                  80

Gly Leu Tyr Ser Ala Ala Gly Asn Ser Phe Ala Phe Ala Ala Pro Val
                85                  90                  95

Ser Ala Pro Asp Leu Thr Thr Cys Gly Pro Ala Asp Lys Pro Asp Gly
            100                 105                 110

Ser Thr Ile Asp Cys Cys Pro Pro Ile Thr Thr Thr Ile Ile Asp Phe
        115                 120                 125

Lys Leu Pro Asp Arg Gly Pro Leu Arg Thr Arg Ile Ala Ala Gln Asp
130                 135                 140

Val Ala Lys Asn Pro Ala Tyr Leu Ala Lys Tyr Lys Lys Ala Ile Glu
145                 150                 155                 160

Leu Met Arg Ala Leu Pro Asp Asp Pro Arg Ser Leu Val Gln Gln
                165                 170                 175

Ala Lys Val His Cys Ser Tyr Cys Asp Gly Gly Tyr Pro Gln Val Gly
            180                 185                 190

Tyr Ser Asp Leu Glu Ile Gln Val His Phe Cys Trp Leu Phe Phe Pro
        195                 200                 205

Phe His Arg Trp Tyr Leu Tyr Phe Tyr Glu Lys Ile Met Gly Glu Leu
210                 215                 220

Ile Gly Asp Pro Thr Phe Ala Leu Pro Phe Trp Asn Arg Asp Ala Pro
225                 230                 235                 240

Ala Gly Met Tyr Ile Pro Glu Ile Phe Thr Asp Thr Ser Ser Ser Leu
                245                 250                 255

Tyr Asp Gln Asn Arg Asn Thr Ala His Gln Pro Pro Lys Leu Leu Asp
            260                 265                 270

Leu Asn Tyr Gly Gly Thr Asp Asp Val Asp Ala Thr Arg Ile
        275                 280                 285

Lys Glu Asn Leu Thr Thr Met Tyr Gln Gln Met Val Ser Lys Ala Thr
290                 295                 300

Ser His Arg Leu Phe Tyr Gly Glu Pro Tyr Ser Ala Gly Asp Glu Pro
305                 310                 315                 320

Asp Pro Gly Ala Gly Asn Ile Glu Thr Thr Pro His Asn Asn Ile His
                325                 330                 335

Leu Trp Val Gly Asp Pro Thr Gln Thr Asn Gly Glu Asp Met Gly Thr
            340                 345                 350

Phe Tyr Ser Ala Gly Arg Asp Pro Leu Phe Tyr Ser His His Ser Asn
        355                 360                 365
```

Val Asp Arg Met Trp Ser Ile Tyr Lys Asp Lys Leu Gly Gly Thr Asp
    370                 375                 380

Ile Glu Asn Thr Asp Trp Leu Asp Ala Glu Phe Leu Phe Tyr Asp Glu
385                 390                 395                 400

Lys Lys Asn Leu Val Arg Val Lys Val Arg Asp Ser Leu Asp Thr Lys
                405                 410                 415

Lys Leu Gly Tyr Val Tyr Asp Glu Lys Val Pro Ile Pro Trp Leu Lys
                420                 425                 430

Ser Lys Pro Thr Leu Val Ser Arg Arg Ile Arg Glu Arg Pro Gln Phe
            435                 440                 445

Ile Phe Asp Leu Thr Thr Thr Phe Pro Ala Thr Leu Ser Asp Thr Ile
    450                 455                 460

Ser Val Glu Val Thr Arg Pro Ser Ala Thr Lys Arg Thr Ala Ala Gln
465                 470                 475                 480

Lys Lys Ala His Asp Glu Val Leu Val Ile Lys Gly Ile Glu Phe Ala
                485                 490                 495

Gly Asn Glu Pro Val Lys Phe Asp Val Tyr Val Asn Asp Asp Ala Glu
                500                 505                 510

Ser Leu Ala Gly Lys Asp Lys Ser Glu Phe Ala Gly Ser Phe Val His
            515                 520                 525

Val Pro His Lys His Lys Lys Asn Ile Lys Thr Asn Leu Arg Leu Ser
    530                 535                 540

Ile Met Ser Leu Leu Glu Glu Leu Asp Ala Glu Thr Asp Ser Ser Leu
545                 550                 555                 560

Val Val Thr Leu Val Pro Lys Val Gly Lys Gly Pro Ile Thr Ile Gly
                565                 570                 575

Gly Phe Ser Ile Glu Leu Ile Asn Thr Thr
            580                 585

<210> SEQ ID NO 20
<211> LENGTH: 1850
<212> TYPE: DNA
<213> ORGANISM: Malus sp.

<400> SEQUENCE: 20
atggcttcta tgtcagctcc actcgtcacc tccgccacaa gtatcatccc cacaacttcc      60
ctctcccctt tctcccaaaa gtatcaccga atatccttat ttggaaaccc taggcattcc     120
aatttacaag ctgtctcatg caaagccaca ataatagta gtgaccaaaa caaaaaccct      180
tccactagct ccaacgatca cgaccatgaa aacccttctc cagtaaacct agacagaaga     240
aatgtactta taggtctcgg aagcctatac ggtggagtgg ctggtcttgg cagcgacccc     300
ttcgctgttg caaagccagt gtcgccgcct gacctagcca atgcggagc tgcggacttt      360 ccaagtggag cagtcccgac caactgttgc ccgccaacgt cccaaaaaat cgtagacttc     420
aaattcccct ccctaccaa actccgcgtc aggccggcag ctcacaccgt ggataaagcc      480
tacatcgaaa atattcaaa agccatcgag ctcatgaaag ccctcccgga cgacgatccg      540
cgtagcttca cccagcaagc cgatatccac tgtgcctatt gcgacggcgc gtacgaccaa     600
gtcggcttcc ccaacctcga gctccaaatc atcaatgct ggcttttctt ccccttccat      660
cgttactacc tatacttcca cgaaagaatc ttggccaaac tcatatacga tccgacgttc     720
gcgttgccgt tttggaactg ggacgcgcca gctggcatgc aactccctgc cttgttcgct     780
aacccggact ctccgcttta cgacgagctt cgcgctgcca gccatcagcc gccgactctc     840

```
atcgatcttg acttcaacgg cacggatgaa acaatgtcca acgatgctca aatcgaagcc    900
aaccgcaaaa ttatgtatag gcagatggtt tccaactcca agaaaccgct gttgttcttt    960
ggttctccct acagggctgg cactgaacca gatccagggg gcggttcaat cgaaacgacc   1020
ccacatggtc cggttcattt atggaccgga gataacacgc aacctaattt tgaagacatg   1080
gggaattttt actccgctgg aagggatcca atattttttt cgcaccattc gaatatagat   1140
cgaatgtgga atatttggaa aagtataggg actaaaaata aagatattaa cgataggatt   1200
ggttggatac ggggttttg ttttatgacg agaatgctga gcttgttagg gtcacggtga   1260
gggacactct tgataataaa aagctagggt atacgtatga agatgttgag attccatggc   1320
tcaagtctag accgacgcca cgtcggacaa agcttgcgag aaaggcaaag gcggctggag   1380
tggcgaaggc ggctggagtg gcgaaggccg ctgagacgac gtcatcaggg aaggtggtgg   1440
cgggtaaaga ttttccaata aatttggaga cgaagataag tacggtggtg tcaaggccga   1500
agccgaagaa gaggagcaag aaggagaaag aggatgagga ggagatattg gtgattcagg   1560
ggattgagct tgacaaagat gtggctgtga agtttgatgt gtatgtgaat gacgtggacg   1620
atgaggatgc ggcaccgagt ggacccgaca agagcgagtt tgctgggagt tttgtgagtg   1680
tgccacataa gcagaaggaa aagagcaaga gttgtttaag gttggggtta acggacctgt   1740
tggaggattt gggtgctgaa gatgatgaga gtgtggtggt gactttagtg cccaggtacg   1800
gcgctcaggc tgttaagatc ggtagcatca aaattgagtt tcttgcttga              1850
```

<210> SEQ ID NO 21
<211> LENGTH: 616
<212> TYPE: PRT
<213> ORGANISM: Malus sp.

<400> SEQUENCE: 21

Met Ala Ser Met Ser Ala Pro Leu Val Thr Ser Ala Thr Ser Ile Ile
1               5                   10                  15

Pro Thr Thr Ser Leu Ser Pro Phe Ser Gln Lys Tyr His Arg Ile Ser
            20                  25                  30

Leu Phe Gly Asn Pro Arg His Ser Asn Leu Gln Ala Val Ser Cys Lys
        35                  40                  45

Ala Thr Asn Asn Ser Ser Asp Gln Asn Lys Asn Pro Ser Thr Ser Ser
    50                  55                  60

Asn Asp His Asp His Glu Asn Pro Ser Pro Val Asn Leu Asp Arg Arg
65                  70                  75                  80

Asn Val Leu Ile Gly Leu Gly Ser Leu Tyr Gly Gly Val Ala Gly Leu
                85                  90                  95

Gly Ser Asp Pro Phe Ala Val Ala Lys Pro Val Ser Pro Asp Leu
            100                 105                 110

Ala Lys Cys Gly Ala Ala Asp Phe Pro Ser Gly Ala Val Pro Thr Asn
        115                 120                 125

Cys Cys Pro Pro Thr Ser Gln Lys Ile Val Asp Phe Lys Phe Pro Ser
    130                 135                 140

Pro Thr Lys Leu Arg Val Arg Pro Ala Ala His Thr Val Asp Lys Ala
145                 150                 155                 160

Tyr Ile Glu Lys Tyr Ser Lys Ala Ile Glu Leu Met Lys Ala Leu Pro
                165                 170                 175

Asp Asp Asp Pro Arg Ser Phe Thr Gln Gln Ala Asp Ile His Cys Ala
            180                 185                 190

Tyr Cys Asp Gly Ala Tyr Asp Gln Val Gly Phe Pro Asn Leu Glu Leu

```
            195                 200                 205
Gln Ile His Gln Cys Trp Leu Phe Phe Pro Phe His Arg Tyr Tyr Leu
    210                 215                 220
Tyr Phe His Glu Arg Ile Leu Ala Lys Leu Ile Tyr Asp Pro Thr Phe
225                 230                 235                 240
Ala Leu Pro Phe Trp Asn Trp Asp Ala Pro Ala Gly Met Gln Leu Pro
            245                 250                 255
Ala Leu Phe Ala Asn Pro Asp Ser Pro Leu Tyr Asp Glu Leu Arg Ala
            260                 265                 270
Ala Ser His Gln Pro Pro Thr Leu Ile Asp Leu Asp Phe Asn Gly Thr
            275                 280                 285
Asp Glu Thr Met Ser Asn Asp Ala Gln Ile Glu Ala Asn Arg Lys Ile
            290                 295                 300
Met Tyr Arg Gln Met Val Ser Asn Ser Lys Lys Pro Leu Leu Phe Phe
305                 310                 315                 320
Gly Ser Pro Tyr Arg Ala Gly Thr Glu Pro Asp Pro Gly Gly Gly Ser
            325                 330                 335
Ile Glu Thr Thr Pro His Gly Pro Val His Leu Trp Thr Gly Asp Asn
            340                 345                 350
Thr Gln Pro Asn Phe Glu Asp Met Gly Asn Phe Tyr Ser Ala Gly Arg
            355                 360                 365
Asp Pro Ile Phe Phe Ser His His Ser Asn Ile Asp Arg Met Trp Asn
            370                 375                 380
Ile Trp Lys Ser Ile Gly Thr Lys Asn Lys Asp Ile Asn Asp Lys Asp
385                 390                 395                 400
Trp Leu Asp Thr Gly Phe Leu Phe Tyr Asp Glu Asn Ala Glu Leu Val
            405                 410                 415
Arg Val Thr Val Arg Asp Thr Leu Asp Asn Lys Lys Leu Gly Tyr Thr
            420                 425                 430
Tyr Glu Asp Val Glu Ile Pro Trp Leu Lys Ser Arg Pro Thr Pro Arg
            435                 440                 445
Arg Thr Lys Leu Ala Arg Lys Ala Lys Ala Ala Gly Val Ala Lys Ala
450                 455                 460
Ala Gly Val Ala Lys Ala Ala Glu Thr Thr Ser Ser Gly Lys Val Val
465                 470                 475                 480
Ala Gly Lys Asp Phe Pro Ile Asn Leu Glu Thr Lys Ile Ser Thr Val
            485                 490                 495
Val Ser Arg Pro Lys Pro Lys Lys Arg Ser Lys Lys Glu Lys Glu Asp
            500                 505                 510
Glu Glu Glu Ile Leu Val Ile Gln Gly Ile Glu Leu Asp Lys Asp Val
            515                 520                 525
Ala Val Lys Phe Asp Val Tyr Val Asn Asp Val Asp Asp Glu Asp Ala
            530                 535                 540
Ala Pro Ser Gly Pro Asp Lys Ser Glu Phe Ala Gly Ser Phe Val Ser
545                 550                 555                 560
Val Pro His Lys Gln Lys Glu Lys Ser Lys Ser Cys Leu Arg Leu Gly
            565                 570                 575
Leu Thr Asp Leu Leu Glu Asp Leu Gly Ala Glu Asp Asp Glu Ser Val
            580                 585                 590
Val Val Thr Leu Val Pro Arg Tyr Gly Ala Gln Ala Val Lys Ile Gly
            595                 600                 605
Ser Ile Lys Ile Glu Phe Leu Ala
            610                 615
```

<210> SEQ ID NO 22
<211> LENGTH: 1782
<212> TYPE: DNA
<213> ORGANISM: Malus sp.

<400> SEQUENCE: 22

| | | | | | |
|---|---|---|---|---|---|
| atgacgtctc | tttcacctcc | ggtagtcacc | accccaccg | ttcccaaccc | cgccacaaaa | 60 |
| cctctctccc | ccttctctca | aaacaactcc | caagtttccc | tactcacaaa | gcccaagcgt | 120 |
| tcctttgcac | gtaaggtctc | atgcaaagcc | acaaacaatg | accaaaatga | tcaagcacag | 180 |
| tccaaactag | acaggagaaa | tgtgcttctt | ggtcttggag | gtctatacgg | cgtggcgggt | 240 |
| atgggcacag | acccgttcgc | ttttgccaag | cctatagccc | caccagacgt | atctaaatgt | 300 |
| ggtcctgcag | acttgccaca | gggtgcagtg | cccaccaact | gctgcccgcc | gccttccaca | 360 |
| aaaatcattg | actttaagct | gcctgccccc | gccaaactcc | gcatcaggcc | accggctcac | 420 |
| gccgttgacc | aagcctacag | ggacaaatac | tacaaagcga | tggagctcat | gaaggcccta | 480 |
| cccgacgacg | acccacgtag | cttcaagcaa | caggcagccg | tgcattgcgc | ttattgcgac | 540 |
| ggcgcctatg | accaagtcgg | gttcccgaaa | ctcgagctcc | aaatccacaa | ctcatggctc | 600 |
| ttcttcccgt | tccaccgtta | ctacttgtac | tttttcgaga | gatcctagg | caaactcatt | 660 |
| aacgacccga | cattcgcttt | gccgttctgg | aactgggact | cgccagccgg | catgccactg | 720 |
| cccgcaattt | acgctgatcc | aaagtcccct | ctctacgaca | agctccgatc | tgccaatcat | 780 |
| cagccccga | ctctggtcga | tctcgattac | aacgggaccg | aggacaatgt | gtcaaaggaa | 840 |
| accacaatca | acgccaatct | caaaatcatg | tacaggcaaa | tggtgtccaa | ttccaagaat | 900 |
| gctaagttgt | tctttgggaa | cccgtacagg | gcagggacg | agcctgaccc | tggtggcggc | 960 |
| tccatcgagg | ggacaccaca | cgcgccggtt | catttatgga | ccggtgacaa | cacccagccc | 1020 |
| aactttgagg | acatgggaa | ttttactcc | gctggtcggg | accccatatt | ttttgcacac | 1080 |
| cattcgaatg | tcgatcgaat | gtggagtatt | tggaaaactc | ttggaggtaa | gagaactgat | 1140 |
| cttactgact | cggactggtt | ggactccgga | ttcttgtttt | acaacgagaa | cgcagagtta | 1200 |
| gtccgagtca | aggtcaggga | ctgcttggag | accaaaaatc | ttgggtatgt | ataccaagat | 1260 |
| gtggacattc | cttggctcag | ctccaagcca | acaccgcgaa | gggcgaaagt | tgcattgagc | 1320 |
| aaagtagcga | agaagctggg | agttgcacac | gcagctgttg | cgtcgtccag | caaggtggtg | 1380 |
| gcaggcactg | agttcccgat | aagtctgggg | tcgaagataa | gcacggtggt | gaagagaccg | 1440 |
| aagcagaaga | agaggagcaa | gaaggccaag | gaggatgagg | aggagatatt | ggtgattgag | 1500 |
| ggaatcgagt | ttgacaggga | cgtggctgtg | aagtttgatg | tgtatgtgaa | tgacgtcgat | 1560 |
| gacttgccga | gtgggcctga | caagacgag | tttgccggaa | gctttgtaag | tgtgccgcac | 1620 |
| agccacaagc | acaagaagaa | gatgaacact | attttgaggt | tagggttgac | agatttgttg | 1680 |
| gaggaaattg | aggcggagga | cgatgacagc | gtggtggtga | ctttggtgcc | caagttcggc | 1740 |
| gctgtcaaga | ttggtggtat | caagattgaa | tttgcttctt | ag | | 1782 |

<210> SEQ ID NO 23
<211> LENGTH: 593
<212> TYPE: PRT
<213> ORGANISM: Malus sp.

<400> SEQUENCE: 23

Met Thr Ser Leu Ser Pro Pro Val Val Thr Thr Pro Thr Val Pro Asn
1               5                   10                  15

Pro Ala Thr Lys Pro Leu Ser Pro Phe Ser Gln Asn Asn Ser Gln Val
            20                  25                  30

Ser Leu Leu Thr Lys Pro Lys Arg Ser Phe Ala Arg Lys Val Ser Cys
        35                  40                  45

Lys Ala Thr Asn Asn Asp Gln Asn Asp Gln Ala Gln Ser Lys Leu Asp
50                  55                  60

Arg Arg Asn Val Leu Leu Gly Leu Gly Gly Leu Tyr Gly Val Ala Gly
65                  70                  75                  80

Met Gly Thr Asp Pro Phe Ala Phe Ala Lys Pro Ile Ala Pro Pro Asp
                85                  90                  95

Val Ser Lys Cys Gly Pro Ala Asp Leu Pro Gln Gly Ala Val Pro Thr
            100                 105                 110

Asn Cys Cys Pro Pro Pro Ser Thr Lys Ile Ile Asp Phe Lys Leu Pro
        115                 120                 125

Ala Pro Ala Lys Leu Arg Ile Arg Pro Pro Ala His Ala Val Asp Gln
130                 135                 140

Ala Tyr Arg Asp Lys Tyr Tyr Lys Ala Met Glu Leu Met Lys Ala Leu
145                 150                 155                 160

Pro Asp Asp Asp Pro Arg Ser Phe Lys Gln Gln Ala Ala Val His Cys
                165                 170                 175

Ala Tyr Cys Asp Gly Ala Tyr Asp Gln Val Gly Phe Pro Glu Leu Glu
            180                 185                 190

Leu Gln Ile His Asn Ser Trp Leu Phe Phe Pro Phe His Arg Tyr Tyr
        195                 200                 205

Leu Tyr Phe Phe Glu Lys Ile Leu Gly Lys Leu Ile Asn Asp Pro Thr
210                 215                 220

Phe Ala Leu Pro Phe Trp Asn Trp Asp Ser Pro Ala Gly Met Pro Leu
225                 230                 235                 240

Pro Ala Ile Tyr Ala Asp Pro Lys Ser Pro Leu Tyr Asp Lys Leu Arg
                245                 250                 255

Ser Ala Asn His Gln Pro Pro Thr Leu Val Asp Leu Asp Tyr Asn Gly
            260                 265                 270

Thr Glu Asp Asn Val Ser Lys Glu Thr Thr Ile Asn Ala Asn Leu Lys
        275                 280                 285

Ile Met Tyr Arg Gln Met Val Ser Asn Ser Lys Asn Ala Lys Leu Phe
290                 295                 300

Phe Gly Asn Pro Tyr Arg Ala Gly Asp Glu Pro Asp Pro Gly Gly Gly
305                 310                 315                 320

Ser Ile Glu Gly Thr Pro His Ala Pro Val His Leu Trp Thr Gly Asp
                325                 330                 335

Asn Thr Gln Pro Asn Phe Glu Asp Met Gly Asn Phe Tyr Ser Ala Gly
            340                 345                 350

Arg Asp Pro Ile Phe Phe Ala His His Ser Asn Val Asp Arg Met Trp
        355                 360                 365

Ser Ile Trp Lys Thr Leu Gly Gly Lys Arg Thr Asp Leu Thr Asp Ser
370                 375                 380

Asp Trp Leu Asp Ser Gly Phe Leu Phe Tyr Asn Glu Asn Ala Glu Leu
385                 390                 395                 400

Val Arg Val Lys Val Arg Asp Cys Leu Glu Thr Lys Asn Leu Gly Tyr
                405                 410                 415

Val Tyr Gln Asp Val Asp Ile Pro Trp Leu Ser Ser Lys Pro Thr Pro
            420                 425                 430

```
Arg Arg Ala Lys Val Ala Leu Ser Lys Val Ala Lys Lys Leu Gly Val
            435                 440                 445
Ala His Ala Ala Val Ala Ser Ser Ser Lys Val Ala Gly Thr Glu
    450                 455                 460
Phe Pro Ile Ser Leu Gly Ser Lys Ile Ser Thr Val Val Lys Arg Pro
465                 470                 475                 480
Lys Gln Lys Lys Arg Ser Lys Ala Lys Glu Asp Glu Glu Ile
                485                 490                 495
Leu Val Ile Glu Gly Ile Glu Phe Asp Arg Asp Val Ala Val Lys Phe
                500                 505                 510
Asp Val Tyr Val Asn Asp Val Asp Leu Pro Ser Gly Pro Asp Lys
            515                 520                 525
Thr Glu Phe Ala Gly Ser Phe Val Ser Val Pro His Ser His Lys His
    530                 535                 540
Lys Lys Lys Met Asn Thr Ile Leu Arg Leu Gly Leu Thr Asp Leu Leu
545                 550                 555                 560
Glu Glu Ile Glu Ala Glu Asp Asp Asp Ser Val Val Val Thr Leu Val
                565                 570                 575
Pro Lys Phe Gly Ala Val Lys Ile Gly Gly Ile Lys Ile Glu Phe Ala
            580                 585                 590
Ser

<210> SEQ ID NO 24
<211> LENGTH: 1846
<212> TYPE: DNA
<213> ORGANISM: Malus sp.

<400> SEQUENCE: 24
taccaccacc accatgggca cttactcttc tctgatcatc tccaccaatt ccttctctgc      60
cttcctccca aacaaatccc aactttcctt ctctggaaaa agcaagcact acattgcacg     120
tagatcatca atatattgca aagccacaaa ccctaattat aataatgagc aagatcaaca     180
acaatcttct aatttgttgg gaaaattgga caggagaaat gtcctaattg gcctgggcgg     240
cctctacggg gccaccaccc tcgccccaaa gccgttggcc tttgccaacc cgctggctcc     300
acccgaccta accaaatgta agccggccga aatcaccacc ggaggtgaaa ctgtggaatg     360
ctgtccaccg gtctccacaa agatcaaaac cttcactccg gaccagtcta tcccactgcg     420
gacgaggcct gccgcccatt tggtcacgga cgagtacttg gccaagttca gaaaagctca     480
agccctcatg cgtgccttac ccgaagacga cccgcgtagc atggttcaac aagctaaagt     540
tcactgtgcc tactgcaatg gtgcttatcc acaagtaggg tttccggaca ttgacatcca     600
aatccacttc tcctggcttt tctttccttt ccaccgcatg tacttgtatt tctacgagag     660
aatccttggc aagctcattg atgacccaac tttcgctctc ccatactgga attgggactc     720
tcctgacggt tttccaattc ccgacattta cacagataca acttccccac tctatgatca     780
gtaccgaaac gccgaccacc agcccccgt gctggtggat tcagctacg gtggaaccga     840
tgatgacgtg gacgaccaga caagaataga tgagaatcta gccatcatgt accggcaaat     900
ggtttccggt gccaaaactc ccatctatt tttcggccat gagtacaggg caggagacac     960
aacaacaggg acttacgccg gcaccattga gaacagtcct cataataaca tccatctctg    1020
gtgcggtgac ccgaaccaga cccaccacga agacatgggt aacttctact ccgccggtcg    1080
gatccctgtt tacgcccacc attgcagtga ccgcatgtgg aacgtttgga aaaccctcgg    1140
aggcaagcgc aaggacccca ccgacaccga ttggcttgac gctgagtttc tgttctacga    1200
```

-continued

```
tgaaaacgcc gagcttgtga gctgtaaagt tcgggacagc ctcaaacctg agaaagatct    1260
tcgttatact tacgagcctg ttagtgttcc gtggctgttc accaagccaa ccgctcgtaa    1320
gccaaagagc aagacaaaag ccaaggtggg ggctacccag ctgacgacaa agttcccggc    1380
cacgtttgat tcgaagacga cggtggaggt ggcgaggccg aagccgcgga agaggaccaa    1440
gaaggagaag atcgacgagg aggaggtgct gatcattaag gacatcgaat tcgagagcaa    1500
cgaggcggtg aagttcgatg tgtttattaa tgatgatgct gagtcgctca gtaggaagga    1560
caaatccgag tttgctggga gttttgtgca cgtgccgcat aaccagaaga ctgggacgaa    1620 gaaaagacg  aacttaaaac tggggatcac ggacttgttg gaggatttgg gtgtggagga    1680
tgatagcagt gtgctggtga cgttggtgcc tagggtttcg aactcgccta tcaccattgg    1740
tgggtttaag atcgagtatt cttcttgatc aaaaagtatg gttaagtaat taaataattt    1800
catagtggaa tggcctgctt tcatgcatgc ccttgtgttt agttaa                   1846
```

<210> SEQ ID NO 25
<211> LENGTH: 588
<212> TYPE: PRT
<213> ORGANISM: Malus sp.

<400> SEQUENCE: 25

```
Thr Thr Thr Thr Met Gly Thr Tyr Ser Ser Leu Ile Ile Ser Thr Asn
1               5                   10                  15

Ser Phe Ser Ala Phe Leu Pro Asn Lys Ser Gln Leu Ser Phe Ser Gly
            20                  25                  30

Lys Ser Lys His Tyr Ile Ala Arg Arg Ser Ser Ile Tyr Cys Lys Ala
        35                  40                  45

Thr Asn Pro Asn Tyr Asn Asn Glu Gln Asp Gln Gln Ser Ser Asn
    50                  55                  60

Leu Leu Gly Lys Leu Asp Arg Arg Asn Val Leu Ile Gly Leu Gly Gly
65                  70                  75                  80

Leu Tyr Gly Ala Thr Thr Leu Ala Pro Lys Pro Leu Ala Phe Ala Asn
                85                  90                  95

Pro Leu Ala Pro Pro Asp Leu Thr Lys Cys Lys Pro Ala Glu Ile Thr
            100                 105                 110

Thr Gly Gly Glu Thr Val Glu Cys Cys Pro Val Ser Thr Lys Ile
        115                 120                 125

Lys Thr Phe Thr Pro Asp Gln Ser Ile Pro Leu Arg Thr Arg Pro Ala
130                 135                 140

Ala His Leu Val Thr Asp Glu Tyr Leu Ala Lys Phe Lys Lys Ala Gln
145                 150                 155                 160

Ala Leu Met Arg Ala Leu Pro Glu Asp Asp Pro Arg Ser Met Val Gln
                165                 170                 175

Gln Ala Lys Val His Cys Ala Tyr Cys Asn Gly Ala Tyr Pro Gln Val
            180                 185                 190

Gly Phe Pro Asp Ile Asp Ile Gln Ile His Phe Ser Trp Leu Phe Phe
        195                 200                 205

Pro Phe His Arg Met Tyr Leu Tyr Phe Tyr Glu Arg Ile Leu Gly Lys
    210                 215                 220

Leu Ile Asp Asp Pro Thr Phe Ala Leu Pro Tyr Trp Asn Trp Asp Ser
225                 230                 235                 240

Pro Asp Gly Phe Pro Ile Pro Ile Tyr Thr Asp Thr Thr Ser Pro
                245                 250                 255
```

Leu Tyr Asp Gln Tyr Arg Asn Ala Asp His Gln Pro Pro Val Leu Val
            260                 265                 270

Asp Leu Ser Tyr Gly Gly Thr Asp Asp Val Asp Asp Gln Thr Arg
        275                 280                 285

Ile Asp Glu Asn Leu Ala Ile Met Tyr Arg Gln Met Val Ser Gly Ala
290                 295                 300

Lys Thr Pro His Leu Phe Phe Gly His Glu Tyr Arg Ala Gly Asp Thr
305                 310                 315                 320

Thr Thr Gly Thr Tyr Ala Gly Thr Ile Glu Asn Ser Pro His Asn Asn
                325                 330                 335

Ile His Leu Trp Cys Gly Asp Pro Asn Gln Thr His His Glu Asp Met
                340                 345                 350

Gly Asn Phe Tyr Ser Ala Gly Arg Ile Pro Val Tyr Ala His His Cys
            355                 360                 365

Ser Asp Arg Met Trp Asn Val Trp Lys Thr Leu Gly Gly Lys Arg Lys
370                 375                 380

Asp Pro Thr Asp Thr Asp Trp Leu Asp Ala Glu Phe Leu Phe Tyr Asp
385                 390                 395                 400

Glu Asn Ala Glu Leu Val Ser Cys Lys Val Arg Asp Ser Leu Lys Pro
                405                 410                 415

Glu Lys Asp Leu Arg Tyr Thr Tyr Glu Pro Val Ser Val Pro Trp Leu
            420                 425                 430

Phe Thr Lys Pro Thr Ala Arg Lys Pro Lys Ser Lys Thr Lys Ala Lys
        435                 440                 445

Val Gly Ala Thr Gln Leu Thr Thr Lys Phe Pro Ala Thr Phe Asp Ser
450                 455                 460

Lys Thr Thr Val Glu Val Ala Arg Pro Lys Pro Arg Lys Arg Thr Lys
465                 470                 475                 480

Lys Glu Lys Ile Asp Glu Glu Val Leu Ile Ile Lys Asp Ile Glu
                485                 490                 495

Phe Glu Ser Asn Glu Ala Val Lys Phe Asp Val Phe Ile Asn Asp Asp
            500                 505                 510

Ala Glu Ser Leu Ser Arg Lys Asp Lys Ser Glu Phe Ala Gly Ser Phe
        515                 520                 525

Val His Val Pro His Asn Gln Lys Thr Gly Thr Lys Lys Thr Asn
530                 535                 540

Leu Lys Leu Gly Ile Thr Asp Leu Leu Glu Asp Leu Gly Val Glu Asp
545                 550                 555                 560

Asp Ser Ser Val Leu Val Thr Leu Val Pro Arg Val Ser Asn Ser Pro
                565                 570                 575

Ile Thr Ile Gly Gly Phe Lys Ile Glu Tyr Ser Ser
            580                 585

<210> SEQ ID NO 26
<211> LENGTH: 407
<212> TYPE: DNA
<213> ORGANISM: Malus sp.

<400> SEQUENCE: 26
cgaattggca ttggggaccc aaccttcgcc ctccccttct ggaactggga cgcaccagct      60
ggaatgtaca ttcctgagat tttcactgat acgtcgtcat ccctctacga ccagtataga     120
aatgcagcgc atcagccccc gaagctctta gactttaata acagcgggac cgacgataac     180
gtcgacgacg caacacgaat caaagagaac ttaacaacaa tgtaccagca gatggtgtca     240

```
aaggccactt ctcacagact cttttttgga gagccctaca gcgcagggga cgacccaagt    300
cctggtgccg gaaacattga gagcattccc cataacaata ttcactttg gactggcgac     360 ccaacccaga caaatgggga agacatgggg aattttttact ccgctgg                 407
```

<210> SEQ ID NO 27
<211> LENGTH: 457
<212> TYPE: DNA
<213> ORGANISM: Malus sp.

<400> SEQUENCE: 27

```
tttctttccc gttccaccgt tactacttat acttccacga aagaatcttg gccaaactca     60
tagacgatcc gacgttcgcg ttgccgtttt ggaactggga cgcgccagct ggcatgcaac    120
tccctgcctt gttcgctaac ccggactctc cgctttacga cgagcttcgc gctgccagcc   180
atcagccgcc gactctcatc gatcttgact tcaacggcac ggatgaaaca atgtccaacg   240
atgctcaaat cgaagccaac ctcaaaatta tgtataggca gatggtttcc aactccaaga   300
aaccgctgtt gttctttggt tcgccctaca gggctggcac tgaaccagat ccagggggcg   360
gttcaatcga aacgacccca catggtccgg ttcatttatg ggccggagat aacacgcaac   420
ctaattttga agacatgggg aattttttact ccgctgg                           457
```

<210> SEQ ID NO 28
<211> LENGTH: 457
<212> TYPE: DNA
<213> ORGANISM: Malus sp.

<400> SEQUENCE: 28

```
tcttcttccc gttccaccgt tactatctct acttttttcga aagatccta ggcaaactca    60 ttaacgaccc gacattcgct ttgccgttct ggaactggga ctcgccagcc ggcatgccac   120
tgcccgcgat ttacgctgat ccaaagtccc ctctctacga caagctccga tctgccaatc   180
atcagccccc gactctggtc gatctcgatt acaacgggac cgaggacaat gtgtcaaagg   240
aaaccacaat caacgccaat ctcaaaatca tgtacaggca aatggtgtcc aattccaaga   300
atgctaagtt gttctttggg aacccgtaca gggcagggga caagcccgac cctggtggcg   360
gctccatcga ggggacacca cacgcgccgg ttcatttatg gaccggtgac aacacccagc   420
ccaactttga ggatatgggg aattttttact ccgctgg                           457
```

<210> SEQ ID NO 29
<211> LENGTH: 453
<212> TYPE: DNA
<213> ORGANISM: Malus sp.

<400> SEQUENCE: 29

```
ttcctttcca ccgcatgtac ttgtatttct acgagagaat ccttggcaag ctcattgatg    60
acccaacttt cgctctccca tactggaatt gggactctcc tgacggtttt ccaattcccg   120
acatttacac agatacaact tccccactct atgatcagta ccgaaacgcc gaccaccagc   180
cccccgtgct ggtggatctc agctacggtg gaaccgatga tgacgtggac gaccagacaa   240
gaatagatga gaacctagcc atcatgtacc ggcaagtggt ttccggtgcc aaaactcccc   300
atctattttt cggccatgag tacagggcag gagacacaac aacagggacc tacgccggca   360
ccattgagaa cagtcctcat aataacatcc atctctggtg cggtgacccg aaccagaccc   420
accacgaaga catgggtaac ttctactccg cgg                               453
```

```
<210> SEQ ID NO 30
<211> LENGTH: 200
<212> TYPE: DNA
<213> ORGANISM: Malus sp.

<400> SEQUENCE: 30
ccacatgtgg ccctgccgac aagccagacg ggtccaccat cgattgttgc ccacccatca      60
cgaccaccat catcgacttc aaactccccg accgaggccc actccgcaca aggatcgctg     120
cccaggacgt tgcaaaaaac cctgcatact tggctaaata caaaaaggcc atcgagctga     180
tgcgggcact tccagatgac                                                 200

<210> SEQ ID NO 31
<211> LENGTH: 200
<212> TYPE: DNA
<213> ORGANISM: Malus sp.

<400> SEQUENCE: 31
aatgcggagc tgcggacttt ccaagtggag cagtcccgac caactgttgc ccgccaacgt      60
cccaaaaaat cgtagacttc aaattcccct ccccctaccaa actccgcgtc aggccggcag    120
ctcacaccgt ggataaagcc tacatcgaaa aatattcaaa agccatcgag ctcatgaaag     180
ccctcccgga cgacgatccg                                                 200

<210> SEQ ID NO 32
<211> LENGTH: 200
<212> TYPE: DNA
<213> ORGANISM: Malus sp.

<400> SEQUENCE: 32
aatgtggtcc tgcagacttg ccacagggtg cagtgcccac caactgctgc ccgccgcctt      60
ccacaaaaat cattgacttt aagctgcctg cccccgccaa actccgcatc aggccaccgg    120
ctcacgccgt tgaccaagcc tacagggaca aatactacaa agcgatggag ctcatgaagg    180
ccctacccga cgacgaccca                                                 200

<210> SEQ ID NO 33
<211> LENGTH: 200
<212> TYPE: DNA
<213> ORGANISM: Malus sp.

<400> SEQUENCE: 33
aatgtaagcc ggccgaaatc accaccggag gtgaaactgt ggaatgctgt ccaccggtct      60
ccacaaagat caaaaccttc actccggacc agtctatccc actgcggacg aggcctgccg    120
cccatttggt cacggacgag tacttggcca agttcaagaa agctcaagcc ctcatgcgtg    180
ccttacccga agacgacccg                                                 200

<210> SEQ ID NO 34
<211> LENGTH: 171
<212> TYPE: DNA
<213> ORGANISM: Malus sp.

<400> SEQUENCE: 34
gtcacactaa ttacaacaaa cttaattaat ttccgctga tttggattta accaagttag       60
ctaaagcacc ttgcggcccc attgcaccta agtttggatc tcggttttgt agactagatt    120
gtattagaat atcatattga gggcttgtat atattttgaa caatatttca g             171

<210> SEQ ID NO 35
```

```
<211> LENGTH: 1822
<212> TYPE: DNA
<213> ORGANISM: Malus sp.

<400> SEQUENCE: 35
cgaattggca ttggggaccc aaccttcgcc ctcccttct ggaactggga cgcaccagct      60
ggaatgtaca ttcctgagat tttcactgat acgtcgtcat ccctctacga ccagtataga    120
aatgcagcgc atcagccccc gaagctctta gactttaata acagcgggac cgacgataac    180
gtcgacgacg caacacgaat caaagagaac ttaacaacaa tgtaccagca gatggtgtca    240
aaggccactt ctcacagact ctttttgga gagccctaca gcgcagggga cgacccaagt    300
cctggtgccg aaacattga gagcattccc cataacaata ttcactttg gactggcgac     360 ccaacccaga caaatgggga agacatgggg aatttttact ccgctggaat cactagtgaa    420
ttcgatttct ttcccgttcc accgttacta cttatacttc cacgaaagaa tcttggccaa    480
actcatagac gatccgacgt tcgcgttgcc gttttggaac tgggacgcgc agctggcat     540 gcaactccct gccttgttcg ctaacccgga ctctccgctt tacgacgagc ttcgcgctgc    600
cagccatcag ccgccgactc tcatcgatct tgacttcaac ggcacggatg aaacaatgtc    660
caacgatgct caaatcgaag ccaacctcaa aattatgtat aggcagatgg tttccaactc    720
caagaaaccg ctgttgttct ttggttcgcc ctacagggct ggcactgaac cagatccagg    780
gggcggttca atcgaaacga ccccacatgg tccggttcat ttatgggccg gagataacac    840
gcaacctaat tttgaagaca tggggaattt ttactccgct ggaatcacta gtgaattcga    900
tatcttcttc ccgttccacc gttactatct ctactttttc gagaagatcc taggcaaact    960
cattaacgac ccgacattcg ctttgccgtt ctggaactgg gactcgccag ccggcatgcc   1020
actgcccgcg atttacgctg atccaaagtc ccctctctac gacaagctcc gatctgccaa   1080
tcatcagccc ccgactctgg tcgatctcga ttacaacggg accgaggaca atgtgtcaaa   1140
ggaaaccaca atcaacgcca atctcaaaat catgtacagg caaatggtgt ccaattccaa   1200
gaatgctaag ttgttctttg gaacccgta cagggcaggg acaagcccg accctggtgg    1260 cggctccatc gagggacac cacacgcgcc ggttcattta tggaccggtg acaacaccca   1320
gcccaacttt gaggatatgg ggaatttta ctccgctggt atcaagcttt tccttccac    1380 cgcatgtact tgtatttcta cgagagaatc cttggcaagc tcattgatga cccaactttc   1440
gctctcccat actggaattg ggactctcct gacggttttc caattcccga catttacaca   1500
gatacaactt ccccactcta tgatcagtac cgaaacgccg accaccagcc cccgtgctg    1560 gtggatctca gctacggtgg aaccgatgat gacgtggacg accagacaag aatagatgag   1620
aacctagcca tcatgtaccg gcaagtggtt tccggtgcca aaactcccca tctattttc    1680 ggccatgagt acagggcagg agacacaaca acagggacct acgccggcac cattgagaac   1740
agtcctcata taacatcca tctctggtgc ggtgacccga accagaccca ccacgaagac    1800
atgggtaact tctactccgc gg                                            1822

<210> SEQ ID NO 36
<211> LENGTH: 1771
<212> TYPE: DNA
<213> ORGANISM: Malus sp.

<400> SEQUENCE: 36
ccacatgtgg ccctgccgac aagccagacg ggtccaccat cgattgttgc ccacccatca     60
cgaccaccat catcgacttc aaactccccg accgaggccc actccgcaca aggatcgctg    120
```

-continued

```
cccaggacgt tgcaaaaaac cctgcatact tggctaaata caaaaaggcc atcgagctga    180
tgcgggcact tccagatgac aatgcggagc tgcggacttt ccaagtggag cagtcccgac    240
caactgttgc ccgccaacgt cccaaaaaat cgtagacttc aaattcccct cccctaccaa    300
actccgcgtc aggccggcag ctcacaccgt ggataaagcc tacatcgaaa atattcaaa    360 agccatcgag ctcatgaaag ccctcccgga cgacgatccg aatgtggtcc tgcagacttg    420
ccacagggtg cagtgcccac caactgctgc ccgccgcctt ccacaaaaat cattgactt    480 aagctgcctg ccccgccaa actccgcatc aggccaccgg ctcacgccgt tgaccaagcc    540
tacagggaca atactacaa agcgatggag ctcatgaagg ccctacccga cgacgaccca    600
aatgtaagcc ggccgaaatc accaccggag gtgaaactgt ggaatgctgt ccaccggtct    660
ccacaaagat caaaaccttc actccggacc agtctatccc actgcggacg aggcctgccg    720
cccatttggt cacggacgag tacttggcca agttcaagaa agctcaagcc ctcatgcgtg    780
ccttacccga agacgacccg gtcacactaa ttacaacaaa cttaattaat ttcccgctga    840
tttggattta accaagttag ctaaagcacc ttgcggcccc attgcaccta gtttggatc    900 tcggttttgt agactagatt gtattagaat atcatattga gggcttgtat atattttgaa    960
caatatttca gcgggtcgtc ttcgggtaag gcacgcatga gggcttgagc tttcttgaac   1020
ttggccaagt actcgtccgt gaccaaatgg gcggcaggcc tcgtccgcag tgggatagac   1080
tggtccggag tgaaggtttt gatctttgtg gagaccggtg gacagcattc cacagtttca   1140
cctccggtgg tgatttcggc cggcttacat ttgggtcgtc gtcgggtagg gccttcatga   1200
gctccatcgc tttgtagtat ttgtccctgt aggcttggtc aacggcgtga gccggtggcc   1260
tgatgcggag tttggcgggg gcaggcagct taaagtcaat gattttttgtg gaaggcggcg   1320 ggcagcagtt ggtgggcact gcaccctgtg gcaagtctgc aggaccacat tcggatcgtc   1380 gtccggagg gctttcatga gctcgatggc ttttgaatat ttttcgatgt aggctttatc   1440
cacggtgtga gctgccggcc tgacgcggag tttggtaggg gaggggaatt tgaagtctac   1500 gatttttgg gacgttggcg ggcaacagtt ggtcggact gctccacttg gaaagtccgc   1560
agctccgcat tgtcatctgg aagtgcccgc atcagctcga tggcctttttt gtatttagcc   1620 aagtatgcag ggttttttgc aacgtcctgg gcagcgatcc ttgtgcggag tgggcctcgg   1680
tcggggagtt tgaagtcgat gatggtggtc gtgatgggtg ggcaacaatc gatggtggac   1740
ccgtctggct tgtcggcagg gccacatgtg g    1771
```

<210> SEQ ID NO 37
<211> LENGTH: 1761
<212> TYPE: DNA
<213> ORGANISM: Malus sp.

<400> SEQUENCE: 37

```
atgacttcat ctcccttacc accaacttct acaatggccg ccctgcactc caccaccaca     60
accaccctct tccgctctcc tttattccca aacaagtccc agactccact gcaacgaaaa    120
cccaaacaat gccttgcggg cagagtgcgc tgcaaagcaa caaaaggtga caatgataac    180
ctagaccagg cttagcaag actcgacagg aggaacatgc tgataggttt aggcactggg    240
ggtctctaca gtgcggcagg aaactcattt gcttttgcag caccggtatc cgccccagac    300
ctgaccacat gtgccctgc cgacaagcca gacgggtcca ccatcgattg ttgcccaccc    360
atcacgacca ccatcatcga cttcaaactc cccgaccgag gcccactccg cacaaggatc    420
```

```
gctgcccagg acgttgcaaa aaaccctgca tacttggcta aatacaaaaa ggccatcgag    480
ctgatgcggg cacttccaga tgacgacccg cgcagtctcg tccaacaggc caaagtccat    540
tgctcctact gcgacggtgg atacccacaa gtcggatatt cagatttgga gatccaagtt    600
cacttctgtt ggctattctt cccgttccat cgttggtacc tctacttcta cgagaaaatc    660
atgggcgagc tcattgggga cccaaccttc gccctcccct tctggaacag ggacgcgcca    720
gctggcatgt acattcctga gattttcacc gatacgtcgt catccctcta cgaccagaac    780
agaaatacag cgcatcagcc cccgaagctc ctggacttga attatggcgg gaccgacgat    840
gacgtcgacg acgcgacacg aatcaaagag aacctaacaa cgatgtacca gcagatggtg    900
tcgaaggcca cttctcacag actattctac ggagagccct atagcgcagg ggacgaacca    960
gatcctggcg ccggaaacat tgagaccact ccccataaca atattcacct ttgggttggc   1020
gacccaaccc agacaaacgg ggaggacatg gggacctttt actctgcggg gagggatccg   1080
ctgttttact ctcaccattc caacgtggac cgcatgtggt ctatatataa agataagttg   1140
ggaggtacgg acatagaaaa taccgactgg ctggacgcag agttcttatt ctacgacgag   1200
aaaaagaatc tcgtgcgcgt caaggttcgg gactcgctcg cactaaaaa actcgggtac   1260 gtgtacgacg agaaagtccc aatcccatgg ctgaagtcga agccgacgct cgtaagtcga   1320
cgaataagag aaaggccaca gttcatcttc gatcttacta caacgttccc tgctacattg   1380
tcggatacaa tcagcgtcga ggtgacaagg ccgtctgcga cgaagcggac agctgcccag   1440
aagaaggcac atgacgaggt gctggtgatt aaggggattg agtttgccgg gaatgagcct   1500
gtgaagttcg acgtgtatgt gaacgatgac gcggaatcgc tggctgggaa agacaagtcg   1560
gagtttgctg ggagttttgt tcacgtgccg cataagcata agaaaaatat taagacgaac   1620
ctgcgactga gcattatgag cttgttggag gagttggatg cggagacaga cagcagtttg   1680
gtggtgactt tggtgccgaa agttgggaag gggccaatca ccatcggagg gtttagcatt   1740
gagctcatta atactaccta a                                             1761

<210> SEQ ID NO 38
<211> LENGTH: 407
<212> TYPE: DNA
<213> ORGANISM: Malus sp.

<400> SEQUENCE: 38
cgaattggca ttggggaccc aaccttcgcc ctccccttct ggaactggga cgcaccagct     60
ggaatgtaca ttcctgagat tttcactgat acgtcgtcat ccctctacga ccagtataga    120
aatgcagcgc atcagccccc gaagctctta gactttaata acagcgggac cgacgataac    180
gtcgacgacg caacacgaat caaagagaac ttaacaacaa tgtaccagca gatggtgtca    240
aaggccactt ctcacagact ctttttttgga gagccctaca gcgcagggga cgacccaagt    300
cctggtgccg aaacattgag agcattccc cataacaata ttcactttg gactggcgac     360 ccaacccaga caaatgggga agacatgggg aattttttact ccgctgg                 407

<210> SEQ ID NO 39
<211> LENGTH: 1851
<212> TYPE: DNA
<213> ORGANISM: Malus sp.

<400> SEQUENCE: 39
atggcttcta tgtcagctcc actcgtcacc tccgccacaa gtatcatccc cacaacttcc     60
ctctcccctt tctcccaaaa gtatcaccga atatccttat ttggaaaccc taggcattcc    120
```

-continued

```
aatttacaag ctgtctcatg caaagccaca aataatagta gtgaccaaaa caaaaaccct      180
tccactagct ccaacgatca cgaccatgaa aaccctctc cagtaaacct agacagaaga       240
aatgtactta taggtctcgg aagcctatac ggtggagtgg ctggtcttgg cagcgacccc     300
ttcgctgttg caaagccagt gtcgccgcct gacctagcca aatgcggagc tgcggacttt     360
ccaagtggag cagtcccgac caactgttgc ccgccaacgt cccaaaaaat cgtagacttc    420
aaattcccct cccctaccaa actccgcgtc aggccggcag ctcacaccgt ggataaagcc    480
tacatcgaaa aatattcaaa agccatcgag ctcatgaaag ccctcccgga cgacgatccg    540
cgtagcttca cccagcaagc cgatatccac tgtgcctatt gcgacggcgc gtacgaccaa    600
gtcggcttcc ccaacctcga gctccaaatc catcaatgct ggcttttctt ccccttccat    660
cgttactacc tatacttcca cgaaagaatc ttggccaaac tcatatacga tccgacgttc    720
gcgttgccgt tttggaactg ggacgcgcca gctggcatgc aactccctgc cttgttcgct    780
aacccggact ctccgcttta cgacgagctt cgcgctgcca gccatcagcc gccgactctc    840
atcgatcttg acttcaacgg cacggatgaa acaatgtcca acgatgctca aatcgaagcc    900
aaccgcaaaa ttatgtatag gcagatggtt tccaactcca agaaaccgct gttgttcttt    960
ggttctccct acagggctgg cactgaacca gatccagggg gcggttcaat cgaaacgacc   1020
ccacatggtc cggttcattt atggaccgga gataacacgc aacctaattt tgaagacatg   1080
gggaattttt actccgctgg aagggatcca atatttttt cgcaccattc gaatatagat    1140
cgaatgtgga atatttggaa aagtatagg actaaaaata aagatattaa cgataaggat    1200
tggttggata cggggttttt gttttatgac gagaatgctg agcttgttag ggtcacggtg   1260
agggacactc ttgataataa aaagctaggg tatacgtatg aagatgttga gattccatgg   1320
ctcaagtcta gaccgacgcc acgtcggaca aagcttgcga gaaaggcaaa ggcggctgga   1380
gtggcgaagg cggctggagt ggcgaaggcc gctgagacga cgtcatcagg gaaggtggtg   1440
gcgggtaaag atttttccaat aaatttggag acgaagataa gtacggtggt gtcaaggccg  1500
aagccgaaga gaggagcaa gaaggagaaa gaggatgagg aggagatatt ggtgattcag    1560
gggattgagc ttgacaaaga tgtggctgtg aagtttgatg tgtatgtgaa tgacgtggac   1620
gatgaggatg cggcaccgag tggacccgac aagagcgagt ttgctgggag ttttgtgagt   1680
gtgccacata agcagaagga aaagagcaag agttgtttaa ggttggggtt aacggacctg   1740
ttggaggatt tgggtgctga agatgatgag agtgtggtgg tgactttagt gcccaggtac   1800
ggcgctcagg ctgttaagat cggtagcatc aaaattgagt tcttgcttg a              1851
```

<210> SEQ ID NO 40
<211> LENGTH: 457
<212> TYPE: DNA
<213> ORGANISM: Malus sp.

<400> SEQUENCE: 40

```
tttctttccc gttccaccgt tactacttat acttccacga aagaatcttg gccaaactca     60
tagacgatcc gacgttcgcg ttgccgtttt ggaactggga cgcgccagct ggcatgcaac   120
tccctgcctt gttcgctaac ccggactctc cgctttacga cgagcttcgc gctgccagcc   180
atcagccgcc gactctcatc gatcttgact tcaacggcac ggatgaaaca atgtccaacg   240
atgctcaaat cgaagccaac ctcaaaatta tgtataggca gatggtttcc aactccaaga   300
aaccgctgtt gttctttggt tcgccctaca gggctggcac tgaaccagat ccaggggggcg   360
```

| gttcaatcga aacgacccca catggtccgg ttcatttatg ggccggagat aacacgcaac | 420 |
| ctaattttga agacatgggg aatttttact ccgctgg | 457 |

<210> SEQ ID NO 41
<211> LENGTH: 1782
<212> TYPE: DNA
<213> ORGANISM: Malus sp.

<400> SEQUENCE: 41

| atgacgtctc tttcacctcc ggtagtcacc acccccaccg ttcccaaccc cgccacaaaa | 60 |
| cctctctccc ccttctctca aaacaactcc caagtttccc tactcacaaa gcccaagcgt | 120 |
| tcctttgcac gtaaggtctc atgcaaagcc acaaacaatg accaaaatga tcaagcacag | 180 |
| tccaaactag acaggagaaa tgtgcttctt ggtcttggag gtctatacgg cgtggcgggt | 240 |
| atgggcacag acccgttcgc ttttgccaag cctatagccc caccagacgt atctaaatgt | 300 |
| ggtcctgcag acttgccaca gggtgcagtg cccaccaact gctgcccgcc gccttccaca | 360 |
| aaaatcattg actttaagct gcctgccccc gccaaactcc gcatcaggcc accggctcac | 420 |
| gccgttgacc aagcctacag ggacaaatac tacaaagcga tggagctcat gaaggcccta | 480 |
| cccgacgacg acccacgtag cttcaagcaa caggcagccg tgcattgcgc ttattgcgac | 540 |
| ggcgcctatg accaagtcgg gttcccagaa ctcgagctcc aaatccacaa ctcatggctc | 600 |
| ttcttcccgt tccaccgtta ctacttgtac tttttcgaga gatcctagg caaactcatt | 660 |
| aacgacccga cattcgcttt gccgttctgg aactgggact cgccagccgg catgccactg | 720 |
| cccgcaattt acgctgatcc aaagtcccct ctctacgaca agctccgatc tgccaatcat | 780 |
| cagcccccga ctctggtcga tctcgattac aacgggaccg aggacaatgt gtcaaaggaa | 840 |
| accacaatca acgccaatct caaaatcatg tacaggcaaa tggtgtccaa ttccaagaat | 900 |
| gctaagttgt tctttgggaa cccgtacagg gcagggggacg agcctgaccc tggtggcggc | 960 |
| tccatcgagg ggacaccaca cgcgccggtt catttatgga ccggtgacaa cacccagccc | 1020 |
| aactttgagg acatggggaa ttttttactcc gctggtcggg accccatatt ttttgcacac | 1080 |
| cattcgaatg tcgatcgaat gtggagtatt tggaaaactc ttggaggtaa agaactgat | 1140 |
| cttactgact cggactggtt ggactccgga ttcttgtttt acaacgagaa cgcagagtta | 1200 |
| gtccgagtca aggtcaggga ctgcttggag accaaaaatc ttgggtatgt ataccaagat | 1260 |
| gtggacattc cttggctcag ctccaagcca acaccgcgaa gggcgaaagt tgcattgagc | 1320 |
| aaagtagcga agaagctggg agttgcacac gcagctgttg cgtcgtccag caaggtggtg | 1380 |
| gcaggcactg agttcccgat aagtctgggg tcgaagataa gcacggtggt gaagagaccg | 1440 |
| aagcagaaga gaggagcaa gaaggccaag gaggatgagg aggagatatt ggtgattgag | 1500 |
| ggaatcgagt ttgacaggga cgtggctgtg aagtttgatg tgtatgtgaa tgacgtcgat | 1560 |
| gacttgccga gtgggcctga caagacgag tttgccggaa gctttgtaag tgtgccgcac | 1620 |
| agccacaagc acaagaagaa gatgaacact attttgaggt tagggttgac agatttgttg | 1680 |
| gaggaaattg aggcggagga cgatgacagc gtggtggtga cttttggtgcc caagttcggc | 1740 |
| gctgtcaaga ttggtggtat caagattgaa tttgcttctt ag | 1782 |

<210> SEQ ID NO 42
<211> LENGTH: 456
<212> TYPE: DNA
<213> ORGANISM: Malus sp.

<400> SEQUENCE: 42

```
tctcttcccg ttccaccgtt actatctcta cttttcgag aagatcctag gcaaactcat      60
taacgacccg acattcgctt tgccgttctg gaactggac tcgccagccg gcatgccact     120
gcccgcgatt tacgctgatc caaagtcccc tctctacgac aagctccgat ctgccaatca    180
tcagcccccg actctggtcg atctcgatta caacgggacc gaggacaatg tgtcaaagga    240
aaccacaatc aacgccaatc tcaaaatcat gtacaggcaa atggtgtcca attccaagaa    300
tgctaagttg ttctttggga acccgtacag ggcaggggac aagcccgacc ctggtggcgg    360
ctccatcgag gggacaccac acgcgccggt tcatttatgg accggtgaca cacccagcc     420 caactttgag gatatgggga atttttactc cgctgg                              456

<210> SEQ ID NO 43
<211> LENGTH: 1768
<212> TYPE: DNA
<213> ORGANISM: Malus sp.

<400> SEQUENCE: 43
taccaccacc accatgggca cttactcttc tctgatcatc tccaccaatt ccttctctgc     60
cttcctccca aacaaatccc aactttcctt ctctggaaaa agcaagcact acattgcacg    120
tagatcatca atatattgca aagccacaaa ccctaattat aataatgagc aagatcaaca    180
acaatcttct aatttgttgg gaaaattgga caggagaaat gtcctaattg gcctgggcgg    240
cctctacggg gccaccaccc tcgccccaaa gccgttggcc tttgccaacc cgctggctcc    300
acccgaccta accaaatgta agccggccga aatcaccacc ggaggtgaaa ctgtggaatg    360
ctgtccaccg gtctccacaa agatcaaaac cttcactccg gaccagtcta tcccactgcg    420
gacgaggcct gccgcccatt tggtcacgga cgagtacttg gccaagttca agaaagctca    480
agccctcatg cgtgccttac ccgaagacga cccgcgtagc atggttcaac aagctaaagt    540
tcactgtgcc tactgcaatg gtgcttatcc acaagtaggg tttccggaca ttgacatcca    600
aatccacttc tcctggcttt tctttccttt ccaccgcatg tacttgtatt tctacgagag    660
aatccttggc aagctcattg atgacccaac tttcgctctc ccatactgga attgggactc    720
tcctgacggt tttccaattc ccgacattta cacagataca acttccccac tctatgatca    780
gtaccgaaac gccgaccacc agcccccgt gctggtggat tcagctacg gtggaaccga    840 tgatgacgtg gacgaccaga caagaataga tgagaatcta gccatcatgt accggcaaat    900
ggtttccggt gccaaaactc cccatctatt tttcggccat gagtacaggg caggagacac    960
aacaacaggg acttacgccg gcaccattga gaacagtcct cataataaca tccatctctg   1020
gtgcggtgac ccgaaccaga cccaccacga agacatgggt aacttctact ccgccggtcg   1080
gatccctgtt tacgcccacc attgcagtga ccgcatgtgg aacgtttgga aaaccctcgg   1140
aggcaagcgc aaggaccca ccgacaccga ttggcttgac gctgagtttc tgttctacga    1200
tgaaaacgcc gagcttgtga gctgtaaagt tcggacagc ctcaaacctg agaaagatct   1260
tcgttatact tacgagcctg ttagtgttcc gtggctgttc accaagccaa ccgctcgtaa   1320
gccaaagagc aagacaaaag ccaaggtggg ggctacccag ctgacgacaa agttcccggc   1380
cacgtttgat tcgaagacga cggtggaggt ggcgaggccg aagccgcgga agaggaccaa   1440
gaaggagaag atcgacgagg aggaggtgct gatcattaag gacatcgaat tcgagagcaa   1500
cgaggcggtg aagttcgatg tgtttattaa tgatgatgct gagtcgctca gtaggaagga   1560
caaatccgag tttgctggga gttttgtgca cgtgccgcat aaccagaaga ctgggacgaa   1620
```

| | |
|---|---:|
| gaaaaagacg aacttaaaac tggggatcac ggacttgttg gaggatttgg gtgtggagga | 1680 |
| tgatagcagt gtgctggtga cgttggtgcc tagggtttcg aactcgccta tcaccattgg | 1740 |
| tgggtttaag atcgagtatt cttcttga | 1768 |

<210> SEQ ID NO 44
<211> LENGTH: 453
<212> TYPE: DNA
<213> ORGANISM: Malus sp.

<400> SEQUENCE: 44

| | |
|---|---:|
| ttcctttcca ccgcatgtac ttgtatttct acgagagaat ccttggcaag ctcattgatg | 60 |
| acccaacttt cgctctccca tactggaatt gggactctcc tgacggtttt ccaattcccg | 120 |
| acatttacac agatacaact tccccactct atgatcagta ccgaaacgcc gaccaccagc | 180 |
| cccccgtgct ggtggatctc agctacggtg gaaccgatga tgacgtggac gaccagacaa | 240 |
| gaatagatga gaacctagcc atcatgtacc ggcaagtggt ttccggtgcc aaaactcccc | 300 |
| atctattttt cggccatgag tacagggcag gagacacaac aacagggacc tacgccggca | 360 |
| ccattgagaa cagtcctcat aataacatcc atctctggtg cggtgacccg aaccagaccc | 420 |
| accacgaaga catgggtaac ttctactccg cgg | 453 |

<210> SEQ ID NO 45
<211> LENGTH: 1761
<212> TYPE: DNA
<213> ORGANISM: Malus sp.

<400> SEQUENCE: 45

| | |
|---|---:|
| atgacttcat ctcccttacc accaacttct acaatggccg ccctgcactc caccaccaca | 60 |
| accaccctct tccgctctcc tttattccca aacaagtccc agactccact gcaacgaaaa | 120 |
| cccaaacaat gccttgcggg cagagtgcgc tgcaaagcaa caaaggtgaa caatgataac | 180 |
| ctagaccagg gcttagcaag actcgacagg aggaacatgc tgataggttt aggcactggg | 240 |
| ggtctctaca gtgcggcagg aaactcattt gcttttgcag caccggtatc cgccccagac | 300 |
| ctgaccacat gtggccctgc cgacaagcca gacgggtcca ccatcgattg ttgcccaccc | 360 |
| atcacgacca ccatcatcga cttcaaactc cccgaccgag gcccactccg cacaaggatc | 420 |
| gctgcccagg acgttgcaaa aaaccctgca tacttggcta atacaaaaa ggccatcgag | 480 |
| ctgatgcggg cacttccaga tgacgacccg cgcagtctcg tccaacaggc caaagtccat | 540 |
| tgctcctact gcgacggtgg ataccacaa gtcggatatt cagatttgga gatccaagtt | 600 |
| cacttctgtt ggctattctt cccgttccat cgttggtacc tctacttcta cgagaaaatc | 660 |
| atgggcgagc tcattgggga cccaaccttc gccctcccct tctggaacag ggacgcgcca | 720 |
| gctggcatgt acattcctga gattttcacc gatacgtcgt catccctcta cgaccagaac | 780 |
| agaaatacag cgcatcagcc cccgaagctc ctggacttga attatggcgg gaccgacgat | 840 |
| gacgtcgacg acgcgacacg aatcaaagag aacctaacaa cgatgtacca gcagatggtg | 900 |
| tcgaaggcca cttctcacag actattctac ggagagccct atagcgcagg ggacgaacca | 960 |
| gatcctggcg ccgaaacat tgagaccact ccccataaca atattcacct tgggttggc | 1020 |
| gacccaaccc agacaaacgg ggaggacatg gggaccttt actctgcggg gagggatccg | 1080 |
| ctgtttttact ctcaccattc caacgtggac cgcatgtggt ctatatataa agataagttg | 1140 |
| ggaggtacgg acatagaaaa taccgactgg ctggacgcag agttcttatt ctacgacgag | 1200 |
| aaaaagaatc tcgtgcgcgt caaggttcgg gactcgctcg acactaaaaa actcgggtac | 1260 |

```
gtgtacgacg agaaagtccc aatcccatgg ctgaagtcga agccgacgct cgtaagtcga    1320
cgaataagag aaaggccaca gttcatcttc gatcttacta caacgttccc tgctacattg    1380
tcggatacaa tcagcgtcga ggtgacaagg ccgtctgcga cgaagcggac agctgcccag    1440
aagaaggcac atgacgaggt gctggtgatt aaggggattg agtttgccgg gaatgagcct    1500
gtgaagttcg acgtgtatgt gaacgatgac gcggaatcgc tggctgggaa agacaagtcg    1560
gagtttgctg ggagttttgt tcacgtgccg cataagcata agaaaaatat taagacgaac    1620
ctgcgactga gcattatgag cttgttggag gagttggatg cggagacaga cagcagtttg    1680
gtggtgactt tggtgccgaa agttgggaag gggccaatca ccatcggagg gtttagcatt    1740
gagctcatta atactaccta a                                              1761

<210> SEQ ID NO 46
<211> LENGTH: 200
<212> TYPE: DNA
<213> ORGANISM: Malus sp.

<400> SEQUENCE: 46
ccacatgtgg ccctgccgac aagccagacg ggtccaccat cgattgttgc ccacccatca      60
cgaccaccat catcgacttc aaactccccg accgaggccc actccgcaca aggatcgctg     120
cccaggacgt tgcaaaaaac cctgcatact tggctaaata caaaaaggcc atcgagctga     180
tgcgggcact tccagatgac                                                 200

<210> SEQ ID NO 47
<211> LENGTH: 1851
<212> TYPE: DNA
<213> ORGANISM: Malus sp.

<400> SEQUENCE: 47
atggcttcta tgtcagctcc actcgtcacc tccgccacaa gtatcatccc cacaacttcc      60
ctctcccctt tctcccaaaa gtatcaccga atatccttat ttggaaaccc taggcattcc     120
aatttacaag ctgtctcatg caaagccaca aataatagta gtgaccaaaa caaaaaccct     180
tccactagct ccaacgatca cgaccatgaa aaccttctc cagtaaacct agacagaaga     240
aatgtactta taggtctcgg aagcctatac ggtggagtgg ctggtcttgg cagcgacccc     300
ttcgctgttg caaagccagt gtcgccgcct gacctagcca aatgcggagc tgcggacttt     360
ccaagtggag cagtcccgac caactgttgc ccgccaacgt cccaaaaaat cgtagacttc     420
aaattcccct ccctaccaa actccgcgtc aggccggcag ctcacaccgt ggataaagcc     480
tacatcgaaa aatattcaaa agccatcgag ctcatgaaag ccctccccgga cgacgatccg     540 cgtagcttca cccagcaagc cgatatccac tgtgcctatt gcgacggcgc gtacgaccaa     600
gtcggcttcc ccaacctcga gctccaaatc catcaatgct ggcttttctt cccccttccat     660 cgttactacc tatacttcca cgaaagaatc ttggccaaac tcatatacga tccgacgttc     720
gcgttgccgt tttggaactg ggacgcgcca gctggcatgc aactccctgc cttgttcgct     780
aacccggact ctccgcttta cgacgagctt cgcgctgcca gccatcagcc gccgactctc     840
atcgatcttg acttcaacgg cacgatgaa acaatgtcca acgatgctca aatcgaagcc     900
aaccgcaaaa ttatgtatag gcagatggtt tccaactcca agaaaccgct gttgttctt     960 ggttctccct acagggctgg cactgaacca gatccagggg gcggttcaat cgaaacgacc    1020
ccacatggtc cggttcattt atggaccgga gataacacgc aacctaattt tgaagacatg    1080
```

| | |
|---|---|
| gggaatttttt actccgctgg aagggatcca atatttttt cgcaccattc gaatatagat | 1140 |
| cgaatgtgga atatttggaa aagtataggg actaaaaata aagatattaa cgataaggat | 1200 |
| tggttggata cggggttttt gttttatgac gagaatgctg agcttgttag ggtcacggtg | 1260 |
| agggacactc ttgataataa aaagctaggg tatacgtatg aagatgttga gattccatgg | 1320 |
| ctcaagtcta gaccgacgcc acgtcggaca aagcttgcga gaaaggcaaa ggcggctgga | 1380 |
| gtggcgaagg cggctggagt ggcgaaggcc gctgagacga cgtcatcagg gaaggtggtg | 1440 |
| gcgggtaaag attttccaat aaatttggag acgaagataa gtacggtggt gtcaaggccg | 1500 |
| aagccgaaga gaggagcaa gaaggagaaa gaggatgagg aggagatatt ggtgattcag | 1560 |
| gggattgagc ttgacaaaga tgtggctgtg aagtttgatg tgtatgtgaa tgacgtggac | 1620 |
| gatgaggatg cggcaccgag tggacccgac aagagcgagt ttgctgggag ttttgtgagt | 1680 |
| gtgccacata agcagaagga aaagagcaag agttgtttaa ggttggggtt aacggacctg | 1740 |
| ttggaggatt tgggtgctga agatgatgag agtgtggtgg tgactttagt gcccaggtac | 1800 |
| ggcgctcagg ctgttaagat cggtagcatc aaaattgagt ttcttgcttg a | 1851 |

<210> SEQ ID NO 48
<211> LENGTH: 200
<212> TYPE: DNA
<213> ORGANISM: Malus sp.

<400> SEQUENCE: 48

| | |
|---|---|
| aatgcggagc tgcggacttt ccaagtggag cagtcccgac caactgttgc ccgccaacgt | 60 |
| cccaaaaaat cgtagacttc aaattcccct cccctaccaa actccgcgtc aggccggcag | 120 |
| ctcacaccgt ggataaagcc tacatcgaaa atattcaaa agccatcgag ctcatgaaag | 180 |
| ccctcccgga cgacgatccg | 200 |

<210> SEQ ID NO 49
<211> LENGTH: 1782
<212> TYPE: DNA
<213> ORGANISM: Malus sp.

<400> SEQUENCE: 49

| | |
|---|---|
| atgacgtctc tttcacctcc ggtagtcacc acccccaccg ttcccaaccc cgccacaaaa | 60 |
| cctctctccc ccttctctca aaacaactcc caagtttccc tactcacaaa gcccaagcgt | 120 |
| tccttttgcac gtaaggtctc atgcaaagcc acaaacaatg accaaaatga tcaagcacag | 180 |
| tccaaactag acaggagaaa tgtgcttctt ggtcttggag gtctatacgg cgtggcgggt | 240 |
| atgggcacag acccgttcgc ttttgccaag cctatagccc caccagacgt atctaaatgt | 300 |
| ggtcctgcag acttgccaca gggtgcagtg cccaccaact gctgcccgcc gccttccaca | 360 |
| aaaatcattg actttaagct gcctgcccc gccaaactcc gcatcaggcc accggctcac | 420 |
| gccgttgacc aagcctacag ggacaaatac tacaaagcga tggagctcat gaaggccta | 480 |
| cccgacgacg acccacgtag cttcaagcaa caggcagccg tgcattgcgc ttattgcgac | 540 |
| ggcgcctatg accaagtcgg gttcccagaa ctcgagctcc aaatccacaa ctcatggctc | 600 |
| ttcttcccgt tccaccgtta ctacttgtac tttttcgaga agatcctagg caaactcatt | 660 |
| aacgacccga cattcgcttt gccgttctgg aactgggact cgccagccgg catgccactg | 720 |
| cccgcaattt acgctgatcc aaagtcccct ctctacgaca agctccgatc tgccaatcat | 780 |
| cagccccga ctctggtcga tctcgattac aacgggaccg aggacaatgt gtcaaaggaa | 840 |
| accacaatca acgccaatct caaaatcatg tacaggcaaa tggtgtccaa ttccaagaat | 900 |

-continued

```
gctaagttgt tctttgggaa cccgtacagg gcagggacg agcctgaccc tggtggcggc     960
tccatcgagg ggacaccaca cgcgccggtt catttatgga ccggtgacaa cacccagccc    1020
aactttgagg acatgggaa ttttttactcc gctggtcggg accccatatt ttttgcacac    1080
cattcgaatg tcgatcgaat gtggagtatt tggaaaactc ttggaggtaa agaactgat     1140 cttactgact cggactggtt ggactccgga ttcttgtttt acaacgagaa cgcagagtta    1200
gtccgagtca aggtcaggga ctgcttggag accaaaaatc ttgggtatgt ataccaagat    1260
gtggacattc cttggctcag ctccaagcca acaccgcgaa gggcgaaagt tgcattgagc    1320
aaagtagcga agaagctggg agttgcacac gcagctgttg cgtcgtccag caaggtggtg    1380
gcaggcactg agttcccgat aagtctgggg tcgaagataa gcacggtggt gaagagaccg    1440
aagcagaaga agaggagcaa gaaggccaag gaggatgagg aggagatatt ggtgattgag    1500
ggaatcgagt ttgacaggga cgtggctgtg aagtttgatg tgtatgtgaa tgacgtcgat    1560
gacttgccga gtgggcctga caagacgag tttgccggaa gctttgtaag tgtgccgcac     1620
agccacaagc acaagaagaa gatgaacact attttgaggt tagggttgac agatttgttg    1680
gaggaaattg aggcggagga cgatgacagc gtggtggtga ctttggtgcc caagttcggc    1740
gctgtcaaga ttggtggtat caagattgaa tttgcttctt ag                       1782

<210> SEQ ID NO 50
<211> LENGTH: 200
<212> TYPE: DNA
<213> ORGANISM: Malus sp.

<400> SEQUENCE: 50
aatgtggtcc tgcagacttg ccacagggtg cagtgcccac caactgctgc ccgccgcctt      60
ccacaaaaat cattgactttt aagctgcctg cccccgccaa actccgcatc aggccaccgg    120
ctcacgccgt tgaccaagcc tacagggaca aatactacaa agcgatggag ctcatgaagg    180
ccctacccga cgacgaccca                                                200

<210> SEQ ID NO 51
<211> LENGTH: 1768
<212> TYPE: DNA
<213> ORGANISM: Malus sp.

<400> SEQUENCE: 51
taccaccacc accatgggca cttactcttc tctgatcatc tccaccaatt ccttctctgc      60
cttcctccca aacaaatccc aactttcctt ctctggaaaa agcaagcact acattgcacg     120
tagatcatca atatattgca aagccacaaa ccctaattat aataatgagc aagatcaaca    180
acaatcttct aatttgttgg gaaaattgga caggagaaat gtcctaattg gcctgggcgg    240
cctctacggg gccaccaccc tcgccccaaa gccgttggcc tttgccaacc cgctggctcc    300
acccgaccta accaaatgta agccggccga aatcaccacc ggaggtgaaa ctgtggaatg    360
ctgtccaccg gtctccacaa agatcaaaac cttcactccg gaccagtcta tcccactgcg    420
gacgaggcct gccgcccatt tggtcacgga cgagtacttg gccaagttca agaaagctca    480
agccctcatg cgtgccttac ccgaagacga cccgcgtagc atggttcaac aagctaaagt    540
tcactgtgcc tactgcaatg gtgcttatcc acaagtaggg tttccggaca ttgacatcca    600
aatccacttc tcctggctttt ctttcctttt ccaccgcatg tacttgtatt tctacgagag    660
aatccttggc aagctcattg atgacccaac tttcgctctc ccatactgga attgggactc    720
```

```
tcctgacggt tttccaattc ccgacattta cacagataca acttccccac tctatgatca    780
gtaccgaaac gccgaccacc agcccccgt gctggtggat ctcagctacg gtggaaccga    840
tgatgacgtg gacgaccaga caagaataga tgagaatcta gccatcatgt accggcaaat    900
ggtttccggt gccaaaactc cccatctatt tttcggccat gagtacaggg caggagacac    960
aacaacaggg acttacgccg gcaccattga gaacagtcct cataataaca tccatctctg   1020
gtgcggtgac ccgaaccaga cccaccacga agacatgggg aacttctact ccgccggtcg   1080
gatccctgtt tacgcccacc attgcagtga ccgcatgtgg aacgtttgga aaaccctcgg   1140
aggcaagcgc aaggacccca ccgacaccga ttggcttgac gctgagtttc tgttctacga   1200
tgaaaacgcc gagcttgtga gctgtaaagt tcgggacagc ctcaaacctg agaaagatct   1260
tcgttatact tacgagcctg ttagtgttcc gtggctgttc accaagccaa ccgctcgtaa   1320
gccaaagagc aagacaaaag ccaaggtggg ggctacccag ctgacgacaa agttcccggc   1380
cacgtttgat tcgaagacga cggtggaggt ggcgaggccg aagccgcgga agaggaccaa   1440
gaaggagaag atcgacgagg aggaggtgct gatcattaag gacatcgaat tcgagagcaa   1500
cgaggcggtg aagttcgatg tgtttattaa tgatgatgct gagtcgctca gtaggaagga   1560
caaatccgag tttgctggga gttttgtgca cgtgccgcat aaccagaaga ctgggacgaa   1620
gaaaaagacg aacttaaaac tggggatcac ggacttgttg gaggatttgg gtgtggagga   1680
tgatagcagt gtgctggtga cgttggtgcc tagggtttcg aactcgccta tcaccattgg   1740
tgggtttaag atcgagtatt cttcttga                                      1768

<210> SEQ ID NO 52
<211> LENGTH: 200
<212> TYPE: DNA
<213> ORGANISM: Malus sp.

<400> SEQUENCE: 52
aatgtaagcc ggccgaaatc accaccggag gtgaaactgt ggaatgctgt ccaccggtct     60
ccacaaagat caaaaccttc actccggacc agtctatccc actgcggacg aggcctgccg    120
cccatttggt cacggacgag tacttggcca agttcaagaa agctcaagcc ctcatgcgtg    180
ccttacccga agacgacccg                                                200

<210> SEQ ID NO 53
<211> LENGTH: 148
<212> TYPE: DNA
<213> ORGANISM: plasmid element

<400> SEQUENCE: 53
ctgatgggct gcctgtatcg agtggtgatt ttgtgccgag ctgccggtcg gggagctgtt     60
ggctggctgg tggcaggata tattgtggtg taaacaaatt gacgcttaga caacttaata    120
acacattgcg gacgttttta atgtactg                                       148

<210> SEQ ID NO 54
<211> LENGTH: 345
<212> TYPE: DNA
<213> ORGANISM: plasmid element

<400> SEQUENCE: 54
aaactgaagg cgggaaacga caatctgatc atgagcggag aattaaggga gtcacgttat     60 gaccccccgcc gatgacgcgg gacaagccgt tttacgtttg gaactgacag aaccgcaacg    120
ttgaaggagc cactcagccg cgggtttctg gagtttaatg agctaagcac atacgtcaga    180
```

```
aaccattatt gcgcgttcaa aagtcgccta aggtcactat cagctagcaa atatttcttg      240
tcaaaaatgc tccactgacg ttccataaat tcccctcggt atccaattag agtctcatat      300
tcactctcaa tccaaataat ctgcaccgga tctggatcgt ttcgc                      345
```

<210> SEQ ID NO 55
<211> LENGTH: 795
<212> TYPE: DNA
<213> ORGANISM: plasmid element

<400> SEQUENCE: 55

```
atgattgaac aagatggatt gcacgcaggt tctccggccg cttgggtgga gaggctattc       60
ggctatgact gggcacaaca gacaatcggc tgctctgatg ccgccgtgtt ccggctgtca      120
gcgcaggggc gcccggttct ttttgtcaag accgacctgt ccggtgccct gaatgaactg      180
caggacgagg cagcgcggct atcgtggctg gccacgacgg gcgttccttg cgcagctgtg      240
ctcgacgttg tcactgaagc gggaagggac tggctgctat tgggcgaagt gccggggcag      300
gatctcctgt catctcacct tgctcctgcc gagaaagtat ccatcatggc tgatgcaatg      360
cggcggctgc atacgcttga tccggctacc tgcccattcg accaccaagc gaaacatcgc      420
atcgagcgag cacgtactcg gatggaagcc ggtcttgtcg atcaggatga tctggacgaa      480
gagcatcagg ggctcgcgcc agccgaactg ttcgccaggc tcaaggcgcg catgcccgac      540
ggcgatgatc tcgtcgtgac ccatggcgat gcctgcttgc cgaatatcat ggtggaaaat      600
ggccgctttt ctggattcat cgactgtggc cggctgggtg tggcggaccg ctatcaggac      660
atagcgttgg ctacccgtga tattgctgaa gagcttggcg gcgaatgggc tgaccgcttc      720
ctcgtgcttt acggtatcgc cgctcccgat tcgcagcgca tcgccttcta tcgccttctt      780
gacgagttct tctga                                                       795
```

<210> SEQ ID NO 56
<211> LENGTH: 163
<212> TYPE: DNA
<213> ORGANISM: plasmid element

<400> SEQUENCE: 56

```
gatcgttcaa acatttggca ataaagtttc ttaagattga atcctgttgc cggtcttgcg       60
atgattatca tataatttct gttgaattac gttaagcatg taataattaa catgtaatgc      120
atgacgttat ttatgagatg gttttttatg attagagtcc cgc                        163
```

<210> SEQ ID NO 57
<211> LENGTH: 651
<212> TYPE: DNA
<213> ORGANISM: plasmid element

<400> SEQUENCE: 57

```
tctagataag gatccacgaa gcttgcatgc ctgcaggtcc gatctgagac ttttcaacaa       60
agggtaatat cgggaaacct cctcggattc cattgcccag ctatctgtca cttcatcaaa      120
aggacagtag aaaaggaagg tggcacctac aaatgccatc attgcgataa aggaaaggct      180
atcgttcaag atgcctctgc cgacagtggt cccaaagatg gacccccacc cacgaggagc      240
atcgtggaaa aagaagacgt tccaaccacg tcttcaaagc aagtggattg atgtgatggt      300
ccgatctgag acttttcaac aaagggtaat atcgggaaac ctcctcggat tccattgccc      360
agctatctgt cacttcatca aaaggacagt agaaaaggaa ggtggcacct acaaatgcca      420
```

```
tcattgcgat aaaggaaagg ctatcgttca agatgcctct gccgacagtg gtcccaaaga      480
tggaccccca cccacgagga gcatcgtgga aaaagaagac gttccaacca cgtcttcaaa      540
gcaagtggat tgatgtgata tctccactga cgtaagggat gacgcacaat cccactatcc      600
ttcgcaagac ccttcctcta tataaggaag ttcatttcat ttggagagga g              651

<210> SEQ ID NO 58
<211> LENGTH: 1888
<212> TYPE: DNA
<213> ORGANISM: plasmid element

<400> SEQUENCE: 58
gagcccagtc acgacgttgt aaaacgacgg ccagtgagcg cgcgtaatac gactcctata      60
gggcgaattg gcattgggga cccaaccttc gccctcccct tctggaactg ggacgcacca     120
gctggaatgt acattcctga gattttcact gatacgtcgt catccctcta cgaccagtat     180
agaaatgcag cgcatcagcc cccgaagctc ttagacttta ataacagcgg gaccgacgat     240
aacgtcgacg acgcaaacacg aatcaaagag aacttaacaa caatgtacca gcagatggtg     300
tcaaaggcca cttctcacag actctttttt ggagagccct acagcgcagg ggacgaccca     360
agtcctggtg ccggaaacat tgagagcatt ccccataaca atattcactt ttggactggc     420
gacccaaccc agacaaatgg ggaagacatg gggaattttt actccgctgg aatcactagt     480
gaattcgatt tctttcccgt tccaccgtta ctacttatac ttccacgaaa gaatcttggc     540
caaactcata gacgatccga cgttcgcgtt gccgttttgg aactgggacg cgccagctgg     600
catgcaactc cctgccttgt tcgctaaccc ggactctccg ctttacgacg agcttcgcgc     660
tgccagccat cagccgccga ctctcatcga tcttgacttc aacggcacgg atgaaacaat     720
gtccaacgat gctcaaatcg aagccaacct caaaattatg tataggcaga tggttttccaa    780 ctccaagaaa ccgctgttgt ctttggttc gccctacagg gctggcactg aaccagatcc     840 aggggcggt tcaatcgaaa cgaccccaca tggtccggtt catttatggg ccggagataa     900
cacgcaacct aattttgaag acatggggaa tttttactcc gctggaatca ctagtgaatt     960
cgatatcttc ttcccgttcc accgttacta tctctacttt tcgagaaga tcctaggcaa    1020 actcattaac gacccgacat cgctttgcc gttctggaac tgggactcgc cagccggcat    1080
gccactgccc gcgatttacg ctgatccaaa gtcccctctc tacgacaagc tccgatctgc    1140
caatcatcag cccccgactc tggtcgatct cgattacaac gggaccgagg acaatgtgtc    1200
aaaggaaacc acaatcaacg ccaatctcaa aatcatgtac aggcaaatgg tgtccaattc    1260
caagaatgct aagttgttct ttgggaaccc gtacagggca ggggacaagc ccgaccctgg    1320
tggcggctcc atcgagggga caccacacgc gccggttcat ttatgaaccg gtgacaaacac    1380 ccagcccaac tttgaggata tggggaattt ttactccgct ggtatcaagc ttttcctttc    1440
caccgcatgt acttgtattt ctacgagaga atccttggca agctcattga tgacccaact    1500
ttcgctctcc catactggaa ttgggactct cctgacggtt ttccaattcc cgacatttac    1560
acagatacaa cttccccact ctatgatcag taccgaaacg ccgaccacca gccccccgtg    1620
ctggtggatc tcagctacgg tggaaccgat gatgacgtgg acgaccagac aagaatagat    1680
gagaacctag ccatcatgta ccggcaagtg gtttccggtg ccaaaactcc ccatctattt    1740
ttcggccatg agtacagggc aggagacaca acaacaggga cctacgccgg caccattgag    1800
aacagtcctc ataataacat ccatctctgg tgcggtgacc cgaaccagac ccaccacgaa    1860
gacatgggta acttctactc cgcggctc                                        1888
```

<210> SEQ ID NO 59
<211> LENGTH: 253
<212> TYPE: DNA
<213> ORGANISM: plasmid element

<400> SEQUENCE: 59

```
gatcgttcaa acatttggca ataaagtttc ttaagattga atcctgttgc cggtcttgcg      60
atgattatca tataatttct gttgaattac gttaagcatg taataattaa catgtaatgc     120
atgacgttat ttatgagatg ggttttatg attagagtcc cgcaattata catttaatac      180
gcgatagaaa acaaaatata gcgcgcaaac taggataaat tatcgcgcgc ggtgtcatct     240
atgttactag atc                                                        253
```

<210> SEQ ID NO 60
<211> LENGTH: 136
<212> TYPE: DNA
<213> ORGANISM: plasmid element

<400> SEQUENCE: 60

```
aaactatcag tgtttgacag gatatattgg cgggtaaacc taagagaaaa gagcgtttat      60
tagaataatc ggatatttaa aagggcgtga aaaggtttat ccgttcgtcc atttgtatgt     120
gcatgccaac cacagg                                                     136
```

<210> SEQ ID NO 61
<211> LENGTH: 163
<212> TYPE: DNA
<213> ORGANISM: plasmid element

<400> SEQUENCE: 61

```
tcctgtggtt ggcatgcaca tacaaatgga cgaacggata aacctttca cgcccttta       60
aatatccgat tattctaata aacgctcttt tctcttaggt ttacccgcca atatatcctg     120
tcaaacactg atagtttaaa ctgaaggcgg gaaacgacaa tct                       163
```

<210> SEQ ID NO 62
<211> LENGTH: 1612
<212> TYPE: DNA
<213> ORGANISM: plasmid element

<400> SEQUENCE: 62

```
ggcgcgccaa gctacttacc tcttatataa aaagaaaaa gtgtttctaa tatatactca       60
atttaaataa aatattttca atcaaattta gataacaaat acttatcaat atgaggtcaa     120
taacaataaa aaataatgt aaaaaaaagg agcaatacat aatataagaa aaagattaa      180
agtgcgatta tcaacgagta ttataccta atttgctaat atttaaactc ttatatttaa     240
ggttatgttc acaatatact taaaaagcgc tatattagag catatattaa ttaataaaaa     300
agaaaatgct aaatgatcaa aaaattaga tagaaaatta agaaaattat aatatttttt     360
tattttaaaa taaattgata tattctttat tttttagtta aaatgtatta agttaaaag    420
aataaaaata ttttaaaaaa taaaataaca taaataaaat atcattctaa ttaaattcag     480
accaaatttt ttccccagat tttggccaat acctaaaata aaattaagtt atttttagta     540
tatttttta cattgaccta cattttctca gttttttcta aaggagcgtg taagcgtcaa     600
cctcattctc ctaattttcc ccaccacata aataaaaga aacggtagct tttgcgtgtt     660
gttttgctac actacacctc attattacac gtgtcatcat ataattggct aaccctatga     720
```

```
ggcggtttcg tctagagtcg gccatgccat ctataaaagg aacctttctg cacctcattt      780
tttcatcttc tatctgactt ctattataat ttctctcaat tgcctttaaa tttctctttc      840
aaggttagaa atcttctcta ttttttggtt tttgtctgtt tagattctcg aattagctaa      900
gcaggtgctg ttaaagccct aaaatttgag ttttttttcc gttgttttga tgaaaaagcc      960
cctaatttga gttttttttcc gtcgatttga tgccaaaggt ttaaaattag agttttttcg    1020
tcggtttgat tctaaaggcc caaaatgtgg ggttttccgg gtgatttgat gataatgccc     1080
tagaatttga gttttttttat ggtggtttga tgaaaaaggt cttgaatttg attttttttt    1140
tccggttgat ttgatgaaaa agccctagaa tttgtgattt ttcgtcggtt tgattctaaa    1200
gccctaaaat ttgaggtttt ccggttgttt tgatgaaaaa gccctaaaat ttgagttttt    1260
tccccgtgtt ttagattgtt tggttttaat tctcgaatca gttaatcagg gagtgtgaaa    1320
agccctataa tttgagtttt tttccgttgt tctgattgtt gtttttatga ctttgcagat    1380
gcagatcttt gtgaaaactc tcaccggaaa gaccatcacc ctagaggtgg aaagttctga    1440
tacaatcgac aacgttaagg ctaagattca ggataaggaa gggattcccc cggatcagca    1500
aaggcttatc ttcgccggaa agcagttgga ggacggacgt actctagctg attacaacat    1560
ccagaaggag tctacccctcc atttggttct ccgtctacgt ggtggtggat cc            1612

<210> SEQ ID NO 63
<211> LENGTH: 1771
<212> TYPE: DNA
<213> ORGANISM: plasmid element

<400> SEQUENCE: 63
ccacatgtgg ccctgccgac aagccagacg ggtccaccat cgattgttgc ccacccatca      60
cgaccaccat catcgacttc aaactccccg accgaggccc actccgcaca aggatcgctg     120
cccaggacgt tgcaaaaaac cctgcatact tggctaaata caaaaaggcc atcgagctga     180
tgcgggcact tccagatgac aatgcggagc tgccggacttt ccaagtggag cagtcccgac     240
caactgttgc ccgccaacgt cccaaaaaat cgtagacttc aaattcccct cccctaccaa     300
actccgcgtc aggccggcag ctcacaccgt ggataaagcc tacatcgaaa aatattcaaa      360
agccatcgag ctcatgaaag ccctccccgga cgacgatccg aatgtggtcc tgcagacttg     420
ccacagggtg cagtgcccac caactgctgc ccgccgcctt ccacaaaaat cattgacttt     480
aagctgcctg cccccgccaa actccgcatc aggccaccgg ctcacgccgt tgaccaagcc     540
tacagggaca aatactacaa agcgatggag ctcatgaagg ccctacccga cgacgaccca     600
aatgtaagcc ggccgaaatc accaccggag gtgaaactgt ggaatgctgt ccaccggtct     660
ccacaaagat caaaaccttc actccggacc agtctatccc actgcggacg aggcctgccg     720
cccatttggt cacggacgag tacttggcca agttcaagaa agctcaagcc ctcatgcgtg     780
ccttacccga agacgacccg gtcacactaa ttacaacaaa cttaattaat ttcccgctga     840
tttggattta accaagttag ctaaagcacc ttgcggcccc attgcaccta agtttggatc     900
tcggttttgt agactagatt gtattagaat atcatattga gggcttgtat atattttgaa     960
caatatttca gcgggtcgtc ttcgggtaag gcacgcatga gggcttgagc tttcttgaac    1020
ttggccaagt actcgtccgt gaccaaatgg gcggcaggcc tcgtccgcag tgggatagac    1080
tggtccggag tgaaggtttt gatctttgtg gagaccggtg gacagcattc cacagtttca    1140
cctccggtgg tgatttcggc cggcttacat ttgggtcgtc gtcgggtagg gccttcatga    1200
gctccatcgc tttgtagtat ttgtccctgt aggcttggtc aacggcgtga gccggtggcc    1260
```

```
tgatgcggag tttggcgggg gcaggcagct taaagtcaat gattttttgtg gaaggcggcg   1320 ggcagcagtt ggtgggcact gcaccctgtg gcaagtctgc aggaccacat tcggatcgtc   1380
gtccgggagg gctttcatga gctcgatggc ttttgaatat ttttcgatgt aggctttatc   1440
cacggtgtga gctgccggcc tgacgcgag tttggtaggg gagggaatt tgaagtctac     1500 gattttttgg gacgttggcg ggcaacagtt ggtcgggact gctccacttg aaagtccgc    1560 agctccgcat tgtcatctgg aagtgcccgc atcagctcga tggcctttt gtatttagcc    1620 aagtatgcag gttttttgc aacgtcctgg gcagcgatcc ttgtgcggag tgggcctcgg    1680
tcggggagtt tgaagtcgat gatggtggtc gtgatgggtg ggcaacaatc gatggtggac   1740
ccgtctggct tgtcggcagg gccacatgtg g                                  1771
```

```
<210> SEQ ID NO 64
<211> LENGTH: 361
<212> TYPE: DNA
<213> ORGANISM: plasmid element

<400> SEQUENCE: 64
ctagttttta atgtttagca aatgtcctat cagttttctc ttttttgtcga acggtaattt   60 agagtttttt ttgctatatg gattttcgtt tttgatgtat gtgacaaccc tcgggattgt   120
tgatttattt caaaactaag agttttttgct tattgttctc gtctattttg gatatcaatc   180
ttagttttat atcttttcta gttctctacg tgttaaatgt tcaacacact agcaatttgg   240
ctgcagcgta tggattatgg aactatcaag tctgtgggat cgataaatat gcttctcagg   300
aatttgagat tttacagtct ttatgctcat tgggttgagt ataatatagt aaaaaaatag   360
g                                                                   361
```

```
<210> SEQ ID NO 65
<211> LENGTH: 161
<212> TYPE: DNA
<213> ORGANISM: plasmid element

<400> SEQUENCE: 65
aaaaccaccc cagtacatta aaaacgtccg caatgtgtta ttaagttgtc taagcgtcaa   60
tttgtttaca ccacaatata tcctgccacc agccagccaa cagctccccg accggcagct   120
cggcacaaaa tcaccactcg atacaggcag cccatcagtc c                       161
```

```
<210> SEQ ID NO 66
<211> LENGTH: 457
<212> TYPE: DNA
<213> ORGANISM: Pyrus sp.

<400> SEQUENCE: 66
tcttcttccc gttccaccgt tactacttgt acttttcga aagatccta ggcaaactca     60 ttaacgaccc gacattcgct atgccgttct ggaactggga ctcgccagcc ggcatgccac    120
tgcccgcgat ttacgctaat ccaaggtccc ctctctacga caagttccga tctgccaaac    180
atcagccgcc aactttggtc gatctcgatt acaacgggac cgaggacaac gtgtcaaagg    240
aaaccacaat caacgccaat ctcaaaatca tgtacaggca aatggtgtcc aattccaaga    300
atgctcggtt gttctttggg aacccgtaca gggcagggga cgagcctgac cctggtggcg    360
gctccatcga gggcacccca cacggccggt tcattatg gaccggtgac aacacccagc     420
ccaactttga ggacatgggg aattttttact ccgctgg                            457
```

<210> SEQ ID NO 67
<211> LENGTH: 458
<212> TYPE: DNA
<213> ORGANISM: Pyrus sp.

<400> SEQUENCE: 67

```
ttcttcttcc cgttccaccg ttactattta tacttctacg aaagaatctt agccaaactc      60
atcgacgatc tgatgttcgc gttaccgttt tggaactggg acgcgccagc tggcatgcaa     120
ctccctgcct tgtacgccaa ccccgactct cccctatacg acgagctccg cgcttcaagc     180
catcagccgc cgactctcat cgatctggac ttcaacggta cggatgaaac aatgtccaac     240
gacgtttaaa tcgacgccaa cctcaaaatc atgtataggc agatggtttc caactccaag     300
aaaccgctgt tgttctttgg ttcgcctttg agagctggca ctgaaccaga tccagggtcc     360
ggttcaatcg aaggtacccc acatggtcca gttcataggt ggaccggaga taacacgcaa     420
cctaattttg aggacatggg gaattttac tccgctgg                              458
```

<210> SEQ ID NO 68
<211> LENGTH: 456
<212> TYPE: DNA
<213> ORGANISM: Pyrus sp.

<400> SEQUENCE: 68

```
cttcttccca ttccaccgtt actatctata cttctacgaa agaatcttgg gcaaactcat      60
aggcgatccg acgttcgcgt tgccgttttg gaactacgac gcgccagctg gcatgcaaat     120
ccctgccttg tacactaacc cggactctcc gctttacgac aagttccgcg ctgccagcca     180
tcagccgccg actctcatcg atcttgactt caacggcacg gatgaaacaa tttccaacga     240
tgctcgaatc gacgccaacc tcaaactcat gtataggcag atgatttcca acgccaagaa     300
acagctgttg ttctttggtg cgcccttgag ggctggcact gaaccagatc cagggcaggg     360
ttcaatcgaa acggcccac atggtccggt tcatttatgg accggagata acacgcaacc     420
taatattgaa gacatgggga atttttactc cgctgg                               456
```

<210> SEQ ID NO 69
<211> LENGTH: 34
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 69

```
tcttcttccc nttccaccgt tactayytnt aytt                                  34
```

<210> SEQ ID NO 70
<211> LENGTH: 29
<212> TYPE: DNA
<213> ORGANISM: Artificial
<220> FEATURE:
<223> OTHER INFORMATION: Primer

<400> SEQUENCE: 70

```
ccagcggagt aaaaattccc catrtcytc                                        29
```

<210> SEQ ID NO 71
<211> LENGTH: 20
<212> TYPE: DNA
<213> ORGANISM: Artificial
<220> FEATURE:
<223> OTHER INFORMATION: Primer

<400> SEQUENCE: 71
gcgttgattg tggtttcctt                                          20

<210> SEQ ID NO 72
<211> LENGTH: 20
<212> TYPE: DNA
<213> ORGANISM: Artificial
<220> FEATURE:
<223> OTHER INFORMATION: Primer

<400> SEQUENCE: 72
tcccgttcca ccgttactac                                          20

<210> SEQ ID NO 73
<211> LENGTH: 24
<212> TYPE: DNA
<213> ORGANISM: Artificial
<220> FEATURE:
<223> OTHER INFORMATION: Primer

<400> SEQUENCE: 73
gccgtcgacc gacgacgacc cacg                                     24

<210> SEQ ID NO 74
<211> LENGTH: 27
<212> TYPE: DNA
<213> ORGANISM: Artificial
<220> FEATURE:
<223> OTHER INFORMATION: Primer

<400> SEQUENCE: 74
gccgtcgaca gctgagccca aggaatg                                  27

<210> SEQ ID NO 75
<211> LENGTH: 20
<212> TYPE: DNA
<213> ORGANISM: Artificial
<220> FEATURE:
<223> OTHER INFORMATION: Primer

<400> SEQUENCE: 75
acaatcccac tatccttcgc                                          20

<210> SEQ ID NO 76
<211> LENGTH: 19
<212> TYPE: DNA
<213> ORGANISM: Artificial
<220> FEATURE:
<223> OTHER INFORMATION: Primer

<400> SEQUENCE: 76
cctggatctg gttcagtgc                                           19

<210> SEQ ID NO 77
<211> LENGTH: 18
<212> TYPE: DNA
<213> ORGANISM: Artificial
<220> FEATURE:

<223> OTHER INFORMATION: Primer

<400> SEQUENCE: 77
ttcgctaacc cggactct                                                 18

<210> SEQ ID NO 78
<211> LENGTH: 22
<212> TYPE: DNA
<213> ORGANISM: Artificial
<220> FEATURE:
<223> OTHER INFORMATION: Primer

<400> SEQUENCE: 78
cgggttccca agaacaact ta                                             22

<210> SEQ ID NO 79
<211> LENGTH: 27
<212> TYPE: DNA
<213> ORGANISM: Artificial
<220> FEATURE:
<223> OTHER INFORMATION: Primer

<400> SEQUENCE: 79
gccaagcttt tcctttccac cgcatgt                                       27

<210> SEQ ID NO 80
<211> LENGTH: 20
<212> TYPE: DNA
<213> ORGANISM: Artificial
<220> FEATURE:
<223> OTHER INFORMATION: Primer

<400> SEQUENCE: 80
tatgataatc atcgcaagac                                               20

<210> SEQ ID NO 81
<211> LENGTH: 19
<212> TYPE: DNA
<213> ORGANISM: Artificial
<220> FEATURE:
<223> OTHER INFORMATION: Primer

<400> SEQUENCE: 81
cctgcttgcc gaatatcat                                                19

<210> SEQ ID NO 82
<211> LENGTH: 20
<212> TYPE: DNA
<213> ORGANISM: Artificial
<220> FEATURE:
<223> OTHER INFORMATION: Primer

<400> SEQUENCE: 82
gaaatctcgt gatggcaggt                                               20

<210> SEQ ID NO 83
<211> LENGTH: 22
<212> TYPE: DNA
<213> ORGANISM: Artificial
<220> FEATURE:
<223> OTHER INFORMATION: Primer

<400> SEQUENCE: 83
gaacaagatg gattgcacgc ag                                            22

```
<210> SEQ ID NO 84
<211> LENGTH: 22
<212> TYPE: DNA
<213> ORGANISM: Artificial
<220> FEATURE:
<223> OTHER INFORMATION: Primer

<400> SEQUENCE: 84
ctgatgctct tcgtccagat ca                                              22

<210> SEQ ID NO 85
<211> LENGTH: 20
<212> TYPE: DNA
<213> ORGANISM: Artificial
<220> FEATURE:
<223> OTHER INFORMATION: Primer

<400> SEQUENCE: 85
gcgttgattg tggtttcctt                                                 20

<210> SEQ ID NO 86
<211> LENGTH: 20
<212> TYPE: DNA
<213> ORGANISM: Artificial
<220> FEATURE:
<223> OTHER INFORMATION: Primer

<400> SEQUENCE: 86
tcccgttcca ccgttactac                                                 20

<210> SEQ ID NO 87
<211> LENGTH: 20
<212> TYPE: DNA
<213> ORGANISM: Artificial
<220> FEATURE:
<223> OTHER INFORMATION: Primer

<400> SEQUENCE: 87
agggagtgtg aaaagcccta                                                 20

<210> SEQ ID NO 88
<211> LENGTH: 20
<212> TYPE: DNA
<213> ORGANISM: Artificial
<220> FEATURE:
<223> OTHER INFORMATION: Primer

<400> SEQUENCE: 88
ggggagtttg aagtcgatga                                                 20

<210> SEQ ID NO 89
<211> LENGTH: 20
<212> TYPE: DNA
<213> ORGANISM: Artificial
<220> FEATURE:
<223> OTHER INFORMATION: Primer

<400> SEQUENCE: 89
gaaagctgcc tgttccaaag                                                 20

<210> SEQ ID NO 90
<211> LENGTH: 20
<212> TYPE: DNA
<213> ORGANISM: Artificial
<220> FEATURE:
<223> OTHER INFORMATION: Primer
```

<400> SEQUENCE: 90
gaaagagcct gatgcactcc                                                      20

<210> SEQ ID NO 91
<211> LENGTH: 20
<212> TYPE: DNA
<213> ORGANISM: Artificial
<220> FEATURE:
<223> OTHER INFORMATION: Primer

<400> SEQUENCE: 91
cggctccgtc gatactatgt                                                      20

<210> SEQ ID NO 92
<211> LENGTH: 20
<212> TYPE: DNA
<213> ORGANISM: Artificial
<220> FEATURE:
<223> OTHER INFORMATION: Primer

<400> SEQUENCE: 92
gcagcggtat ttttcgatca                                                      20

<210> SEQ ID NO 93
<211> LENGTH: 20
<212> TYPE: DNA
<213> ORGANISM: Artificial
<220> FEATURE:
<223> OTHER INFORMATION: Primer

<400> SEQUENCE: 93
gggactcgct cgacactaaa                                                      20

<210> SEQ ID NO 94
<211> LENGTH: 20
<212> TYPE: DNA
<213> ORGANISM: Artificial
<220> FEATURE:
<223> OTHER INFORMATION: Primer

<400> SEQUENCE: 94
tcacctcgac gctgattgta                                                      20

<210> SEQ ID NO 95
<211> LENGTH: 20
<212> TYPE: DNA
<213> ORGANISM: Artificial
<220> FEATURE:
<223> OTHER INFORMATION: Primer

<400> SEQUENCE: 95
gggactcgct cgacactaaa                                                      20

<210> SEQ ID NO 96
<211> LENGTH: 20
<212> TYPE: DNA
<213> ORGANISM: Artificial
<220> FEATURE:
<223> OTHER INFORMATION: Primer

<400> SEQUENCE: 96
tcgtcatgtg ccttcttctg                                                      20

<210> SEQ ID NO 97
<211> LENGTH: 20

```
<212> TYPE: DNA
<213> ORGANISM: Artificial
<220> FEATURE:
<223> OTHER INFORMATION: Primer

<400> SEQUENCE: 97
gtgaatgacg tggacgatga                                              20

<210> SEQ ID NO 98
<211> LENGTH: 20
<212> TYPE: DNA
<213> ORGANISM: Artificial
<220> FEATURE:
<223> OTHER INFORMATION: Primer

<400> SEQUENCE: 98
catcatcttc agcacccaaa                                              20

<210> SEQ ID NO 99
<211> LENGTH: 20
<212> TYPE: DNA
<213> ORGANISM: Artificial
<220> FEATURE:
<223> OTHER INFORMATION: Primer

<400> SEQUENCE: 99
catcttcagc acccaaatcc                                              20

<210> SEQ ID NO 100
<211> LENGTH: 20
<212> TYPE: DNA
<213> ORGANISM: Artificial
<220> FEATURE:
<223> OTHER INFORMATION: Primer

<400> SEQUENCE: 100
tgaatgacgt ggacgatgag                                              20

<210> SEQ ID NO 101
<211> LENGTH: 20
<212> TYPE: DNA
<213> ORGANISM: Artificial
<220> FEATURE:
<223> OTHER INFORMATION: Primer

<400> SEQUENCE: 101
agtttgccgg aagctttgta                                              20

<210> SEQ ID NO 102
<211> LENGTH: 20
<212> TYPE: DNA
<213> ORGANISM: Artificial
<220> FEATURE:
<223> OTHER INFORMATION: Primer

<400> SEQUENCE: 102
tgatgcctgg gttgacataa                                              20

<210> SEQ ID NO 103
<211> LENGTH: 20
<212> TYPE: DNA
<213> ORGANISM: Artificial
<220> FEATURE:
<223> OTHER INFORMATION: Primer

<400> SEQUENCE: 103
```

```
agtttgccgg aagctttgta                                       20

<210> SEQ ID NO 104
<211> LENGTH: 20
<212> TYPE: DNA
<213> ORGANISM: Artificial
<220> FEATURE:
<223> OTHER INFORMATION: Primer

<400> SEQUENCE: 104
ttgatgcctg ggttgacata                                       20

<210> SEQ ID NO 105
<211> LENGTH: 20
<212> TYPE: DNA
<213> ORGANISM: Artificial
<220> FEATURE:
<223> OTHER INFORMATION: Primer

<400> SEQUENCE: 105
tagtgttccg tggctgttca                                       20

<210> SEQ ID NO 106
<211> LENGTH: 20
<212> TYPE: DNA
<213> ORGANISM: Artificial
<220> FEATURE:
<223> OTHER INFORMATION: Primer

<400> SEQUENCE: 106
tcctcctcgt cgatcttctc                                       20

<210> SEQ ID NO 107
<211> LENGTH: 20
<212> TYPE: DNA
<213> ORGANISM: Artificial
<220> FEATURE:
<223> OTHER INFORMATION: Primer

<400> SEQUENCE: 107
tagtgttccg tggctgttca                                       20

<210> SEQ ID NO 108
<211> LENGTH: 20
<212> TYPE: DNA
<213> ORGANISM: Artificial
<220> FEATURE:
<223> OTHER INFORMATION: Primer

<400> SEQUENCE: 108
ctgagcgact cagcatcatc                                       20
```

GENETICALLY MODIFIED REDUCED-BROWNING FRUIT-PRODUCING PLANT AND PRODUCED FRUIT THEREOF, AND METHOD OF OBTAINING SUCH

CROSS-REFERENCE TO RELATED APPLICATIONS

This application is a continuation of U.S. patent application Ser. No. 16/248,057, filed Jan. 15, 2019, which is a continuation of U.S. patent application Ser. No. 15/404,236, filed Jan. 12, 2017, now U.S. Pat. No. 10,227,602, issued Mar. 12, 2019; which is a continuation of U.S. patent application Ser. No. 14/049,952, filed Oct. 9, 2013, now U.S. Pat. No. 9,580,723, issued Feb. 28, 2017; which is a continuation of U.S. patent application Ser. No. 12/919,735, filed Aug. 26, 2010, now U.S. Pat. No. 8,563,805, issued Oct. 22, 2013, which is a national stage application under 35 U.S.C. § 371 of International Patent Application No. PCT/CA2009/000212, filed Feb. 26, 2009, which claims the benefit of and priority from U.S. Provisional Patent Application No. 61/031,821, filed Feb. 27, 2008, which are hereby incorporated by reference in their entirety.

FIELD OF THE INVENTION

This invention relates to a genetically modified fruit-producing plant, plant cell, seed, seedling, progeny thereof, or produced fruit thereof, which plant produces a reduced-browning fruit. This invention further relates to a method of obtaining such.

BACKGROUND OF THE INVENTION

Browning of Fruit

Browning of apples and other fruit from damage, such as cuts, bruises, slicing, juicing, cell death, or any other form of damage that disrupts cell membranes, is believed to be caused by the enzymatic reaction catalyzed by Polyphenol Oxidase (PPO). The brown pigment is a polymer formed from the non-enzymatic condensation of quinones, with lesser amounts of amino acids and proteins, into lignin-like compounds. The quinones are synthesized from di-phenols in the enzymatic reaction catalyzed by PPO (Whitaker and Lee, 1995). Most PPOs also have monophenolase activity and convert monophenols to di-phenols (Mar-Sojo et al., 1998). The cause of browning has been understood for some time, yet the solution to reducing browning remains an on-going problem for industry.

Browning reduces quality by causing detrimental flavor and nutritional changes (Eskin, 1990). With the explosive growth of the fresh-cut produce sector, lost opportunities have become more evident given that, for instance, browning limits the use of apple and other fruits in commercial fresh cut produce products. It is thus a significant problem limiting the widespread introduction of fresh cut produce products such as prepared apple slices.

Browning is also a major consideration in the manufacture of juice, and brown bruises are a significant cause of reduced grade for growers and of lost value for institutional processors (restaurants, hospitals, etc.) and retailers, who have to accept these losses or try to minimize them through the implementation of improved handling practices.

Approaches to Control Browning

Various approaches to control vegetable and fruit browning have been described and resulted in mixed success, due to a variety of reasons, including cost and amount of handling. For a general review of strategies for reducing fruit browning, see e.g.: Friedman (1991), Iyengar and McEvily, (1992), Whitaker and Lee (1995), McEvily et al. (1992), Sapers (1993), Weemaes (1998), Martinez and Whitaker (1995), and Brushett (2006).

U.S. Pat. No. 5,939,117 (Cheng et al.) and U.S. Pat. No. 5,925,395 (Cheng) describes an anti-browning/anti-oxidant dip treatment. Fresh-cut apple slices which have been treated with an anti-browning/anti-oxidant dip, are described as having reduced browning. However, the off-flavoring and high cost of the anti-browning/anti-oxidant dip solution has limited their commercial success. Furthermore, anti-oxidant dip solutions do not deal effectively with secondary browning that results from the cutting knife and skin deformation prior to cutting and other secondary browning reactions, which lead to a thin brown line under the skin on the apple slice and other market detracting attributes.

Other approaches to control browning have been described, including but not limited to, cultivation in low oxygen atmosphere and low temperature (Heimdal et al., 1995); treatment with calcium ascorbate, glutathione, cysteine and citrate (Jiang et al., 1998); treatment with sulfites and sub optimal pH and high-pressure carbon dioxide (Chen et al., 1992); treatment of fresh cut apple slices with natural products (Buta et al., 1999); and a treatment with a 10% solution of honey (Osmianski and Lee, 1990).

Murata et al. (2000 and 2001) report that by suppression of a single PPO gene homologous to the apple PPO gene APO5 they obtained apple shoots and callus having reduced PPO activity which exhibit low browning potential in vitro. However, these references do not disclose a reduced browning fruit-producing plant or reduced-browning apple nor whether suppression of a single PPO gene homologous to APO5 would be sufficient to obtain such a reduced-browning fruit-producing plant or reduced-browning apple.

SUMMARY OF THE INVENTION

In one aspect, the invention relates to a genetically modified fruit-producing plant, said plant having sufficiently reduced total Polyphenol Oxidase (PPO) activity relative to a wild type of said plant to reduce browning in the fruit of said plant relative to said wild type, wherein the reduced total PPO activity results from a reduction in activity of at least two PPO isoenzymes in said plant relative to said wild type, or a cell, seed, seedling, part, tissue, cell, fruit or progeny of said plant.

In another aspect, the invention relates to a method for producing a genetically modified fruit-producing plant, said plant having sufficiently reduced total Polyphenol Oxidase (PPO) activity relative to a wild type of said plant to reduce browning in the fruit of said plant relative to said wild type, said method comprising reducing the activity of at least two PPO isoenzymes in said plant relative to said wild type.

In another aspect, the invention relates to a nucleic acid construct comprising: a promoter; a first nucleic acid sequence comprising at least 200 contiguous nucleotides of a nucleic acid molecule encoding a polypeptide of SEQ ID NO: 19; a second nucleic acid sequence comprising at least 200 contiguous nucleotides of a nucleic acid molecule encoding a polypeptide of SEQ ID NO: 21; a third nucleic acid sequence comprising at least 200 contiguous nucleotides of a nucleic acid molecule encoding a polypeptide of SEQ ID NO: 23; and a fourth nucleic acid sequence comprising at least 200 contiguous nucleotides of a nucleic acid molecule set forth in SEQ ID NO: 24 and encoding a polypeptide of SEQ ID NO: 25; wherein the first, second, third and fourth nucleic acid molecules are operably linked to said promoter in sense orientation.

In another aspect, the invention relates to a nucleic acid construct encoding an mRNA capable of forming a stem loop structure, the nucleic acid construct comprising, from 5' to 3': a promoter, a first set of nucleic acid sequences, a spacer, and a second set of nucleic acid sequences, said first set of nucleic acid sequences comprising: a first nucleic acid sequence comprising at least 200 contiguous nucleotides of a nucleic acid molecule encoding a polypeptide of SEQ ID NO: 19; a second nucleic acid sequence comprising at least 200 contiguous nucleotides of a nucleic acid molecule encoding a polypeptide of SEQ ID NO: 21; a third nucleic acid sequence comprising at least 200 contiguous nucleotides of a nucleic acid molecule encoding a polypeptide of SEQ ID NO: 23; and a fourth nucleic acid sequence comprising at least 200 contiguous nucleotides of a nucleic acid molecule encoding a polypeptide of SEQ ID NO: 25; wherein the first, second, third and fourth nucleic acid sequences are operably linked to said promoter in sense orientation; said second set of nucleic acid sequences comprising: said first, second, third and fourth nucleic acid sequences operably linked to said promoter in anti-sense orientation; wherein the first and second sets of nucleic acid molecules are separated by the spacer.

In another aspect, the invention relates to a genetically modified plant cell transformed with the nucleic acid construct as described above.

In another aspect, the invention relates to a genetically modified plant comprising the genetically modified plant cell as described above.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention:

FIG. 1A-1D show nucleic acid sequence and amino acid sequence alignments between AP14 [SEQ ID NO:2 and 4] and PGO3 [SEQ ID NO:1 and 3], with Clustal W™ (1.83).

FIG. 2A-2E show cloned novel partial sequences and/or nucleic acid sequence fragments of known apple PPO isoenzyme encoding sequences: APO5 [SEQ ID NO:5]; PPO3 [SEQ ID NO:6]; PPO7 [SEQ ID NO:7]; PPO2 [SEQ ID NO:8]; PPOJ [SEQ ID NO:9]; GPO3 [SEQ ID NO:10]; AP14 [SEQ ID NO:11]; pSR7 [SEQ ID NO:12]; APO3 5' [SEQ ID NO:13]; APO9 5' [SEQ ID NO:14]; APO3 3' [SEQ ID NO:15]; APO9 3' [SEQ ID NO:16]; and pSR8 [SEQ ID NO:17].

FIG. 3 shows sequence identity (%) obtained through a multiple nucleic acid sequence alignments of apple PPO encoding sequences with Clustal W™ (1.82).

FIG. 4A-4D show nucleic acid sequence and amino acid sequence of four apple PPO encoding sequences: PPO2 [SEQ ID NO:18] PPO2 (translation) [SEQ ID NO:19]; GPO3 [SEQ ID NO:20]; GPO3 (translation) [SEQ ID NO:21]; APO5 [SEQ ID NO:22]; APO5 (translation) [SEQ ID NO:23]; pSR7 [SEQ ID NO:24]; and pSR7 (translation) [SEQ ID NO:25].

FIG. 5A-5B: A. shows nucleic acid fragment of four PPO encoding sequences used for constructing PGAS: PPO2 [SEQ ID NO:26]; GPO3 [SEQ ID NO:27]; APO5 [SEQ ID NO:28]; and PSR7 [SEQ ID NO:29]. B. shows the nucleic acid fragments used in the construction of PGAS2: PPO2 [SEQ ID NO:30]; GPO3 [SEQ ID NO:31]; APO5 [SEQ ID NO:32]; PSR7 [SEQ ID NO:33]; and ACO2 [SEQ ID NO:34].

FIG. 6A-6B. A. shows the nucleic acid sequence of the PGAS transgene fragment in the sense orientation [SEQ ID NO:35]. B. shows the nucleic acid sequence of the PGAS2 transgene fragment [SEQ ID NO:36].

FIG. 7A-7X. A-L show nucleic acid sequence alignment between the apple PPO isoenzyme encoding genomic sequences and the corresponding nucleic acid sequences used for constructing PGAS: PPO2 [SEQ ID NO:37] and PPO2_PGAS [SEQ ID NO:38]; GPO3 [SEQ ID NO:39] and GPO3_PGAS [SEQ ID NO:40]; APO5 [SEQ ID NO:41] and APO5_PGAS [SEQ ID NO:42]; pSR7 [SEQ ID NO:43] and pSR7_PGAS [SEQ ID NO:44]. M-X show nucleic acid sequence alignment between the apple PPO isoenzyme encoding genomic sequences and the corresponding nucleic acid sequences used for constructing PGAS2: PPO2 [SEQ ID NO:45] and PPO2 PGAS2 [SEQ ID NO:46]; GPO3 [SEQ ID NO:47] and GPO3_PGAS2 [SEQ ID NO:48]; APO5 [SEQ ID NO:49] and APO5_PGAS2 [SEQ ID NO:50]; pSR7 [SEQ ID NO:51] and pSR7_PGAS2 [SEQ ID NO:52].

FIG. 9A-9E: A-C show nucleic acid sequence of the T-DNA elements of GEN-03 which are typically transferred into a plant following a transformation event: LB [SEQ ID NO:53]; $P_{NOS}$ [SEQ ID NO:54]; nptII [SEQ ID NO:55]; $T_{NOS}$ [SEQ ID NO:56]; $P_{CAMV35S}$ [SEQ ID NO:57]; PGAS [SEQ ID NO:58]; $T_{NOS}$ [SEQ ID NO:59]; and RB [SEQ ID NO:60]. D-E shows the nucleic acid sequence of the elements for PGAS2: RB [SEQ ID NO:61]; $P_{SUL409S}$ [SEQ ID NO:62]; PGAS2 [SEQ ID NO:63]; $T_{UB13}$ [SEQ ID NO:64]; and LB [SEQ ID NO:65].

FIG. 10A-10D show PPO suppression or activity in examples of GEN-03 (A and B) and OSF-02 (C and D) genetic events.

FIG. 11 shows an illustrative example of the results obtained from a detailed examination of the reduced-browning phenotype of genetic events sent to field trial.

FIG. 12 shows an illustrative example of a controlled bruised response of genetic events (743 and 784) sent to field trial relative to control events.

FIG. 13 shows an illustrative example of a reduced-browning phenotype of juice produced from genetic events (743 and 784) sent to field trial relative to control events.

FIG. 14A-14C show an illustrative example of measurement of PPO gene expression, total PPO activity, and change in luminosity in immature fruit obtained from genetic events sent to field trial, in two independent experiments (I and II).

FIG. 15 shows the nucleic acid sequence of three pear PPO encoding sequences: PearGB [SEQ ID NO:66]; Pear1 [SEQ ID NO:67] and Pear2 [SEQ ID NO:68].

FIG. 16 shows sequence identity (%) obtained through a multiple nucleic acid sequence alignment of apple and pear PPO encoding sequences with Clustal W™ (1.82).

FIG. 17 shows the relationship between PPO activity in tissue culture leaf material (TC), PPO activity in immature fruit tissue (2005), Impact Bruising (2005 and 2006) and PPO gene expression in immature fruit (2005).

DETAILED DESCRIPTION

Figure 8A:
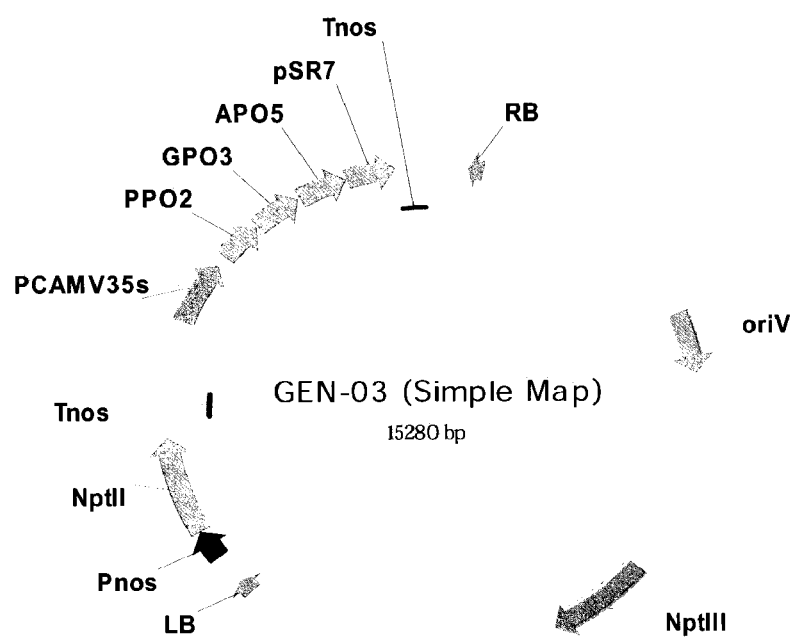
FIG. 8A-8B: A. shows an illustrative representation of GEN-03 comprising the PGAS transgene fragment in the sense orientation; and B. illustrates OSF-02, where P=PPO2; G=GPO3; A=APO5; and S=pSR7.

The invention provides a genetically modified fruit-producing plant, seed, seedling, progeny thereof, or produced fruit thereof, which genetically modified plant produces a reduced-browning fruit by having a reduced Polyphenol Oxidase (PPO) activity relative to control fruit-producing plant, seed, seedling, progeny thereof, or produced fruit thereof. The invention also provides a method of obtaining such genetically modified fruit-producing plant.

Polyphenol Oxidase (PPO) Expression in Plants

PPOs are copper-containing metalloenzymes that catalyze the oxidation of phenols to produce quinones. Quinones may subsequently react with amino acids and proteins to form brown and black pigments, resulting in the browning of produce, including without limitation, fruits and vegetables. PPOs are localized to the plastid in plants, whereas the phenolic substrates of the enzymes are sequestered in vacuoles. This compartmentalization prevents a PPO from reacting with its substrate unless the plant cells are damaged and the enzyme and its substrate are mixed.

PPO gene expression has been described in diverse genera of animals, plants, fungi and bacteria (for a review, see Mayer (2006)).

Any plant that expresses PPO and is susceptible to bruising, or produces fruit that is susceptible to bruising may be used in the context of the invention.

Among plants, PPO has been described, without limitation, in fruit-producing plants (e.g. apricot, apple, banana, pear), vegetables (e.g. artichoke, cabbage, potato, tomato), flowers (e.g. orchid); herbs (e.g. oregano); grains (e.g. wheat); and others (e.g. red clover).

The invention has application in any fruit-producing plant that expresses PPO. Such plants include, without limitation, apple, apricot, avocado, banana, blackberry, blueberry, cherry, cranberry, custard apple, date, durian, fig, grapefruit, grape, jack fruit, kiwi fruit, lychee, mandarin, mangosteen, mango, melon, nashi, nectarine, orange, papaya or paw paw, passionfruit, peach, pear, persimmon, pineapple, plum, pomegranate, pomelo, raspberry, rhubarb, star fruit, strawberry, tamarillo, and tangerine plants or trees (as used herein the term "plant" is intended to encompass also fruit-producing trees). The invention encompasses also cells, seeds, seedlings, parts, tissues, fruit and progeny of such plants.

In one embodiment the plant is an apple plant. The following are examples of PPO genes described in apple, and which may be targeted for reduction of PPO activity:

U.S. Pat. No. 6,936,748 (Robinson and Dry) described the cloning of PPO genes from potato tubers, grape, apple and broad bean. Apple PPO genes pSR7 and pSR8 were identified in addition to a partial sequence of a genomic clone, GALPO3, which appears to be very similar to the apple PPO gene, APO3.

Boss et al. (1995) screened an apple cDNA library with pSR8 and isolated six clones, including the PPO gene APO5. In personal communications with Boss, it was noted that other apple PPO clones, APO1, APO2, APO3 and APO9, were similar or identical to each other and 70% identical to APO5.

Haruta et al. (1998) isolated and characterized two apple PPO clones PPO3 and PPO7 that are nearly identical to APO5.

Kim et al. (2001) teaches that apple PPO gene PPO2 is 96% identical to pSR8. PPO2 has less homology with the other apple isoenzymes than they have to each other. PPO2 is not closely related to peach or cherry PPOs but somewhat related to a PPO sequence from apricot.

In many plant species, PPO genes are organized in multigene families. For example, Kruger et al (1976) reported 12 isoenzymes of PPO in wheat. Newman et al (1993) reported at least six PPO genes in tomato, with homologies ranging from 70-96%. Boss et al (1995) reported at least four PPO genes in apple.

The invention involves reducing activity of at least two PPO isoenzymes in a fruit-producing plant. As used herein, the term "PPO isoenzyme" encompasses enzymes that differ in amino acid sequence but catalyze the same chemical reaction. In biochemistry, isoenzymes (or isozymes) are isoforms (closely related variants) of enzymes. In many cases, homologous genes encode isoenzymes.

In an embodiment, the plant is an apple plant (Malus x domestica). The invention may be practiced in any variety of apple, such as, for example, Golden Delicious, Granny Smith, Fuji, Gala, MacIntosh, PPO isoenzymes in apple, the activity of which may be reduced in accordance with the invention, include, without limitation, any two or more of APO5 (Boss et al. (1995); pSR7; (Robinson (1993)); pSR8 (PPO2) (Robinson (1993)); PPO2 (HortResearch; Kim et al. (2001)); GPO3 (HortResearch, Boss), APO; PPO3 and PPO7 (Haruta et al. (1998)).

In an embodiment, PPO2 comprises, consists of, or consists essentially of the amino acid sequence set forth in SEQ ID NO: 19. In an embodiment, GPO3 comprises, consists of, or consists essentially of the amino acid sequence set forth in SEQ ID NO: 21. In an embodiment, APO5 comprises, consists of, or consists essentially of the amino acid sequence set forth in SEQ ID NO: 23. In an embodiment, PSR7 comprises, consists of, or consists essentially of the amino acid sequence set forth in SEQ ID NO 25.

It is anticipated that some apple varieties or indeed even other fruit-producing plant species may contain variants of PPO2, GPO3, APO5 and PSR7 that may be targeted for reduction in activity in accordance with the invention. Accordingly, the PPO isoenzyme may have an amino acid sequence that possesses at least 60%, at least 70%, at least 80%, at least 90%, at least 95%, at least 96%, at least 97%, at least 98% or at least 99% sequence identity to SEQ ID NO: 19, 21, 23 or 25. Preferably such variant sequences are species or allelic variants of the PPO2, GPO3, APO5 or PSR7 sequence as set forth in SEQ ID NO: 19, 21, 23 and 25, respectively.

The PPO isoenzyme may also be a fragment of a PPO isoenzyme as described above, the fragment possessing PPO activity. Such fragments may comprise e.g. at least 10, at least 20, at least 30, at least 40, at least 50, at least 60, at least 70, at least 80, at least 90, at least 100, at least 150, at least 200, at least 250, or at least 300 amino acids.

In an embodiment, the PPO isoenzyme described herein is a polypeptide that retains at least some PPO activity of any one of the apple isoenzymes APO5, GPO3, PPO2 or pSR7 but differs in sequence from any one of these by one or more amino acid insertions, deletions, or substitutions, particularly conservative amino acid substitutions. As used herein, the expression "conservative amino acid substitutions" refers to the substitution of one amino acid for another at a given location in the polypeptide, where the substitution occurs without substantial loss of the relevant function. Conservative substitutions generally involve substitution of an amino acid residue with another amino acid residue on the basis of relative similarity of side-chain substituents, for example, their size, charge, hydrophobicity, hydrophilicity, and the like. Specific, non-limiting examples of a conservative substitution include the following examples:

| Original Residue | Conservative Substitutions |
|---|---|
| Ala | Ser |
| Arg | Lys |

| Original Residue | Conservative Substitutions |
|---|---|
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

As used herein, the term "polypeptide" encompasses any chain of naturally or non-naturally occurring amino acids (either D- or L-amino acids), regardless of length (e.g., at least 5, 6, 8, 10, 12, 14, 16, 18, 20, 25, 30, 40, 50, 100 or more amino acids) or post-translational modification (e.g., glycosylation or phosphorylation) or the presence of e.g. one or more non-amino acyl groups (for example, sugar, lipid, etc.) covalently linked to the peptide, and includes, for example, natural proteins, synthetic or recombinant polypeptides and peptides, hybrid molecules, peptoids, peptidomimetics, etc. As used herein, the terms "polypeptide", "peptide" and "protein" may be used interchangeably.

Other apple PPO isoenzymes may be identified for use in the context of the invention. As disclosed herein, a degenerate primer approach was used to identify novel PPO gene sequences. Other approaches to identify novel PPO isoenzymes are known in the art include, but not limited to, use of degenerate primers to screen an expression library from plants that produce fruit susceptible to browning; and the use of bioinformatics to virtually identify other PPO genes.

Following the identification of a candidate PPO gene, it may be disrupted in a fruit producing plant and the produced fruit may be assessed for altered fruit-browning properties, with any of the approaches disclosed herein.

Other approaches to identify PPO isoenzymes include, without limitation, screening cDNA, genomic or bac libraries with PPO probes from apple or other species. Alternatively, sequences could be identified in the apple genome sequence soon to be published (IASMA—Istituto Agrario San Michele all'Adige).

When the invention is practiced in a pear plant, non-limiting examples of PPO isoenzymes that may be targeted for reduced activity include without limitation PPOs encoded by PearGB [SEQ ID NO:66]; Pear1 [SEQ ID NO:67] and Pear2 [SEQ ID NO:68], or fragments or variants thereof as described above.

Reduction of PPO Activity or Expression

PPO expression and/or activity in genetically modified plants of the present invention may be reduced by any method that results in reduced activity of at least two PPO isoenzymes in the plant. This may be achieved by e.g. by altering PPO at the DNA, mRNA and/or protein levels.

As used herein, "activity" refers to the biochemical reaction of an enzyme with its cognate substrate. In the context of the invention, reduced PPO activity may result from reduced protein levels of a PPO isoenzyme and/or reduced rate at which a PPO isoenzyme catalyzes its reaction with a substrate.

Total PPO activity may be determined, without limitation, by using the polyphenol oxidase specific activity assay of Broothaerts et al (2000), or a modification thereof, for example, the assay adapted for use in microtitre plate format. PPO specific activity may be expressed in terms of U/mg protein. Substrates that may be used in the assay to determine PPO specific activity are known in the art, and include, without limitation, 4-methyl catechol.

In one embodiment, PPO expression and/or activity may be altered by targeting genomic PPO genes. For example, the endogenous PPO gene may be altered by, without limitation, knocking-out one or more PPO genes; or knocking-in a heterologous DNA to disrupt one or more PPO genes. The skilled person would understand that these approaches may be applied to the coding sequences, the promoter or other regulatory elements necessary for gene transcription.

In another embodiment, PPO expression and/or activity may be altered by targeting PPO mRNA transcripts. In this regard, levels of PPO mRNA transcripts may be reduced by methods known in the art including, but not limited to, co-suppression, antisense expression, small hair pin (shRNA) expression (Zhao et al.), interfering RNA (RNAi) expression (Matzke et al.), double stranded (dsRNA) expression (Karkare et al.), inverted repeat dsRNA expression (Otani et al.), micro interfering RNA (miRNA) (Willmann and Poethig, or Pikaard), simultaneous expression of sense and antisense sequences (Karkare et al.), or a combination thereof, targeted at least two PPO isoenzymes encoding genes.

The phenomenon of co-suppression in plants relates to the introduction of transgenic copies of a gene resulting in reduced expression of the transgene as well as the endogenous gene (Napoli et al (1990); van der Krol et al. (1990). The observed effect depends on sequence identity between the transgene and the endogenous gene.

RNA interference/silencing relates to the silencing of genes by the introduction of double stranded RNA. RNA is both an initiator and target in the process (Fire et al, (1998); Lindbo et al, (1993); Montgomery et al, (1998)). This mechanism targets RNA from viruses and transposons and also plays a role in regulating development and genome maintenance. Briefly, double stranded RNA is cleaved by the enzyme dicer resulting in short fragments of 21-23 bp (siRNA). One of the two strands of each fragment is incorporated into the RNA-induced silencing complex (RISC). The RISC associated RNA strand pairs with mRNA and induces cleavage of the mRNA. Alternatively, RISC associated RNA strand pairs with genomic DNA resulting in epigenetic changes that affect gene transcription. Micro RNA (miRNA) is a type of RNA transcribed from the genome itself and works in a similar way. Similarly, shRNA may be cleaved by dicer and associate with RISC resulting in mRNA cleavage.

Antisense suppression of gene expression does not involve the catalysis of mRNA degradation, but instead involves single-stranded RNA fragments binding to mRNA and blocking protein translation.

Both antisense and sense suppression are mediated by silencing RNAs (sRNAs) produced from either a sense-antisense hybrid or double stranded RNA (dsRNA) generated by an RNA-dependent RNA polymerase (Jorgensen 2006). Majors classes or sRNAs include short-interfering RNAs (siRNAs) and microRNAs (miRNAs) which differ in their biosynthesis.

Processing of dsRNA precursors by Dicer-Like complexes yields 21-nucleotide siRNAs and miRNAs guide cleavage of target transcripts from within RNA-induced silencing complexes (RISC).

Preferably PPO expression may be suppressed using an synthetic gene or an unrelated gene that contained about 21 bp regions of high homology (preferably 100% homology) to the PPO gene.

See, for example, Jorgensen R A, Doetsch N, Muller A, Que Q, Gendler, K and Napoli C A (2006) A paragenetic perspective on integration of RNA silencing into the epigenome and in the biology of higher plants. Cold Spring Harb. Symp. Quant. Biol. 71:481-485.

For a review, see for example, Ossowski S, Schwab R and Weigel D (2008) Gene silencing in plants using artificial microRNAs and other small RNAs. The Plant Journal 53:674-690.

In a further embodiment, PPO activity may be altered by targeting one or more PPO isoenzymes at the protein level. For example, a PPO isoenzyme activity may be altered by affecting the post-translational modification of the enzyme; or by the introduction of a heterologous protein (e.g. a mutated form of one or more PPO isoenzymes may be expressed such that it associates with the wildtype PPO isoenzyme and alters its activity; or an antibody that binds specifically to one or more PPO isoenzymes).

As used herein, "expression" or "expressing" refers to production of any detectable level of a product encoded by the coding sequence. In the context of the invention, reduced PPO expression may result from reduced transcription of a PPO gene or from reduced translation of PPO mRNA transcripts.

In one embodiment, a genetically modified fruit producing plant of the invention comprises, stably integrated into its genome a first nucleic acid molecule heterologous to the plant, the presence of the first nucleic acid molecule reducing expression of a first PPO isoenzyme; and a second nucleic acid molecule heterologous to the plant, the presence of the second nucleic acid molecule in the plant reducing expression of a second PPO isoenzyme.

In one embodiment, a genetically modified plant of the present invention may further comprise a third nucleic acid molecule heterologous to the plant, the presence of said third nucleic acid molecule reducing expression of a third PPO isoenzyme.

In another embodiment, the genetically modified plant of the present invention may further comprise a fourth nucleic acid molecule heterologous to the plant, the presence of the fourth nucleic acid molecule reducing expression of a fourth PPO isoenzyme.

If a plant expresses additional PPO isoenzymes, additional heterologous nucleic acid molecules (e.g. fifth, sixth, seventh and eighth heterologous nucleic acid molecules) may also be used to reduce expression of such PPO isoenzymes.

A nucleic acid molecule that reduces the expression and/or activity of any PPO isoenzyme may be used in the context of the invention. For instance, suitable apple PPO isoenzymes that may be targeted in apple plants to reduce browning in the fruit of the plant include those described above.

Further, a nucleic acid sequence comprising a nucleic acid sequence that is at least 65%, at least 70%, at least 75%, at least 80%, at least 85%, at least 90%, at least 95%, at least 96%, at least 97%, at least 98% or at least 99% identical to the nucleic acid sequence of any known apple or other fruit PPO isoenzyme may be suitable for use in the context of the invention.

Fragments of nucleic acid sequences encoding fruit PPO isoenzymes may be used. Such fragments may have lengths of at least 20, at least 50, at least 100, at least 150, at least 200, at least 300 or at least 400 contiguous nucleotides of a nucleic acid sequence encoding a PPO. Alternatively such fragments may have a minimum length of at least 20, at least 25, at least 30, at least 35, at least 40, at least 45, or at least 50 contiguous nucleotides and a maximum length less than 3000, less than 2000, less than 1750, less than 1500, less than 1250, less than 1000, less than 750 or less than 500 contiguous nucleotides or any combination of such minimum and maximum lengths of a nucleic acid sequence encoding a PPO.

In one aspect, a nucleic acid molecule may comprise PPO2 (SEQ ID NO: 18); GPO3 (SEQ ID NO: 20); APO5 (SEQ ID NO: 22); pSR7 (SEQ ID NO: 24); a species variant thereof; an allelic variant thereof; a non-natural variant thereof; or a fragment thereof.

In one embodiment, a fragment of PPO2 as set forth in SEQ ID NO: 26; a fragment of GPO3 as set forth in SEQ ID NO: 27; a fragment of APO5 as set forth in SEQ ID NO: 28; and a fragment of pSR7 as set forth in SEQ ID NO: 29 may be suitable for use in the context of the invention.

In another embodiment, a fragment of PPO2 as set forth in SEQ ID NO: 30; a fragment of GPO3 as set forth in SEQ ID NO: 31; a fragment of APO5 as set forth in SEQ ID NO: 32; and a fragment of pSR7 as set forth in SEQ ID NO: 33 may be suitable for use in the context of the invention.

The gene fragments PPO2, GPO3, APO5, and pSR7 described herein are merely illustrative. Gene fragments suitable for use in the context of the invention may differ in sequence, in length and in location relative to those noted above may be suitable for use in the context of the invention.

For example, a gene fragment (such as a fragment of e.g. PPO2, GPO3, APO5, or pSR7) may comprise at least 20, at least 40, at least 60, at least 80, at least 100, at least 150, at least 200, at least 150, at least 300, at least 350, at least 400, at least 450 or at least 500 contiguous nucleotides of said genes. A gene fragment of PPO2, GPO3, APO5 and/or pSR7 may be 5' or 3' of the fragments of those genes disclosed herein.

Nucleic acid molecules that are substantially identical to the PPO2, GPO3, APO5, and pSR7 genes disclosed herein, may also be used in the context of the invention. As used herein, one nucleic acid molecule may be "substantially identical" to another if the two molecules have at least 60%, at least 70%, at least 80%, at least 82.5%, at least 85%, at least 87.5%, at least 90%, at least 92.5%, at least 95%, at least 96%, at least 97%, at least 98%, or at least 99% sequence identity. In one embodiment, the two nucleic acid molecules each comprise at least 20 identical contiguous nucleotides.

In various embodiments of the invention, the at least two heterologous nucleic acid molecules are selected from: at least 20, at least 50, at least 100, at least 150, at least 200, at least 300 or at least 400 contiguous nucleotides of a nucleic acid sequence possessing at least 80%, at least 90% or 100% sequence identity to the nucleic acid sequence set forth in SEQ ID NO: 18;

at least 20, at least 50, at least 100, at least 150, at least 200, at least 300 or at least 400 contiguous nucleotides of a nucleic acid sequence possessing at least 80%, at least 90% or 100% sequence identity to the nucleic acid sequence set forth in SEQ ID NO: 20;

at least 20, at least 50, at least 100, at least 150, at least 200, at least 300 or at least 400 contiguous nucleotides of a nucleic acid sequence possessing at least 80%, at least 90% or 100% sequence identity to the nucleic acid sequence set forth in SEQ ID NO: 22; and at least 20, at least 50, at least 100, at least 150, at least 200, at least 300 or at least 400 contiguous nucleotides of a nucleic acid sequence possessing at least 80%, at least 90% or 100% sequence identity to the nucleic sequence set forth in SEQ ID NO: 24.

In other embodiments of the invention, the at least two heterologous nucleic acid molecules are selected from:

a nucleic acid molecule with a minimum length of at least 20, at least 25, at least 30, at least 35, at least 40, at least 45, or at least 50 contiguous nucleotides and a maximum length less than 1750, less than 1500, less than 1250, less than 1000, less than 750 or less than 500 contiguous nucleotides or any combination of such minimum and maximum lengths of a nucleic acid sequence possessing at least 80%, at least 90% or 100% sequence identity to the nucleic acid sequence set forth in SEQ ID NO: 18;

a nucleic acid molecule with a minimum length of at least 20, at least 25, at least 30, at least 35, at least 40, at least 45, or at least 50 contiguous nucleotides and a maximum length less than 1750, less than 1500, less than 1250, less than 1000, less than 750 or less than 500 contiguous nucleotides or any combination of such minimum and maximum lengths of a nucleic acid sequence possessing at least 80%, at least 90% or 100% sequence identity to the nucleic acid sequence set forth in SEQ ID NO: 20;

a nucleic acid molecule with a minimum length of at least 20, at least 25, at least 30, at least 35, at least 40, at least 45, or at least 50 contiguous nucleotides and a maximum length less than 1750, less than 1500, less than 1250, less than 1000, less than 750 or less than 500 contiguous nucleotides or any combination of such minimum and maximum lengths of a nucleic acid sequence possessing at least 80%, at least 90% or 100% sequence identity to the nucleic acid sequence set forth in SEQ ID NO: 22; and a nucleic acid molecule with a minimum length of at least 20, at least 25, at least 30, at least 35, at least 40, at least 45, or at least 50 contiguous nucleotides and a maximum length less than 1750, less than 1500, less than 1250, less than 1000, less than 750 or less than 500 contiguous nucleotides or any combination of such minimum and maximum lengths of a nucleic acid sequence possessing at least 80%, at least 90% or 100% sequence identity to the nucleic sequence set forth in SEQ ID NO: 24.

The term "identity" refers to sequence similarity between two polypeptide or polynucleotide molecules. Identity can be determined by comparing each position in the aligned sequences. A degree of identity between amino acid or nucleic acid sequences is a function of the number of identical or matching amino acids or nucleic acids at positions shared by the sequences, for example, over a specified region. Optimal alignment of sequences for comparisons of identity may be conducted using a variety of algorithms, as are known in the art, including the Clustal W™ program, available at http://clustalw.genome.ad.jp, the local homology algorithm of Smith and Waterman, 1981, Adv. Appl. Math 2: 482, the homology alignment algorithm of Needleman and Wunsch, 1970, J. Mol. Biol. 48:443, the search for similarity method of Pearson and Lipman, 1988, Proc. Natl. Acad. Sci. USA 85:2444, and the computerised implementations of these algorithms (such as GAP, BESTFIT, FASTA and TFASTA in the Wisconsin Genetics Software Package, Genetics Computer Group, Madison, WI, U.S.A.). Sequence identity may also be determined using the BLAST algorithm (e.g. BLASTn and BLASTp), described in Altschul et al., 1990, J. Mol. Biol. 215:403-10 (using the published default settings). Software for performing BLAST analysis is available through the National Center for Biotechnology Information (through the Internet at http://www.ncbi.nlm.nih.gov/). For instance, sequence identity between two nucleic acid sequences can be determined using the BLASTn algorithm at the following default settings: expect threshold 10; word size 11; match/mismatch scores 2, −3; gap costs existence 5, extension 2. Sequence identity between two amino acid sequences may be determined using the BLASTp algorithm at the following default settings: expect threshold 10; word size 3; matrix BLOSUM 62; gap costs existence 11, extension 1. In another embodiment, the person skilled in the art can readily and properly align any given sequence and deduce sequence identity/homology by mere visual inspection.

In the alternative, two nucleic acid sequences encoding PPO isoenzymes may be substantially complementary (or are homologues/have identity) if the two sequences hybridize to each other under moderately stringent, or preferably stringent, conditions. Hybridization to filter-bound sequences under moderately stringent conditions may, for example, be performed in 0.5 M $NaHPO_4$, 7% sodium dodecyl sulfate (SDS), 1 mM EDTA at 65° C., and washing in 0.2×SSC/0.1% SDS at 42° C. (see Ausubel, et al. (eds), 1989, Current Protocols in Molecular Biology, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M $NaHPO_4$, 7% SDS, 1 mM EDTA at 65° C., and washing in 0.1×SSC/0.1% SDS at 68° C. (see Ausubel, et al. (eds), 1989, supra). Hybridization conditions may be modified in accordance with known methods depending on the sequence of interest (see Tijssen, 1993, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York). Generally, stringent conditions are selected to be about 5° C. lower than the thermal melting point for the specific sequence at a defined ionic strength and pH.

The first, second, third and/or fourth or additional nucleic acid molecules may be present in a single genetic construct or in multiple constructs. In one embodiment, the first, second, third and/or fourth or additional nucleic acid molecules may be arranged in the sense orientation relative to a promoter. In another embodiment, the first, second, third and/or fourth or additional nucleic acid molecules may be arranged in the anti-sense orientation relative to a promoter. In a further embodiment, a genetic construct may comprise at least two nucleic acid molecules in both the sense and anti-sense orientations, relative to a promoter. A genetic construct comprising nucleic acids in both the sense and anti-sense orientations may result in mRNA transcripts capable of forming stem-loop structures.

One or more of the nucleic acid molecules may be under transcriptional control of the same promoter.

A genetic construct comprising nucleic acids in both orientations relative to a promoter may further comprise a spacer to separate the nucleic acid molecules in sense orientation and those in the anti-sense orientation. As used herein, a "spacer" may comprise at least 2, at least 5, at least 10, at least 20, at least 30, at least 40, at least 50, at least 75, at least 100, at least 150, or at least 200 nucleotides. In one embodiment, the spacer may be an intron, such as an intron from a PPO gene.

In the context of the present invention, the nucleic acid molecules may comprise nucleic acid that is heterologous to the plant in which PPO activity is reduced. As used herein, "heterologous", "foreign" and "exogenous" DNA and RNA are used interchangeably and refer to DNA or RNA that does not occur naturally as part of the plant genome in which it is present or which is found in a location or locations in the genome that differ from that in which it occurs in nature. Thus, heterologous or foreign DNA or RNA is nucleic acid that is not normally found in the host genome in an identical context (i.e. linked to identical 5' and 3' sequences). In one aspect, heterologous DNA may be the same as the host DNA but introduced into a different place in the host genome and/or has been modified by methods known in the art, where the modifications include, but are not limited to, insertion in a vector, linked to a foreign promoter and/or other regulatory elements, or repeated at multiple copies. In another aspect, heterologous DNA may be from a different organism, a different species, a different genus or a different kingdom, as the host DNA. Further, the heterologous DNA may be a transgene. As used herein, "transgene" refers to a segment of DNA containing a gene sequence that has been isolated from one organism and introduced into a different organism.

As used herein, "nucleotide sequence", "polynucleotide sequence", "nucleic acid" or "nucleic acid molecule" may refer to a polymer of DNA or RNA which can be single or double stranded and optionally containing synthetic, non-natural or altered nucleotide bases capable of incorporation into DNA or RNA polymers. "Nucleic acid", "nucleic acid sequence", "polynucleotide sequence" or "nucleic acid molecule" may encompass genes, cDNA, DNA and RNA encoded by a gene. Nucleic acids, nucleic acid sequences, polynucleotide sequence and nucleic acid molecule may comprise at least 3, at least 10, at least 100, at least 1000, at least 5000, or at least 10000 nucleotides or base pairs.

As used herein, a "fragment", a "fragment thereof", "gene fragment" or a "gene fragment thereof" refers to a portion of a "nucleotide sequence", "polynucleotide sequence", "nucleic acid" or "nucleic acid molecule" that may still reduce total PPO gene expression and/or fruit browning. In one embodiment, the fragment comprises at least 20, at least 40, at least 60, at least 80, at least 100, at least 150, at least 200, at least 150, at least 300, at least 350, at least 400, at least 450 or at least 500 contiguous nucleotides.

As used herein, a "non-natural variant" refers to nucleic acid sequences native to an organism but comprising modifications to one or more of its nucleotides. Nucleic acids may be modified by any chemical and/or biological means known in the art including, but not limited to, reaction with any known chemicals such as alkylating agents, browning sugars, etc; conjugation to a linking group (e.g. PEG); methylation; oxidation; ionizing radiation; or the action of chemical carcinogens. Such nucleic acid modifications may occur during synthesis or processing or following treatment with chemical reagents known in the art.

As used herein, a "species variant" refers to an alternate form of the same PPO gene as found in different species of the same genus. The term may also refer to an alternate form of the same PPO gene as found in different varieties of the same species, for example, of a plant.

As used herein, an "allelic variant" refers to an alternate form of the same gene at a specific location of the genome.

As used herein, "wildtype" may refer to a plant or plant material that was not transformed with a nucleic acid molecule or construct, as described herein. A "wildtype" may also refer to a plant or plant material in which total PPO activity was not reduced from a reduction in activity of at least two PPO isoenzymes.

The person skilled in the art will also readily understand that although in the foregoing illustrative examples partial PPO coding sequences were used to construct the PPO suppression transgene, complete PPO coding sequences, alternative PPO coding sequences, 5'UTR and/or 3'UTR, or mutated derivatives of these sequences can also be used.

The skilled person would appreciate that the reduction in activity of at least two PPO isoenzymes may not be limited by the number of different nucleic acid molecules introduced into a plant or plant cell. In one embodiment, one nucleic acid molecule may target one or more PPO isoenzyme genes. For example, one nucleic acid molecule may target at least one, at least two, at least three, or more PPO isoenzyme genes. In another example, 3 gene segments may be used to effect suppression of 4 PPO isoenzyme gene targets: 1 segment specific for PPO2, 1 segment specific for pSR7, and 1 segment capable of targeting both APO5 and GPO3 (for example, due to microhomology). In another embodiment, one or more nucleic acid molecules may be used to target one PPO isoenzyme gene. In a further embodiment, one nucleic acid molecule may target one PPO isoenzyme gene.

The maximum number of nucleic acid molecules that may be used in the context of the invention may be limited only by the maximum size of the construct that may be delivered to a target plant or plant cell using a given transformation method.

The skilled person would also appreciate that a nucleic acid molecule comprising the sequence of a PPO gene promoter and/or other regulatory elements may be used in the context of the invention. In an embodiment, a heterologous nucleic acid molecule comprising sequences of a PPO gene promoter and/or regulatory element may be used to bias the cellular machinery away from an endogenous PPO gene promoter thus resulting in reduced PPO gene expression.

Suppression Construct

A construct of the invention comprising a first, second, third and/or fourth nucleic acid molecule may further comprise a promoter and other regulatory elements, for example, an enhancer, a silencer, a polyadenylation site, a transcription terminator, a selectable marker or a screenable marker.

As used herein, a "vector" or a "construct" may refer to any recombinant polynucleotide molecule such as a plasmid, cosmid, virus, vector, autonomously replicating polynucleotide molecule, phage, or linear or circular single-stranded or double-stranded DNA or RNA polynucleotide molecule, derived from any source. A "vector" or a "construct" may comprise a promoter, a polyadenylation site, an enhancer or silencer and a transcription terminator, in addition to a nucleotide sequence encoding a gene or a gene fragment of interest. As used herein, a "transformation vector" may refer to a vector used in the transformation of, or in the introduction of DNA into, cells, plants or plant materials.

As used herein, a "promoter" refers to a nucleotide sequence that directs the initiation and rate of transcription of a coding sequence (reviewed in Roeder, Trends Biochem Sci, 16: 402, 1991). The promoter contains the site at which RNA polymerase binds and also contains sites for the binding of other regulatory elements (such as transcription factors). Promoters may be naturally occurring or synthetic (see Datla et al. Biotech Ann. Rev 3:269, 1997 for review of plant promoters). Further, promoters may be species specific (for example, active only in *B. napus*); tissue specific (for example, the napin, phaseolin, zein, globulin, dlec2, γ-kafirin seed specific promoters); developmentally specific (for example, active only during embryogenesis); constitutive (for example maize ubiquitin, rice ubiquitin, rice actin, *Arabidopsis* actin, sugarcane bacilliform virus, CsVMV and CaMV 35S, *Arabidopsis* polyubiquitin, *Solanum bulbocastanum* polyubiquitin, *Agrobacterium tumefaciens*-derived nopaline synthase, octopine synthase, and mannopine synthase gene promoters); or inducible (for example the stilbene synthase promoter and promoters induced by light, heat, cold, drought, wounding, hormones, stress and chemicals). A promoter includes a minimal promoter that is a short DNA sequence comprised of a TATA box or an Inr element, and other sequences that serve to specify the site of transcription initiation, to which regulatory elements are added for control of expression. A promoter may also refer to a nucleotide sequence that includes a minimal promoter plus DNA elements that regulates the expression of a coding sequence, such as enhancers and silencers. Thus in one aspect, the expression of the constructs of the present invention may be regulated by selecting a species specific, a tissue specific, a development specific or an inducible promoter.

Enhancers and silencers are DNA elements that affect transcription of a linked promoter positively or negatively, respectively (reviewed in Blackwood and Kadonaga, Science, 281: 61, 1998).

Polyadenylation site refers to a DNA sequence that signals the RNA transcription machinery to add a series of the nucleotide A at about 30 bp downstream from the polyadenylation site.

Transcription terminators are DNA sequences that signal the termination of transcription. Transcription terminators are known in the art. The transcription terminator may be derived from *Agrobacterium tumefaciens*, such as those isolated from the nopaline synthase, mannopine synthase, octopine synthase genes and other open reading frame from Ti plasmids. Other terminators may include, without limitation, those isolated from CaMV and other DNA viruses, dlec2, zein, phaseolin, lipase, osmotin, peroxidase, PinII and ubiquitin genes, for example, from *Solanum tuberosum*.

In the context of the invention, the nucleic acid construct may further comprise a selectable marker. Selectable markers may be used to select for plants or plant cells that contain the exogenous genetic material. The exogenous genetic material may include, but is not limited to, an enzyme that confers resistance to an agent such as a herbicide or an antibiotic, or a protein that reports the presence of the construct.

Numerous plant selectable marker systems are known in the art and are consistent with this invention. The following review article illustrates these well known systems: Miki and McHugh; Journal of Biotechnology 107: 193-232; Selectable marker genes in transgenic plants: applications, alternatives and biosafety (2004).

Examples of a selectable marker include, but are not limited to, a neo gene, which codes for kanamycin resistance and can be selected for using kanamycin, NptII, G418, hpt etc.; an amp resistance gene for selection with the antibiotic ampicillin; an hygromycinR gene for hygromycin resistance; a BAR gene (encoding phosphinothricin acetyl transferase) which codes for bialaphos resistance including those described in WO/2008/070845; a mutant EPSP synthase gene, aadA, which encodes glyphosate resistance; a nitrilase gene, which confers resistance to bromoxynil; a mutant acetolactate synthase gene (ALS), which confers imidazolinone or sulphonylurea resistance, ALS, and a methotrexate resistant DHFR gene.

Further, screenable markers that may be used in the context of the invention include, but are not limited to, a β-glucuronidase or uidA gene (GUS), which encodes an enzyme for which various chromogenic substrates are known, green fluorescent protein (GFP), and luciferase (LUX).

The size or length of the nucleic acid construct or elements thereof, are not limited to the specific embodiments described herein. For example, the skilled person would appreciate that the size of a transgene element may be defined instead by transgene element function; and that the promoter element may be determined instead as one that was capable of driving transcription at a sufficient level and in the desired tissues. Similarly, the stem loop structure formed by the mRNA transcribed by a nucleic acid construct of the invention, may comprise a number of gene segments which may vary in length. For example, the stem loop may comprise 3 gene segments of about 21-30 basepairs each, in addition to a spacer, such as an intron (126 bp plus intron).

The skilled person would appreciate that the size of the gene segments may be established by the sum of the element sizes combined and may depend on the transformation method used to deliver the transgene into the target organism. For example, each transformation method (*Agrobacterium*, biolistics, VIGS-based delivery systems) may be limited to theoretical maximum transgene sizes.

Plant Transformation

The present invention is not limited to any particular method for transforming plant cells. Methods for introducing nucleic acids into cells (also referred to herein as "transformation") are known in the art and include, but are not limited to: Viral methods (Clapp. Clin Perinatol, 20: 155-168, 1993; Lu et al. J Exp Med, 178: 2089-2096, 1993; Eglitis and Anderson. Biotechniques, 6: 608-614, 1988; Eglitis et al, Avd Exp Med Biol, 241: 19-27, 1988); physical methods such as microinjection (Capecchi. Cell, 22: 479-488, 1980), electroporation (Wong and Neumann. Biochim Biophys Res Commun, 107: 584-587, 1982; Fromm et al, Proc Natl Acad Sci USA, 82: 5824-5828, 1985; U.S. Pat. No. 5,384,253) and the gene gun (Johnston and Tang. Methods Cell Biol, 43: 353-365, 1994; Fynan et al. Proc Natl Acad Sci USA, 90: 11478-11482, 1993); chemical methods (Graham and van der Eb. Virology, 54: 536-539, 1973; Zatloukal et al. Ann NY Acad Sci, 660: 136-153, 1992); and receptor mediated methods (Curiel et al. Proc Natl Acad Sci USA, 88: 8850-8854, 1991; Curiel et al. Hum Gen Ther, 3: 147-154, 1992; Wagner et al. Proc Natl Acad Sci USA, 89: 6099-6103, 1992).

The introduction of DNA into plant cells by *Agrobacterium* mediated transfer is well known to those skilled in the art. If, for example, the Ti or Ri plasmids are used for the transformation of the plant cell, at least the right border, although more often both the right and the left border of the T-DNA contained in the Ti or Ri plasmid must be linked to the genes to be inserted as flanking region. If agrobacteria are used for the transformation, the DNA to be integrated must be cloned into special plasmids and specifically either into an intermediate or a binary vector. The intermediate vectors may be integrated into the Ti or Ri plasmid of the agrobacteria by homologous recombination due to sequences, which are homologous to sequences in the T-DNA. This also contains the vir-region, which is required for T-DNA transfer. Intermediate vectors cannot replicate in agrobacteria. The intermediate vector can be transferred to *Agrobacterium tumefaciens* by means of a helper plasmid (conjugation). Binary vectors are able to replicate in *E. coli* as well as in agrobacteria. They contain a selection marker gene and a linker or polylinker framed by the right and left T-DNA border region. They can be transformed directly into agrobacteria. The *Agrobacterium* acting as host cell should contain a plasmid carrying a vir-region. The vir-region is required for the transfer of the T-DNA into the plant cell. Additional T-DNA may be present. Such a transformed *Agrobacterium* is used for the transformation of plant cells. The use of T-DNA for the transformation of plant cells has been intensively studied and has been adequately described in standard review articles and manuals on plant transformation. Plant explants cultivated for this purpose with *Agrobacterium tumefaciens* or *Agrobacterium rhizogenes* can be used for the transfer of DNA into the plant cell.

Although *Agrobacterium tumefaciens* LBA4404 transformation has been described, a person skilled in the art will readily understand that any other suitable method of DNA transfer into plant may be used.

Another method for introducing DNA into plant cells is by biolistics. This method involves the bombardment of plant cells with microscopic particles (such as gold or tungsten particles) coated with DNA. The particles are rapidly accelerated, typically by gas or electrical discharge, through the cell wall and membranes, whereby the DNA is released into the cell and incorporated into the genome of the cell. This method is used for transformation of many crops, including corn, wheat, barley, rice, woody tree species and others. Biolistic bombardment has been proven effective in transfecting a wide variety of animal tissues as well as in both eukaryotic and prokaryotic microbes, mitochondria, and microbial and plant chloroplasts (Johnston. Nature, 346: 776-777, 1990; Klein et al. Bio/Technol, 10: 286-291, 1992; Pecorino and Lo. Curr Biol, 2: 30-32, 1992; Jiao et al, Bio/Technol, 11: 497-502, 1993).

Another method for introducing DNA into plant cells is by electroporation. This method involves a pulse of high voltage applied to protoplasts/cells/tissues resulting in transient pores in the plasma membrane which facilitates the uptake of foreign DNA. The foreign DNA enter through the holes into the cytoplasm and then to the nucleus.

Plant cells may be transformed by liposome mediated gene transfer. This method refers to the use of liposomes, circular lipid molecules with an aqueous interior, to deliver nucleic acids into cells. Liposomes encapsulate DNA fragments and then adhere to the cell membranes and fuse with them to transfer DNA fragments. Thus, the DNA enters the cell and then to the nucleus.

Other well-known methods for transforming plant cells which are consistent with the present invention include, but are not limited to, pollen transformation (See University of Toledo 1993 U.S. Pat. No. 5,177,010); Whiskers technology (See U.S. Pat. Nos. 5,464,765 and 5,302,523).

The nucleic acid constructs of the present invention may be introduced into plant protoplasts. Plant protoplasts are cells in which its cell wall is completely or partially removed using either mechanical or enzymatic means, and may be transformed with known methods including, calcium phosphate based precipitation, polyethylene glycol treatment and electroporation (see for example Potrykus et al., Mol. Gen. Genet., 199: 183, 1985; Marcotte et al., Nature, 335: 454, 1988). Polyethylene glycol (PEG) is a polymer of ethylene oxide. It is widely used as a polymeric gene carrier to induce DNA uptake into plant protoplasts. PEG may be used in combination with divalent cations to precipitate DNA and effect cellular uptake. Alternatively, PEG may be complexed with other polymers, such as poly(ethylene imine) and poly L lysine.

A nucleic acid molecule of the present invention may also be targeted into the genome of a plant cell by a number of methods including, but not limited to, targeting recombination, homologous recombination and site-specific recombination (see review Baszcynski et al. Transgenic Plants, 157: 157-178, 2003 for review of site-specific recombination systems in plants). Homologous recombination and gene targeting in plants (reviewed in Reiss. International Review of Cytology, 228: 85-139, 2003) and mammalian cells (reviewed in Sorrell and Kolb. Biotechnology Advances, 23: 431-469, 2005) are known in the art.

As used herein, "targeted recombination" refers to integration of a nucleic acid construct into a site on the genome, where the integration is facilitated by a construct comprising sequences corresponding to the site of integration.

Homologous recombination relies on sequence identity between a piece of DNA that is introduced into a cell and the cell's genome. Homologous recombination is an extremely rare event in higher eukaryotes. However, the frequency of homologous recombination may be increased with strategies involving the introduction of DNA double-strand breaks, triplex forming oligonucleotides or adeno-associated virus.

As used herein, "site-specific recombination" refers to the enzymatic recombination that occurs when at least two discrete DNA sequences interact to combine into a single nucleic acid sequence in the presence of the enzyme. Site-specific recombination relies on enzymes such as recombinases, transposases and integrases, which catalyse DNA strand exchange between DNA molecules that have only limited sequence homology. Mechanisms of site specific recombination are known in the art (reviewed in Grindley et al. Annu Rev Biochem, 75: 567-605, 2006). The recognition sites of site-specific recombinases (for example Cre and att sites) are usually 30-50 bp. The pairs of sites between which the recombination occurs are usually identical, but there are exceptions e.g. attP and attB of λ integrase (Landy. Ann Rev Biochem, 58: 913-949, 1989).

The nucleic acid molecule becomes stably integrated into the plant genome such that it is heritable to daughter cells in order that successive generations of plant cells have reduced PPO expression. This may involve the nucleic acid molecules of the present invention integrating, for instance integrating randomly, into the plant cell genome. Alternatively, the nucleic acid molecules of the present invention may remain as exogenous, self-replicating DNA that is heritable to daughter cells. As used herein, exogenous, self-replicating DNA that is heritable to daughter cells is also considered to be "stably integrated into the plant genome".

Plant Culture

Plant cell culture techniques are known in the art (see for example Fischer et al. Biotechnol Appl Biochem, 30: 109-112, 1999; Doran. Current Opinions in Biotechnology, 11: 199-204, 2000). The skilled person would appreciate that the composition of the culture media, its pH and the incubating conditions, such as temperatures, aeration, $CO_2$ levels, and light cycles, may vary depending on the type of cells.

Plant Selection

After transformation, plant cells may be sub-cloned to obtain clonal populations of cells. Methods of sub-cloning cells are known in the art and include, but are not limited to, limiting dilution of the pool of transformed cells. For example, a construct of the invention may comprise a selectable or screenable marker, as described herein. A cell transformed with a construct comprising a selection marker may be grown under selective pressure to identify those that contain and/or express the construct.

Naturally, it could also be done without any selection marker, although this would involve a fairly high screening expenditure. If marker-free genetically modified plants are desired, there are also strategies available to the person skilled in the art, which allow subsequent removal of the marker gene, such as co-transformation and sequence-specific recombinases.

After preparing clonal populations of transgenic plant cells, the cells may be characterized and selected based on analysis at the level of DNA, RNA and protein. Preferably, transgenic plant cells in which the nucleic acid construct is stably integrated into the cell genome are selected. As used herein, "stably integrated" refers to the integration of genetic material into the genome of the transgenic plant cell and remains part of the plant cell genome over time. The term "stably integrated" may also refer to the persistence of an exogenous replicating DNA that is heritable to daughter cells.

Stable integration of nucleic acid constructs may be influenced by a number of factors including, but not limited to, the transformation method used and the vector containing the gene of interest. The transformation method determines which cell type can be targeted for stable integration. The type of vector used for stable integration defines the integration mechanism, the regulation of transgene expression and the selection conditions for stably expressing cells. After integration, the level and time of expression of the gene of interest may depend on the linked promoter and on the particular integration site.

Plant Regeneration

Once the plant material is transformed, it may be regenerated into plantlets or plants. Plant regeneration by tissue culture techniques is well established. For example, plant regeneration from cultured protoplasts is described in Evans et al, (1983); and Vasil I. R. (1986). Plants have been successfully micropropagated in vitro by organogenesis or somatic embryogenesis including, but not limited to, all major species of sugarcane, sugar beet, cotton, fruit and other trees, legumes and vegetables. The methods for regeneration vary from species to species of plants, but generally a suspension of transformed protoplasts containing copies of the heterologous gene is first provided. Callus tissue is formed and shoots may be induced from callus and subsequently rooted. Alternatively, embryo formation may be induced from a protoplast suspension. These embryos germinate to form mature plants. The culture media will generally contain various amino acids and hormones, such as auxin and cytokinins. Shoots and roots normally develop simultaneously. Efficient regeneration will depend on the type of explant, the physiological condition of the explant and physical and chemical media of the explant during culture, and on the history of the culture. In another alternative, plant material may be micrografted onto rootstocks.

Testing for Reduction of PPO Activity or Expression

Disruption of PPO genes, gene expression, or PPO enzymatic activity may be confirmed by methods known in the art of molecular biology (see e.g. Maniatis et al., (1989)). For example, disruption of PPO genes may be assessed by PCR followed by Southern blot analysis. PPO mRNA levels may, for example, be measured by real time PCR, RT-PCR, Northern blot analysis, micro-array gene analysis, and RNAse protection. PPO protein levels may, without limitation, be measured by enzyme activity assays, ELISA and Western blot analysis. PPO expression may be used as a predictor of reduced fruit browning. PPO enzymatic activity may be assessed biochemically or functionally.

For example, PPO activity may be measured biochemically by methods known in the art including, but not limited to, the detection of products formed by the enzyme in the presence of any number of heterologous substrates, for example, 4-methyl catechol. PPO activity may also be measured functionally, for example, by assessing its effects on fruit browning.

A genetically modified fruit-producing plant of the present invention may result in the reduction of total PPO activity in said plant or its seed, seedling, progeny thereof, or produced fruit thereof, by at least 57%, at least 60%, at least 65%, at least 70%, at least 75%, at least 80%, at least 85%, or of at least 89%, relative to a wild type plant, seed, seedling, progeny thereof, or produced fruit thereof.

The skilled person would appreciate that the reduction in PPO activity may vary depending on a number of factors including, but not limited to, the source of the PPO, the developmental stage of a plant or plant material, the method of cultivation, the harvesting conditions, the experimental conditions and variations thereof.

In one embodiment, the PPO specific activity of tissue culture leaf material produced from the genetically modified fruit-producing plant of the present invention may be reduced by at least 250, at least 500, at least 750, at least 1000, at least 1250, at least 1500, at least 1750, at least 2000 or at least 2250 U/mg of protein as determined with the PPO specific activity assay of Broothaerts et al (2000), or a modification thereof, adapted for use in microtitre plate format; wherein the PPO specific activity of said wildtype of said plant averages 2630 U/mg of protein.

In another embodiment, the PPO specific activity of immature fruit material produced from the genetically modified fruit-producing plant of the present invention may be reduced by at least 10000, at least 15000, at least 20000, at least 25000, at least 30000, at least 35000, at least 40000, at least 45000, at least 50000, at least 55000, at least 60000, at least 65000, or at least 70000 U/mg of protein as determined with the PPO specific activity assay of Broothaerts et al (2000), or a modification thereof, adapted for use in microtitre plate format; wherein the PPO specific activity of said wildtype of said plant averages 75160 U/mg of protein.

A genetically modified fruit-producing plant of the present invention may result in the reduction of total PPO expression in said plant or its seed, seedling, progeny thereof, or produced fruit thereof, by at least 70%, at least 75%, at least 80%, at least 85%, at least 90%, at least 95%, relative to a wild type plant, seed, seedling, progeny thereof, or produced fruit thereof.

Fruit Browning

As used herein, "reduced-browning" (or similar terminology) means that when a fruit, such as an apple, is bruised, sliced, juiced or processed in a manner where cell wall destruction takes place, browning will be detectably less than in a control. Any reduction in fruit browning (such as a reduction in browning visible to the naked eye relative to a control) may be advantageous. In one embodiment, the rate of browning of a fruit produced from a fruit-producing plant of the invention is reduced, relative to a control fruit. In another embodiment, the total quantity or degree of browning of a fruit produced from a fruit-producing plant of the invention is reduced, relative to a control fruit.

For example, an individual eating an apple would likely find it advantageous if the apple browned more slowly than a regular apple as in the case of *Ambrosia*. If that same apple were cut to be packed into a lunch or served on a fruit plate, then the apple would likely have to brown very little over an extended period of time in order to be acceptable.

Also, a consumer may indicate that some browning is acceptable, as this is the normal expectation. However, that same consumer would not purchase an apple from the store if it had any form of bruise at the time of purchase. So that consumer had already made considerable selection against apples that bruise.

Thus, industry would prefer an apple that did not suffer from bruising (which results in shrinkage) or browning (which results in lower consumer satisfaction). In other words, an apple that does not show visible evidence of browning from mechanical damage such as bruising or slicing, may have commercial advantages.

Any detectable level of reduced browning that is detectable to the naked eye may constitute a reduction in browning. Beyond this, reduced browning may be detected by a device, such as a chromameter, even if not visible to the human eye. Reduction in fruit browning may be determined in many ways, including, but not limited to, the difference in luminosity of a fruit tissue that is bruised in comparison to adjacent, unbruised tissue of the same fruit.

Fruit browning may be determined by known methods including, but not limited to, spectroscopy (e.g. light absorption, laser-induced fluorescence spectroscopy, time-delayed integration spectroscopy, large aperture spectrometer); colorimetry (e.g. tristimulus, "spekol" spectrocolorimeter); and visual inspection/scoring. These approaches allow the detection of, among other parameters, changes in luminosity and color of bruised transgenic fruit in comparison to bruised control fruit.

In one embodiment, a bruising apparatus may be used to deliver a controlled bruise to fruit with minimal destruction to the tissue. The particular specifications of such an apparatus are not critical. What is important is that the apparatus permits fruit to be bruised in a consistent manner so that the fruit may be used in controlled scientific studies.

In one embodiment, browning may be measured by the change in luminosity ($\Delta L$) or total change in color ($\Delta E$) assays described herein.

Luminosity may be measured and expressed in terms of any number of models including, but not limited to, the Hunter Lab color space or a related implementation thereof (see, for example, Hunter (1948a and 1948b)). In the Hunter Lab color space, L is a correlate of lightness which ranges from 0-100, where 100 is white and 0 is black; a and b are termed opponent color axes; a represents roughly Redness (positive) and Greenness (Negative), b is positive for yellow colors and negative for blue colors.

$\Delta L$ represents the change in luminosity between the unbruised apple (trt1) and the bruised apple flesh (trt2). A decrease in luminosity of 2.0 units ($\Delta L=-2.0$) or greater, using the Hunter color space model, is generally visible to the eye.

$\Delta E$ represents the change in total color between the unbruised apple and the bruised apple flesh. $\Delta E$ is calculated from the formulae:

$$\Delta L = L_{trt\,2} - L_{trt\,1}$$

$$\Delta a = L_{trt\,2} - L_{trt\,1}$$

$$\Delta b = L_{trt\,2} - L_{trt\,1}$$

$$\Delta E = \sqrt{(\Delta\Delta L^2) + (\Delta\Delta a^2) + (\Delta\Delta b^2)}$$

A threshold for determining that a fruit has a reduced-browning phenotype is obtained when the $\Delta L$ (i.e. difference in luminosity between a bruised area of a fruit and adjacent unbruised tissue) is less than about 0.5, less than about 1.0, less than about 1.5, less than about 2.0, less than about 2.5, less than about 3.0, less than about 3.5, or less than about 4.0, using the Hunter color space model.

In one embodiment, in Golden Delicious apples, a decrease in luminosity of about 2.0 ($\Delta L=-2.0$) is generally visible to the eye. For other apple species and/or varieties the $\Delta L$ value that represents a visible bruise may vary slightly from this depending on a number of factors, including, but not limited to, the natural flesh color of the apple (a and b color opponents). In another embodiment, an apple may be detectably low-browning to the naked eye if the decrease in luminosity is between about 2.1 to 3.5 units.

Fruit browning may also be considered with respect to a wildtype or control fruit and a test fruit produced from a reduced-browning plant of the invention. In an example, a control fruit and a test fruit produced from a reduced-browning plant of the invention are bruised in the same, or substantially the same way. Subsequently, the change in luminosity $\Delta L$ of each fruit is measured by detecting the luminosity at the site of bruising in comparison to the luminosity at an adjacent, unbruised site, resulting in a control $\Delta L$ and a test sample $\Delta L$. The test sample fruit may be considered reduced-browning if the test sample $\Delta L$ is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 20%, at least 25%, at least 30%, at least 35%, at least 40%, at least 45%, at least 50%, at least 60%, at least 70%, at least 80% or at least 90% less than the control $\Delta L$.

The skilled person would appreciate that browning may vary depending on a number of factors including, but not limited to, the manner and ambient conditions in which a fruit or plant material is bruised. For example, a fruit bruised at 2° C. may show different browning characteristics from a fruit bruised at 18° C., as detected by the eye or by an instrument, such as a chromameter, or like devices.

The skilled person would also appreciate that fruit and/or other plant material may be bruised in any number of ways. In one embodiment, fruit may be bruised according to the Controlled Bruising Procedure as follows.

Controlled Bruising Procedure

Summary

A controlled bruise is delivered to fruit (e.g. apples) in a controlled manner with minimal destruction of tissue using an impact device as described herein. Bruise response is reported as Change in Luminosity ($\Delta L$), or Total Change in Colour ($\Delta E$) between the bruised and non-bruised tissue as measured using a Minolta Chroma Meter.

Equipment and Materials

The Impact Device

The Impact Device comprises the Impact Device itself, plus a shallow container of glass beads into which the fruit is set, prior to being bruised. The Impact Device comprises a wooden block with a rounded impact surface that can be dropped from a consistent and adjustable height. A bruise, as delivered by the Impact Device could, alternatively, be produced by dropping a marble or steel ball down a tube, of a specific length, which is placed on the surface of the fruit. A shallow dish full of glass beads, into which the fruit is placed, provides a cushion to prevent damage to the underside of the fruit during impact to the top side of the fruit.

The fruit is ideally bruised with minimum tissue damage. Excessive impact can damage tissue and produce a Change in Luminosity that is unrelated to the bruising.

Colour Meter

A colour meter, e.g. a Minolta colour meter, is used to measure bruising. The meter is calibrated according to manufacturer's instructions against a white background.

Procedure

Fruit is removed from storage and allowed to come to room temperature for 2 hours. Positions of the bruises are marked with a felt pen on the fruit skin. Each fruit is bruised 5× and allowed to sit at room temperature for 3 hours for the bruise to form. The fruit are peeled over the bruise areas without removing the pen marking or cutting deeply into the flesh of the fruit. Each peeled area is measured on the non-bruised area adjacent to the bruise (trt 1) and directly on the bruised area (trt 2). Bruising, or Change in Luminosity ($\Delta L$) is calculated as: $\Delta L = trt2 - trt1$.

For further details concerning measurement of fruit bruising additional information, see e.g. Rojas-Graü M. A. et al. (2006); Gnanasekharan V. et al. (1992); and McGuire R. G. (1992).

Uses of Fruit with Reduced Browning

Fruits, vegetables and/or plants of the present invention may have commercial advantages. For example, reduced-browning produce that are easily bruised would retain the appearance of undamaged fruit, thus retaining its commercial value. In other examples, the juice of fruits and vegetables; or cut fruits and vegetables of the present invention would not require treatment with chemicals or other products to prevent browning, thus retaining the flavour and wholesomeness of the product. Accordingly, the genetically modified fruit-producing plants of the present invention may have commercial advantages in the food industry, for example, grocery, baked goods, beverages and snack industries; in advertisements and the advertising industry; in television programs (e.g. cooking shows); and in any business in which fruits and vegetables susceptible to browning are featured or displayed.

The invention is further illustrated by the following, non-limiting examples.

Examples

1. Reduction of a Single PPO Gene in Apples

In an illustrative example, the inventors have used a 250 bp fragment of AP14 between the Cu binding sites (or that includes one of the Cu binding sites) in the antisense orientation under control of the CAMV35S promoter ($P_{CAMV35S}$) and Nopaline Synthase terminator ($T_{NOS}$), which fragment was cloned into the binary vector pBIN-PLUS (van Engelen et al. 1995) to create the vector GEN-01. It was believed that the homology between all PPO sequences was sufficient that targeting any one of them would result in sufficient reduction of total PPO expression.

AP14 is highly homologous to GPO3 at the 5' end. Over the region of AP14 cloned and sequenced, AP14 is 90% identical to GPO3 at the nucleotide sequence level, and 81% identical to GPO3 at the amino acid level (FIG. 1). However, there is a change in the AP14 coding sequence that generates a translational stop codon in the AP14 sequence, and approximately 43 base pair (bp) downstream of this stop codon, there is a 7 base pair deletion in AP14, relative to GPO3, that would create a frameshift in the coding region. Therefore, it was thought that AP14 is likely a pseudogene copy of GPO3.

The inventors have also used a PPO suppression transgene in which approximately 800 bp of APO5 was placed in the antisense orientation under control of the CAMV35S promoter ($P_{CAMV35S}$) and Nopaline Synthase terminator ($T_{NOS}$) and cloned into the binary vector pBINPLUS to create the vector GEN-02, which was based on information that showed that APO5 was the predominant species present in immature fruit. Additionally, Haruta et al. (1998) had reported reduced browning in leaf tissue caused by antisense construct that carried PPO3, a homolog of APO5.

The inventors produced over 200 GEN-01 and 400 GEN-02 genetically modified lines and have identified no lines with significantly reduced PPO Activity or reduced browning phenotype.

2. Cloning and Sequencing of Apple PPO Genes

It was recognized that apple PPO activity was encoded by more than one PPO gene sequence although the sequences had not all been cloned and the family had not been clearly established.

Robinson (1993) identified pSR7 and pSR8 (later to be identified as PPO2), HortResearch found PPO2, GPO3, APO5 and pSR7 in their apple EST library (personal communication). Boss et al. (1995) identified APO5 and Haruta et al. (1998) identified PPO3 and PPO7 (APO5 homologs). Kim et al. (2001) identified PPO2. Boss also identified GPO3 (unpublished).

The inventors used PCR using degenerate PPO primers to screen apple for novel PPO gene sequences. Using this approach, GPO3, APO5 and AP14 were identified in genomic DNA; GPO3, APO5 and PPO2 (PPOJ) were identified in apple fruit and apple leaf cDNA; and GPO3 and pSR7 were identified in an immature apple fruit cDNA library (Eugentech).

TABLE I

| PPO Gene Sequence | Source | Genbank Accession | Sequence |
|---|---|---|---|
| APO5 | Boss et al. 1995 HR_PPO2 | L29450 | Complete |
| PPO3 | Haruta et al. 1998 | D87669 | Complete |
| PPO7 | Haruta et al. 1998 | D87670 | |
| PPO2 | Kim et al. 2001 HR_PPO3 | AF380300 | Complete |
| PPOJ | Okanagan Specialty Fruits | | |
| pSR8 | Robinson (WO9302195) | A27663 | Partial |
| GPO3 | Boss (personal communication) HR_PPO1 | | Partial Complete |
| AP14 | Okanagan Specialty Fruits | | |
| pSR7 | Robinson (WO9302195) HR_PPO4/5, HR_PPO8 Okanagan Specialty Fruits | A27661 | Partial Complete |
| APO3 (5' APO3 sequence.) | Boss (personal communication) | | Partial |
| APO9 (5' APO9 sequence.) | Boss (personal communication) | | Partial |
| APO3 (3' APO3 sequence.) | Boss (personal communication) | | Partial |
| APO9 (3' APO9 sequence.) | Boss (personal communication) | | Partial |

The apple PPO gene sequences thus obtained (FIG. 2) were aligned using Clustal W™ (FIG. 3) and were sorted into four groups using ContigExpress™ (Vector NTI™ Suite 9.0.0, Invitrogen) and the groups were named for the PPO sequence type.

Referring to FIG. 3, sequences APO95 and APO93 are 5' and 3' non-overlapping fragments of the same clone. Similarly, sequences APO35 and APO33 are 5' and 3' non-overlapping fragments of the same clone. The 3' sequences are identical while the 5' ends do not overlap. Based on the 3' sequence, it is assumed that the APO9 and APO3 clones are the same. Where APO9 overlaps the GPO3 sequence, they are 87% identical. Where APO3 overlaps the GPO3 sequence, they are 94% identical.

According to the alignment results obtained, it is expected that certain sequences are likely the same gene, or are likely equivalent from an antisense point of view (see Table II).

TABLE II

| Antisense Group | Targets |
| --- | --- |
| PPO2 | PPO2, PPOJ, pSR8 |
| GPO3 | GPO3, AP14, APO9, APO3 |
| APO5 | APO5, PPO3, PPO7 |
| pSR7 | pSR7 |

Accordingly, the four apple PPO gene groups are: APO5 (includes APO5, PPO3 and PPO7), GPO3 (includes GALPO3, APO3, APO9 and AP14), PPO2 (includes PPO2 and pSR8) and pSR7 (FIG. 4). Alignment of the four PPO genes (PPO2, GPO3, APO5 and pSR7) with Clustal W showed an overall homology/identity between these sequences of 61 to 75% (see Table III).

TABLE III

| Homology/identity of the four apple PPO genes | | | | |
| --- | --- | --- | --- | --- |
|  | PPO2 | GPO3 | APO5 | pSR7 |
| PPO2 | 100 | 61 | 63 | 66 |
| GPO3 |  | 100 | 75 | 62 |
| APO5 |  |  | 100 | 65 |
| pSR7 |  |  |  | 100 |

RNA Extraction from Tissue

Total RNA for RT-PCR was isolated from various apple tissues using a novel cellulose method (Weirsma 2001, submitted). Briefly, 2 g of frozen ground tissue was weighed out into a frozen 50 ml centrifuge tube. Extraction buffer (10 ml) preheated to 65° C. was added and the mixture was incubated for 1 minute at 65° C. to melt the tissue. The mixture was extracted one time with 5 ml of chloroform: isoamyl alcohol (24:1) with shaking for 10 minutes at room temperature. After centrifugation, the aqueous layer was filtered through miracloth into a fresh 50 ml centrifuge tube. Ethanol was added to the aqueous layer to a final concentration of 30% and 0.5 g CC41 (Whatman) cellulose powder was added. The mixture was shaken for 45 minutes on ice. The mixture was applied to a BioRad Econo-column and washed with approximately 250 ml of STE (30% STE: 0.1 M NaCl, 0.05 M Tris and 30% ethanol). After washing, the column was allowed to go dry and residual STE was purged from the column using a 60 ml syringe. ssRNA was eluted from the column with three elutions of 2, 1, and 1 ml of sterile double distilled water using an air purge in between each elution. Eluates were collected into a cold 50 ml centrifuge tube. Nucleic acids were precipitated by addition of 1/10 volume of 3 M NaAc pH 5.2 and 2.5 volumes of 95% ethanol overnight at −20° C. After centrifugation, the pellet was washed with 70% ethanol and aspirated dry. The RNA was solubilized in 600 µl of sterile RNAse-free water and transferred to a microfuge tube.

The 50 ml centrifuge tube was rinsed with an additional 300 µl of water which was also transferred to the microfuge tube (total volume in microfuge tube=900 µl). The ssRNA was selectively precipitated by addition of ⅓ volume of 8 M LiCl (2M LiCl final) overnight at −20° C. After centrifugation to collect the ssRNA, the ssRNA was solubilized in 400 µl of water. RNA was re-precipitated by addition of 40 µl of 3 M NaAc pH 5.2 and 1 ml of 95% ethanol. The RNA pellet was washed with 70% ethanol, aspirated dry and solubilized in 50 µl of water. The RNA was quantified spectrophotometrically and a sample was run on 1% TAE agarose gel to check integrity of RNA. RNA was stored at −80° C. until used.

EB: 0.2 M glycine, 0.1 M $Na_2HPO_4$, 0.6 M NaCl, 2% SDS, 2% PVP-40 and 5% BME

Degenerate PPO-Specific PCR Primers

PPO-specific degenerate PCR primers were developed using CODEHOP. Briefly, a consensus PPO amino acid sequence was generated from an alignment of the known apple PPO sequences (L29450, D87669, D87670, GALPO3) plus the sequences for apricot (AF020786), sweet potato (AB038994), pokeweed (D45385), tobacco (Y12501), tomato (Z12838), potato (U22922) and grape (Z27411). The alignment was submitted to the BLOCKS multiple alignment processor for arrangement into a format that is accepted by CODEHOP. The BLOCKS output was submitted to CODEHOP for selection of degenerate primers, using the *Malus domestica* codon table for back translation. CODEHOP degenerate primers were selected that were within the Copper binding sites and had similar melting temperatures (Tms). Primer JCA1 (5' TCT TCT TCC CNT TCC ACC GTT ACt ayy tnt ayt t 3') [SEQ ID NO: 69] and primer JCB1 (5' CCA GCG GAG TAA AAA TTC ccc atr tcy tc 3') [SEQ ID NO: 70] were selected. The primer JCA1 was modified to reflect codon usage in apple using the known apple DNA sequences.

Reverse Transcription

Reverse transcription (RT) (first strand synthesis) was carried out using Superscript™ II reverse transcriptase according to the manufacturers' instructions (Invitrogen). Briefly, an RNA/primer mixture was made that contained: 1 µg of total RNA, 1 µl of 10 mM dNTP and 1 µl of 2 µM cDNA primer in a final volume of 10 µl. The mixture was incubate at 65° C. for 5 minutes and then placed on ice for at least 1 minute. To this, 9 µl of a first strand synthesis reaction mixture containing: 4 µl of 5×RT buffer, 2 µl of 50 mM $MgCl_2$, 2 µl of 0.1 M DTT and 1 µl of RNAse Out™ was added. The RT reaction mixture was mixed gently, collected by brief centrifugation and incubated at 42° C. for 2 minutes. To the reaction, 1 µl of Superscript II reverse transcriptase was added and the reaction was incubated at 42° C. for 50 minutes. The reaction was terminated at 70° C. for 15 minutes and cooled on ice. Finally, 1 µl of RNAse H was added and the reaction was incubated at 37° C. for 20 minutes. The cDNA was used directly for PCR.

Hot Start, Touchdown PCR, TA Cloning and Sequencing

Hot start, touchdown PCR was used to amplify chromosomal DNA and cDNA samples. For amplification of genomic DNA, the PCR reaction contained: 1×PCR buffer, 1.5 mM $MgCl_2$, 200 µM dNTP, 1 µM JCA1, 1 µM JCB1, 1.25 U AmpliTaq Gold™, and 100 ng Golden Delicious genomic DNA. For amplification of cDNA, the PCR reaction contained: 1×PCR buffer, 1.5 mM $MgCl_2$, 200 µM dNTP, 1 µM PPO upper, 1 µM PPO lower, 1.25 U AmpliTaq Gold, and 2 µl of cDNA. The reaction was overlaid with oil and cycled. After an initial hot start incubation for 9 minutes at 95° C., the PCR reaction was subjected to 1 cycle of 95° C., 1 min; 70° C., 1 min; and 72° C., 1 min. The initial annealing temperature was reduced in each successive cycle by 2° C. to 62° C. The PCR reaction was subjected to a total of 40 cycles. After cycling, the PCR reaction was subjected to a final extension for 10 minute at 72° C., and then held at 6° C.

PCR products were size fractionated on TAE-agarose. Amplification products were excised from the gel, gel cleaned and ligated into pGEM-T Easy™. The ligation reaction was electroporated into Electromax™ DH10b cells. Plasmids carrying inserted were isolated and the insert was sequenced using M13F and M13R primers (BigDye™, ABI).

3. Reduction of PPO Expression in Apples

In a pivotal review RNA interference, Sharp (2001) suggested that for a transgene to induce silencing of a related but not identical target gene, the two segments must share regions of "identical and uninterrupted sequences of significant length" in the order of 30-35 base pair at a minimum.

Since dsRNA is processed to 21-23 nucleotide segments, Sharp suggests that a single basepair mismatch between the siRNA and target RNA dramatically reduce gene targeting and silencing.

The inventors compared pair-wise, the four PPO apple sequences, within a sliding (conservative) 22 base-pair window for regions of 100% homology.

This pair-wise analysis demonstrated that GPO3 and APO5, having an overall sequence similarity of 75%, have several regions of identical and uninterrupted sequences of significant length as shown below.

TABLE IIIb

| | Number of Regions of 22 bp Micro Homology | | |
|---|---|---|---|
| | GPO3 | APO5 | pSR7 |
| PPO2 | 0 | 0 | 0 |
| GPO3 | | 25 | 1 |
| APO5 | | | 0 |

Table IIIb shows that: there are no regions of 100% micro homology between PPO2 and GPO3, APO5 or pSR7; there are no regions of 100% micro homology between APO5 and pSR7; and that there are 25 regions of 100% micro homology of 22 bp between GPO3 and APO5. These are part of 3 larger regions of 100% homology. There is 1 region of 100% micro homology of 22 bp between GPO3 and pSR7.

4. Construction of PPO Suppression Transgene

In an illustrative example, the inventors used a PPO suppression transgene PGAS (PPO2, GPO3, APO5 and pSR7), cloned in the sense orientation in the pBINPLUS to create GEN-03, to suppress PPO mRNA expression of all four PPO isoenzymes.

The PGAS suppression transgene was constructed using standard molecular biology techniques (Sambrook et al. 1989). Briefly, approximately 0.45 kb individual PPO fragments (PPOJ, GPO3, APO5 and pSR7) (FIG. 5A) were amplified from genomic DNA (GPO3, APO5) or cDNA (PPOJ, pSR7) using degenerate PCR primers, where the fragments include the Copper A and Copper B binding sites. PPOJ and PPO2 are 90% identical and could be the same gene, if for some reason the sequencing was poor. A person skilled in the art would expect that, from a functional perspective, suppression of either gene (PPOJ or PPO2) would be reasonably expected to induce suppression of the other. The fragments were cloned individually and then combined into a single chimeric PPO suppression fragment (PGAS) (FIG. 6A). Since the PPO fragments used in the PGAS transgene were initially amplified using degenerate PCR primers, the 5' and 3' ends of the PPO fragments used in the PGAS transgene may not exactly match the sequence of the endogenous PPO gene (FIG. 7A to 7L).

These PPO gene fragments were in the "sense" orientation under the control of the double enhanced CAMV35S promoter ($P_{CAMV35S}$) and Nopaline Synthase terminator ($T_{NOS}$) to create the PPO suppression transgene ($P_{CAMV35S}$:PGAS:$T_{NOS}$) Approximately 50 bp of the PPOJ sequence was lost during the construction of the vector.

The $P_{CAMV35S}$:PGAS:$T_{NOS}$ transgene was transferred into pBINPLUS to create the plant transformation vector GEN-03 (FIG. 8A). GEN-03 was transferred into *Agrobacterium tumefaciens* LBA4404 in preparation for plant transformation. The elements of the GEN-03 T-DNA region that are transferred to the plant are described in (FIG. 9A-9C).

Figure 8B:
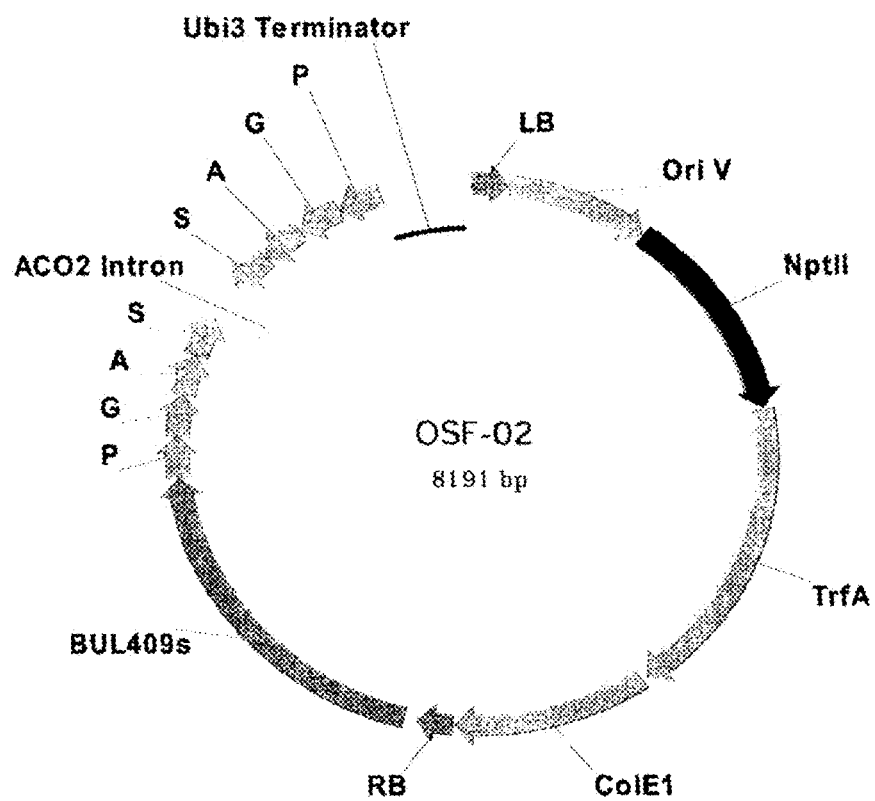

In another illustrative example, the inventors constructed an alternate PPO suppression transgene (PGAS2) (FIGS. 6B and 8B) having a 1771 bp chimeric PPO Suppression sequence comprising 200 bp fragment of each of four apple PPO genes (PPO2, GPO3, APO5 and pSR7; FIG. 5B), followed at its 3' terminal by an apple intron, followed at the intron's 3' terminal by inverted 200 bp fragment of each of pSR7, APO5, GPO3 and PPO2 (the same fragments as those used in 5' of the intron). The fragments of PPO2, GPO3, APO5 and pSR7 used in the PGAS2 transgene were aligned with their respective genes (FIG. 7M-7X). The elements of the PGAS2 transgene are described in (FIG. 9D-9F); which was used to create the OSF-02 transformation vector (FIG. 8B). RNA transcribed from this 1771 bp chimeric PPO Suppression sequence is expected to generate a dsRNA stem of 800 bp with an intron loop. The transgene was under the control of the BUL409s promoter and the Ubiquitin 3 terminator (Garbarino and Belknap 1994).

The BUL409s promoter is a polyubiquitin promoter from the wild potato *Solanum bulbocastanum* containing 5' regulatory sequences (784 bp), the 5' untranslated region (59 bp), an intron (535 bp) and an ubiquitin coding domain (228 bp) (Bill Belknap, USDA Albany).

The Ubiquitin 3 terminator is the polyubiquitin terminator from potato *Solanum tuberosum* (DQ320121) (Garbarino and Belknap 1994).

5. Apple Transformation

A. GEN-03

The GEN-03 vector (having the $P_{CAMV35S}$:PGAS:$T_{NOS}$ transgene) was transformed into apple varieties Golden Delicious (also abbreviated as "GD"), Granny Smith (also abbreviated as "GS"), Fuji (also abbreviated as "Fu") and Gala (also abbreviated as "Ga"), using *Agrobacterium tumefaciens* LBA4404 transformation.

Briefly, leaves of 3-week-old apple tissue culture plantlets were excised and cut into segments perpendicular to the mid-rib. Leaf segments were inoculated with *Agrobacterium tumefaciens* LBA4404 carrying the recombinant vector GEN-03 at a density of $3 \times 10^8$ cells/ml for 5 to 10 minutes. Leaf segments were blotted on filter paper to remove excess bacterial cells and placed onto co-cultivation medium with the adaxial surfaces in contact with the medium for 4 days (dark). Infected leaf segments were washed and placed onto regeneration medium containing 6 mg/ml kanamycin with the adaxial surfaces in contact for 4 weeks (2 weeks dark, 2 weeks light). Leaf segments were transferred to regeneration medium containing 50 mg/ml kanamycin (4 weeks). Transformed shoots were transferred to proliferation medium with 50 mg/ml kanamycin (4 weeks). Surviving shoots were transferred to proliferation medium.

The selection marker (NptII) confers resistance to the antibiotic kanamycin. Cells that received and integrated the selection marker obtained the ability to regenerate in the presence of kanamycin. Shoots that arose from callus after the transformation process typically arose from a single cell that integrated the selection marker. These shoots were presumed to be homogenous.

Each shoot represented a unique transformation event and was genetically distinct. Individual shoots were given unique EventID numbers to identify the distinct genetic event (see Table IV). All plant material (tissue culture plants, field trees, tissue samples and apples) that arose from these single genetics events retained the EventID number.

TABLE IV

EventID and PlantID Numbers (GEN-03)

| | |
|---|---|
| Event | A genetically distinct transformation event. |
| EventID | Event Identification Number. A unique identification number assigned to each Event. Example: 705 |
| Plant | A tree either self-rooted or grafted. |
| PlantID | Plant Identification Number. A unique identification number assigned to each Plant. Example: 705-0001 The first plant of event number 705 |

B. OSF-02

The OSF-02 vector (having the PBUL409s:PGAS2:TUBI3 transgene) was transformed into apple varieties Golden Delicious, Granny Smith, Fuji and Gala, using *Agrobacterium tumefaciens* LBA4404 transformation.

Briefly, leaves of specially prepared Leaf Expansion Culture plants were excised and wounded with non-traumatic forceps (manufacturer). Wounded leaves were inoculated with *Agrobacterium tumefaciens* LBA4404 carrying the recombinant vector OSF-02 for 5 minutes. Leaves are blotted on filter paper to remove excess bacterial cells and placed onto co-cultivation medium right side up for 3 days at 25° C. (dark). Infected leaves were washed. The tip and base were cut from each leaf and the remaining leaf sliced into three sections. Leaf segments were transferred to regeneration medium (without antibiotics or other selection agents) and set in the dark for 3 weeks. Plates containing the transformed leaf segments were transferred to the growth room (without light). After 1 week, the lights were turned on. Over the next 3 to 6 weeks, regenerating shoots were transferred to proliferation medium (Cornell University).

Genetically modified plants were identified by PCR.

Sterile techniques may be used as described herein.

Alternatively, using sterile techniques in a laminar flow hood, 3-4 fully expanded, young leaves (10-20 mg) in good condition were taken from shoot cultures that were 3-4 weeks old and placed into labelled 96-Deepwell plates. The plates were transferred to the −80° C. freezer and then freeze dried for 24 hours at <100 m Torr. Plant genomic DNA was isolated from leaf tissue on an automated DNA extraction system using the "Slipstream MES" protocol (HortResearch).

Genomic DNA was amplified in a PCR reaction using PCR primers that are specific for endogenous APO5, the PGAS or PGAS2 transgene, the nptII selection marker (GEN-03) or vector backbone (OSF-02) (TABLE V-b1 and V-b2).

The BUL409s promoter (OBI-04/1313-1706) is unique to the PGAS2 transgene.

The backbone nptII sequence (nptII Backbone set 1) is present in the backbone of the OSF-02 vector. This sequence is not normally present in apple and will only be present in transgenic Events where the LB was bypassed (subjected to read through) during T-DNA transfer (during transformation).

6. PCR Screening for Genetically Modified Lines

Genetically modified lines were identified by PCR. Briefly, using sterile techniques in the laminar flow hood, 3-4 fully expanded, young tissue culture leaves in good condition were taken from shoot cultures that were 3-4 weeks old and placed into labeled FastPrep™ tubes. Each tube was placed immediately into liquid nitrogen and each batch of tubes was then transferred to the −80° C. freezer for storage. Plant genomic DNA for PCR was isolated from leaf tissue using CTAB (Lodhi al. 1994). Genomic DNA was amplified in a PCR reaction using the following PCR primers that are specific for endogenous APO5, the PGAS transgene or the nptII selection marker of GEN-03 (TABLE V-a1 and V-a2). For PCR primers used to screen lines for OSF-02, see (TABLE V-b1 and V-b2).

TABLE V

Table V-a1: PCR primers for GEN-03

| Target | Primers | Size (bp) | Screen for Presence of | Genotype Correct |
|---|---|---|---|---|
| APO5 (Set1) | Apo5 Forward/Apo5 Reverse | 250 | PCR Positive Control | Positive |
| APO5 (Set2) | JA4/JA5 | 800 | PCR Positive Control | Positive |
| PGAS (Set1) | CAMV35s/GPO3-R | 953 | CAMV35S:PPO2 Junction | Positive |
| PGAS (Set2) | GPO3-L/APO5-R | 672 | GPO3:APO5 Junction | Positive |

TABLE V-continued

| Target | Primers | Product Size (bp) | Screen for Presence of | Genotype Correct |
|---|---|---|---|---|
| PGAS (Set3) | pSR7-F (A81)/NOSTERM | 556 | pSR7:NOSTERM Junction | Positive |
| nptII (set1) | nptII Forward/nptII Reverse | 286 | nptII Selection Marker | Positive |
| nptII (Set2) | nptII-F/nptII-R | 483 | nptII Selection Marker | Positive |

Table V-a2: Primer Sequences (GEN-03)

| Target | Primer Name | SEQ ID NO: | Primer Sequence (5' to 3') |
|---|---|---|---|
| APO5 (Set1) | Apo5 Forward | 71 | GCGTTGATTGTGGTTTCCTT |
| | Apo5 Reverse | 72 | TCCCGTTCCACCGTTACTAC |
| APO5 (Set2) | JA4 | 73 | GCC GTC GAC CGA CGA CGA CCC ACG |
| | JA5 | 74 | GCC GTC GAC AGC TGA GCC CAA GGA ATG |
| PGAS (Set1) | CAMV35s | 75 | ACA ATC CCA CTA TCC TTC GC |
| | GPO3-R | 76 | CCT GGA TCT GGT TCA GTG C |
| PGAS (Set2) | GPO3-L | 77 | TTC GCT AAC CCG GAC TCT |
| | APO5-R | 78 | CGG GTT CCC AAA GAA CAA CTT A |
| PGAS (Set3) | pSR7-F (A81) | 79 | GCC AAG CTT TTC CTT TCC ACC GCA TGT |
| | NOSTERM | 80 | TAT GAT AAT CAT CGC AAG AC |
| nptII (Set 1) | nptII Forward | 81 | CCT GCT TGC CGA ATA TCA T |
| | nptII Reverse | 82 | GAA ATC TCG TGA TGG CAG GT |
| nptII (Set 2) | nptII-F | 83 | GAA CAA GAT GGA TTG CAC GCA G |
| | nptII-F | 84 | CTG ATG CTC TTC GTC CAG ATC A |

Table V-b1: PCR primers for OSF-02

| Target | Primers | Product Size (bp) | Screen for Presence of | Genotype Correct |
|---|---|---|---|---|
| APO5 | Apo5 Forward/Apo5 Reverse | 250 | PCR Positive Control | Positive |
| BUL409s | SP/O3I-04/1313-1706/ ASP/OBI-04/1313-1707 | 394 | PGAS2 Transgene | Positive |
| nptII | (Set 1) Left/Right | 172 | Vector Backbone | Negative |
| nptII | (Set 2) Left/Right | 228 | Vector Backbone | Negative |

Table V-b2: Primer Sequences (OSF-02)

| Target | Primer Name | SEQ ID NO: | Primer Sequence (5' to 3') |
|---|---|---|---|
| APO5 | Apo5 Forward | 85 | GCG TTG ATT GTG GTT TCC TT |
| | Apo5 Reverse | 86 | TCC CGT TCC ACC GTT ACT AC |
| BUL409s | SP/OBI-04/1313-1706 | 87 | AGG GAG TGT GAA AAG CCC TA |
| | ASP/OBI-04/1313-1707 | 88 | GGG GAG TTT GAA GTC GAT GA |
| nptII (Set 1) | Left | 89 | GAA AGC TGC CTG TTC CAA AG |
| | Right | 90 | GAA AGA GCC TGA TGC ACT CC |
| nptII (Set 2) | Left | 91 | CGG CTC CGT CGA TAC TAT GT |
| | Right | 92 | GCA GCG GTA TTT TTC GAT CA |

APO5 is normally present in the genomic DNA of apple. A control amplification of an 800 bp fragment from apple genomic DNA with APO5-specific primers (JA4/JA5) showed that the particular DNA sample was amplifiable and that all PCR reaction components were in working order. Accordingly, all apple genomic DNA samples were expected to yield an 800 bp PCR fragment when amplified with these primers and only genomic DNA samples from which the APO5 was amplified were analyzed further.

While APO5 is present in the genomic DNA of untransformed plants, the CAMV35s:PPO2 junction, (CAMV35s/GPO3-R), the GPO3:APO5 junction (GPO3-L/APO5-R), and the pSR7:NOSTERM junction (pSR7-F/NOSTERM) are unique to the PGAS Transgene.

nptII is not normally present in untransformed apple tissue. Amplification of a 483 bp fragment from apple genomic DNA with NptII-specific primers (NptII-f/NptII-R) was evidence that NptII was present and that the tissue was therefore genetically modified tissue.

7. PPO Activity and Gene Expression

Briefly, using sterile techniques in the laminar flow hood, 6-10 fully expanded, young tissue culture leaves (approximately 10 mg) in good condition were taken from shoot cultures that were 3-4 weeks old and placed into labeled FastPrep™ tubes. Each tube was placed immediately into liquid nitrogen and each batch of tubes was then transferred to the −80° C. freezer for storage. Crude PPO was extracted from frozen ground leaf tissue. Total soluble protein was measured using BCA. Total PPO Activity was measured using 4-methyl catechol as substrate. The procedure was a modification of the Polyphenol Oxidase activity assay of Broothaerts et al (2000) adapted to a microtitre plate format.

In tissue culture, a survey of 34 untransformed Golden Delicious control samples, taken throughout the year, but from young healthy culture grown in nearly identical conditions, gave a PPO Specific Activity average of 2613+/−1019, with Specific Activity values ranging from 774-5995 U/mg protein. The Experimental Error of the PPO Assay was approximately 5-10%. Events were subjected to PPO activity screening preferably two times and more preferably >two times at successive sub-culture points.

Total RNA was extracted using a small-scale modification of the cellulose-binding method of Fils-Lycaon et al. (1996). Two g of powdered apple tissue in a 50 ml polypropylene Oak Ridge tube were shaken at room temperature for 45 min with: 9.33 ml GPS buffer (0.2 M Glycine, 0.1 M sodium phosphate (dibasic), 0.6 M NaCl, pH 9.5); 1 ml 20% (w/v) SDS; 0.3 g polyvinylpyrrolidone (PVP-40); 0.75 ml 2-mercaptoethanol; and 4.5 ml buffer-saturated (pH 8) phenol. Two ml of chloroform:isoamyl alcohol (24:1) were added and mixed briefly before centrifuging for 20 min at 14 k×g and 2° C. in a JA17 rotor (Beckman). Ten ml of the aqueous upper layer were carefully removed and filtered through Miracloth™ and 95% ethanol was added to bring the final ethanol concentration to 30% (4.5 ml 95% ethanol added to 10 ml sample). A 0.5 g quantity of cellulose (Whatman CC 51) was added and the slurry was shaken for 45 min on ice to bind the RNA. The cellulose was pelleted by centrifugation for 2 min at room temperature at 800×g, the supernatant discarded and the pellet resuspended in 40 ml 30% STE (30% (v/v) ethanol, 0.1 M NaCl, 50 mM Tris-HCl (pH 8.0), 1 mM EDTA). This wash was repeated five times with the final pellet resuspended in 25 ml 30% STE and poured into a sterile 1.5×15 cm nylon fritted column. The cellulose in the column was washed with an additional 200 ml of 30% STE and the residual buffer was expelled with air. Total RNA was eluted with RNase-free water, then precipitated with ethanol/sodium acetate in the cold and washed with 70% ethanol. The RNA was resuspended in water, residual cellulose was removed by centrifugation and the RNA quantified with RiboGreen™ (Invitrogen, Carlsbad, CA). cDNA was synthesized following a DNase I digestion from 1 μg of total RNA using Superscript II (Invitrogen) and oligo(dT) by a modification of the protocol of Huang et al. (2000). EDTA was added to chelate Mg before denaturation of the DNase I and additional Mg was added with the RT buffer to bring the final unchelated concentration to 5 mM. The RNase H step was omitted. The cDNA was diluted 4-fold with water, EDTA added to give a slight excess (0.5 mM) over Mg and stored at −20 C until use.

Real time PCR analysis was conducted in: 1× AmpliTaq™ Gold Buffer II; 2.5 mM MgCl2; 200 μM each dNTP; 7.5% glycerol; 3.0% DMSO; 1/40,000 SYBRGreen II; 0.5 unit AmpliTaq Gold; 200 nM each primer; cDNA equivalent to 6.25 ng of starting total RNA; and 20 μl final volume.

Primers were designed using Primer 3 (Rozen and Skaletsky, 2000). Primers are given in Table VI.

TABLE VI

| | PCR Primers (5' to 3') | | Size |
|---|---|---|---|
| Target | Primer One | Primer Two | (bp) |
| PPO2 | MaldoPPO2-69 [SEQ ID NO: 93] GGGACTCGCTCGACACTAAA | MaldoPPO2-71 [SEQ ID NO: 94] TCACCTCGACGCTGATTGTA | 177 |
| PPO2 | MaldoPPO2-69 [SEQ ID NO: 95] GGGACTCGCTCGACACTAAA | MaldoPPO2-70 [SEQ ID NO: 96] TCGTCATGTGCCTTCTTCTG | 229 |
| GPO3 | MaldoGPO3-64 [SEQ ID NO: 97] GTGAATGACGTGGACGATGA | MaldoGPO3-65 [SEQ ID NO: 98] CATCATCTTCAGCACCCAAA | 163 |
| GPO3 | MaldoGPO3-66 [SEQ ID N0: 99] CATCTTCAGCACCCAAATCC | MaldoGPO3-67 [SEQ ID NO: 100] TGAATGACGTGGACGATGAG | 159 |
| APO5 | MaldoAPO5-60 [SEQ ID NO: 101] AGTTTGCCGGAAGCTTTGTA | MaldoAPO5-61 [SEQ ID NO: 102] TGATGCCTGGGTTGACATAA | 218 |
| APO5 | MaldoAPO5-60 [SEQ ID NO: 103] AGTTTGCCGGAAGCTTTGTA | MaldoAPO5-62 [SEQ ID NO: 104] TTGATGCCTGGGTTGACATA | 219 |
| pSR7 | MaldopSR7-53 [SEQ ID NO: 105] TAGTGTTCCGTGGCTGTTCA | MaldopSR7-54 [SEQ ID NO: 106] TCCTCCTCGTCGATCTTCTC | 183 |
| pSR7 | MaldopSR7-53 [SEQ ID NO: 107] TAGTGTTCCGTGGCTGTTCA | MaldopSR7-56 [SEQ ID NO: 108] CTGAGCGACTCAGCATCATC | 270 |

A Stratagene Mx3000P instrument was used with cycle conditions of: 10 min 95° C. initial denaturation/enzyme activation; 40 cycles of 30 s at 95° C., 45 s at 60° C., 30 s at 72° C.; and with detection at the end of the 60° C. step. Dissociation curves were routinely run to ensure that single products were produced. Baselines and thresholds were set manually. Relative expression was calculated using the method of Pfaffl (2001) with efficiencies determined by the slopes of calibration curves using dilutions of cDNA as template. Normalization was done using an average of the expression values for the genes for protein disulphide isomerase (MdPDI1) and polyubiquitin (MdUBI2) which showed low variation in expression among the fruit samples. Measurement variation was maximized by using two cDNA synthesis reactions for each tissue and using these in separate real time PCR runs for the duplicate values plotted. Relative copy numbers were plotted on a logarithmic scale.

8. Micrografting

Lines showing highly reduced total PPO activity in tissue culture were grafted onto M9 (Malling 9) rootstocks and advanced into field trials according to Lane et al. (2003).

9. Controlled Bruising of Apples

Mature fruits were harvested from control and genetically modified apple lines and returned to laboratory for analysis. Fruits were subjected to a series of tests to determine whether the expected reduced browning phenotype followed the marked reduction in total PPO gene expression and total PPO activity. The inventors measured gene expression by quantitative PCR, total PPO activity, and browning response to slicing, impact bruising and juicing.

A special bruising apparatus was designed at PARC Summerland to deliver a controlled bruise to the apple with minimal destruction to the tissue. Apples were bruised in a consistent manner using the improvised Impact Device. Bruise response was reported as Change in Luminosity ($\Delta L$) or Total Change in Color ($\Delta E$) between the bruised and non-bruised tissue as measured using a Minolta Chroma Meter.

10. Results

A total of 184 Events were determined to be genetically modified by PCR screening. Of these, a total of 175 kanamycin-resistant Events were subjected to PPO activity screening (Events 717, 720, 721, 723-727, 735-737, 850, 881, 883, 884, 887 and 888 were not tested).

In one experiment, twelve GEN-03 Events plus untransformed control Golden Delicious or Granny Smith were selected for field trials (FIG. 10A). Some of these showed reduced-browning potential and others were sent as controls. In another experiment, twenty additional GEN-03 Events were selected for field trials (FIG. 10B). In other experiments, 10 OSF-02 Events were selected for field trials (FIG. 10C). In another experiment, 18 OSF-2 Events were selected for field trials (FIG. 10D).

Thirty-two GEN-03 Events were micrografted onto rootstocks (Malling 9), grown in the greenhouse/screenhouse and transferred into the field. Plants were grown in the field under standard commercial tree fruit management conditions.

Control and genetically modified fruits were harvested from the field trial and assessed. It is known that PPO gene expression is the highest and PPO protein is produced in immature fruit. Therefore, gene expression and Total PPO activity were measured in immature fruit harvested in the spring.

Detailed data from eight Events is provided to illustrate the relationship between total PPO activity in tissue culture leaf material, gene expression and total PPO activity in immature fruit and the desired non-browning phenotype achieved in mature apple fruit (FIG. 11).

Based on the herein described relationship between low tissue culture total PPO activity and the reduced-browning fruit phenotype, the inventors reasonably predicted that 13 Golden Delicious Events (702, 703, 705, 707, 730, 743, 752, 792, 801, 831, 842, 845 and 846), 1 Granny Smith Event (784), and 1 Fuji Event (872) should produce a reduced-browning fruit phenotype. In fact, Event 792 showed a reduced total PPO activity of 66% (FIG. 14B) and a $\Delta L$ of −1.1 and −0.5 in two independent experiments (FIG. 14C).

Three Golden Delicious Events (705, 707 and 743) had been selected initially showing reduction in total PPO activity in tissue culture of approximately 80%-90% relative to a control fruit. In immature fruit tissue, these Events showed significant reduction in gene expression of all four PPO genes. The suppression was more complete closer to the ends of the transgene and especially toward the 3' end (pSR7). Decreased gene expression in immature fruit tissue was reflected in marked reduction in total PPO Activity of approximately 75-92%. Apples harvested from these Events were of a reduced-browning phenotype (low change in luminosity). Images of the "Controlled Bruising" provided in FIG. 12 clearly show that the change in luminosity that was measured in the reduced-browning Events was barely visible to the eye.

Juice produced from Event 743 did not significantly brown (FIG. 13 top). Even when left overnight at room temperature, while the untransformed control was darkened considerably within 15 minutes. It was also observed that the wet bruising often associated with damaged apple flesh did not occur in the reduced-browning Events.

The results obtained for Golden Delicious apples were similarly obtained in Granny Smith apple (784) (FIG. 13 bottom).

Many other Events were sent to the field for evaluation and the detailed results are reported in FIGS. 14A-14C.

Recovery of a large number of Golden Delicious Events reflects the emphasis on this apple variety for proof of concept of the reduced-browning technology and the amount of Golden Delicious material pushed through the transformation procedure, and should not be construed as limiting the invention.

REFERENCES

1. Boss P K, Gardner R C, Janssen B J, Ross G S. (1995) An apple Polyphenol Oxidase cDNA is up-regulated in wounded tissues. Plant Molecular Biology 27(2):429-33.
2. Brushett, Lynda, Lacasse, Stephen (2006) Regional Market Analysis for Fresh-cut Apple Slices. Cooperative Development Institute, Deerfield M A
3. Buta J G, Moline H E, Spaulding D W and Wang C Y (1999) Extending storage life of fresh-cut apples using natural products and their derivatives. Journal of Agriculture and Food Chemistry 47: 1-6.
4. Chen J S, Balaban M O, Wei C I, Marshall M R and Hsu W Y (1992) Inactivation of Polyphenol Oxidase by high pressure carbon dioxide. Journal of Agriculture and Food Chemistry 40: 2345-2349.
5. CLUSTAL W (1.82) Multiple Sequence Alignments (http://bioweb.pasteur.fr/seqanal/interfaces/clustalw-simple.html)
6. Eskin M (1990) Biochemistry of food spoilage: enzymatic browning. In: Eskin, M. (Ed.), Biochemistry of Foods, Academic Press, Inc., pp. 401-432.
7. Evans et al, Handbook of Plant Cell Cultures, Vol. 1: (MacMillan Publishing Co. New York, 1983.
8. Fire, A. et al. Nature 391: 706-811, 1998.
9. Friedman M (1991) Prevention of adverse effects of food browning. Advances in Experimental Medical Biology 289: 171-215.

10. Garbarino and Belknap (1994) Isolation of a ubiquitin-ribosomal protein gene (ubi3) from potato and expression of its promoter in genetically modified plants. Plant Mol Biol. 1994 January; 24(1): 119-27.
11. Gnanasekharan V. et al. (1992) Detection of Color Changes in Green Vegetables. Journal of Food Science. 57: 149-154.
12. Haruta M, Murata M, Hiraide A, Kadokura H, Yamasaki M, Sakuta M, Shimizu S, and Homma S (1998) Cloning genomic DNA encoding apple Polyphenol Oxidase and comparison of the gene product in *Escherichia coli* and in apple. Bioscience Biotechnology Biochemistry 62: 358-362.
13. Heimdal H, Kuhn B F, Poll L, and Larsen L M (1995) Biochemical changes and sensory quality of shredded and MA-packaged iceberg lettuce. Journal of Food Science 60: 1265-1268.
14. Hunter, Richard Sewall (July 1948a). "Photoelectric Color-Difference Meter". JOSA 38 (7): 661.
15. Hunter, Richard Sewall (December 1948b). "Accuracy, Precision, and Stability of New Photo-electric Color-Difference Meter". JOSA 38 (12): 1094.
16. Jiang, Y., Fu, J., Jiang, Y., & Fu, J. R., (1998). Inhibition of Polyphenol Oxidase and the browning control of litchi fruit by glutathione and citric acid. Food Chemistry, 62, 49-52.
17. Jorgensen R A, Doetsch N, Muller A, Que Q, Gendler, K and Napoli C A (2006) A paragenetic perspective on integration of RNA silencing into the epigenome and in the biology of higher plants. Cold Spring Harb. Symp. Quant. Biol. 71:481-485.
18. Karkare et al. Appl Biochem Biotechnol. 2004 October; 119(1): 1-12.
19. Kim J Y, Seo Y S, Kim J E, Sung S-K, Song K-J, An G and Kim W T (2001) Two Polyphenol Oxidases are differentially expressed during vegetative and reproductive development and in response to wounding in the Fuji apple. Plant Science 161: 1145-1152.
20. Kruger et al., Cereal Chem, 53: 201-213, 1976.
21. Lane W D, Bhagwat B, Armstrong J D and Wahlgren S (2003) Apple micrografting protocol to establish genetically modified clones on field ready rootstock. Biotechnology 13(4):641-646.
22. Lindbo, J. A. et al. Plant Cell 5: 1749-1759, 1993.
23. Lodhi, M. A. et al. (1994) A simple and efficient method for DNA extraction from grapevine cultivars and *Vitis* species. Plant Mol. Biol. Reporter 12: 6-13
24. Maniatis T, Fritsch E F and Sambrook J (1989) Molecular Cloning: A Laboratory Manual, 2nd Ed., Cold Spring Harbor Laboratory, Cold Spring Harbor (NY).
25. Mar-Sojo M, Nunez-Delicado E, Garcia-Carmona F, and Sanchez-Ferrer A. (1998) Monophenolase activity of latent banana pulp Polyphenol Oxidase. Journal of Agriculture and Food Chemistry 46: 4931-4936.
26. Martinez M V and Whitaker J R (1995) The biochemistry and control of enzymatic browning. Trends in Food Science and Technology 6: 195-200.
27. Matzke et al. Curr Opin Plant Biol. 2007 October; 10(5): 512-9. Epub 2007 Aug. 16. Review.
28. Mayer, Phytochemistry 67: 2318-2331, 2006.
29. McEvily A J, Iyengar R and Otwell W S (1992) Inhibition of enzymatic browning in foods and beverages. Critical Reviews in Food Science and Nutrition 32: 253-273.
30. McGuire R. G. (1992) Reporting of Objective Color Measurements. HortScience 27: 1254-1255.
31. Montgomery, M. K. et al. PNAS 95: 15502-15507, 1998.
32. Murata et al., J. Agric. Food Chem, 48: 5243-5248, 2000.
33. Murata et al., Biosci. Biotechnol Biochem, 65: 383-388, 2001.
34. Napoli et al., Plant Cell 2: 279-289, 1990.
35. Newman et al., Plant Mol Biol, 21: 1035-101, 1993.
36. Osmianski J and Lee C Y (1990) Inhibition of Polyphenol Oxidase activity and browning by honey. Journal of Agricultural and Food Chemistry 38: 1892-1895.
37. Ossowski S, Schwab R and Weigel D (2008) Gene silencing in plants using artificial microRNAs and other small RNAs. The Plant Journal 53:674-690.
38. Otani et al. Plant Cell Rep. 2007 October; 26(10): 1801-7. Epub 2007 Jul. 12.
39. Pikaard. Cold Spring Harb Symp Quant Biol. 2006; 71: 473-80.
40. Rojas-Graü M. A. et al. (2006) Browning Inhibition in Fresh-cut 'Fuji' Apple Slices by Natural Antibrowning Agents. Journal of Food Science. 71: S59-S65.
41. Sambrook J, Fritsch E F and Maniatis T (1989) Molecular Cloning: A Laboratory Manual (Second Edition). Cold Spring Harbor Laboratory Press.
42. Sapers G M (1993) Browning of foods: control by sulfites, antioxidants, and other means. Food Technology 47: 75-84.
43. Sharp P A (2001) RNA interference. Genes and Development 15: 485-90.
44. Simon Piers Robinson (CSIRO) U.S. Pat. No. 5,846,531 Jun. 5, 2001, WO93/02195 February 1993, WO94/0367 February 1994, WO96/37617 November 1996.
45. van der Krol, A. R. et al. Plant Cell 2: 291-299, 1990.
46. Vasil I. R. (ed), Cell Culture and Somatic Cell Genetics of Plants, Acad. Press, Orlando, Vol. I, 1984, and Vol. III, 1986.
47. Weemaes C (1998) Temperature and/or pressure inactivation of Polyphenol Oxidases for preservation of enzymatic browning in foods: a kinetic. Nr. 380 aan de Faculteit Landbouwkundige en Toegepaste Biologische Wetenschappen van de K. U. Leuven.
48. Whitaker J R and Lee C Y (1995) Recent advances in chemistry of enzymatic browning: an overview. In: Lee C Y and Whitaker J R (Eds), Enzymatic browning and its prevention, American Chemical Society Wash. D. C. pp. 2-7.
49. Willmann and Poethig. Curr Opin Plant Biol. 2007 October; 10(5):503-11. Epub 2007 Aug. 20. Review.
50. Zhao et al. Acta Biochim Biophys Sin (Shanghai). 2006 January; 38(1):22-8.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

As used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

The invention claimed is:

1. A genetically modified apple plant comprising a heterologous nucleic acid molecule comprising two or more of:
   a first nucleic acid sequence comprising at least 50 contiguous nucleotides of SEQ ID NO:18;
   a second nucleic acid sequence comprising at least 50 contiguous nucleotides of SEQ ID NO:20;
   a third nucleic acid sequence comprising at least 50 contiguous nucleotides of SEQ ID NO:22; and
   a fourth nucleic acid sequence comprising at least 50 contiguous nucleotides of SEQ ID NO:24;
   wherein when two or more of the first, second, third, and fourth nucleic acid sequences are present, each is capable of reducing expression of a corresponding first, second, third, or fourth polyphenol oxidase (PPO) isoenzymes, such that fruit of said apple plant has reduced browning potential relative to fruit of a wild type apple plant, and wherein the reduced browning potential results from reduction in expression of two or more genes encoding polyphenol oxidase (PPO) isoenzymes in said genetically modified apple plant compared to said wild type apple plant, and
   wherein at least one of the two or more nucleic acid sequences comprises the second or the fourth nucleic acid sequence.

2. The genetically modified apple plant of claim 1, wherein the heterologous nucleic acid molecule comprises three or more of the first, second, third, and fourth nucleic acid sequences.

3. The genetically modified apple plant of claim 1, wherein the heterologous nucleic acid molecule comprises all four of the first, second, third, and fourth nucleic acid sequences.

4. The genetically modified apple plant of claim 1, wherein the heterologous nucleic acid molecule is operably linked to a promoter.

5. The genetically modified apple plant of claim 1, wherein the heterologous nucleic acid molecule encodes an mRNA molecule capable of forming a stem-loop structure.

6. The genetically modified apple plant of claim 1, wherein the browning of fruit produced from said genetically modified apple plant is reduced by at least 50% relative to the wild type apple plant.

7. A genetically modified apple plant cell, seed, seedling, part, tissue, fruit, or progeny of the genetically modified apple plant of claim 1.

8. A genetically modified apple plant fruit from the genetically modified apple plant of claim 1.

9. A beverage comprising juice from the genetically modified apple plant fruit of claim 8.

10. A genetically modified apple plant part from the genetically modified apple plant of claim 1.

11. A foodstuff comprising the genetically modified apple plant part of claim 10.

12. A genetically modified apple plant comprising a heterologous nucleic acid molecule comprising three or more of:
   a first nucleic acid sequence comprising at least 50 contiguous nucleotides of SEQ ID NO:18;
   a second nucleic acid sequence comprising at least 50 contiguous nucleotides of SEQ ID NO:20;
   a third nucleic acid sequence comprising at least 50 contiguous nucleotides of SEQ ID NO:22; and
   a fourth nucleic acid sequence comprising at least 50 contiguous nucleotides of SEQ ID NO:24;
   wherein when three or more of the first, second, third, and fourth nucleic acid sequences are present, each is capable of reducing expression of a corresponding first, second, third, or fourth polyphenol oxidase (PPO) isoenzyme, such that fruit of said apple plant has reduced browning potential relative to fruit of a wild type apple plant, and wherein the reduced browning potential results from reduction in expression of three or more genes encoding polyphenol oxidase (PPO) isoenzymes in said genetically modified apple plant compared to said wild type apple plant.

13. The genetically modified apple plant of claim 12, wherein the heterologous nucleic acid molecule is operably linked to a promoter, and
   wherein the heterologous nucleic acid molecule encodes an mRNA molecule capable of forming a stem-loop structure.

14. The genetically modified apple plant of claim 12, wherein the browning of fruit produced from said genetically modified apple plant is reduced by at least 50% relative to the wild type apple plant.

15. A genetically modified apple plant cell, seed, seedling, part, tissue, fruit, or progeny of the genetically modified apple plant of claim 12.

16. A genetically modified apple plant fruit from the genetically modified apple plant of claim 12.

17. A beverage comprising juice from the genetically modified apple plant fruit of claim 16.

18. A genetically modified apple plant part from the genetically modified apple plant of claim 12.

19. A foodstuff comprising the genetically modified apple plant part of claim 18.

\* \* \* \* \*